(12) United States Patent
Mudryk et al.

(10) Patent No.: US 8,049,019 B2
(45) Date of Patent: Nov. 1, 2011

(54) SUBSTITUTED PYRROLIDINE-2-ONE COMPOUNDS

(75) Inventors: Boguslaw M. Mudryk, East Windsor, NJ (US); Michael E. Randazzo, East Windsor, NJ (US); Rulin Zhao, Pennington, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 76 days.

(21) Appl. No.: 12/606,255

(22) Filed: Oct. 27, 2009

(65) Prior Publication Data
US 2010/0113489 A1 May 6, 2010

Related U.S. Application Data

(62) Division of application No. 11/782,742, filed on Jul. 25, 2007, now Pat. No. 7,629,351.

(60) Provisional application No. 60/896,026, filed on Mar. 21, 2007, provisional application No. 60/834,235, filed on Jul. 28, 2006.

(51) Int. Cl.
*C07D 207/00* (2006.01)
(52) U.S. Cl. .................................. 548/550; 549/345
(58) Field of Classification Search .................. 548/550; 549/345
See application file for complete search history.

(56) References Cited

U.S. PATENT DOCUMENTS

| | | | |
|---|---|---|---|
| 6,706,712 | B2 | 3/2004 | Cherney |
| 6,974,836 | B2 | 12/2005 | Carter et al. |
| 7,087,604 | B2 | 8/2006 | Cherney |
| 7,157,470 | B2 | 1/2007 | Smallheer et al. |
| 7,163,937 | B2 | 1/2007 | Carter et al. |
| 7,183,270 | B2 | 2/2007 | Cherney et al. |
| 7,230,133 | B2 | 6/2007 | Carter |
| 2003/0171218 | A1 | 9/2003 | Bojack et al. |
| 2004/0186143 | A1 | 9/2004 | Carter et al. |
| 2004/0235836 | A1 | 11/2004 | Cherney |
| 2005/0043392 | A1 | 2/2005 | Carter |
| 2005/0054626 | A1 | 3/2005 | Carter et al. |
| 2005/0054627 | A1 | 3/2005 | Carter et al. |
| 2005/0065147 | A1 | 3/2005 | Carter |
| 2006/0069123 | A1 | 3/2006 | Xia et al. |
| 2007/0197516 | A1 | 8/2007 | Carter |

FOREIGN PATENT DOCUMENTS

| | | |
|---|---|---|
| EP | 0 550 924 | 7/1993 |
| JP | 63-83082 | 4/1988 |
| WO | WO 97/05111 | 2/1997 |
| WO | WO 97/43257 | 11/1997 |
| WO | WO 98/01426 | 1/1998 |
| WO | WO 99/00362 | 1/1999 |
| WO | WO 99/07678 | 2/1999 |
| WO | WO 99/37304 | 7/1999 |
| WO | WO 99/38844 | 8/1999 |
| WO | WO 99/40914 | 8/1999 |
| WO | WO 99/46991 | 9/1999 |
| WO | WO 01/10799 | 2/2001 |
| WO | WO 01/17992 | 3/2001 |
| WO | WO 02/04416 | 1/2002 |
| WO | WO 02/060859 | 8/2002 |
| WO | WO 02/078679 | 10/2002 |
| WO | WO 02/102372 | 12/2002 |
| WO | WO 03/005824 | 1/2003 |
| WO | WO 03/075853 | 9/2003 |
| WO | WO 2004/022536 | 3/2004 |
| WO | WO 2004/071460 | 8/2004 |
| WO | WO 2004/098516 | 11/2004 |
| WO | WO 2004/110376 | 12/2004 |

(Continued)

OTHER PUBLICATIONS

Abbadie, C. et al., "Impaired neuropathic pain responses in mice lacking the chemokine receptor CCR2", Proceedings of the National Academy of Sciences, vol. 100, No. 13, pp. 7947-7952 (2003).

(Continued)

*Primary Examiner* — James O Wilson
*Assistant Examiner* — Douglas M Willis
(74) *Attorney, Agent, or Firm* — Laurelee A. Duncan

(57) ABSTRACT

The present invention provides a novel antagonist or partial agonists/antagonist of MCP-1 receptor activity: N-((1R,2S,5R)-5-(tert-butylamino)-2-((S)-2-oxo-3-(6-(trifluoromethyl)quinazolin-4-ylamino) pyrrolidin-1-yl)cyclohexyl)acetamide, or a pharmaceutically acceptable salt, solvate or prodrug, thereof, having an unexpected combination of desirable pharmacological characteristics. Crystalline forms of the present invention are also provided. Pharmaceutical compositions containing the same and methods of using the same as agents for the treatment of inflammatory diseases, allergic, autoimmune, metabolic, cancer and/or cardiovascular diseases is also an objective of this invention. The present disclosure also provides a process for preparing compounds of Formula (I), including N-((1R,2S,5R)-5-(tert-butylamino)-2-((S)-2-oxo-3-(6-(trifluoromethyl)quinazolin-4-ylamino)pyrrolidin-1-yl)cyclohexyl)acetamide:

I

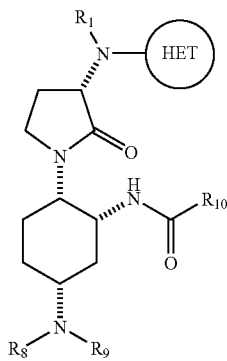

wherein $R^1$, $R^8$, $R^9$, $R^{10}$, and

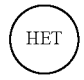

are as described herein. Compounds that are useful intermediates of the process are also provided herein.

1 Claim, 27 Drawing Sheets

FOREIGN PATENT DOCUMENTS

| WO | WO 2005/021500 | 3/2005 |
|----|----|----|
| WO | WO 2006/013427 | 2/2006 |

OTHER PUBLICATIONS

Abdi, R. et al., "Differential Role of CCR2 in Islet and Heart Allograft Rejection: Tissue Specificity of Chemokine/Chemokine Receptor Function in Vivo", The Journal of Immunology, vol. 172, pp. 767-775 (2004).

Andres, P.G. et al., "Mice with a Selective Deletion of the CC Chemokine Receptors 5 or 2 are Protected from Dextran Sodium Sulfate-Mediated Colitis: Lack of CC Chemokine Receptor 5 Expression Results in a NK1.1$^+$ Lymphocyte-Associated Th2-Type Immune Response in the Intestine", The Journal of Immunology, vol. 164, pp. 6303-6312 (2000).

Antoniades, H.N. et al., "Expression of monocyte chemoattractant protein 1 mRNA in human idiopathic pulmonary fibrosis", Proc. Natl. Acad. Sci. USA, vol. 89, pp. 5371-5375 (1992).

Baba, M. et al., "Identification of CCR6, the Specific Receptor for a Novel Lymphocyte-directed CC Chemokine LARC", The Journal of Biological Chemistry, vol. 272, No. 23, pp. 14893-14898 (1997).

Belperio, J.A. et al., "Critical role for the chemokine MCP-1/CCR2 in the pathogenesis of bronchiolitis obliterans syndrome", The Journal of Clinical Investigation, vol. 108, No. 4, pp. 547-556 (2001).

Berman, J.W. et al., "Localization of Monocyte Chemoattractant Peptide-1 Expression in the Central Nervous System in Experimental Autoimmune Encephalomyelitis and Trauma in the Rat", The Journal of Immunology, vol. 156, pp. 3017-3023 (1996).

Bonini, J.A. et al., "Cloning, Expression, and Chromosomal Mapping of a Novel Human CC-Chemokine Receptor (CCR10) that Displays High-Affinity Binding for MCP-1 and MCP-3", DNA and Cell Biology, vol. 16, No. 10, pp. 1249-1256 (1997).

Boring, L. et al., "Decreased lesion formation in CCR2$^{-/-}$ mice reveals a role for chemokines in the initiation of atherosclerosis", Nature, vol. 394, pp. 894-897 (1998).

Boring, L. et al., "Impaired Monocyte Migration and Reduced Type 1 (Th1) Cytokine Responses in C-C Chemokine Receptor 2 Knockout Mice", The Journal of Clinical Investigation, vol. 100, No. 10, pp. 2552-2561 (1997).

Brodmerkel, C.M. et al., "Discovery and Pharmacological Characterization of a Novel Rodent-Active CCR2 Antagonist, INCB3344", The Journal of Immunology, vol. 175, pp. 5370-5378 (2005).

Brühl, H. et al., "Dual Role of CCR2 during Initiation and Progression of Collagen-Induced Arthritis: Evidence for Regulatory Activity of CCR2$^+$ T Cells", The Journal of Immunology, vol. 172, pp. 890-898 (2004).

Bruun, J.M. et al., "Monocyte Chemoattractant Protein-1 Release is Higher in Visceral than Subcutaneous Human Adipose Tissue (AT): Implication of Macrophages Resident in the AT", The Journal of Clinical Endocrinology & Metabolism, vol. 90, No. 4, pp. 2282-2289 (2005).

Bush, E. et al., "CC Chemokine Receptor 2 is Required for Macrophage Infiltration and Vascular Hypertrophy in Angiotensin II-Induced Hypertension", Hypertension, vol. 36, pp. 360-363 (2000).

Carter, P.H., "Chemokine receptor antagonism as an approach to anti-inflammatory therapy: 'just right' or plain wrong?", Current Opinion in Chemical Biology, vol. 6, pp. 510-525 (2002).

Charo, I.F. et al., "Molecular cloning and functional expression of two monocyte chemoattractant protein 1 receptors reveals alternative splicing of the carboxyl-terminal tails", Proc. Natl. Acad. Sci. USA, vol. 91, pp. 2752-2756 (1994).

Charo, I.F. et al., "The Many Roles of Chemokines and Chemokine Receptors in Inflammation", The New England Journal of Medicine, vol. 354, No. 6, pp. 610-621 (2006).

Chen, A. et al., "Diet Induction of Monocyte Chemoattractant Protein-1 and its Impact on Obesity", Obesity Research, vol. 13, No. 8, pp. 1311-1320 (2005).

Chen, H., "Cellular inflammatory responses: Novel insights for obesity and insulin resistance", Pharmacological Research, vol. 53, pp. 469-477 (2006).

Chow, F.Y. et al., "Monocyte chemoattractant protein-1-induced tissue inflammation is critical for the development of renal injury but not type 2 diabetes in obese *db/db* mice", Diabetologia, vol. 50, pp. 471-480 (2007).

Cipollone, F. et al., "Elevated Circulating Levels of Monocyte Chemoattractant Protein-1 in Patients with Restenosis After Coronary Angioplasty", Arterioscler. Thromb. Vasc. Biol., vol. 21, pp. 327-334 (2001).

Combadiere, C. et al., "Cloning and Functional Expression of a Human Eosinophil CC Chemokine Receptor", The Journal of Biological Chemistry, vol. 270, No. 27, pp. 16491-16494 (1995).

Connor, R.I. et al., "Change in Coreceptor Use Correlates with Disease Progression in HIV-1-Infected Individuals", J. Exp. Med., vol. 185, No. 4, pp. 621-628 (1997).

Connor, S.J. et al., "CCR2 expressing CD4$^+$ lymphocytes are preferentially recruited to the ileum in Crohn's disease", Gut, vol. 53, pp. 1287-1294 (2004).

Conti, I. et al., "CCL2 (monocyte chemoattractant protein-1) and cancer", Seminars in Cancer Biology, vol. 14, pp. 149-154 (2004).

Costain, W.J. et al., "Modulatory effects of PLG and its peptidomimetics on haloperidol-induced catalepsy in rats", Peptides, vol. 20, pp. 761-767 (1999).

Craig, M.J. et al., "CCL2 (Monocyte Chemoattractant Protein-1) in cancer bone metastases", Cancer Metastasis Rev., vol. 25, pp. 611-619 (2006).

Dandona, P. et al., "A Rational Approach to Pathogenesis and Treatment of Type 2 Diabetes Mellitus, Insulin Resistance, Inflammation, and Atherosclerosis", The American Journal of Cardiology, vol. 90, No. 5A, pp. 27G-33G (2002).

Dawson, J. et al., "Targeting monocyte chemoattractant protein-1 signalling in disease", Expert Opin. Ther. Targets, vol. 7, No. 1, pp. 35-48 (2003).

Dawson, T.C. et al., "Absence of CC chemokine receptor-2 reduces atherosclerosis in apolipoprotein E-deficient mice", Atherosclerosis, vol. 143, pp. 205-211 (1999).

Deleuran, M. et al., "Localization of monocyte chemotactic and activating factor (MCAF/MCP-1) in psoriasis", Journal of Dermatological Science, vol. 13, pp. 228-236 (1996).

Dimitrijevic, O.B. et al., "Absence of the Chemokine Receptor CCR2 Protects Against Cerebral Ischemia/Reperfusion Injury in Mice", Stroke, vol. 38, pp. 1345-1353 (2007).

Doranz, B.J. et al., "A Dual-Tropic Primary HIV-1 Isolate that Uses Fusin and the β-Chemokine Receptors CKR-5, CKR-3, and CKR-2b as Fusion Cofactors", Cell, vol. 85, pp. 1149-1158 (1996).

Dresser, G.K. et al., "Pharmacokinetic-Pharmacodynamic Consequences and Clinical Relevance of Cytochrome P450 3A4 Inhibition", Clin. Pharmacokinet., vol. 38, No. 1, pp. 41-57 (2000).

Eckel, R.H. et al., "The metabolic syndrome", The Lancet, vol. 365, pp. 1415-1428 (2005).

Egashira, K. et al., "Importance of Monocyte Chemoattractant Protein-1 Pathway in Neointimal Hyperplasia After Periarterial Injury in Mice and Monkeys", Circulation Research, vol. 90, pp. 1167-1172 (2002).

Evans, M.C. et al., "Synthesis and Dopamine Receptor Modulating Activity of Novel Peptidomimetics of L-Prolyl-L-leucyl-glycinamide Featuring α, α-Disubstituted Amino Acids", Journal of Medicinal Chemistry, vol. 42, No. 8, pp. 1441-1447 (1999).

Feria, M. et al., "The CCR2 receptor as a therapeutic target", Expert Opin. Ther. Patents, vol. 16, No. 1, pp. 49-57 (2006).

Ferreira, A.M. et al., "Diminished Induction of Skin Fibrosis in Mice with MCP-1 Deficiency", Journal of Investigative Dermatology, vol. 126, pp. 1900-1908 (2006).

Fife, B.T. et al., "CC Chemokine Receptor 2 is Critical for Induction of Experimental Autoimmune Encephalomyelitis", J. Exp. Med., vol. 192, No. 6, pp. 899-905 (2000).

Frangogiannis, N. G. et al., "Critical Role of Monocyte Chemoattractant Protein-1/CC Chemokine Ligand 2 in the Pathogenesis of Ischemic Cardiomyopathy", Circulation, vol. 115, pp. 584-592 (2007).

Gao, Z. et al., "Unraveling the Chemistry of Chemokine Receptor Ligands", Chemical Reviews, vol. 103, No. 9, pp. 3733-3752 (2003).

Gaupp, S. et al., "Experimental Autoimmune Encephalomyelitis (EAE) in CCR2$^{-/-}$ Mice", American Journal of Pathology, vol. 162, No. 1, pp. 139-150 (2003).

Gerhardt, C.C. et al., "Chemokines control fat accumulation and leptin secretion by cultured human adipocytes", Molecular and Cellular Endocrinology, vol. 175, pp. 81-92 (2001).

Gharaee-Kermani, M. et al., "CC-chemokine receptor 2 required for bleomycin-induced pulmonary fibrosis", Cytokine, vol. 24, pp. 266-276 (2003).

Giles, R. et al., "Can We Target the Chemokine Network for Cancer Therapeutics?", Current Cancer Drug Targets, vol. 6, No. 8, pp. 659-670 (2006).

Gillitzer, R. et al., "MCP-1 mRNA Expression in Basal Keratinocytes of Psoriatic Lesions", The Journal of Investigative Dermatology, vol. 101, No. 2, pp. 127-131 (1993).

Gong, J.-H. et al., "An Antagonist of Monocyte Chemoattractant Protein 1 (MCP-1) Inhibits Arthritis in the MRL-*lpr* Mouse Model", J. Exp. Med., vol. 186, No. 1, pp. 131-137 (1997).

Gonzalo, J.-A. et al., "The Coordinated Action of CC Chemokines in the Lung Orchestrates Allergic Inflammation and Airway Hyperresponsiveness", J. Exp. Med., vol. 188, No. 1, pp. 157-167 (1998).

Gosling, J. et al., "MCP-1 deficiency reduces susceptibility to atherosclerosis in mice that overexpress human apolipoprotein B", The Journal of Clinical Investigation, vol. 103, No. 6, pp. 773-778 (1999).

Grimm, M.C. et al., "Enhanced expression and production of monocyte chemoattractant protein-1 in inflammatory bowel disease mucosa", Journal of Leukocyte Biology, vol. 59, pp. 804-812 (1996).

Gu, L. et al., "Absence of Monocyte Chemoattractant Protein-1 Reduces Atherosclerosis in Low Density Lipoprotein Receptor-Deficient Mice", Molecular Cell, vol. 2, pp. 275-281 (1998).

Guo, J. et al., "Repopulation of Apolipoprotein E Knockout Mice with CCR2-Deficient Bone Marrow Progenitor Cells Does Not Inhibit Ongoing Atherslerotic Lesion Development", Arterioscler. Thromb. Vasc. Biol., vol. 25, pp. 1014-1019 (2005).

Guo, J. et al., "Transplantation of Monocyte CC-Chemokine Receptor 2-Deficient Bone Marrow into ApoE3-Leiden Mice Inhibits Atherogenesis", Arterioscler. Thromb. Vasc. Biol., vol. 23, pp. 447-453 (2003).

Hasegawa, H. et al., "Antagonist of Monocyte Chemoattractant Protein 1 Ameliorates the Initiation and Progression of Lupus Nephritis and Renal Vasculitis in MRL/lpr Mice", Arthritis & Rheumatism, vol. 48, No. 9, pp. 2555-2566 (2003).

Hayashidani, S. et al., "Anti-Monocyte Chemoattractant Protein-1 Gene Therapy Attenuates Left Ventricular Remodeling and Failure After Experimental Myocardial Infarction", Circulation, vol. 108, pp. 2134-2140 (2003).

Horiguchi, K. et al., "Selective Chemokine and Receptor Gene Expressions in Allografts that Develop Transplant Vasculopathy", The Journal of Heart and Lung Transplantation, vol. 21, No. 10, pp. 1090-1100 (2002).

Horuk, R., "Molecular properties of the chemokine receptor family", Trends in Pharmacological Sciences, vol. 15, pp. 159-165 (1994).

Horvath, C. et al., "Targeting CCR2 or CD18 Inhibits Experimental In-Stent Restenosis in Primates: Inhibitory Potential Depends on Type of Injury and Leukocytes Targeted", Circulation Research, vol. 90, pp. 488-494 (2002).

Hughes, P.M. et al., "Monocyte Chemoattractant Protein-1 Deficiency is Protective in a Murine Stroke Model", Journal of Cerebral Blood Flow & Metabolism, vol. 22, No. 3, pp. 308-317 (2002).

Iarlori, C. et al., "Interferon β-1b modulates MCP-1 expression and production in relapsing-remitting multiple sclerosis", Journal of Neuroimmunology, vol. 123, pp. 170-179 (2002).

Ishibashi, M. et al., "Critical Role of Monocyte Chemoattractant Protein-1 Receptor CCR2 on Monocytes in Hypertension-Induced Vascular Inflammation and Remodeling", Circulation Research, vol. 94, pp. 1203-1210 (2004).

Izikson, L. et al., "Resistance to Experimental Autoimmune Encephalomyelitis in Mice Lacking the CC Chemokine Receptor (CCR)2", J. Exp. Med., vol. 192, No. 7, pp. 1075-1080 (2000).

Jones, M.L. et al., "Potential Role of Monocyte Chemoattractant Protein 1/JE in Monocyte/Macrophage-Dependent IgA Immune Complex Alveolitis in the Rat", The Journal of Immunology, vol. 149, No. 6, pp. 2147-2154 (1992).

Kamei, N. et al., "Overexpression of Monocyte Chemoattractant Protein-1 in Adipose Tissues Causes Macrophage Recruitment and Insulin Resistance", The Journal of Biological Chemistry, vol. 281, No. 36, pp. 26602-26614 (2006).

Kanda, H. et al., "MCP-1 contributes to macrophage infiltration into adipose tissue, insulin resistance, and hepatic steatosis in obesity", The Journal of Clinical Investigation, vol. 116, No. 6, pp. 1494-1505 (2006).

Karrer, S. et al., "The -2518 Promotor Polymorphism in the MCP-1 Gene is Associated with Systemic Sclerosis", The Journal of Investigative Dermatology, vol. 124, vol. 1, pp. 92-98 (2005).

Kennedy, K.J. et al., "Acute and relapsing experimental autoimmune encephalomyelitis are regulated by differential expression of the CC chemokines macrophage inflammatory protein-1α and monocyte chemotactic protein-1", Journal of Neuroimmunology, vol. 92, pp. 98-108 (1998).

Khan, W.I. et al., "Critical role of MCP-1 in the pathogenesis of experimental colitis in the context of immune and enterochromaffin cells", Am. J. Physiol. Gastrointest. Liver Physiol., vol. 291, pp. G803-G811 (2006).

Kim, J.S. et al., "Expression of monocyte chemoattractant protein-1 and macrophage inflammatory protein-1 after focal cerebral ischemia in the rat", Journal of Neuroimmunology, vol. 56, pp. 127-134 (1995).

Kim, W.J.H. et al., "MCP-1 deficiency is associated with reduced intimal hyperplasia after arterial injury", Biochemical and Biophysical Research Communications, vol. 310, pp. 936-942 (2003).

Kitagawa, K. et al., "Blockade of CCR2 Ameliorates Progressive Fibrosis in Kidney", American Journal of Pathology, vol. 165, No. 1, pp. 237-246 (2004).

Koch, A.E. et al., "Enhanced Production of Monocyte Chemoattractant Protein-1 in Rheumatoid Arthritis", The Journal of Clinical Investigation, vol. 90, pp. 772-779 (1992).

Kurihara, T. et al., "Defects in Macrophage Recruitment and Host Defense in Mice Lacking the CCR2 Chemokine Receptor", J. Exp. Med., vol. 186, No. 10, pp. 1757-1762 (1997).

Kuziel, W.A. et al., "Severe reduction in leukocyte adhesion and monocyte extravasation in mice deficient in CC chemokine receptor 2", Proc. Natl. Acad. Sci. USA, vol. 94, pp. 12053-12058 (1997).

Lee, I. et al., "Blocking the Monocyte Chemoattractant Protein-1/CCR2 Chemokine Pathway Induces Permanent Survival of Islet Allografts through a Programmed Death-1 Ligand-1-Dependent Mechanism", The Journal of Immunology, vol. 171, pp. 6929-6935 (2003).

Liu, T. et al., "Depletion of macrophages reduces axonal degeneration and hyperalgesia following nerve injury", Pain, vol. 86, pp. 25-32 (2000).

Lloyd, C.M. et al., "Rantes and Monocyte Chemoattractant Protein-1 (MCP-1) Play an Important Role in the Inflammatory Phase of Crescentic Nephritis, but Only MCP-1 is Involved in Crescent Formation and Interstitial Fibrosis", J. Exp. Med., vol. 185, No. 7, pp. 1371-1380 (1997).

Lu, B. et al., "Abnormalities in Monocyte Recruitment and Cytokine Expression in Monocyte Chemoattractant Protein 1-deficient Mice", J. Exp. Med., vol. 187, No. 4, pp. 601-608 (1998).

Lu, Y. et al., "CCR2 Expression Correlates with Prostate Cancer Progression", Journal of Cellular Biochemistry, vol. 101, pp. 676-685 (2007).

Lu, Y. et al., "Monocyte Chemotactic Protein-1 (MCP-1) Acts as a Paracrine and Autocrine Factor for Prostate Cancer Growth and Invasion", The Prostate, vol. 66, pp. 1311-1318 (2006).

Lu, Y. et al., "Monocyte Chemotactic Protein-1 Mediates Prostate Cancer-Induced Bone Resorption", Cancer Research, vol. 67, No. 8, pp. 3646-3653 (2007).

Lukacs, N.W. et al., "Differential Recruitment of Leukocyte Populations and Alteration of Airway Hyperreactivity by C-C Family Chemokines in Allergic Airway Inflammation", The Journal of Immunology, vol. 158, pp. 4398-4404 (1997).

Lumeng, C.N. et al., "Increased Inflammatory Properties of Adipose Tissue Macrophages Recruited During Diet-Induced Obesity", Diabetes, vol. 56, pp. 16-23 (2007).

Lumeng, C.N. et al., "Obesity induces a phenotypic switch in adipose tissue macrophage polarization", The Journal of Clinical Investigation, vol. 117, No. 1, pp. 175-184 (2007).

Luster, A.D., "Chemokines—Chemotactic Cytokines that Mediate Inflammation", The New England Journal of Medicine, vol. 338, No. 7, pp. 436-445 (1998).

Napolitano, M. et al., "Molecular Cloning of TER1, a Chemokine Receptor-Like Gene Expressed by Lymphoid Tissues", The Journal of Immunology, vol. 157, pp. 2759-2763 (1996).

Neels, J.G. et al., "Inflamed fat: what starts the fire?", The Journal of Clinical Investigation, vol. 116, No. 1, pp. 33-35 (2006).

Neote, K. et al., "Molecular Cloning, Functional Expression, and Signaling Characteristics of a C-C Chemokine Receptor", Cell, vol. 72, pp. 415-425 (1993).

Ni, W. et al., "New Anti-Monocyte Chemoattractant Protein-1 Gene Therapy Attenuates Atherosclerosis in Apolipoprotein E-Knockout Mice", Circulation, vol. 103, pp. 2096-2101 (2001).

Nomura, S. et al., "Significance of chemokines and activated platelets in patients with diabetes", Clinical and Experimental Immunology, vol. 121, pp. 437-443 (2000).

Ogata, H. et al., "The Role of Monocyte Chemoattractant Protein-1 (MCP-1) in the Pathogenesis of Collagen-Induced Arthritis in Rats", Journal of Pathology, vol. 182, pp. 106-114 (1997).

Okuma, T. et al., "C-C chemokine receptor 2 (CCR2) deficiency improves bleomycin-induced pulmonary fibrosis by attenuation of both macrophage infiltration and production of macrophage-derived matrix metalloproteinases", Journal of Pathology, vol. 204, pp. 594-604 (2004).

Pérez de Lema, G. et al., "Chemokine Receptor Ccr2 Deficiency Reduces Renal Disease and Prolongs Survival in MRL/lpr Lupus-Prone Mice", Journal of the American Society of Nephrology, vol. 16, pp. 3592-3601 (2005).

Pickup, J.C. et al., "Is Type II diabetes mellitus a disease of the innate immune system?", Diabetologia, vol. 41, pp. 1241-1248 (1998).

Power, C.A. et al., "Molecular Cloning and Functional Expression of a Novel CC Chemokine Receptor cDNA from a Human Basophilic Cell Line", The Journal of Biological Chemistry, vol. 270, No. 33, pp. 19495-19500 (1995).

Premack, B.A. et al., "Chemokine receptors: Gateways to inflammation and infection", Nature Medicine, vol. 2, No. 11, pp. 1174-1178 (1996).

Quinones, M.P. et al., "CC chemokine receptor (CCR)-2 prevents arthritis development following infection by Mycobacterium avium", J. Mol. Med., vol. 84, pp. 503-512 (2006).

Quinones, M.P. et al., "Experimental arthritis in CC chemokine receptor 2-null mice closely mimics severe human rheumatoid arthritis", The Journal of Clinical Investigation, vol. 113, No. 6, pp. 856-866 (2004).

Reinecker, H.-C. et al., "Monocyte-Chemoattractant Protein 1 Gene Expression in Intestinal Epithelial Cells and Inflammatory Bowel Disease Mucosa", Gastroenterology, vol. 108, No. 1, pp. 40-50 (1995).

Reynaud-Gaubert, M. et al., "Upregulation of Chemokines in Bronchoalveolar Lavage Fluid as a Predictive Marker of Post-Transplant Airway Obliteration", The Journal of Heart and Lung Transplantation, vol. 21, No. 7, pp. 721-730 (2002).

Rezaie-Majd, A. et al., "Simvastatin Reduces Expression of Cytokines Interleukin-6, Interleukin-8, and Monocyte Chemoattractant Protein-1 in Circulating Monocytes from Hypercholesterolemic Patients", Arterioscler. Thromb. Vasc. Biol., vol. 22, pp. 1194-1199 (2002).

Rollins, B.J., "Chemokines", Blood, vol. 90, No. 3, pp. 909-928 (1997).

Roque, M. et al., "CCR2 Deficiency Decreases Intimal Hyperplasia After Arterial Injury", Arterioscler. Thromb. Vasc. Biol., vol. 22, pp. 554-559 (2002).

Russell, M.E. et al., "Early and persistent induction of monocyte chemoattractant protein 1 in rat cardiac allografts", Proc. Natl. Acad. Sci. USA, vol. 90, pp. 6086-6090 (1993).

Saiura, A. et al., "Antimonocyte Chemoattractant Protein-1 Gene Therapy Attenuates Graft Vasculopathy", Arterioscler. Thromb. Vasc. Biol., vol. 24, pp. 1886-1890 (2004).

Salcedo, R. et al., "Human endothelial cells express CCR2 and respond to MCP-1: direct role of MCP-1 in angiogenesis and tumor progression", Blood, vol. 96, No. 1, pp. 34-40 (2000).

Samad, F. et al., "Tumor necrosis factor $\alpha$ is a key component in the obesity-linked elevation of plasminogen activator inhibitor 1", Proc. Natl. Acad. Sci. USA, vol. 96, pp. 6902-6907 (1999).

Samson, M. et al., "Molecular Cloning and Functional Expression of a New Human CC-Chemokine Receptor Gene", Biochemistry, vol. 35, No. 11, pp. 3362-3367 (1996).

Sartipy, P. et al., "Monocyte chemoattractant protein 1 in obesity and insulin resistance", Proceedings of the National Academy of Sciences, vol. 100, No. 12, pp. 7265-7270 (2003).

Saunders, J. et al., "Opportunities for novel therapeutic agents acting at chemokine receptors", Drug Discovery Today, vol. 4, No. 2, pp. 80-92 (1999).

Schimmer, R.C. et al., "*Streptococcal* Cell Wall-Induced Arthritis: Requirements for IL-4, IL-10, IFN-$\gamma$, and Monocyte Chemoattractant Protein-1", The Journal of Immunology, vol. 160, pp. 1466-1471 (1998).

Schober, A. et al., "Crucial Role of the CCL2/CCR2 Axis in Neointimal Hyperplasia After Arterial Injury in Hyperlipidemic Mice Involves Early Monocyte Recruitment and CCL2 Presentation on Platelets", Circulation Research, vol. 95, pp. 1125-1133 (2004).

Schweickart, V.L. et al., "CCR11 is a Functional Receptor for the Monocyte Chemoattractant Protein Family of Chemokines", The Journal of Biological Chemistry, vol. 275, No. 13, pp. 9550-9556 (2000), and vol. 276, No. 1, p. 856 (2001) (errata sheet).

Shimizu, S. et al., "Anti-monocyte chemoattractant protein-1 gene therapy attenuates nephritis in MRL/lpr mice", Rheumatology, vol. 43, pp. 1121-1128 (2004).

Smith, M.W. et al., "Contrasting Genetic Influence of *CCR2* and *CCR5* Variants on HIV-1 Infection and Disease Progression", Science, vol. 277, pp. 959-965 (1997).

Spagnolo, P. et al., "C-C Chemokine Receptor 2 and Sarcoidosis: Association with Löfgren's Syndrome", American Journal of Respiratory and Critical Care Medicine, vol. 168, pp. 1162-1166 (2003).

Tacke, F. et al., "Monocyte subsets differentially employ CCR2, CCR5, and CX3CR1 to accumulate within atherosclerotic plaques", The Journal of Clinical Investigation, vol. 117, No. 1, pp. 185-194 (2007).

Tatewaki, H. et al., "Blockade of monocyte chemoattractant protein-1 by adenoviral gene transfer inhibits experimental vein graft neointimal formation", Journal of Vascular Surgery, vol. 45, No. 6, pp. 1236-1243 (2007).

Tesch, G.H. et al., "Monocyte Chemoattractant Protein 1-dependent Leukocyte Infiltrates are Responsible for Autoimmune Disease in MRL-Fas*lpr* Mice", J. Exp. Med., vol. 190, No. 12, pp. 1813-1824 (1999).

Tesch, G.H. et al., "Monocyte chemoattractant protein-1 promotes macrophage-mediated tubular injury, but not glomerular injury, in nephrotoxic serum nephritis", The Journal of Clinical Investigation, vol. 103, No. 1, pp. 73-80 (1999).

Tokuyama, H. et al., "The simultaneous blockade of chemokine receptors CCR2, CCR5 and CXCR3 by a non-peptide chemokine receptor antagonist protects mice from dextran sodium sulfate-mediated colitis", International Immunology, vol. 17, No. 8, pp. 1023-1034 (2005).

Trivedi, B.K. et al., Chapter 17: "Chemokines: Targets for Novel Therapeutics", Annual Reports in Medicinal Chemistry, vol. 35, Academic Press, publ., pp. 191-200 (2000).

Tsou, C.-L. et al., "Critical roles for CCR2 and MCP-3 in monocyte mobilization from bone marrow and recruitment to inflammatory sites", The Journal of Clinical Investigation, vol. 117, No. 4, pp. 902-909 (2007).

Tsuruta, S. et al., "Anti-monocyte chemoattractant protein-1 gene therapy prevents dimethylnitrosamine-induced hepatic fibrosis in rats", International Journal of Molecular Medicine, vol. 14, pp. 837-842 (2004).

Vestergaard, C. et al., "Expression of CCR2 on Monocytes and Macrophages in Chronically Inflamed Skin in Atopic Dermatitis and Psoriasis", Acta Derm. Venereol., vol. 84, pp. 353-358 (2004).

Wada, T. et al., "Gene Therapy via Blockade of Monocyte Chemoattractant Protein-1 for Renal Fibrosis", Journal of the American Society of Nephrology, vol. 15, pp. 940-948 (2004).

Weisberg, S.P. et al., "CCR2 modulates inflammatory and metabolic effects of high-fat feeding", The Journal of Clinical Investigation, vol. 116, No. 1, pp. 115-124 (2006).

Weisberg, S.P. et al., "Obesity is associated with macrophage accumulation in adipose tissue", The Journal of Clinical Investigation, vol. 112, No. 12, pp. 1796-1808 (2003).

Wells, T.N.C. et al., "Plagiarism of the host immune system: lessons about chemokine immunology from viruses", Current Opinion in Biotechnology, vol. 8, pp. 741-748 (1997).

Xu, H. et al., "Chronic inflammation in fat plays a crucial role in the development of obesity-related insulin resistance", The Journal of Clinical Investigation, vol. 112, No. 12, pp. 1821-1830 (2003).

Yamamoto, T. et al., "Role of Monocyte Chemoattractant Protein-1 and its Receptor, CCR-2, in the Pathogenesis of Bleomycin-Induced Scleroderma", The Journal of Investigative Dermatology, vol. 121, No. 3, pp. 510-516 (2003).

Yoshie, O. et al., "Novel lymphocyte-specific CC chemokines and their receptors", Journal of Leukocyte Biology, vol. 62, pp. 634-644 (1997).

Youssef, S. et al., "C-C chemokine-encoding DNA vaccines enhance breakdown of tolerance to their gene products and treat ongoing adjuvant arthritis", The Journal of Clinical Investigation, vol. 106, No. 3, pp. 361-371 (2000).

Zlotnik, A. et al., "Chemokines: A New Classification System and Their Role in Immunity", Immunity, vol. 12, pp. 127-127 (2000).

Experimental and simulated powder patterns of N-((1R,2S,5R)-5-(*tert*-butylamino)-2-((S)-2-oxo-3-(6-(trifluoromethyl)quinazolin-4-ylamino)pyrrolidin-1-yl)cyclohexyl)acetamide, hemi-hydrate, Form H0.5-4

Experimental and simulated powder patterns of N-((1R,2S,5R)-5-(*tert*-butylamino)-2-((S)-2-oxo-3-(6-(trifluoromethyl)quinazolin-4-ylamino)pyrrolidin-1-yl)cyclohexyl)acetamide, free base, Form N-2

Experimental and simulated powder patterns of N-((1R,2S,5R)-5-(*tert*-butylamino)-2-((S)-2-oxo-3-(6-(trifluoromethyl)quinazolin-4-ylamino)pyrrolidin-1-yl)cyclohexyl)acetamide, 1.75 moles $H_2O$, Form H1.75-5

Experimental and simulated powder patterns of N-((1R,2S,5R)-5-(*tert*-butylamino)-2-((S)-2-oxo-3-(6-(trifluoromethyl)quinazolin-4-ylamino)pyrrolidin-1-yl)cyclohexyl)acetamide, mono-ethanol solvate, Form E-1

Experimental and simulated powder patterns of N-((1R,2S,5R)-5-(*tert*-butylamino)-2-((S)-2-oxo-3-(6-(trifluoromethyl)quinazolin-4-ylamino)pyrrolidin-1-yl)cyclohexyl)acetamide, mono-acetic acid solvate, Form HAC-1

Experimental and simulated powder patterns of N-((1R,2S,5R)-5-(*tert*-butylamino)-2-((S)-2-oxo-3-(6-(trifluoromethyl)quinazolin-4-ylamino)pyrrolidin-1-yl)cyclohexyl)acetamide, mono-*R*-propylene glycol solvate, Form RPG-3

DSC of N-((1R,2S,5R)-5-(*tert*-butylamino)-2-((S)-2-oxo-3-(6-(trifluoromethyl)quinazolin-4-ylamino)pyrrolidin-1-yl)cyclohexyl)acetamide, hemi-hydrate, Form H0.5-4

TGA of N-((1R,2S,5R)-5-(*tert*-butylamino)-2-((S)-2-oxo-3-(6-(trifluoromethyl)quinazolin-4-ylamino)pyrrolidin-1-yl)cyclohexyl)acetamide, hemi-hydrate, Form H0.5-4

DSC of N-((1R,2S,5R)-5-(*tert*-butylamino)-2-((S)-2-oxo-3-(6-(trifluoromethyl)quinazolin-4-ylamino)pyrrolidin-1-yl)cyclohexyl)acetamide, free base Form N-2

TGA of N-((1R,2S,5R)-5-(*tert*-butylamino)-2-((S)-2-oxo-3-(6-(trifluoromethyl)quinazolin-4-ylamino)pyrrolidin-1-yl)cyclohexyl)acetamide, free base Form N-2

Vapor Sorption Isotherm of N-((1R,2S,5R)-5-(*tert*-butylamino)-2-((S)-2-oxo-3-(6-(trifluoromethyl)quinazolin-4-ylamino)pyrrolidin-1-yl)cyclohexyl)acetamide, free base Form N-2 at 25 °C DSC of N-((1R,2S,5R)-5-(*tert*-butylamino)-2-((S)-2-oxo-3-(6-(trifluoromethyl)quinazolin-4-ylamino)pyrrolidin-1-yl)cyclohexyl)acetamide, 1.75 moles $H_2O$, Form H1.75-5

TGA of N-((1R,2S,5R)-5-(*tert*-butylamino)-2-((S)-2-oxo-3-(6-(trifluoromethyl)quinazolin-4-ylamino)pyrrolidin-1-yl)cyclohexyl)acetamide, 1.75 moles $H_2O$, Form H1.75-5

DSC of N-((1R,2S,5R)-5-(*tert*-butylamino)-2-((S)-2-oxo-3-(6-(trifluoromethyl)quinazolin-4-ylamino)pyrrolidin-1-yl)cyclohexyl)acetamide,
mono-acetic acid solvate, Form HAC-1

TGA of N-((1R,2S,5R)-5-(*tert*-butylamino)-2-((S)-2-oxo-3-(6-(trifluoromethyl)quinazolin-4-ylamino)pyrrolidin-1-yl)cyclohexyl)acetamide, mono-acetic acid solvate, Form HAC-1

DSC of N-((1R,2S,5R)-5-(*tert*-butylamino)-2-((S)-2-oxo-3-(6-(trifluoromethyl)quinazolin-4-ylamino)pyrrolidin-1-yl)cyclohexyl)acetamide, mono-ethanol solvate, E-1

TGA of N-((1R,2S,5R)-5-(*tert*-butylamino)-2-((S)-2-oxo-3-(6-(trifluoromethyl)quinazolin-4-ylamino)pyrrolidin-1-yl)cyclohexyl)acetamide, mono-ethanol solvate, E-1

DSC of N-((1R,2S,5R)-5-(*tert*-butylamino)-2-((S)-2-oxo-3-(6-(trifluoromethyl)quinazolin-4-ylamino)pyrrolidin-1-yl)cyclohexyl)acetamide, mono-R-propylene glycol solvate, Form RPG-3

TGA of N-((1R,2S,5R)-5-(*tert*-butylamino)-2-((S)-2-oxo-3-(6-
(trifluoromethyl)quinazolin-4-ylamino)pyrrolidin-1-yl)cyclohexyl)acetamide,
mono-R-propylene glycol solvate, Form RPG-3

Intradermal challenge model in cynomolgus monkey: Example 1 inhibited
mononuclear cell recruitment to skin 48-hour TG peritonitis in hCCR2 KI mouse: Example 1 inhibition of monocyte/macrophage infiltration into peritoneal cavity hCCR2 KI mouse EAE: Example 1 treatment reduced clinical score

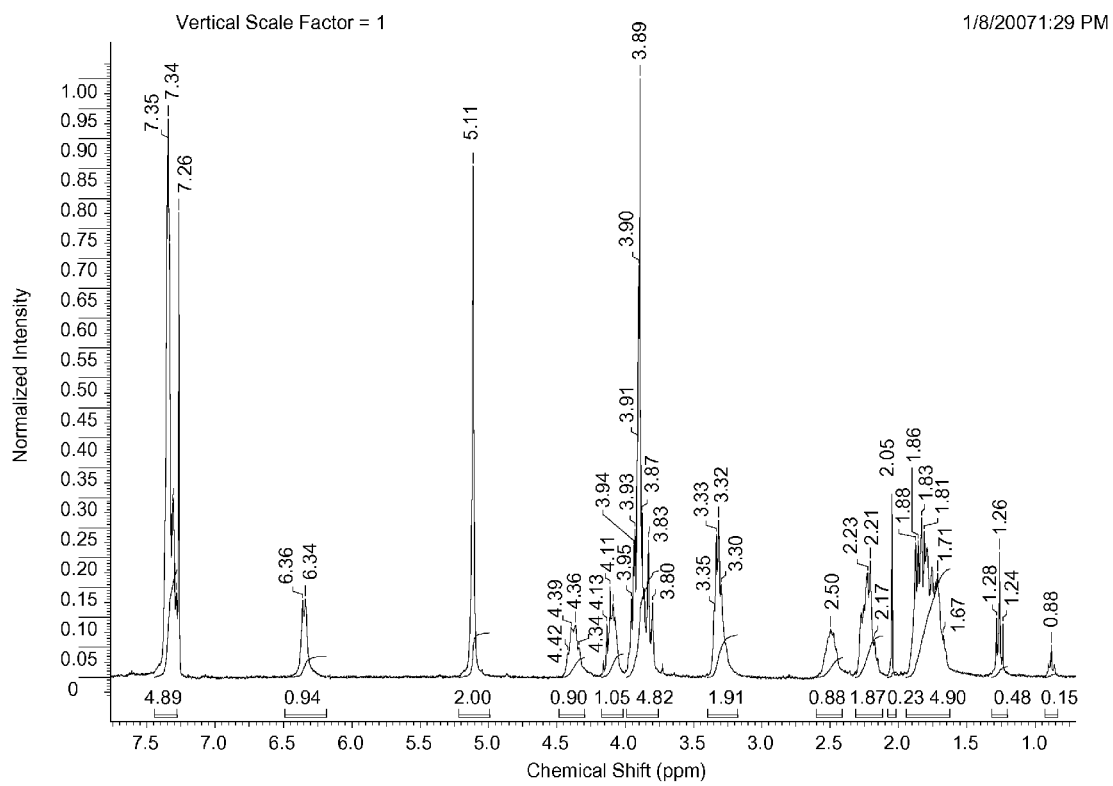
FIG. 23 Proton NMR spectra of Example 1, 2nd Alternative Preparation, Step 3- Compound 7

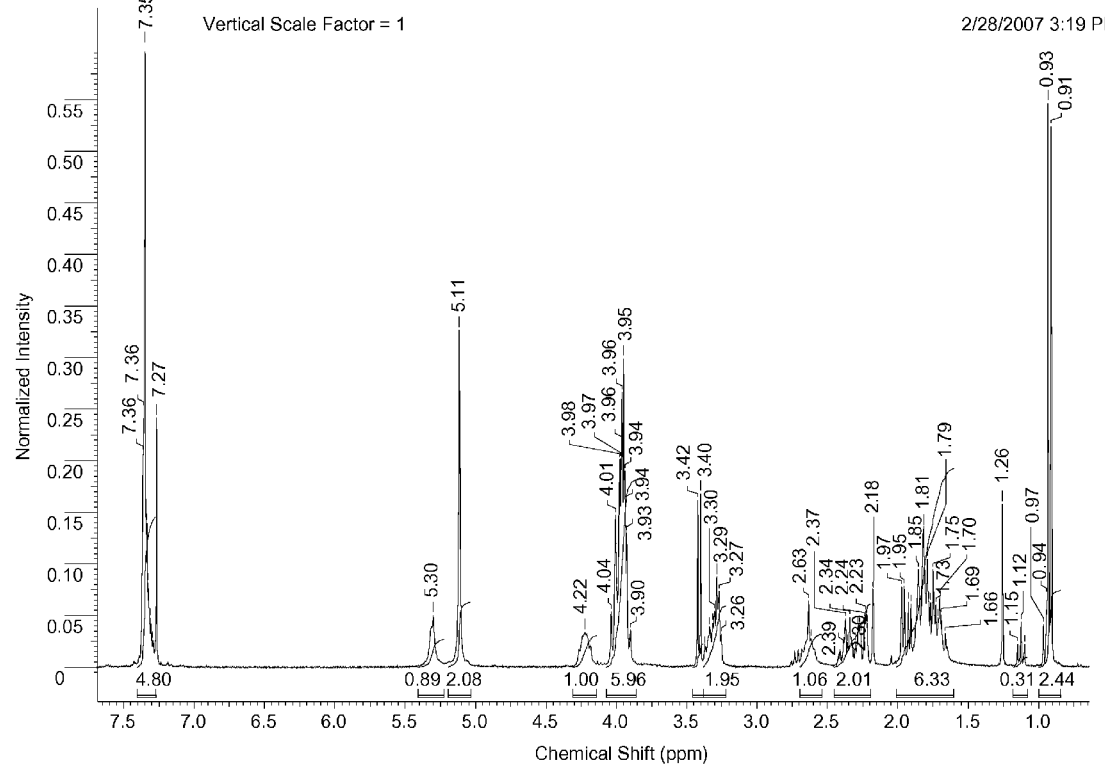
FIG. 24 Proton NMR spectra of Example 1, 2nd Alternative Preparation, Step 4- Compound 8

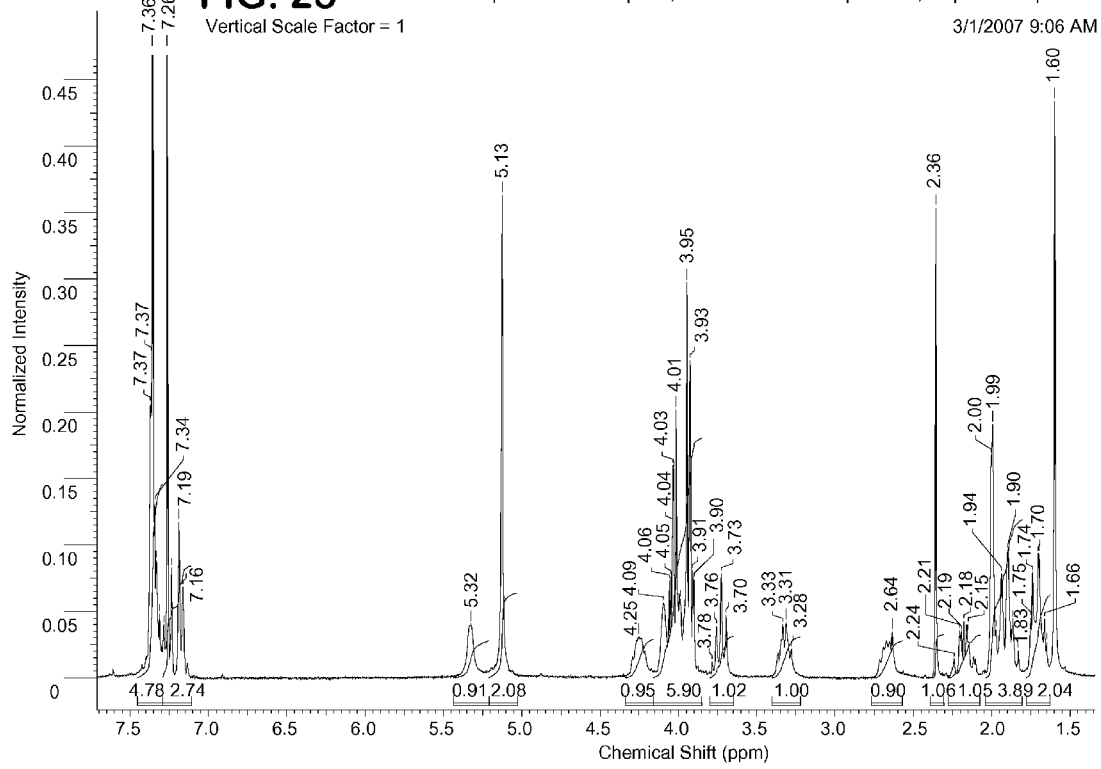
FIG. 25 Proton NMR spectra of Example 1, 2nd Alternative Preparation, Step 4- Compound 9

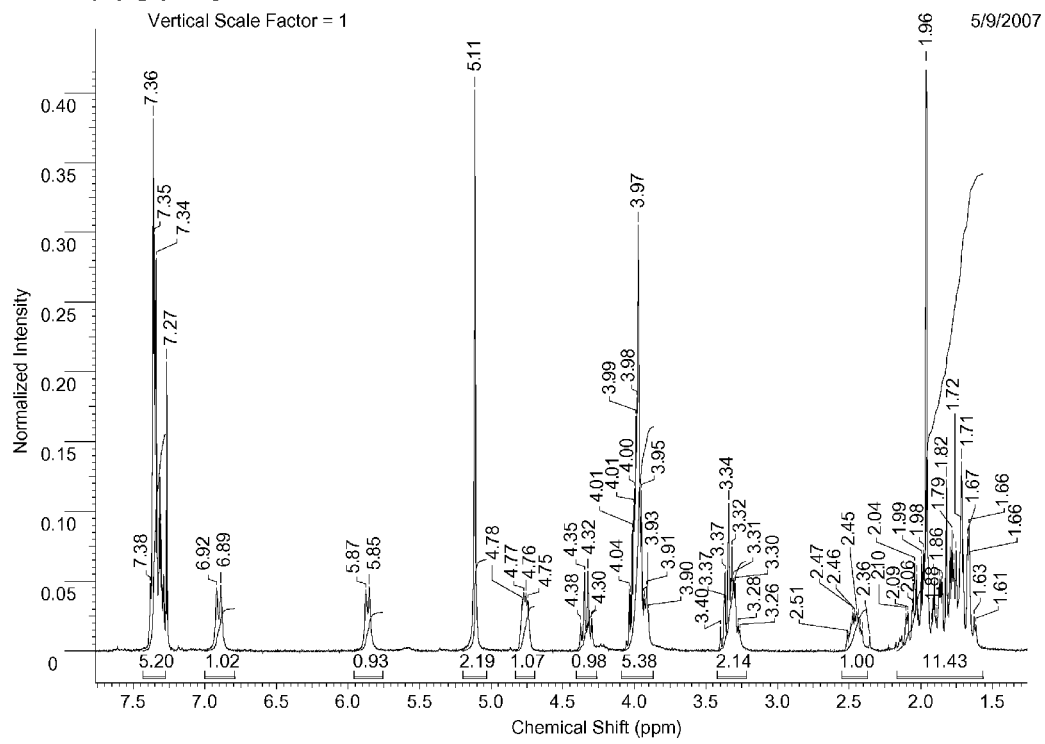
FIG. 26 Proton NMR spectra of Example 1, 2nd Alternative Preparation, Step 4- Compound 10

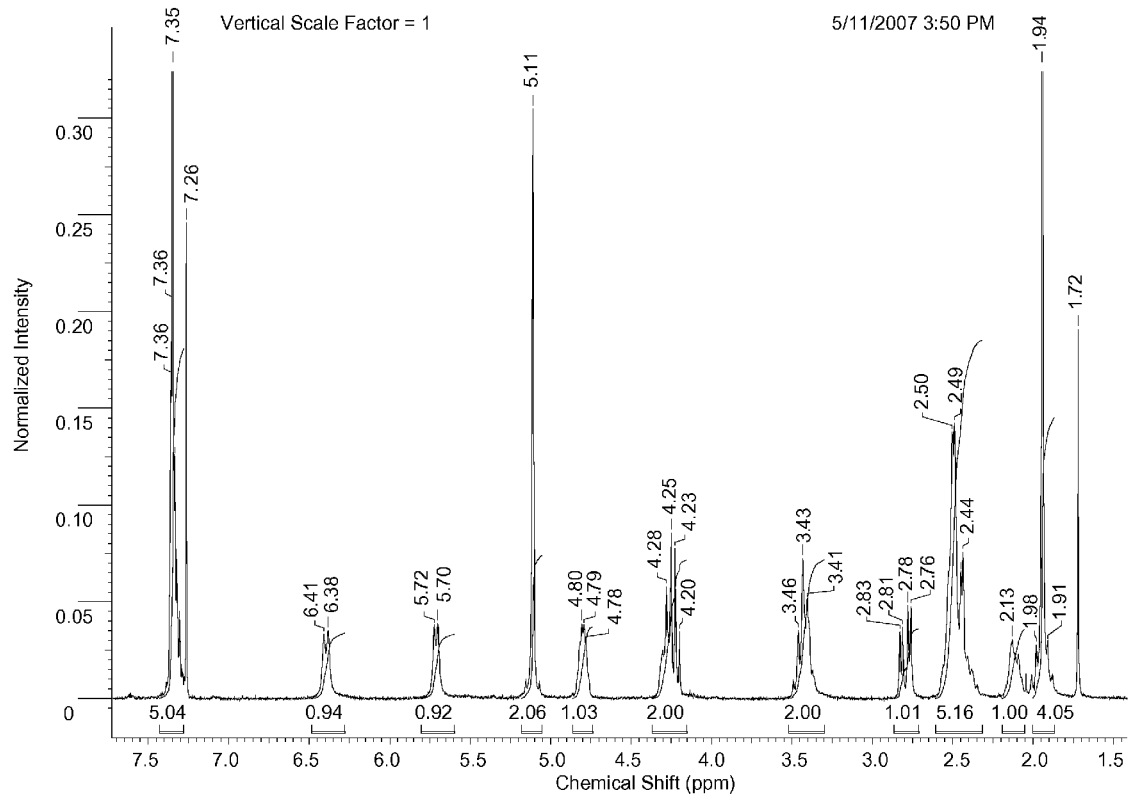
FIG. 27 Proton NMR spectra of Example 1, 2nd Alternative Preparation, Step 5- Compound 11

SUBSTITUTED PYRROLIDINE-2-ONE COMPOUNDS

This application is a divisional of U.S. application Ser. No. 11/782,742 filed Jul. 25, 2007, which claims priority from U.S. Provisional Application No. 60/896,026 filed Mar. 21, 2007 and U.S. Provisional Application Serial No. 60/834,235 filed Jul. 28, 2006, which are incorporated herein by reference.

FIELD OF THE INVENTION

The present invention provides N-((1R,2S,5R)-5-(tert-butylamino)-2-(S)-2-oxo-3-(6-(trifluoromethyl)quinazolin-4-ylamino)pyrrolidin-1-yl)cyclohexyl)acetamide, or a pharmaceutically acceptable salt, solvate or prodrug, thereof, having an unexpected combination of desirable pharmacological characteristics. Crystalline forms of the present invention are also provided. Pharmaceutical compositions containing the same and methods of using the same as agents for the treatment of inflammatory, allergic, autoimmune, metabolic, cancer and/or cardiovascular diseases is also an objective of this invention. The present invention also provides a process for preparing compounds of Formula (I), including N-((1R,2S,5R)-5-(tert-butylamino)-2-((S)-2-oxo-3-(6-(trifluoromethyl)quinazolin-4-ylamino)pyrrolidin-1-yl)cyclohexyl)acetamide:

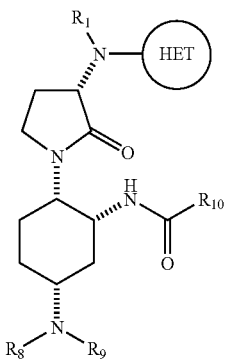

wherein $R^1$, $R^8$, $R^9$, $R^{10}$, and

are as described herein. Compounds that are useful intermediates of the process are also provided herein.

BACKGROUND OF THE INVENTION

Chemokines are chemotactic cytokines, of molecular weight 6-15 kDa, that are released by a wide variety of cells to attract and activate, among other cell types, macrophages, T and B lymphocytes, eosinophils, basophils and neutrophils (reviewed in: Charo and Rasonhoff, *New Eng. J. Med.* 2006, 354, 610-621; Luster, *New Eng. J. Med.* 1998, 338, 436-445; and Rollins, *Blood* 1997, 90, 909-928). There are two major classes of chemokines, CXC and CC, depending on whether the first two cysteines in the amino acid sequence are separated by a single amino acid (CXC) or are adjacent (CC). The CXC chemokines, such as interleukin-8 (IL-8), neutrophil-activating protein-2 (NAP-2) and melanoma growth stimulatory activity protein (MGSA) are chemotactic primarily for neutrophils and T lymphocytes, whereas the CC chemokines, such as RANTES, MIP-1α, MIP-1β, the monocyte chemotactic proteins (MCP-1, MCP-2, MCP-3, MCP-4, and MCP-5) and the eotaxins (-1 and -2) are chemotactic for, among other cell types, macrophages, T lymphocytes, eosinophils, dendritic cells, and basophils. There also exist the chemokines lymphotactin-1, lymphotactin-2 (both C chemokines), and fractalkine (a $CX_3C$ chemokine) that do not fall into either of the major chemokine subfamilies.

The chemokines bind to specific cell-surface receptors belonging to the family of G-protein-coupled seven-transmembrane-domain proteins (reviewed in: Horuk, *Trends Pharm. Sci.* 1994, 15, 159-165) which are termed "chemokine receptors." On binding their cognate ligands, chemokine receptors transduce an intracellular signal though the associated trimeric G proteins, resulting in, among other responses, a rapid increase in intracellular calcium concentration, changes in cell shape, increased expression of cellular adhesion molecules, degranulation, and promotion of cell migration. There are at least ten human chemokine receptors that bind or respond to CC chemokines with the following characteristic patterns(reviewed in Zlotnik and Oshie *Immunity* 2000, 12, 121): CCR-1 (or "CKR-1" or "CC-CKR-1") [MIP-1α, MCP-3, MCP-4, RANTES] (Ben-Barruch, et al., *Cell* 1993, 72, 415-425, and Luster, *New Eng. J. Med.* 1998, 338, 436-445); CCR-2A and CCR-2B (or "CKR-2A"/"CKR-2B" or "CC-CKR-2A"/"CC-CKR-2B") [MCP-1, MCP-2, MCP-3, MCP-4, MCP-5] (Charo, et al., *Proc. Natl. Acad. Sci. USA* 1994, 91, 2752-2756, and Luster, *New Eng. J Med.* 1998, 338, 436-445); CCR-3 (or "CKR-3" or "CC-CKR-3") [eotaxin-1, eotaxin-2, RANTES, MCP-3, MCP-4] (Combadiere, et al., *J. Biol. Chem.* 1995, 270, 16491-16494, and Luster, *New Eng. J. Med.* 1998, 338, 436-445); CCR-4 (or "CKR-4" or "CC-CKR-4") [TARC, MDC] (Power, et al., *J. Biol. Chem.* 1995, 270, 19495-19500, and Luster, *New Eng. J. Med.* 1998, 338, 436-445); CCR-5 (or "CKR-5" OR "CC-CKR-5") [MIP-1α, RANTES, MIP-1β] (Sanson, et al., *Biochemistry* 1996, 35, 3362-3367); CCR-6 (or "CKR-6" or "CC-CKR-6") [LARC] (Baba, et al., *J. Biol. Chem.* 1997, 272, 14893-14898); CCR-7 (or "CKR-7" or "CC-CKR-7") [ELC] (Yoshie et al., *J. Leukoc. Biol.* 1997, 62, 634-644); CCR-8 (or "CKR-8" or "CC-CKR-8") [I-309] (Napolitano et al., J. Immunol., 1996, 157, 2759-2763); CCR-10 (or "CKR-10" or "CC-CKR-10") [MCP-1, MCP-3] (Bonini, et al., *DNA and Cell Biol.* 1997, 16, 1249-1256); and CCR-11 [MCP-1, MCP-2, and MCP-4] (Schweickert, et al., *J. Biol. Chem.* 2000, 275, 90550).

In addition to the mammalian chemokine receptors, mammalian cytomegaloviruses, herpesviruses and poxviruses have been shown to express, in infected cells, proteins with the binding properties of chemokine receptors (reviewed in: Wells and Schwartz, *Curr. Opin. Biotech.* 1997, 8, 741-748). Human CC chemokines, such as RANTES and MCP-3, can cause rapid mobilization of calcium via these virally encoded receptors. Receptor expression may be permissive for infection by allowing for the subversion of normal immune system surveillance and response to infection. Additionally, human chemokine receptors, such as CXCR4, CCR2, CCR3, CCR5 and CCR8, can act as co-receptors for the infection of mammalian cells by microbes as with, for example, the human immunodeficiency viruses (HIV).

The chemokines and their cognate receptors have been implicated as being important mediators of inflammatory, infectious, and immunoregulatory disorders and diseases, including asthma and allergic diseases; as well as autoimmune pathologies, such as rheumatoid arthritis and multiple sclerosis; and metabolic diseases, such as atherosclerosis and diabetes (reviewed Charo and Rasonhoff, *New Eng. J. Med.* 2006, 354, 610-621; Z. Gao and W. A. Metz, *Chem. Rev.* 2003, 103, 3733; P. H. Carter, *Current Opinion in Chemical Biology* 2002, 6, 510; Trivedi, et al, *Ann. Reports Med. Chem.* 2000, 35, 191; Saunders and Tarby, *Drug Disc. Today* 1999, 4, 80; Premack and Schall, *Nature Medicine* 1996, 2, 1174). For example, the chemokine monocyte chemoattractant-1 (MCP-1) and its receptor CC Chemokine Receptor 2 (CCR-2) play a pivotal role in attracting leukocytes to sites of inflammation and in subsequently activating these cells. When the chemokine MCP-1 binds to CCR-2, it induces a rapid increase in intracellular calcium concentration, increased expression of cellular adhesion molecules, and the promotion of leukocyte migration. Demonstration of the importance of the MCP-1/CCR-2 interaction has been provided by experiments with genetically modified mice. MCP-1$^{-/-}$ mice were unable to recruit monocytes into sites of inflammation after several different types of immune challenge (Bao Lu, et al., *J. Exp. Med.* 1998, 187, 601). Likewise, CCR-2 −/− mice were unable to recruit monocytes or produce interferon-γ when challenged with various exogenous agents; moreover, the leukocytes of CCR-2 null mice did not migrate in response to MCP-1 (Landin Boring, et al., *J. Glitz. Invest.* 1997, 100, 2552), thereby demonstrating the specificity of the MCP-1/CCR-2 interaction. Two other groups have independently reported equivalent results with different strains of CCR-2 −/− mice (William A. Kuziel, et al., *Proc. Natl. Acad. Sci. USA* 1997, 94, 12053, and Takao Kurihara, et al., *J. Exp. Med.* 1997, 186, 1757). The viability and generally normal health of the MCP-1 −/− and CCR-2 −/− animals is noteworthy, in that disruption of the MCP-1/CCR-2 interaction does not induce physiological crisis. Taken together, these data lead one to the conclusion that molecules that block the actions of MCP-1/CCR2 would be useful in treating a number of inflammatory and autoimmune disorders (reviewed in: M. Feria and F. Diaz-González, *Exp. Opin. Ther. Patents* 2006, 16, 49; and J. Dawson, W. Miltz, and C. Wiessner, C. *Exp. Opin. Ther. Targets* 2003, 7, 35). This hypothesis has now been validated in a number of different animal disease models, as described below.

It is known that MCP-1 is unregulated in patients with rheumatoid arthritis (Alisa Koch, et al., *J. Clin. Invest.* 1992, 90, 772-779). Moreover, several preclinical studies have demonstrated the potential therapeutic value of antagonism of the MCP-1/CCR2 interaction in treating rheumatoid arthritis. A DNA vaccine encoding MCP-1 was shown recently to ameliorate chronic polyadjuvant-induced arthritis in rats (Sawsan Youssef, et al., *J. Clin. Invest.* 2000, 106, 361). Likewise, the disease symptoms could be controlled via direct administration of antibodies for MCP-1 to rats with collagen-induced arthritis (Hiroomi Ogata, et al., *J. Pathol.* 1997, 182, 106), or streptococcal cell wall-induced arthritis (Ralph C. Schimmer, et al., *J. Immunol.* 1998, 160, 1466). Perhaps most significantly, a peptide antagonist of MCP-1, MCP-1(9-76), was shown both to prevent disease onset and to reduce disease symptoms (depending on the time of administration) in the MRL-lpr mouse model of arthritis (Jiang-Hong Gong, et al., *J. Exp. Med.* 1997, 186, 131). Moreover, it has been demonstrated the administration of small molecule CCR2 antagonists reduced clinical score in rodent models of arthritis (C. M. Brodmerkel, et al, *J. Immunol.* 2005, 175, 5370; and M. Xia, et al. US Patent Application 0069123, 2006). Administration of an anti-CCR2 antibody had varying effects on murine CIA, depending on the time of administration (H. Bruhl, et al. *J. Immunol.* 2004, 172, 890). Recent studies with CCR2−/− mice have suggested that deletion of CCR2 can exacerbate rodent arthritis models in specific experimental circumstances (M. P. Quinones, et al. *J. Clin. Invest.* 2004, 113, 856; M. P. Quinones, et al. *J. Mol. Med.* 2006, 84, 503).

It is known that MCP-1 is upregulated in atherosclerotic lesions, and it has been shown that circulating levels of MCP-1 are reduced through treatment with therapeutic agents (Abdolreza Rezaie-Majd, et al, *Arterioscler. Thromb. Vasc. Biol.* 2002, 22, 1194-1199). Several key studies have demonstrated the potential therapeutic value of antagonism of the MCP-1/CCR2 interaction in treating atherosclerosis. For example, when MCP-1 −/− mice are crossed with LDL receptor-deficient mice, an 83% reduction in aortic lipid deposition was observed (Long Gu, et al., *Mol. Cell* 1998, 2, 275). Similarly, when MCP-1 was genetically ablated from mice which already overexpressed human apolipoprotein B, the resulting mice were protected from atherosclerotic lesion formation relative to the MCP-1 +1+apoB control mice (Jennifa Gosling, et al., *J. Clin. Invest.* 1999, 103, 773). Likewise, when CCR-2 −/− mice are crossed with apolipoprotein E −/− mice, a significant decrease in the incidence of atherosclerotic lesions was observed (Landin Boring, et al, *Nature* 1998, 394, 894; T. C. Dawson, et al. *Atherosclerosis* 1999, 143, 205). Finally, when apolipoprotein E −/− mice are administered a gene encoding a peptide antagonist of CCR2, then lesion size is decreased and plaque stability is increased (W. Ni, et al. *Circulation* 2001, 103, 2096-2101). Transplantation of bone marrow from CCR2−/− mice into ApoE3-Leiden mice inhibited early atherogenesis (J. Guo, et al. *Arterioscler. Thromb. Vase. Biol.* 2003, 23, 447), but had minimal effects on advanced lesions (J. Guo, et al. *Arterioscler. Thromb. Vasc. Biol.* 2005, 25, 1014).

Patients with type 2 diabetes mellitus typically exhibit insulin resistance as one of the hallmark features of the disease. Insulin resistance is also associated with the grouping of abnormalities known as the "metabolic syndrome" or "syndrome X," which includes obesity, atherosclerosis, hypertension, and dyslipidemia (reviewed in: Eckel, et al. *Lancet* 2005, 365, 1415). It is well-recognized that inflammation plays a role in exacerbating the disease process in type 2 diabetes and the "syndrome X" pathologies (reviewed in: Chen, *Pharmacological Research* 2006, 53, 469; Neels and Olefsky, *J. Clin. Invest.* 2006, 116, 33; Danadona and Aljada, *Am J Cardiol.* 2002 90, 27G-33G; Pickup and Crook, *Diabetologia* 1998, 41, 1241). MCP-1 is recognized as playing a role in obesity-induced insulin resistance. In culture, human preadipocytes constitutively expressed MCP-1 (Gerhardt, *Mol. Cell. Endocrinology* 2001, 175, 81). CCR2 is expressed on adipocytes; Addition of MCP-1 to differentiated adipocytes in vitro decreases insulin-stimulated glucose uptake and the expression of several adipogenic genes (LpL, adipsin, GLU-4), aP2, β3-adrenergic receptor, and PPARγ) (P. Sartipy and D. Loskutoff, *Proc. Natl. Acad. Sci USA* 1999, 96, 6902). Patients with type 2 diabetes had greater levels of circulating MCP-1 than non-diabetic controls (S. Nomura, et al. *Clin. Exp. Immunol.* 2000, 121, 437), and release of MCP-1 from adipose tissue could be reduced by treatment with anti-diabetic therapies such as metformin or thiazolidinediones (J. M. Brunn, et al. *J. Clin. Endocrinol. Metab.* 2005, 90, 2282). Likewise, MCP-1 was also overexpressed in murine experimental models of obesity, and was primarily produced by adipose tissue (Sartipy and Loskutoff, *Proc. Natl. Acad. Sci. USA* 2003, 100, 7265). In obese mice, the expression of MCP-1 both preceded and occurred concurrently with the onset of insulin resistance (H. Xu, et al. *J Clin. Invest.* 2003, 112, 1821). Another study showed that the expression of MCP-1 positively correlated with body mass in the perigonadal adipose tissue of mice (Weisberg, et al., *J. Clin. Invest.* 2003, 112, 1796). Consistent with these data, the development of insulin resistance in db/db mice was ameliorated either via genetic deletion of MCP-1 or by gene-induced expression of a dominant negative peptide (H. Kanda, et al. *J Clin. Invest.* 2006, 116, 1494). The logical converse could also be demonstrated: overexpression of MCP-1 in adipose tissue promoted insulin resistance (N. Kamei, et al. *J. Biol. Chem.* 2006, 281, 26602). One conflicting result showing that genetic deletion of MCP-1 does not effect insulin resistance in the db/db mouse has also appeared (F. Y. Chow, et al. *Diabetologia* 2007, 50, 471). Consistent with the data on MCP-1, direct studies with CCR2 (the MCP-1 receptor) have showed that it plays a role in the formation of obesity and obesity-induced insulin resistance. Maintenance of a high fat diet increased the numbers of circulating CCR2$^+$ inflammatory monocytes in both wild-type (C. L. Tsou, et al. *J. Clin. Invest.* 2007, 117, 902) and ApoE$^{-/-}$ mice (F. Tacke, et al. *J. Clin. Invest.* 2007, 117, 185). Genetic deletion of CCR2 reduced numbers of activated macrophages in murine adipose tissue (C. N. Lumeng, et al. *Diabetes* 2007, 56, 16), but did not affect a population of M2 adipose macrophages thought to maintain the "lean" state (C. N. Lumeng, et al. *J. Clin. Invest.* 2007, 117, 175). Genetic deletion of CCR2 reduced diet-induced obesity and improved insulin sensitivity in diet-induced obesity model (S. P. Weisberg, et al. *J. Clin. Invest.* 2006, 116, 115; P Cornelius, R P Gladue, R S Sebastian, WO patent 2006/013427 A2), 2006), depending on experimental conditions (A. Chen, et al. *Obes. Res.* 2005, 13, 1311). Administration of a small molecule CCR2 antagonist also improved insulin sensitivity in this same model (S. P. Weisberg, et al. *J. Clin. Invest.* 2006, 116, 115).

Two studies described the important role of CCR2 in hypertension-induced vascular inflammation, remodeling, and hypertrophy (E Bush et al., *Hypertension* 2000, 36, 360; M Ishibashi, et al. *Circ. Res.* 2004, 94, 1203).

It is known that MCP-1 is upregulated in human multiple sclerosis, and it has been shown that effective therapy with interferon β-1b reduces MCP-1 expression in peripheral blood mononuclear cells, suggesting that MCP-1 plays a role in disease progression (Carla Iarlori, et al., *J. Neuroimmunol.* 2002, 123, 170-179). Other studies have demonstrated the potential therapeutic value of antagonism of the MCP-1/CCR-2 interaction in treating multiple sclerosis; all of these studies have been demonstrated in experimental autoimmune encephalomyelitis (EAE), the conventional animal model for multiple scelerosis. Administration of antibodies for MCP-1 to animals with EAE significantly diminished disease relapse (K. J. Kennedy, et al., *J. Neuroimmunol.* 1998, 92, 98). Furthermore, two reports have shown that CCR-2 −/− mice are resistant to EAE (B. T. Fife, et al., *J. Exp. Med.* 2000, 192, 899; L. Izikson, et al., *J. Exp. Med.* 2000, 192, 1075). A subsequent report extended these initial observations by examining the effects of CCR2 deletion in mice from different strains (S. Gaupp, et al. *Am. J. Pathol.* 2003, 162, 139). Notably, administration of a small molecule CCR2 antagonist also blunted disease progression in C57BL/6 mice (C. M. Brodmerkel, et al. *J. Immunol.* 2005, 175, 5370).

It is known that MCP-1 is upregulated in patients who develop bronchiolitis obliterans syndrome after lung transplantation (Martine Reynaud-Gaubert, et al., *J. of Heart and Lung Transplant.*, 2002, 21, 721-730; John Belperio, et al., *J. Clin. Invest.* 2001, 108, 547-556). In a murine model of bronchiolitis obliterans syndrome, administration of an antibody to MCP-1 led to attenuation of airway obliteration; likewise, CCR2 −/− mice were resistant to airway obliteration in this same model (John Belperio, et al., *J. Clin. Invest.* 2001, 108, 547-556). These data suggest that antagonism of MCP-1/CCR2 may be beneficial in treating rejection of organs following transplantation. In addition, studies have shown that disruption of MCP-1/CCR2 axis was able to prolong the survival of islet transplant (1 Lee et al. *J Immunol* 2003, 171, 6929; R Abdi et al., *J Immunol* 2004, 172, 767). In rat graft models, CCR2 and MCP-1 was shown to be upregulated in grafts that develop graft vasculopathy (K Horiguchi et al., *J Heart Lung Transplant.* 2002, 21, 1090). In another study, anti-MCP-1 gene therapy attenuated graft vasculopathy (A Saiura et al., *Artherioseler Thromb Vase Biol* 2004, 24, 1886). One study described inhibition of experimental vein graft neoinitimal formation by blockage of MCP-1 (H Tatewaki et al., *J Vase Surg.* 2007, 45, 1236).

Other studies have demonstrated the potential therapeutic value of antagonism of the MCP-1/CCR2 interaction in treating asthma. Sequestration of MCP-1 with a neutralizing antibody in ovalbumin-challenged mice resulted in marked decrease in bronchial hyperresponsiveness and inflammation (Jose-Angel Gonzalo, et al., *J. Exp. Med.* 1998, 188, 157). It proved possible to reduce allergic airway inflammation in *Schistosoma mansoni* egg-challenged mice through the administration of antibodies for MCP-1 (Nicholas W. Lukacs, et al., J. Immunol. 1997, 158, 4398). Consistent with this, MCP-1 −/− mice displayed a reduced response to challenge with *Schistosoma mansoni* egg (Bao Lu, et al., *J Exp. Med.* 1998, 187, 601).

Other studies have demonstrated the potential therapeutic value of antagonism of the MCP-1/CCR2 interaction in treating kidney disease. Administration of antibodies for MCP-1 in a murine model of glomerularnephritis resulted in a marked decrease in glomerular crescent formation and deposition of type I collagen (Clare M. Lloyd, et al., *J. Exp. Med.* 1997, 185, 1371). In addition, MCP-1 −/− mice with induced nephrotoxic serum nephritis showed significantly less tubular damage than their MCP-1 +/+ counterparts (Gregory H. Tesch, et al., *J. Clin. Invest.* 1999, 103, 73).

Several studies have demonstrated the potential therapeutic value of antagonism of the MCP-1/CCR2 interaction in treating systemic lupus erythematosus. CCR2$^{-/-}$ mice exhibited prolonged survival and reduced renal disease relative to their WT counterparts in a murine model of systemic lupus erythematosus (G. Perez de Lema, et al. *J. Am. Soc. Neph.* 2005, 16, 3592). These data are consistent with the disease-modifying activity found in recent studies on genetic deletion of MCP-1 (S. Shimizu, et al. *Rheumatology (Oxford)* 2004, 43, 1121; Gregory H. Tesch, et al., *J. Exp. Med.* 1999, 190, 1813) or administration of a peptide antagonist of CCR2 (H. Hasegawa, et al. *Arthritis & Rheumatism* 2003, 48, 2555) in rodent models of lupus.

A remarkable 30-fold increase in CCR2$^+$ lamina propria lymphocytes was observed in the small bowels from Crohn's patients relative to non-diseased ileum (S. T. Connor, et al. *Gut* 2004, 53, 1287). Also of note, there was an expansion in the subset of circulating CCR2$^+$/CD14$^+$/CD56$^+$ monocytes in patients with active Crohn's disease relative to controls. Several rodent studies have demonstrated the potential therapeutic value of antagonism of the MCP-1/CCR2 interaction in treating Crohn's disease/colitis. CCR-2$^{-/-}$ mice were protected from the effects of dextran sodium sulfate-induced colitis (Pietro G. Andres, et al., *J. Immunol.* 2000, 164, 6303). Administration of a small molecule antagonist of CCR2, CCR5, and CXCR3 (murine binding affinities=24, 236, and 369 nM, respectively) also protected against dextran sodium sulfate-induced colitis (H. Tokuyama, et al. *Int. Immunol.* 2005, 17, 1023). Finally, MCP-1−/− mice showed substantially reduced colonic damage (both macroscopic and histological) in a hapten-induced model of colitis (W. I. Khan, et al. *Am. J. Physiol. Gastrointest. Liver Physiol.* 2006, 291, G803).

Two reports described the overexpression of MCP-1 in the intestinal epithelial cells and bowel mucosa of patients with inflammatory bowel disease (H. C. Reinecker, et al., *Gastroenterology* 1995, 108, 40, and Michael C. Grimm, et al., *J. Leukoc. Biol.* 1996, 59, 804).

One study described the association of promoter polymorphism in the MCP-1 gene with sceroderma (systemic sclerosis) (S Karrer et al., *J Invest Dermatol.* 2005, 124, 92). In related models of tissue fibrosis, inhibition of CCR2/MCP-1 axis reduced fibrosis in skin (T Yamamoto and K Nishioka, *J Invest Dermatol* 2003, 121, 510; A M Ferreira et al., *J Invest Dermatol.* 2006, 126, 1900), lung (T Okuma et al., *J Pathol.* 2004, 204, 594; M Gharaee-Kermani et al., *Cytokine* 2003, 24, 266), kidney (K Kitagawa et al., *Am J Pathol.* 2004, 165, 237; T Wada et al., *J Am Soc Nephrol* 2004, 15, 940), heart (S Hayashidani et al., *Circulation* 2003, 108, 2134), and liver (S Tsuruta et al., *Int J Mol Med.* 2004, 14, 837).

One study has demonstrated the potential therapeutic value of antagonism of the MCP-1/CCR2 interaction in treating alveolitis. When rats with IgA immune complex lung injury were treated intravenously with antibodies raised against rat MCP-1 (JE), the symptoms of alveolitis were partially alleviated (Michael L. Jones, et al., *J. Immunol.* 1992, 149, 2147).

Several studies have shown the potential therapeutic value of antagonism of the MCP-1/CCR2 interaction in treating cancer (reviewed in: M. J. Craig and R. D. Loberg, *Cancer Metastasis Rev.* 2006, 25, 611; I. Conti and B. Rollins, *Seminars in Cancer Biology* 2004, 14, 149; R. Giles and R. D. Loberg, *Curr. Cancer Drug Targets* 2006, 6, 659). When immunodeficient mice bearing human breast carcinoma cells were treated with an anti-MCP-1 antibody, inhibition of lung micrometastases and increases in survival were observed (Rosalba Salcedo, et al., *Blood* 2000, 96, 34-40). Using human clinical tumor specimens, CCR2 expression was associated with prostrate cancer progression (Y. Lu, et al. *J. Cell. Biochem.* 2007, 101, 676). In vitro, MCP-1 expression has been shown to mediate prostate cancer cell growth and invasion (Y. Lu, et al. *Prostate* 2006, 66, 1311); furthermore, MCP-1 expressed by prostate cancer cells induced human bone marrow progenitors for bone resorption (Y. Lu, et al., *Cancer Res.* 2007, 67, 3646).

Multiple studies have described the potential therapeutic value of antagonism of the MCP-1/CCR2 interaction in treating restenosis. In humans, MCP-1 levels correlate directly with risk for restenosis (F. Cipollone, et al. *Arterioseler. Thromb. Vasc. Biol.* 2001, 21, 327). Mice deficient in CCR2 or in MCP-1 showed reductions in the intimal area and in the intima/media ratio (relative to wildtype littermates) after arterial injury (Merce Roque, et al. *Arterioscler. Thromb. Vasc. Biol.* 2002, 22, 554; A. Schober, et al. *Circ. Res.* 2004, 95, 1125; W. J. Kim, et al, *Biochem Biophys Res Commun.* 2003, 310, 936). In mice, transfection of a dominant negative inhibitor of MCP-1 in the skeletal muscle (K. Egashira, et al. *Circ. Res.* 2002, 90, 1167) also reduced intimal hyperplasia after arterial injury. Blockade of CCR2 using a neutralizing antibody reduced neointimal hyperplasia after stenting in primates (C. Horvath, et al. *Circ. Res.* 2002, 90, 488).

Two reports describe the overexpression of MCP-1 rats with induced brain trauma (J. S. King, et al., *J. Neuroimmunol.* 1994, 56, 127, and Joan W. Berman, et al., *J. Immunol.* 1996, 156, 3017). In addition, studies have shown that both CCR2$^{-/-}$ (O. B. Dimitrijevic, et al. *Stroke* 2007, 38, 1345) and MCP-1$^{-/-}$ mice (P. M. Hughes, et al. *J. Cereb. Blood Flow Metab.* 2002, 22, 308) are partially protected from ischemia/reperfusion injury.

It is known that monocytes/macrophages play an important role in the development of neuropathic pain (Liu T, van Rooijen N, Tracey D J, *Pain* 2000, 86, 25). Consistent with this notion, a potential role for CCR2 in the treatment of both inflammatory and neuropathic pain has been described recently. CCR2$^{-/-}$ mice showed altered responses to inflammatory pain relative to their WT counterparts, including reduced pain behavior after intraplantar formalin injection and slightly reduced mechanical allodynia after intraplantar CFA injection (C. Abbadie, et al. *Proc. Natl. Acad. Sci., USA* 2003, 100, 7947). In addition, CCR2$^{-/-}$ mice did not display significant mechanical allodynia after sciatic nerve injury. Likewise, a small molecule CCR2 antagonist reduced mechanical allodynia to ~80% of pre-injury levels after oral administration (C. Abbadie, J. A. Lindia, and H. Wang, WO PCT 110376, 2004).

One study described the critical role of MCP-1 in ischemic cardiomyopathy (N. G. Frangogiannis, et al., *Circulation* 2007, 115, 584). Another study described the attenuation of experimetal heart failure following inhibition of MCP-1 (S Hayashidani et al., *Circulation* 2003, 108, 2134).

Other studies have provided evidence that MCP-1 is overexpressed in various disease states not mentioned above. These reports provide correlative evidence that MCP-1 antagonists could be useful therapeutics for such diseases. Another study has demonstrated the overexpression of MCP-1 in rodent cardiac allografts, suggesting a role for MCP-1 in the pathogenesis of transplant arteriosclerosis (Mary E. Russell, et al, *Proc. Natl. Acad. Sci. USA* 1993, 90, 6086). The overexpression of MCP-1 has been noted in the lung endothelial cells of patients with idiopathic pulmonary fibrosis (Harry N. Antoniades, et al., *Proc. Natl. Acad. Sci. USA* 1992, 89, 5371). Similarly, the overexpression of MCP-1 has been noted in the skin from patients with psoriasis (M. Deleuran, et al., *J. Dermatol. Sci.* 1996, 13, 228, and R. Gillitzer, et al., *J. Invest. Dermatol.* 1993, 101, 127); correlative findings with predominance of CCR2+ cells have also been reported (C. Vestergaard, et al. *Acta Derm. Venerol.* 2004, 84, 353). Finally, a recent report has shown that MCP-1 is overexpressed in the brains and cerebrospinal fluid of patients with HIV-1-associated dementia (Alfredo Garzino-Demo, WO 99/46991).

In addition, CCR2 polymorphism has been shown to be associated with sarcoidosis at least in one subset of patients (P. Spagnolo, et al. *Am J Respir Grit Care Med.* 2003, 168, 1162).

It should also be noted that CCR-2 has been implicated as a co-receptor for some strains of HIV (B. J. Doran, et al., *Cell* 1996, 85, 1149). It has also been determined that the use of CCR-2 as an HIV co-receptor can be correlated with disease progression (Ruth I. Connor, et al., *J. Exp. Med.* 1997, 185, 621). This finding is consistent with the recent finding that the presence of a CCR-2 mutant, CCR2-64I, is positively correlated with delayed onset of HIV in the human population (Michael W. Smith, et al., *Science* 1997, 277, 959). Although MCP-1 has not been implicated in these processes, it may be that MCP-1 antagonists that act via binding to CCR-2 may have beneficial therapeutic effects in delaying the disease progression to AIDS in HIV-infected patients.

It should be noted that CCR2 is also the receptor for the human chemokines MCP-2, MCP-3, and MCP-4 (Luster, *New Eng. J. Med.* 1998, 338, 436-445). Since the new compounds of formula (I) described herein antagonize MCP-1 by binding to the CCR-2 receptor, it may be that these compounds of formula (I) are also effective antagonists of the actions of MCP-2, MCP-3, and MCP-4 that are mediated by CCR-2. Accordingly, when reference is made herein to "antagonism of MCP-1," it is to be assumed that this is equivalent to "antagonism of chemokine stimulation of CCR-2."

Accordingly, compounds that modulate chemokine activity could demonstrate a wide range of utilities in treating inflammatory, allergic, autoimmune, metabolic, cancer and/or cardiovascular diseases. Patent publication WO2005021500 A1 (incorporated herein by reference and assigned to present applicant) discloses compounds that modulate MCP-1, MCP-2, MCP-3 and MCP-4 activity via CCR2. The reference also discloses various processes to prepare these compounds including multistep syntheses that include the introduction and subsequent removal of protecting groups.

It is desirable to find new compounds with improved pharmacological characteristics compared with known chemokine modulators. For example, it is desirable to find new compounds with improved CCR-2 inhibitory activity and selectivity for CCR-2 versus other G protein-coupled receptors (i.e. 5HT2A receptor). It is also desirable to find compounds with advantageous and improved characteristics in one or more of the following categories:

(a) pharmaceutical properties (i.e. solubility, permeability, amenability to sustained release formulations);

(b) dosage requirements (e.g., lower dosages and/or once-daily dosing);

(c) factors which decrease blood concentration peak-to-trough characteristics (i.e. clearance and/or volume of distribution);

(d) factors that increase the concentration of active drug at the receptor (i.e. protein binding, volume of distribution);

(e) factors that decrease the liability for clinical drug-drug interactions (cytochrome P450 enzyme inhibition or induction, such as CYP 2D6 inhibition, see G. K. Dresser, J. D. Spence, D. G. Bailey, *Clin. Pharmacokinet.* 2000, 38, 41-57, which is hereby incorporated by reference);

(f) factors that decrease the potential for adverse side-effects (e.g. pharmacological selectivity beyond G protein-coupled receptors, potential chemical or metabolic reactivity, limited CNS penetration, and/or ion-channel selectivity). It is especially desirable to find compounds having a desirable combination of the aforementioned pharmacological characteristics.

It is also desirable in the art to provide new and/or improved processes to prepare such compounds. These processes may be characterized, without limitation, by a) facile adaptation to larger scale production, such as pilot plant or manufacturing scales; b) process steps and/or techniques enabling improvements in the purity (including chiral purity), stability and/or ease of handling of intermediates and/or final compounds; and/or c) fewer process steps.

SUMMARY OF THE INVENTION

The present invention provides a novel antagonist or partial agonist/antagonist of MCP-1 receptor activity: N-((1R,2S,5R)-5-(tert-butylamino)-2-((S)-2-oxo-3-(6-(trifluoromethyl)quinazolin-4-ylamino)pyrrolidin-1-yl)cyclohexyl)acetamide, or a pharmaceutically acceptable salt, solvate or prodrug, thereof, having an unexpected combination of desirable pharmacological characteristics. Crystalline forms of the present invention are also provided. Pharmaceutical compositions containing the same and methods of using the same as agents for the treatment of inflammatory diseases, allergic, autoimmune, metabolic, cancer and/or cardiovascular diseases is also an objective of this invention. The present disclosure also provides a process for preparing compounds of Formula (I), including N-((1R,2S,5R)-5-(tert-butylamino)-2-((S)-2-oxo-3-(6-(trifluoromethyl)quinazolin-4-ylamino)pyrrolidin-1-yl)cyclohexyl)acetamide:

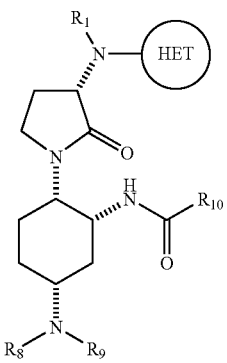

wherein $R^1$, $R^8$, $R^9$, $R^{10}$, and

are as described herein. Compounds that are useful intermediates of the process are also provided herein.

The present disclosure also provides the use of N-((1R,2S,5R)-5-(tert-butylamino)-2-((S)-2-oxo-3-(6-(trifluoromethyl)quinazolin-4-ylamino)pyrrolidin-1-yl)cyclohexyl)acetamide, or a pharmaceutically acceptable salt, solvate or prodrug, for the manufacture of a medicament for the treatment of inflammatory diseases, allergic, autoimmune, metabolic, cancer and/or cardiovascular diseases.

BRIEF DESCRIPTION OF THE DRAWINGS

FIG. 23. Proton NMR spectra of Example 1, $2^{nd}$ Alternative Preparation, Step 3—Compound 7.

FIG. 24. Proton NMR spectra of Example 1, $2^{nd}$ Alternative Preparation, Step 4—Compound 8.

FIG. 25. Proton NMR spectra of Example 1, $2^{nd}$ Alternative Preparation, Step 4—Compound 9.

FIG. 26. Proton NMR spectra of Example 1, $2^{nd}$ Alternative Preparation, Step 4—Compound 10

FIG. 27. Proton NMR spectra of Example 1, $2^{nd}$ Alternative Preparation, Step 5—Compound 11.

DETAILED DESCRIPTION

Figure 1:
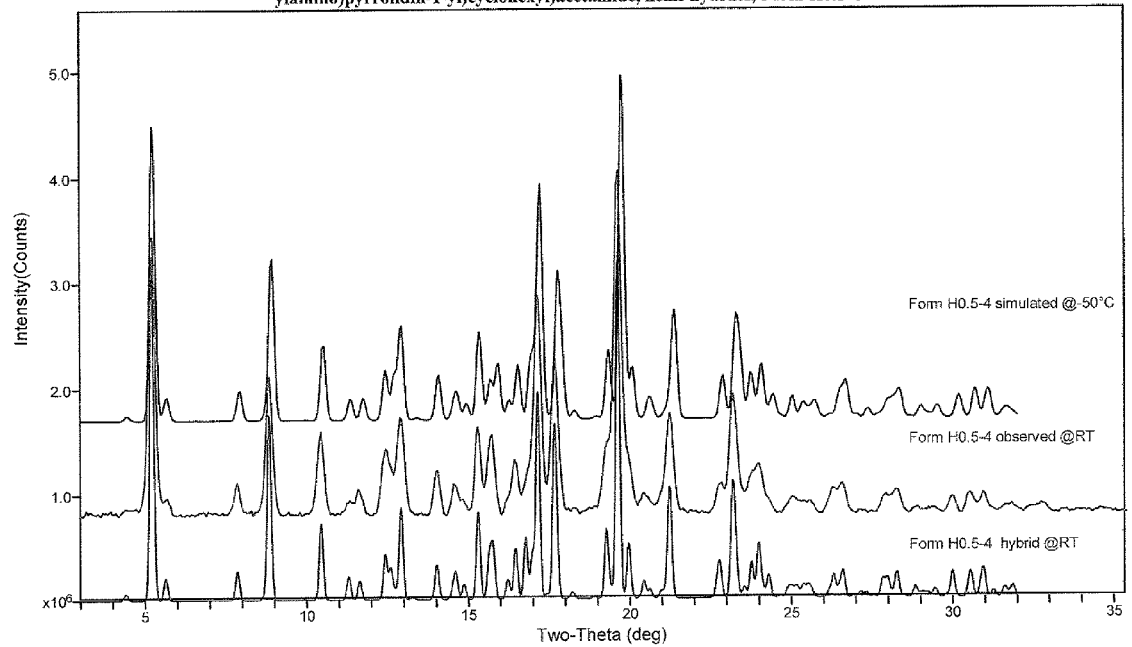
FIG. 1. Experimental and simulated powder patterns of N-((1R,2S,5R)-5-(tert-butylamino)-2-((S)-2-oxo-3-(6-(trifluoromethyl)quinazolin-4-ylamino)pyrrolidin-1-yl)cyclohexyl)acetamide, hemi-hydrate, Form H0.5-4.

The present invention provides a novel antagonist or partial agonist/antagonist of MCP-1 receptor activity: N-((1R,2S,5R)-5-(tert-butylamino)-2-((S)-2-oxo-3-(6-(trifluoromethyl)quinazolin-4-ylamino)pyrrolidin-1-yl)cyclohexyl)acetamide, or a pharmaceutically acceptable salt, solvate or prodrug, thereof, having an unexpected combination of desirable pharmacological characteristics. Crystalline forms of the present invention are also provided. Pharmaceutical compositions containing the same and methods of using the same as agents for the treatment of inflammatory, allergic, autoimmune, metabolic, cancer and/or cardiovascular diseases is also an objective of this invention. The present invention also provides a process for preparing compounds of Formula (I), including N-((1R,2S,5R)-5-(tert-butylamino)-2-((S)-2-oxo-3-(6-(trifluoromethyl)quinazolin-4-ylamino)pyrrolidin-1-yl)cyclohexyl)acetamide:

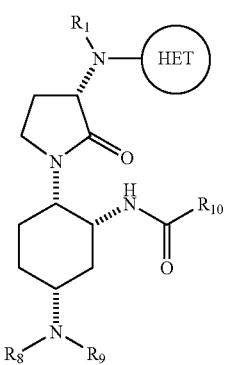

wherein $R^1$, $R^8$, $R^9$, $R^{10}$, and

are as described herein. Compounds that are useful intermediates of the process are also provided herein.

[N-((1R,2S,5R)-5-(tert-butylamino)-2-((S)-2-oxo-3-(6-(trifluoromethyl)quinazolin-4-ylamino)pyrrolidin-1-yl)cyclohexyl)acetamide, unexpectedly demonstrates a desirable combination of pharmacological characteristics including a surprisingly high degree of oral bioavailability in combination with indications that it is highly efficacious and has excellent safety criteria.

Known modulators of CCR2 receptors, such as those disclosed in patent publication WO2005021500 published Mar. 10, 2005 (U.S. Pat. No. 7,163,937, issued Jan. 16, 2007, assigned to present Applicant) that demonstrate an adequate degree of membrane permeability (a critical factor of oral bioavailability), are not sufficiently efficacious, as measured by their CCR2-binding ability (a measure of efficacy), and/or they lack appropriate criteria for safety as indicated by ion channel selectivity as measured by hERG and Na+ ion channel studies.

In contrast, as illustrated by the data presented herein in the section titled "Comparative Pharmacological Characteristics", infra, the relatively polar molecule, N-((1R,2S,5R)-5-(tert-butylamino)-2-((S)-2-oxo-3-(6-(trifluoromethyl)quinazolin-4-ylamino)pyrrolidin-1-yl)cyclohexyl)acetamide demonstrates a surprisingly high degree of membrane permeability, and yet maintains potent CCR2 binding ability along with excellent ion channel selectivity.

Accordingly, the present invention provides a new chemokine modulator having improved pharmacological characteristics that is expected to be useful in treating inflammatory, allergic, autoimmune, metabolic, cancer and/or cardiovascular diseases.

Embodiments

In one embodiment, the disclosure is directed to N-((1R,2S,5R)-5-(tert-butylamino)-2-((S)-2-oxo-3-(6-(trifluoromethyl)quinazolin-4-ylamino)pyrrolidin-1-yl)cyclohexyl)acetamide, and pharmaceutically acceptable salts, thereof.

Another embodiment is a crystalline form of N-((1R,2S,5R)-5-(tert-butylamino)-2-((S)-2-oxo-3-(6-(trifluoromethyl)quinazolin-4-ylamino)pyrrolidin-1-yl)cyclohexyl)acetamide, free base.

Another embodiment is a crystalline form of N-((1R,2S,5R)-5-(tert-butylamino)-2-((S)-2-oxo-3-(6-(trifluoromethyl)quinazolin-4-ylamino)pyrrolidin-1-yl)cyclohexyl)acetamide, free base, wherein the crystalline form comprising the N-2 Form.

Another embodiment is the N-2 Form characterized by (or having) unit cell parameters substantially equal to the following:
  Cell dimensions:
  a=18.7240(4)
  b=8.0171(2)
  c=19.6568(5)
  α=90
  β=114.935(2))
  γ=90
  V(Å$^3$)=2675.7(1)
  Space group P2$_1$2$_1$2$_1$
  Molecules/unit cell 2
wherein said crystal is at a temperature of about +22° C. (RT).

Another embodiment in the N-2 Form characterized by (or having) a powder x-ray diffraction pattern comprising three or more of 2θ values (CuKα λ=1.5418 Å) selected from 5.5, 9.1, 12.1, 14.0 and 19.2, at a temperature of about 22° C.

Another embodiment is the N-2 Form characterized by (or having) a powder x-ray diffraction pattern further comprising four or more of 2θ values (CuKα λ=1.5418 Å) selected from 5.5, 9.1, 12.1, 14.0 and 19.2 at a temperature of about 22° C.

Another embodiment is the N-2 Form characterized by (or having) fractional atomic coordinates substantially as listed in Table 3.

Figure 2:
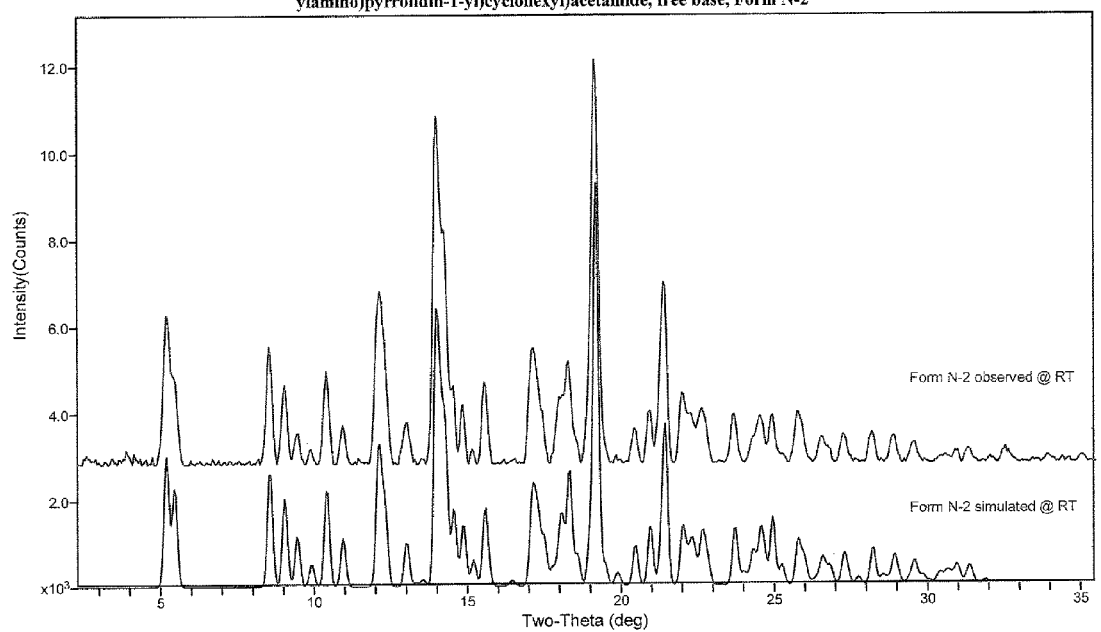
FIG. 2. Experimental and simulated powder patterns of N-((1R,2S,5R)-5-(tert-butylamino)-2-((S)-2-oxo-3-(6-(trifluoromethyl)quinazolin-4-ylamino)pyrrolidin-1-yl)cyclohexyl)acetamide, free base, Form N-2.

Another embodiment is the N-2 Form characterized by (or having) a powder x ray diffraction pattern substantially according to FIG. 2.

Figure 3:
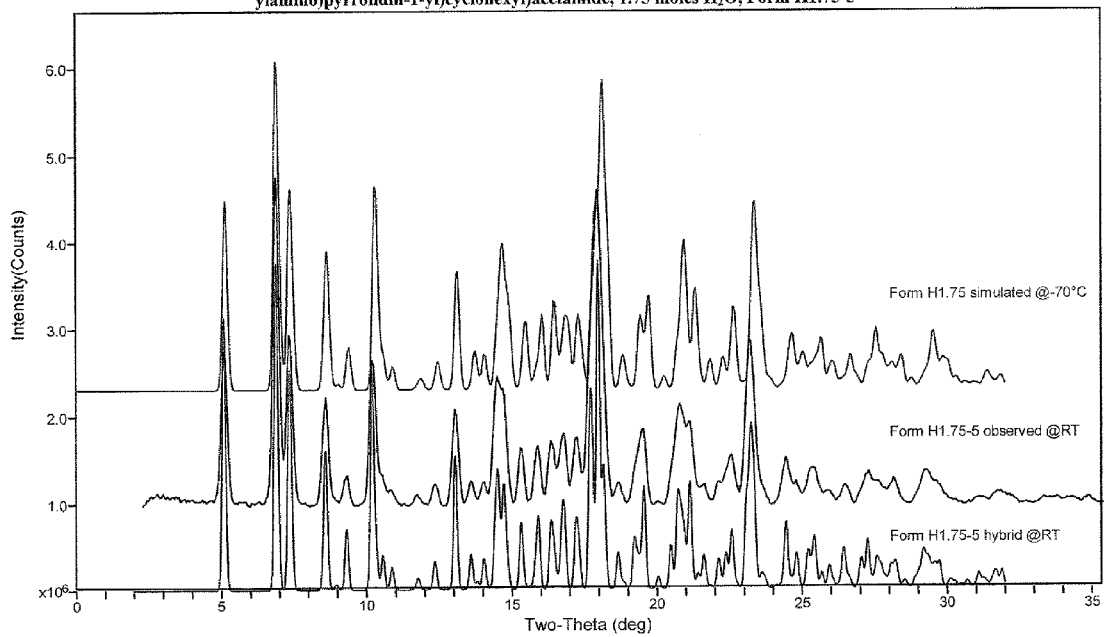
FIG. 3. Experimental and simulated powder patterns of N-((1R,2S,5R)-5-(tert-butylamino)-2-((S)-2-oxo-3-(6-(trifluoromethyl)quinazolin-4-ylamino)pyrrolidin-1-yl)cyclohexyl)acetamide, 1.75 moles $H_2O$, Form H1.75-5.

Another embodiment is a crystalline form of N-((1R,2S,5R)-5-(tert-butylamino)-2-((S)-2-oxo-3-(6-(trifluoromethyl)quinazolin-4-ylamino)pyrrolidin-1-yl)cyclohexyl)acetamide, free base, comprising Form. H1.75-5 (1.75 moles of water), characterized by the unit cell parameters found in Table 1; 3 or 4 or more 2θ values (CuKα λ=1.5418 Å) selected from Table 9; fractional atomic coordinate substantially as listed in Table 4 and/or a powder x-ray diffraction pattern substantially according to FIG. 3.

Another embodiment is a crystalline form of N-((1R,2S,5R)-5-(tert-butylamino)-2-((S)-2-oxo-3-(6-(trifluoromethyl)quinazolin-4-ylamino)pyrrolidin-1-yl)cyclohexyl)acetamide, free base, comprising Form H0.5-4 (hemi-hydrate) characterized by the unit cell parameters found in Table 1; 3 or 4 or more 2θ values (CuKα λ=1.5418 Å) selected from Table 9; fractional atomic coordinate substantially as listed in Table 2 and/or a powder x-ray diffraction pattern substantially according to FIG. 1.

Figure 4:
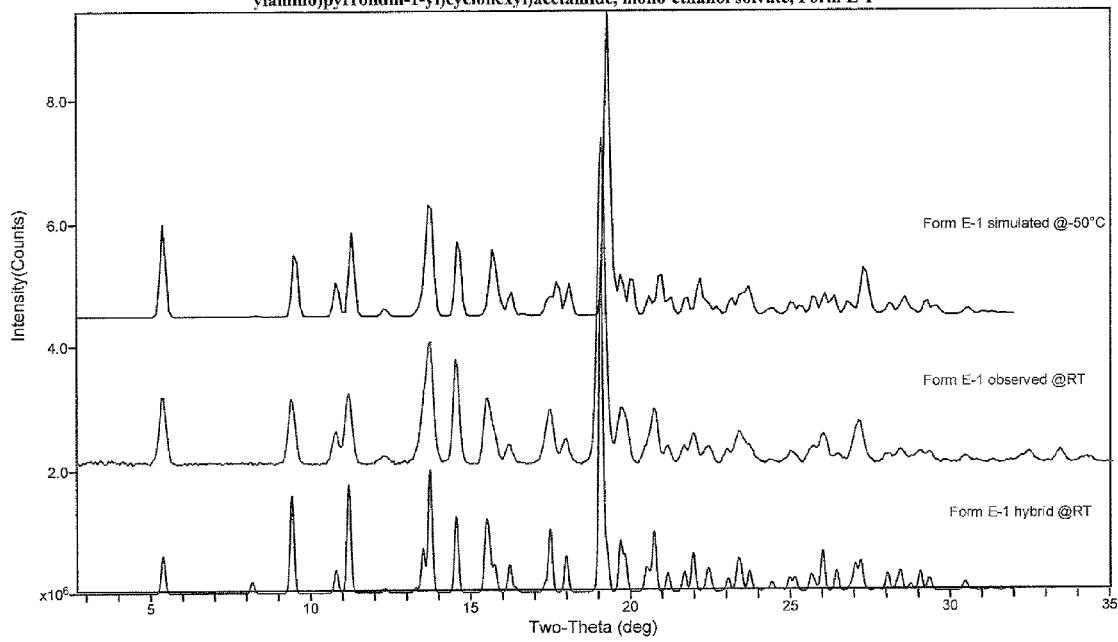
FIG. 4. Experimental and simulated powder patterns of N-((1R,2S,5R)-5-(tert-butylamino)-2-((S)-2-oxo-3-(6-(trifluoromethyl)quinazolin-4-ylamino)pyrrolidin-1-yl)cyclohexyl)acetamide, mono-ethanol solvate, Form E-1.

Another embodiment is a crystalline form of N-((1R,2S,5R)-5-(tert-butylamino)-2-((S)-2-oxo-3-(6-(trifluoromethyl)quinazolin-4-ylamino)pyrrolidin-1-yl)cyclohexyl)acetamide, free base, comprising Form E-1 (mono-ethanol solvate) characterized by the unit cell parameters found in Table 1; 3 or 4 or more 2θ values (CuKα λ=1.5418 Å) selected from Table 9; fractional atomic coordinate substantially as listed in Table 5 and/or a powder x-ray diffraction pattern substantially according to FIG. 4.

Figure 5:
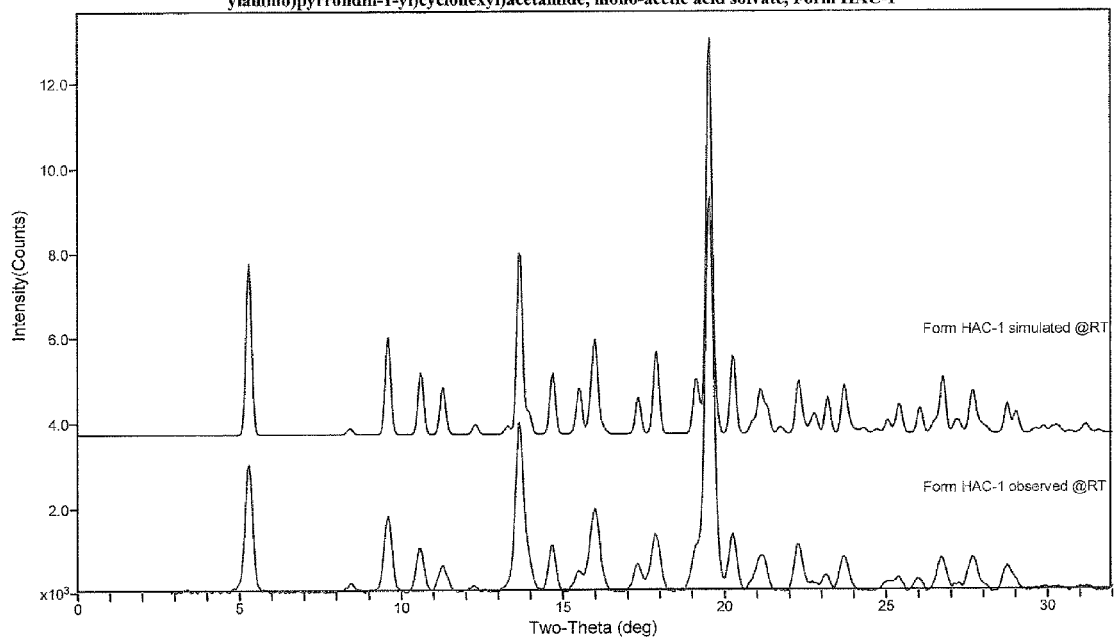
FIG. 5. Experimental and simulated powder patterns of N-((1R,2S,5R)-5-(tert-butylamino)-2-((S)-2-oxo-3-(6-(trifluoromethyl)quinazolin-4-ylamino)pyrrolidin-1-yl)cyclohexyl)acetamide, mono-acetic acid solvate, Fowl HAC-1.

Another embodiment is a crystalline form of N-((1R,2S,5R)-5-(tert-butylamino)-2-((S)-2-oxo-3-(6-(trifluoromethyl)quinazolin-4-ylamino)pyrrolidin-1-yl)cyclohexyl)acetamide, free base, comprising Form HAC-1 (mono-acetic acid solvate) characterized by the unit cell parameters found in Table 1; 3 or 4 or more 2θ values (CuKα λ=1.5418 Å) selected from Table 9; fractional atomic coordinate substantially as listed in Table 6 and/or a powder x-ray diffraction pattern substantially according to FIG. 5.

Another embodiment is a crystalline form patterns of N-((1R,2S,5R)-5-(tert-butylamino)-2-((S)-2-oxo-3-(6-(trifluoromethyl)quinazolin-4-ylamino)pyrrolidin-1-yl)cyclohexyl)acetamide, free base, comprising Form IPA-1 (mono-isopropanol solvate) characterized by the unit cell parameters found in Table 1; 3 or 4 or more 2θ values (CuKα λ=1.5418 Å) selected from Table 9; and/or fractional atomic coordinates substantially as listed in Table 7.

Figure 6:
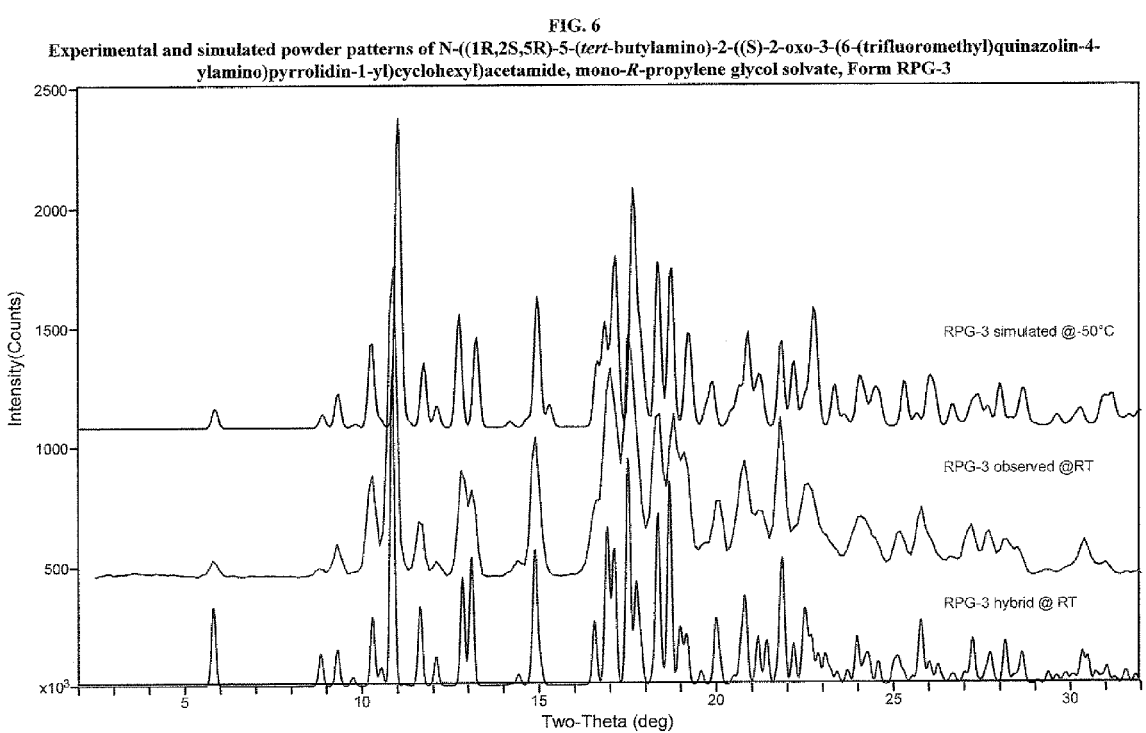
FIG. 6. Experimental and simulated powder patterns of N-(1R,2S,5R)-5-(tert-butylamino)-2-((S)-2-oxo-3-(6-(trifluoromethyl)quinazolin-4-ylamino)pyrrolidin-1-yl)cyclohexyl)acetamide, mono-R-propylene glycol solvate, Form RPG-3.
Figure 7:
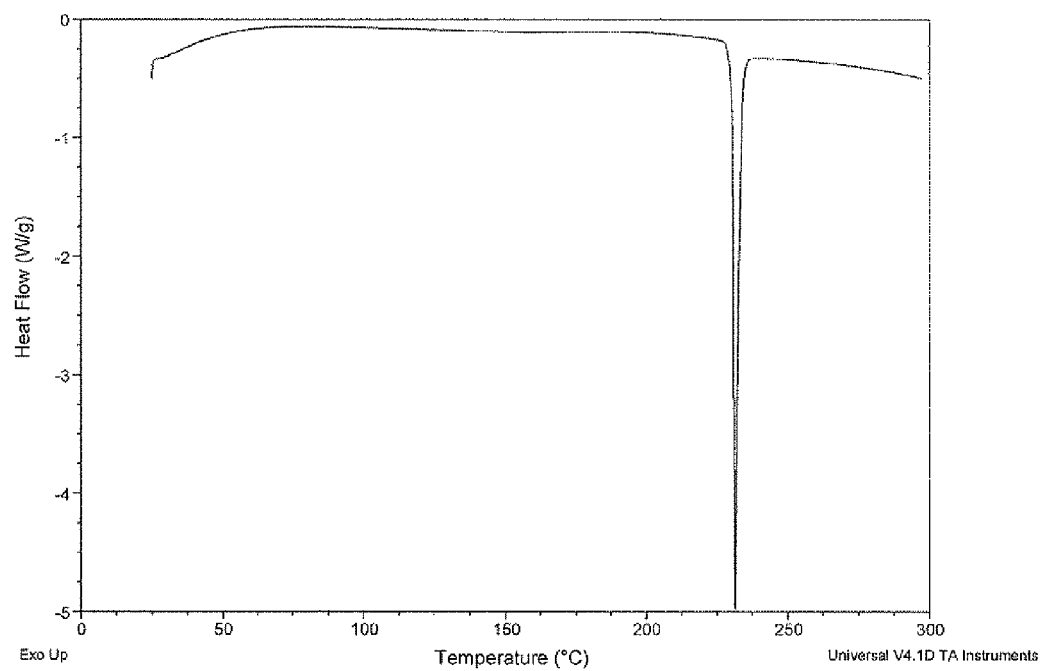
FIG. 7. DSC of N-((1R,2S,5R)-5-(tert-butylamino)-2-((S)-2-oxo-3-(6-(trifluoromethyl)quinazolin-4-ylamino)pyrrolidin-1-yl)cyclohexyl)acetamide, hemi-hydrate, Form H0.5-4.
Figure 8:
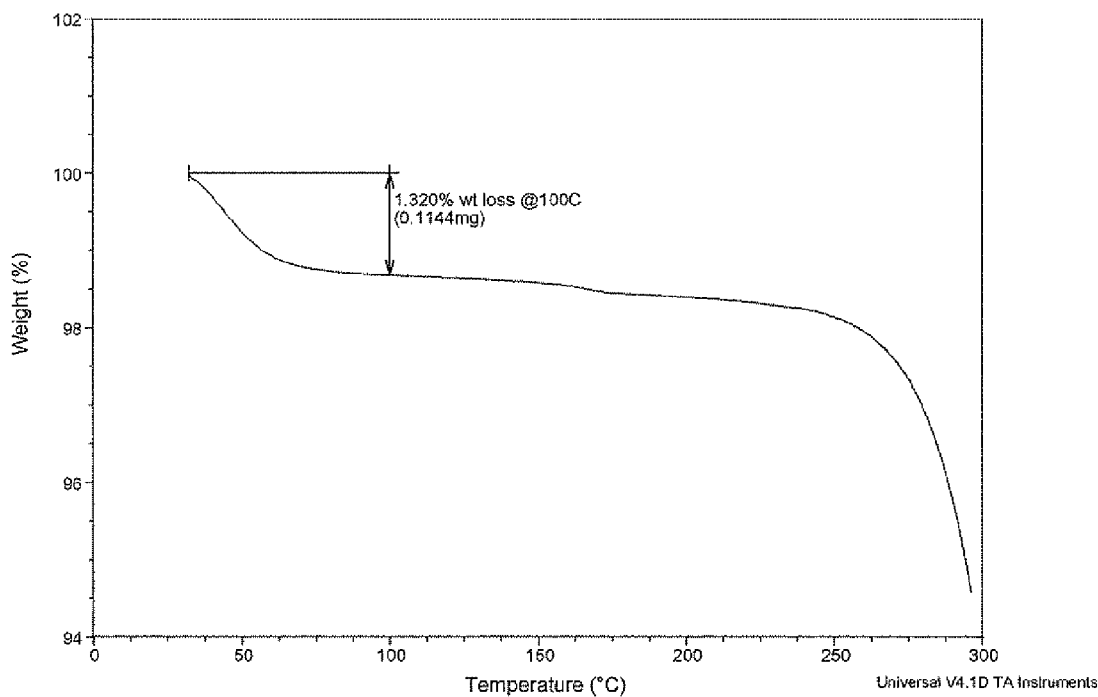
FIG. 8. TGA of N-((1R,2S,5R)-5-(tert-butylamino)-2-((S)-2-oxo-3-(6-(trifluoromethyl)quinazolin-4-ylamino)pyrrolidin-1-yl)cyclohexyl)acetamide, hemi-hydrate, Form H0.5-4.
Figure 9:
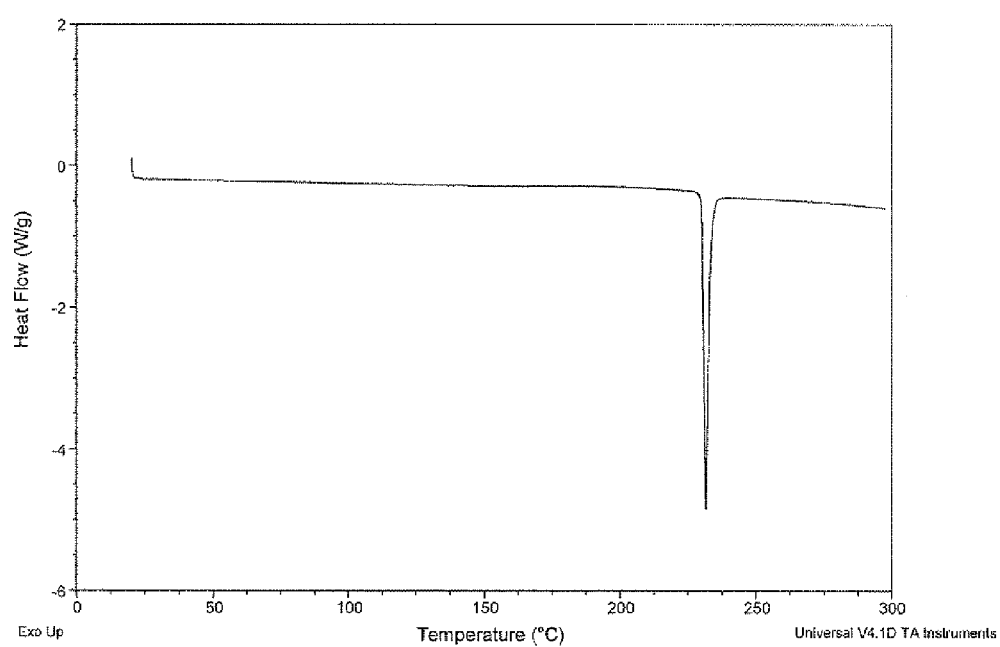
FIG. 9. DSC of N-((1R,2S,5R)-5-(tert-butylamino)-2-((S)-2-oxo-3-(6-(trifluoromethyl)quinazolin-4-ylamino)pyrrolidin-1-yl)cyclohexyl)acetamide, free base, Form N-2.
Figure 10:
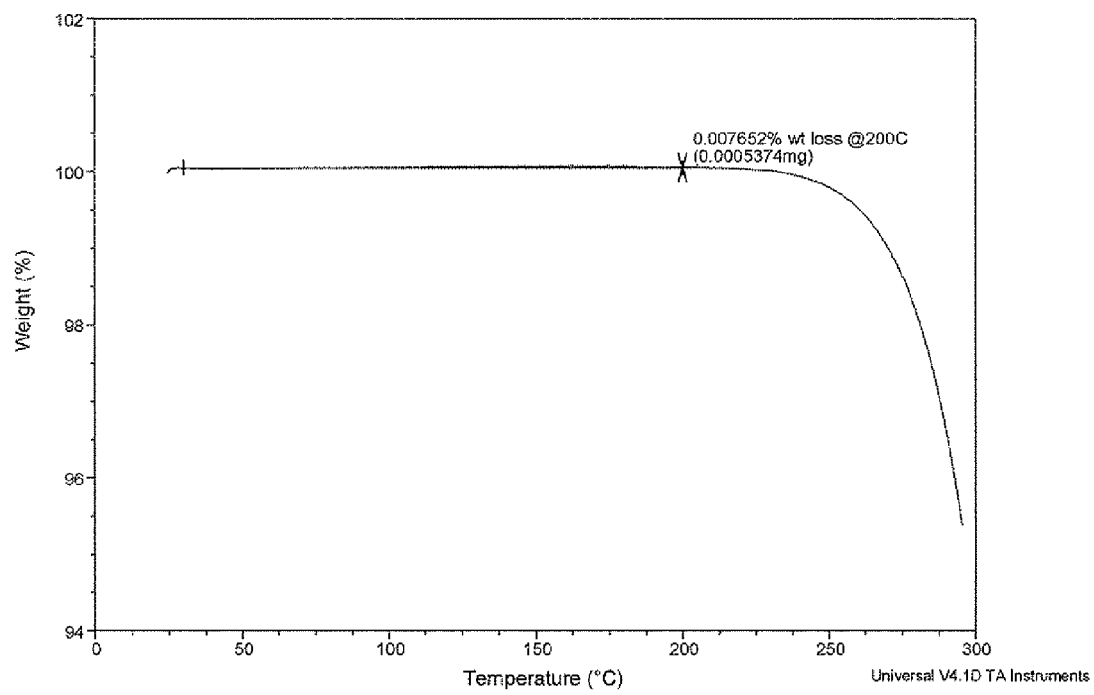
FIG. 10. TGA of N-((1R,2S,5R)-5-(tert-butylamino)-2-((S)-2-oxo-3-(6-(trifluoromethyl)quinazolin-4-ylamino)pyrrolidin-1-yl)cyclohexyl)acetamide, free base, Form N-2.

Another embodiment is a crystalline fowl of N-((1R,2S,5R)-5-(tert-butylamino)-2-((S)-2-oxo-3-(6-(trifluoromethyl)quinazolin-4-ylamino)pyrrolidin-1-yl)cyclohexyl)acetamide, free base comprising Form RPG-3 (mono-R-propylene glycol solvate) characterized by the unit cell parameters found in Table 1; 3 or 4 or more 2θ values (CuKα λ=1.5418 Å) selected from Table 9; fractional atomic coordinate substantially as listed in Table 8 and/or a powder x-ray diffraction pattern substantially according to FIG. 6.

Another embodiment is a pharmaceutical composition, comprising a pharmaceutically acceptable carrier and a compound of the Examples.

Another embodiment is a method for modulation of chemokine or chemokine receptor activity comprising administering to a patient in need thereof a therapeutically effective amount of a compound of the Examples.

Another embodiment is a method for modulation of CCR-2 receptor activity comprising administering to a patient in need thereof a therapeutically effective amount of a compound of the Examples.

Another embodiment is a method for modulation of MCP-1, MCP-2, MCP-3 and MCP-4, and MCP-5 activity that is mediated by the CCR2 receptor comprising administering to a patient in need thereof a therapeutically effective amount of a compound of the Examples.

Another embodiment is a method for modulation of MCP-1 activity comprising administering to a patient in need thereof a therapeutically effective amount of a compound of the Examples.

Another embodiment is a method for inhibiting CCR2 and CCR5 activity comprising administering to a patient in need thereof a therapeutically effective amount of a compound of the Examples.

Another embodiment is a method for treating disorders, comprising administering to a patient in need thereof a therapeutically effective amount of a compound of the Examples said disorders being selected from diabetes, obesity, metabolic syndrome, stroke, neuropathic pain, ischemic cardiomyopathy, psoriasis, hypertension, scheroderma, osteoarthritis, aneurism, fever, cardiovascular disease, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerulonephritis, asthma, multiple sclerosis, atherosclerosis, vasculitis, vulnerable plaques, rheumatoid arthritis, restenosis, venous neointimal hyperplasia, dialysis-graft neointimal hyperplasia, arterio-venous shunt intimal hyperplasia, organ transplantation, chronic allograft nephropathy, and cancer.

Another embodiment is a method for treating disorders, comprising administering to a patient in need thereof a therapeutically effective amount of a compound of the Examples, wherein said disorders are selected from diabetes, obesity, Crohn's disease, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerulonephritis, asthma, multiple sclerosis, atherosclerosis, and rheumatoid arthritis, restenosis, organ transplantation, and cancer.

Another embodiment is a method for treating disorders, comprising administering to a patient in need thereof a therapeutically effective amount of a compound of the Examples, wherein said disorders are selected from diabetes, obesity, Crohn's disease, systemic lupus erythematosus, glomerulonephritis, multiple sclerosis, atherosclerosis, restenosis, and organ transplantation.

Another embodiment is a method for treating disorders, comprising administering to a patient in need thereof a therapeutically effective amount of a compound of the Examples, wherein said disorders are selected from multiple sclerosis, atherosclerosis, Crohn's disease, and diabetes.

Another embodiment is a method for treating disorders, comprising administering to a patient in need thereof a therapeutically effective amount of a compound of the Examples, wherein said disorders are selected from restenosis, organ transplantation, and cancer.

Another embodiment is a method for treating diabetes, comprising administering to a patient in need thereof a therapeutically effective amount of a compound of the Examples.

Another embodiment is a method for treating Crohns's disease, comprising administering to a patient in need thereof a therapeutically effective amount of a compound of the Examples.

Another embodiment is a method for treating multiple sclerosis, comprising administering to a patient in need thereof a therapeutically effective amount of a compound of the Examples.

Another embodiment is a method for treating atherosclerosis, comprising administering to a patient in need thereof a therapeutically effective amount of a compound of the Examples.

Another embodiment is a method for treating restenosis, comprising administering to a patient in need thereof a therapeutically effective amount of a compound of the Examples.

Another embodiment is a method for treating organ transplantation, comprising administering to a patient in need thereof a therapeutically effective amount of a compound of the Examples.

Another embodiment is a method for treating cancer, comprising administering to a patient in need thereof a therapeutically effective amount of a compound of the Examples.

Another embodiment is a method for treating cancer, wherein the cancer is selected from breast cancer, liver cancer, prostate cancer and melanoma.

Another embodiment is a method for treating inflammatory, allergic, autoimmune, metabolic, cancer and/or cardiovascular diseases comprising administering to a patient in need thereof a therapeutically effective amount of a compound of the Examples.

Another embodiment is a method for treating inflammatory, allergic, autoimmune, metabolic, cancer and/or cardiovascular diseases which are at least partially mediated by CCR-2, comprising administering to a patient in need thereof a therapeutically effective amount of a compound of the Examples.

Another embodiment is a method for modulation of CCR2 activity comprising administering to a patient in need thereof a therapeutically effective amount of a compound of the Examples.

Another embodiment is a method for modulation of MIP-1β and RANTES activity that is mediated by the CCR5 receptor comprising administering to a patient in need thereof a therapeutically effective amount of a compound of the Examples.

Another embodiment is a compound of Examples in the preparation of a medicament for the treatment of diabetes, obesity, metabolic syndrome, stroke, neuropathic pain, ischemic cardiomyopathy, psoriasis, hypertension, scheroderma, osteoarthritis, aneurism, fever, cardiovascular disease, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerulonephritis, asthma, multiple sclerosis, atherosclerosis, vasculitis, vulnerable plaques, rheumatoid arthritis, restenosis, venous neointimal hyperplasia, dialysis-graft neointimal hyperplasia, arterio-venous shunt intimal hyperplasia, organ transplantation, chronic allograft nephropathy, and cancer.

Another embodiment is a compound of the Examples for use in therapy.

The invention may be embodied in other specific forms without departing from the spirit or essential attributes thereof. This invention also encompasses all combinations of alternative aspects and embodiments of the invention noted herein. It is understood that any and all embodiments may be taken in conjunction with any other embodiment to describe additional embodiments of the present invention. Furthermore, any elements of an embodiment (including preferred aspects) are meant to be combined with any and all other elements from any of the embodiments to describe additional embodiments.

Process Embodiments

The present disclosure also provides a novel process for making compounds of formula I:

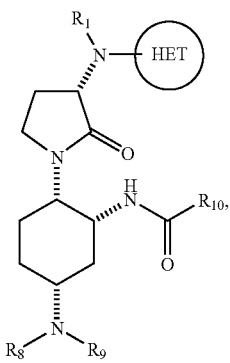

including N-((1R,2S,5R)-5-(tert-butylamino)-2-((S)-2-oxo-3-(6-(trifluoromethyl)quinazolin-4-ylamino)pyrrolidin-1-yl)cyclohexyl)acetamide, or a pharmaceutically acceptable salt thereof.

In a 1$^{st}$ embodiment, the present disclosure provides a novel process for preparing a compound of formula IV, the process comprising:

coupling an amino acid derivative of structure I, or a salt thereof, with a cyclohexanone of formula II, or a salt thereof (see preparation in WO ; 2005021500), to afford a compound of structure IV, or a salt thereof having a substituted amide side chain

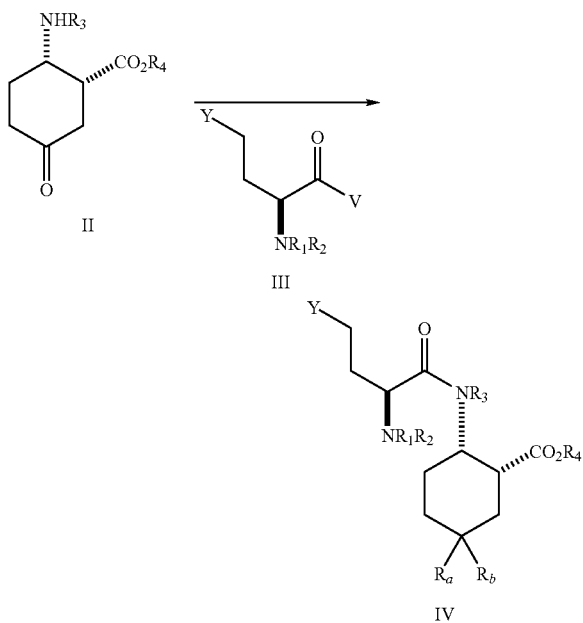

wherein:

$R_a$ and $R_b$ are independently $C_{1-6}$ alkoxy;

or $R_a$ and $R_b$ together with the carbon to which they are both attached combine to form a carbonyl, a thiocarbonyl, a cyclic acetal or cyclic thioacetal, wherein the cyclic acetal or cyclic thioacetal is selected from —O—Z—O— and —S—Z—S—, Z is —(CT$_1$T$_2$)$_2$—, —(CT$_1$T$_2$)$_3$—, or

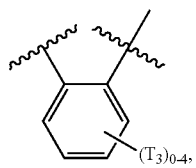

and $T_1$, $T_2$ and $T_3$ at each occurrence is independently selected from hydrogen, $C_{1-4}$alkyl, $C_{2-4}$alkenyl, halogen, hydroxy, cyano, nitro, $CF_3$, $OC_{1-4}$alkyl, $OCF_3$, and C(=O) $C_{1-4}$alkyl (preferably $T_1$, $T_2$ and $T_3$ are each hydrogen);

$R_1$, $R_2$ and $R_3$ are independently hydrogen or an amine-protecting group;

$R_4$ is lower $C_{1-6}$alkyl or optionally substituted benzyl;

Y is halogen, SMe, S(Me)$^+$R$_{12}$, or OSO$_2$R$_{13}$;

V is OH, halogen or OSO$_2$R$_{13}$; R$_{12}$ is hydrogen, $C_{1-6}$alkyl, —(CH$_2$)C(O)O $C_{1-6}$alkyl, or —(CH$_2$)C(O)O $C_{1-6}$alkyl; and $R_{13}$ at each occurrence is $C_{1-6}$alkyl.

Preferred amine-protecting groups are groups that can be removed by hydrolysis or hydrogenolysis under standard conditions. Such groups include without limitation, a carbobenzyloxy (Cbz) group, a tert-butyloxycarbonyl (BOC), a fluorenylmethyloxycarbonyl (FMOC) group, a benzyl (Bn) group or a p-methoxybenzyl (PMB) group. More preferred are Cbz, BOC, or Bn groups (especially Cbz and Bn).

In a 2$^{nd}$ embodiment, the present disclosure provides a novel process wherein:

$R_a$ and $R_b$ together with the carbon atoms to which they are both attached combine to form a carbonyl or a 1,3-dioxolane group (especially a 1,3-dioxolane group);

$R_1$ is hydrogen;
$R_2$ is Cbz;
$R_3$ is hydrogen;
$R_4$ is $C_{1-6}$alkyl;
Y is S(Me); and
V is OH.

In a 3$^{rd}$ embodiment, where Y is —SMe, the disclosure provides a process further comprising alkylating the compound of formula IV with a group $R_{12}X$, where X is a halogen, to form a sulfonium salt thereof. The alkylating agent is preferably methyl iodide.

In a 4$^{th}$ embodiment, the disclosure provides a process wherein cyclohexanone of formula IV is a toluenesulfonate salt.

In a 5$^{th}$ embodiment, the disclosure provides a process wherein the compound of formula IV is a sulfonium salt.

In a 6$^{th}$ embodiment, the disclosure provides a process wherein the coupling is conducted under an inert atmosphere, such as nitrogen or argon (preferably nitrogen) in an aprotic solvent such as proprionitrile, isopropyl acetate, n-butyl acetate, tert-butyl acetate or acetonitrile (especially acetonitrile and/or ethyl acetate).

In a 7$^{th}$ embodiment, the disclosure provides a process wherein the coupling can be achieved by the contacting a compound of formula II with a diimide coupling reagent in the presence of an activator, and a tertiary amine base. The diimide coupling reagent includes regeants, for example such as EDAC. Examples of activators includes HOBt ((said term includes hydrates thereof) and N',N'-4-dimethylamino-pyridine. A tertiary amine base, includes for example, triethylamine, N-N-disopropyl-N-ethyl amine and tri-n-propylamine.

In a 8$^{th}$ embodiment, the disclosure provides a process wherein the diimide coupling reagent is EDAC, the activator, is HOBt, (said term includes hydrates thereof) and the tertiary amine base is triethylamine.

In a 9th embodiment, disclosure provides a process wherein the mole ratios of a compound of formula II to the diimide coupling reagent to the activator to the tertiary amine about one to about 0.090-1.50 to about 0.95-1.50 to about 2.00 to 3.00, respectively. Said mole ratios are preferably one to about 0.095-1.05 to about 0.95-1.10 and to about 2.10 to 2.20, respectively.

In a 10th embodiment, the disclosure provides a novel process for preparing a compound of formula V having an ester moiety:

IV →

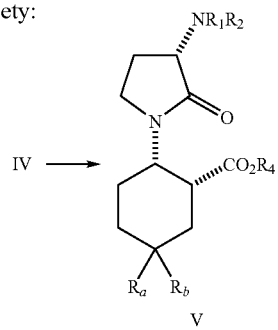

V the process, comprising:
cyclizing the amino acid derivative side chain of a compound of formula IV, or a salt thereof, to afford a compound of formula V having an ester moiety.

In an 11th embodiment where $R_a$ and $R_b$ are independently $C_{1-6}$alkoxy, or $R_a$ and $R_b$ together with the carbon to which they are both attached combine to form a a thiocarbonyl, a cyclic acetal or cyclic thioacetal, the disclosure provides a process which optionally further comprises the step of hydrolyzing the $R_a$ and $R_b$ groups so that the combination of the $R_a$ and $R_b$ together with the carbon to which they are both attached form a carbonyl. Hydrolyzing can be conducted in a solvent such as acetone, butanone, acetonitrile and isopropanol, or aqueous solutions thereof, and is preferably conducted in aqueous acetone. Preferably, the hydrolysis step follows the cylization step.

In a 12th embodiment, the disclosure provides a process wherein the cyclization is conducted by combining a compound of formula IV, or a salt thereof, with a base in the presence of a solvent. Such bases may be, for example without limitation, cesium carbonate, cesium bicarbonate, potassium carbonate, sodium tert-butylate, sodium hexamethyldisilazide, and preferably cesium carbonate.

In a 13th embodiment, the disclosure provides a process wherein the cyclization is conducted under an inert atmosphere, such as nitrogen or argon (preferably nitrogen) in a solvent including, for example without limit, DMSO, DMF, DMA, N-methylpyrrolidone, sulfolane (especially DMSO and/or DMF).

In a 14th embodiment, the disclosure provides process for preparing a compound of formula VI:

V →

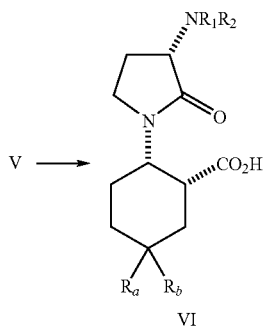

VI the process comprising:
hydrolyzing the ester moiety of the compound of formula V with a hydrolyzing agent to form the acid of compound VI at temperatures from about −5 to about 5° C. Ester hydrolyzing agents are well know to those of skill in the art and include alkali metal hydroxides, MOH, where M is Li, Na or K, preferably the hydrolyzing agent is aqueous NaOH. Preferably the hydrolyzing step is performed under biphasic conditions with an organic solvent that is partially miscible in water. Preferred organic solvents are acylic or cyclic ethers including THF, 2-methyl THF, 1,2-dimethoxyethane, 1,4-dioxane, especially THF.

Alternatively, in a 15th embodiment, where $R_a$ and $R_b$ together with the atom to which they are both attached combine to form a carbonyl, the disclosure provides a process for preparing a compound of formula VII:

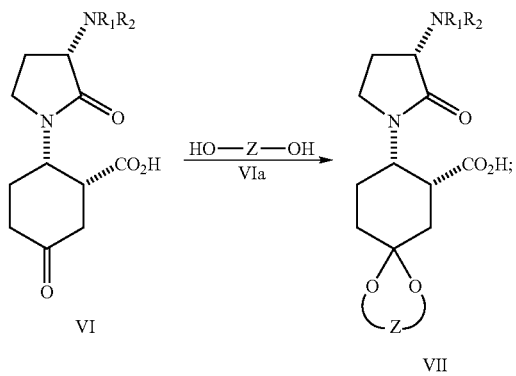

the process comprising:
reacting a compound of formula VIa, HO—Z—OH, with a compound of formula IV (optionally in situ) in the presence of an acid catalyst to give a compound of formula VII, wherein Z is —$(CT_1T_2)_{2-}$, —$(CT_1T_2)_{3-}$, or

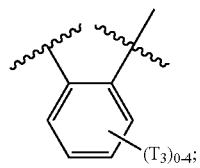

and $T_1$, $T_2$ and $T_3$ at each occurrence is independently selected from hydrogen, $C_{1-4}$alkyl, $C_{2-4}$alkenyl, halogen, hydroxy, cyano, nitro, $CF_3$, $OC_{1-4}$alkyl, $OCF_3$, and $C(=O)$ $C_{1-4}$alkyl (preferably $T_1$, $T_2$ and $T_3$ are each hydrogen).

Preferably the compound of formula VIa is ethylene glycol and the acid catalyst is p-toluenesulfonic acid, or a hydrate thereof.

In a 16th embodiment, the disclosure provides a process for preparing a compound of formula VIII:

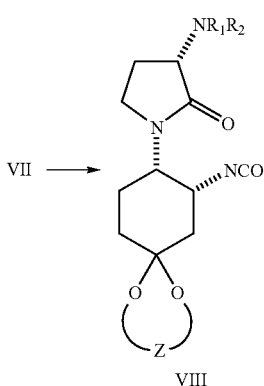

VII → the process comprising:

transforming the ketal of formula VII to an intermediate isocyanate of formula VIII. The transformation is preferably conducted via a Curtius rearrangement.

In a 17th embodiment, the disclosure provides a process wherein the transforming step is conducted via a Curtius rearrangement comprising the steps of:

a) mixing a substantially anhydrous solution of formula VII with a base (the base is for example, without limitation, an alkylamine, especially a tertiary amine, preferably triethylamine);

b) adding a haloformate (for example, a chloroformate, preferably i-BuO$_2$CCl) to the solution at a temperature of from about −10° C. to about 0° C. to form a mixed anhydride of the acid of formula VII;

c) treating the mixed anhydride with an azide reagent (preferably NaN$_3$) in the presence of a phase transfer catalyst (preferably a tetralkylammonium salt such as tetrabutylammonium bromide at about 5 mol %) at a temperature of about −10° C. to about 0° C. to form the acid azide of formula VIIa:

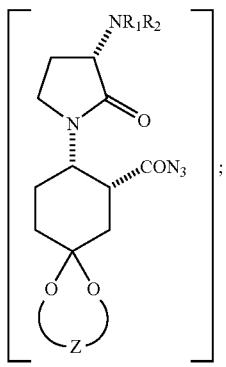

and d) heating a substantially anhydrous solution of the acyl azide of formula VIIa to form the corresponding isocyanate of formula VIII. Preferably the substantially anhydrous solution of acyl azide is dried over molecular sieves.

In a 18th embodiment, the disclosure provides a process for preparing a compound of formula IX having a ketal moiety:

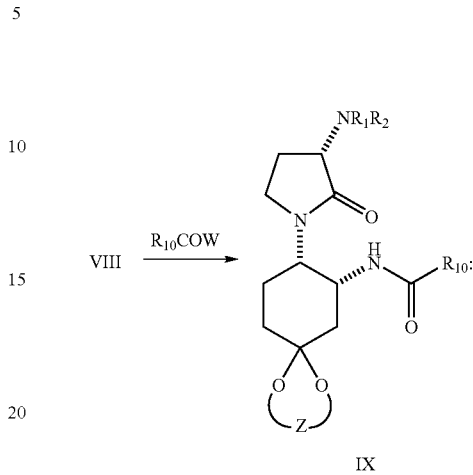

the process comprising:

contacting the isocyanate of formula VIII (optionally in situ) with a compound of formula R$_{10}$COW (e.g. acetic acid) in the presence of a corresponding acid anhydride (i.e. (R$_{10}$CO)$_2$O) to to form the amide of formula IX wherein:

R$_{10}$ is C$_{1-6}$alkyl (R$_{10}$ is preferably methyl): and

W is OH or OC$_{1-6}$alkyl.

In a 19th embodiment the disclosure provides a process for preparing a compound of formula X:

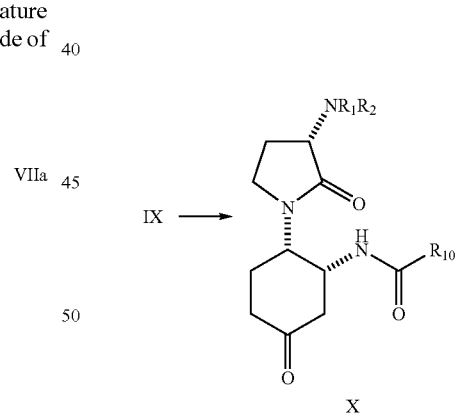

the process comprising:

hydrolyzing the ketal moiety of the amide of formula IX to form a compound of formula X. Ketal hydrolyzing conditions and reagents are well known to those of skill in the art. Preferably hydrolysis is conducted by heating a solution of compound IX having a ketal moiety in an organic solvent (for example acetone) and hydrochloric acid (about 1 N) at about 45° C. to about 55° C. for about 2-4 hours.

In a 20th embodiment, the disclosure provides a process for preparing a compound of formula XI:

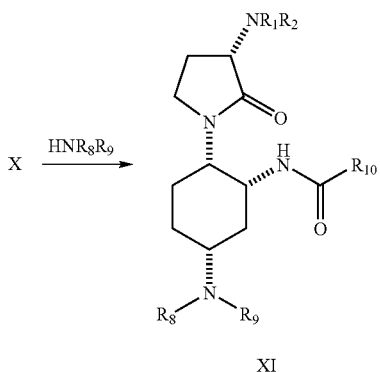

XI

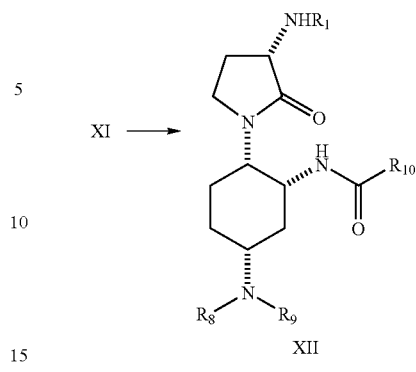

XII the process comprising:

reductively aminating the compound of formula X with an amine of formula $HNR_8R_9$ in the presence of a Lewis Acid followed by a reducing agent to form a compound of formula XI having a pyrollidonyl amine moiety.

In a 21$^{st}$ embodiment, the disclosure provides a process wherein reductively aminating comprises the steps of:

a) adding a Lewis Acid (preferably a titanium reagent including, without limit, $TiCl_2(O\text{-iso-propyl})_2$) to a solution of compound X and the amine having the formula $HNR_8R_9$ in an aprotic solvent to form an imine-enamine of formula XA:

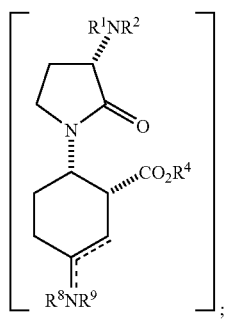

Xa and b) treating the imine-enamine of formula Xa with a reducing agent (preferably borane dimethyl sulfide) to afford the compound of formula XI having a pyrollindonyl amine moiety.

In the foregoing steps, the aprotic solvent can be for example, without limitation, dichloromethane, acetonitrile, DMSO, DMF, and N-methyl-pyrrolidinone (preferably dichloromethane).

In a 22$^{nd}$ embodiment, the disclosure provides a process wherein the amine of formula $HN(R_8)(R_9)$ is preferably tent-butyl amine.

In a 23$^{rd}$ embodiment, the disclosure provides process for preparing a compound of formula XII:

the process comprising:

deprotecting the pyrollidonyl amine of formula XI to form a compound of formula XII.

In a 24$^{th}$ embodiment, the disclosure provides a process wherein the deprotecting step is carried out by hydrogenating a solution of the compound of formula XII in the presence of a catalyst such as palladium. Preferably the hydrogenation is carried out at about 20 to about 40 psig in a solvent, including, without limitation, methanol, over 5% Pd/C catalyst at about 25° C. for about two to about six hours.

In a 25$^{th}$ embodiment, the disclosure provides a process for preparing a compound of formula I comprising coupling the compound of formula XII with a compound of formula

to afford a compound of formula I wherein:

HET is a 3-14 membered heteroaryl ring having one to four heteroatoms selected from N, O or S (preferably one to three heteroatoms, especially one to two nitrogen atoms) in at least one of the rings (HET is preferably a 6-substituted quinazolin-4-yl, more preferably 6-trifluoromethyl-quinazolin-4-yl); and LG is a leaving group selected from halogen or $OSO_2R_{16}$, wherein $R_{16}$ is phenyl, a 5- to 7-membered heteroaryl having one or more atoms selected from N, S, or O, $C_{1-6}$alkyl, or a 3- to 7-membered cycloalkyl, all of which are optionally substituted by one to three groups selected from halogen, $CF_3$ and $C_{1-6}$alkyl (preferably LG is a halogen, especially chlorine).

A leaving group as used herein includes, without limitation, groups such as halogens, mesylate, nonaflates, sulfonates, tosylates and triflates. A preferred leaving group is halogen or $OSO_2R_{16}$, wherein $R_{16}$ is phenyl, a 5- to 7-membered heteroaryl having one or more atoms selected from N, S or O, $C_{1-6}$alkyl, or a 3- to 7-membered cycloalkyl, all of which are optionally substituted by one to three groups selected from halogen, $CF_3$, and $C_{1-6}$alkyl. In the most preferred embodiment LG is a halogen, especially chlorine.

In a 26$^{th}$ embodiment, the disclosure provides a process for preparing a compound of formula X:

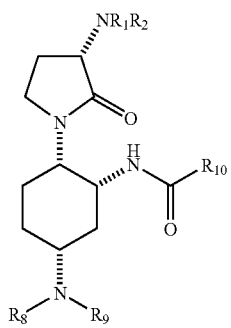

comprising the steps of:

hydrolyzing the ester moiety of the compound of formula V with a hydrolyzing agent to form the acid of compound VI at temperatures from about −5 to about 5° C.:

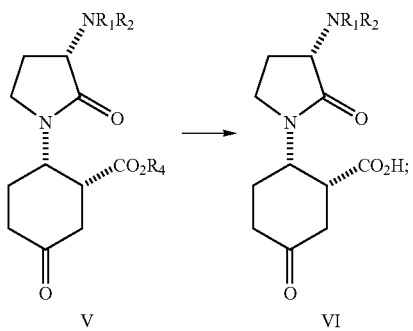

reacting a compound of formula VIa, HO—Z—OH, with a compound of formula IV (optionally in situ) in the presence of an acid catalyst to give a compound of formula VII having a carboxylic acid moiety:

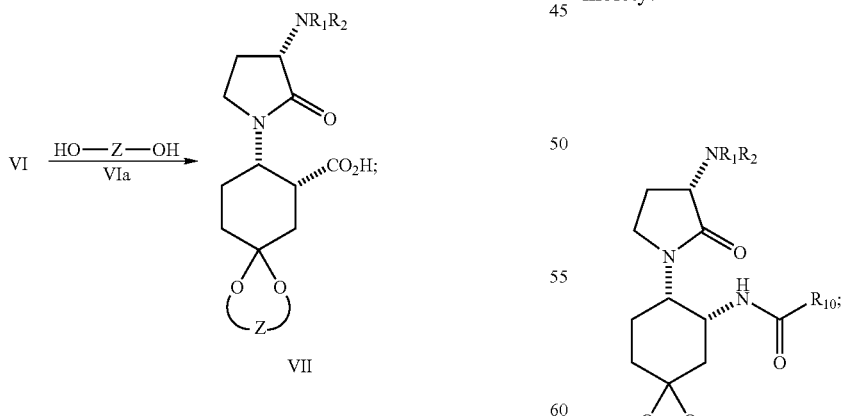

reacting a compound of formula VIa, HO—Z—OH (preferably alkylene glycol, especially ethylene glycol), with a compound of formula IV (optionally in situ) in the presence of an acid catalyst (preferably p-toluenesulfonic acid, or a hydrate thereof) to give a compound of formula VII having a carboxylic acid moiety:

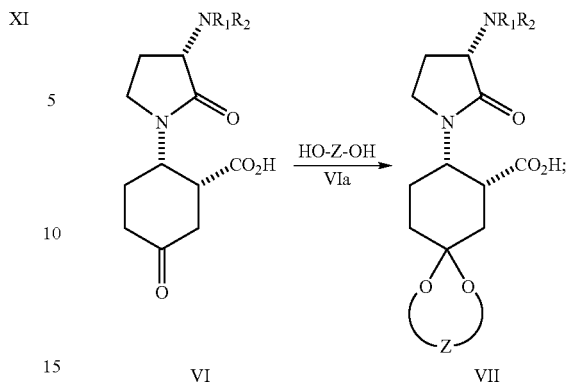

transforming the carboxylic acid moiety of the ketal of formula VII to a corresponding intermediate isocyanate of formula VIII:

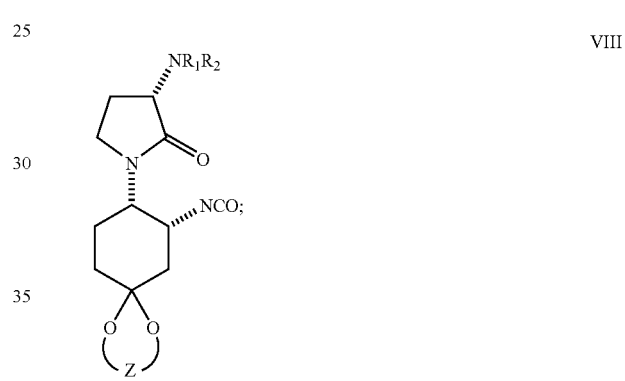

contacting the isocyanate of formula VIII (optionally in situ), with a compound of formula $R_{10}COW$ (e.g. acetic acid) in the presence of a corresponding acid anhydride (i.e. $(R_{10}CO)_2O$) to to form the amide of formula IX having a ketal moiety:

and hydrolyzing the ketal moiety of the amide of formula IX to form the compound of formula X:

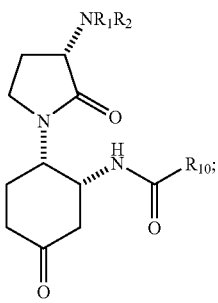

wherein:

$R_1$, and $R_2$ are independently hydrogen or an amine-protecting group;

$R_4$ and $R_{10}$ are independently $C_{1-6}$alkyl or optionally substituted benzyl;

$R_8$ and $R_9$ are independently hydrogen or $C_{1-6}$alkyl;

W is OH or $OC_{1-6}$alkyl;

Z is $-(CT_1T_2)_{2-}$, $-(CT_1T_2)_{3-}$, or

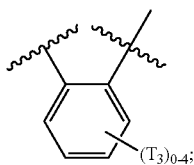

and $T_1$, $T_2$ and $T_3$ at each occurrence are independently selected from hydrogen, $C_{1-4}$alkyl, $C_{2-4}$alkenyl, halogen, hydroxy, cyano, nitro, $CF_3$, $OC_{1-4}$alkyl, $OCF_3$, and $C(=O)C_{1-4}$alkyl.

In a 27th embodiment, the disclosure provides a process for preparing a compound of formula XI wherein:

the compound of formula VII is (7R,8S)-8-((3S)-3-(((benzyloxy)carbonyl)amino)-2-oxo-1-pyrrolidinyl)-1,4-dioxaspiro[4.5]decane-7-carboxylic acid, or a salt thereof;

the compound of formula VIIa is benzyl ((3S)-1-((7R,8S)-7-(azidocarbonyl)-1,4-dioxaspiro[4.5]dec-8-yl)-2-oxo-3-pyrrolidinyl)carbamate, or a salt thereof;

the compound of formula VIII is benzyl ((3S)-1-((7R,8S)-7-isocyanato-1,4-dioxaspiro[4.5]dec-8-yl)-2-oxo-3-pyrrolidinyl)carbamate, or a salt thereof;

the compound of formula IX is benzyl ((3S)-1-((7R,8S)-7-acetamido-1,4-dioxaspiro[4.5]dec-8-yl)-2-oxo-3-pyrrolidinyl)carbamate, or a salt thereof;

the compound of formula X is benzyl ((3S)-1-((1S,2R)-2-acetamido-4-oxocyclohexyl)-2-oxo-3-pyrrolidinyl)carbamate, or a salt thereof; and the compound of formula XI is benzyl ((3S)-1-((1S,2R,4R)-2-acetamido-4-(tert-butylamino)cyclohexyl)-2-oxo-3-pyrrolidinyl)carbamate, or a salt thereof.

In a 28th embodiment, the disclosure provides a process for preparing a compound of formula I:

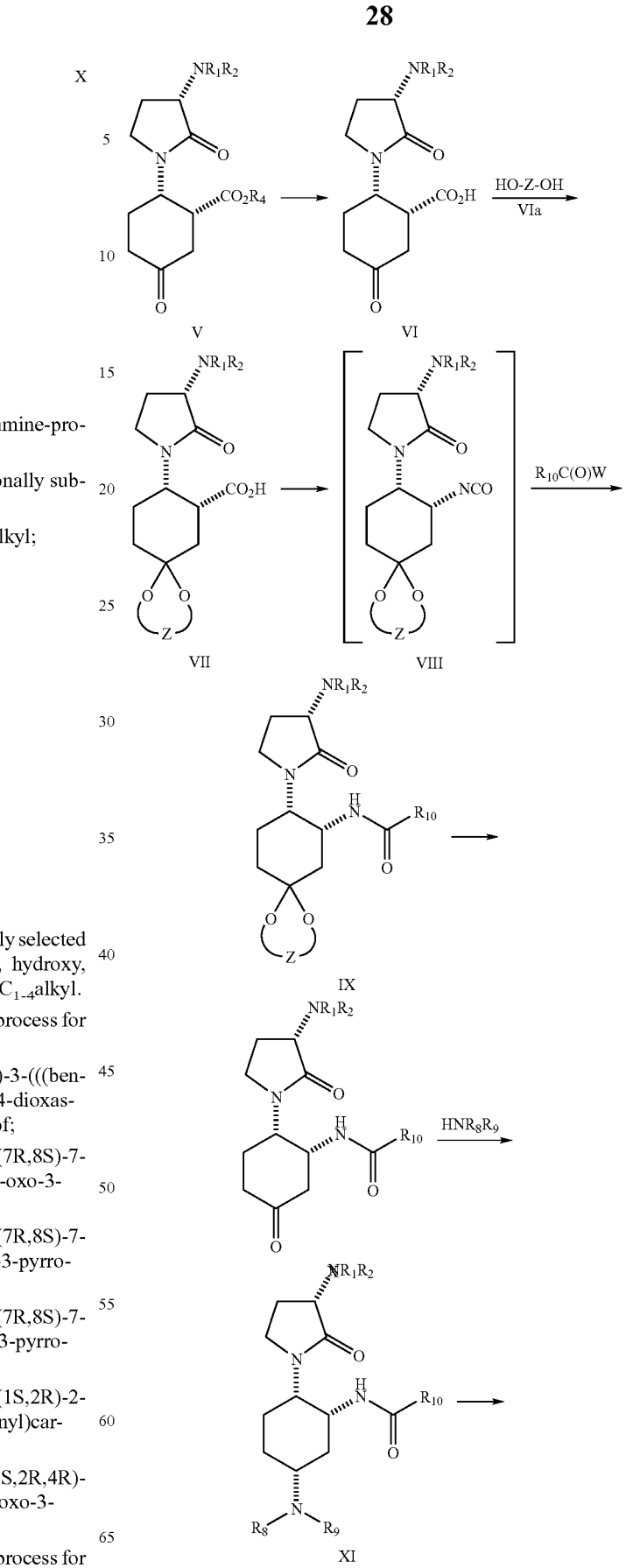

-continued

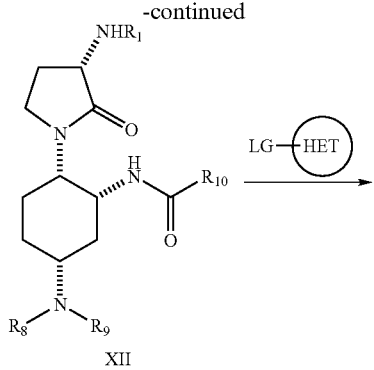

XII

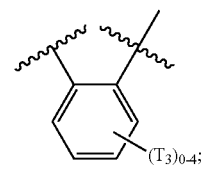

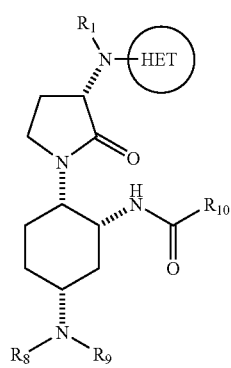

the process comprising:

hydrolyzing the ester moiety of the compound of formula V with a hydrolyzing agent (preferably an alkali hydroxide, especially sodium hydroxide) to form a compound of formula VI;

reacting a compound of formula Va, HO—Z—OH, with the compound of formula VI, optionally in situ, in the presence of acid catalyst (preferably p-toluenesulfonic acid, or a hydrate thereof) to afford a compound of formula VII having a carboxylic acid moiety;

transforming the carboxylic acid moiety of the ketal of formula VII to form a corresponding intermediate isocyanate of formula VIII;

contacting the isocyanate of formula VIII, optionally in situ, with a compound of formula $R_{10}COW$ (preferably acetic acid) in the presence of a corresponding acid anhydride, $(R_{10}CO)_2O$ (preferably acetic anhydride), to form the amide of formula IX having a ketal moiety;

hydrolyzing the ketal moiety of the amide of formula IX to form the compound of formula X; and reductively aminating the compound of formula X with an amine of formula $HNR_8R_9$ (preferably text-butyl amine) in the presence of a Lewis acid (preferably a titanium reagent such as $TiCl_2(O\text{-iso-propyl})_2$) to form a compound of formula XI having a pyrollidonyl amine moiety;

deprotecting the pyrollidinyl amine of formula XI to form a compound of formula XII; and coupling the compound of formula XII with a compound of formula

to afford a compound of formula I;
wherein:
$R_1$, and $R_2$ are independently hydrogen or an amine-protecting group;
$R_4$ and $R_{10}$ are independently $C_{1-6}$alkyl or optionally substituted benzyl;
$R_8$ and $R_9$ are independently hydrogen or $C_{1-6}$alkyl;
W is OH or $OC_{1-6}$alkyl;
Z is —$(CT_1T_2)_{2-}$, —$(CT_1T_2)_{3-}$, or

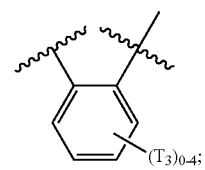

$T_1$, $T_2$ and $T_3$ at each occurrence is independently selected from hydrogen, $C_{1-4}$alkyl, $C_{2-4}$alkenyl, halogen, hydroxy, cyano, nitro, $CF_3$, $OC_{1-4}$alkyl, $OCF_3$, and $C(=O)C_{1-4}$alkyl (preferably Z is —$(CH_2)_2$—);

HET is a 3-14 membered heteroaryl ring having one to four heteroatoms selected from N, O or S (preferably one to three heteroatoms, especially one to two nitrogen atoms) in at least one of the rings (HET is preferably a 6-substituted quinazolin-4-yl, more preferably 6-trifluoromethyl-quinazolin-4-yl); and LG is a leaving group selected from halogen or $OSO_2R_{16}$, wherein $R_{16}$ is phenyl, a 5- to 7-membered heteroaryl having one or more atoms selected from N, S, or O, $C_{1-6}$alkyl, or a 3- to 7-membered cycloalkyl, all of which are optionally substituted by one to three groups selected from halogen, $CF_3$ and $C_{1-6}$alkyl (preferably LG is a halogen, especially chlorine).

In a 29th embodiment, the disclosure provides a compound of formula VI, or a salt thereof:

VI

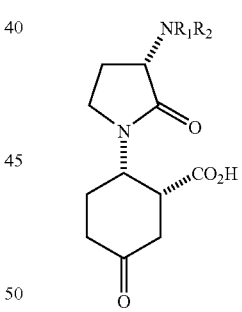

wherein:
$R_1$ and $R_2$ are independently selected from hydrogen and an amine-protecting group selected from BOC, Cbz, and benzyl (preferably $R_1$ is hydrogen and $R_2$ is Cbz);
Z is —$(CT_1T_2)_{2-}$, —$(CT_1T_2)_{3-}$, or and $T_1$, $T_2$ and $T_3$ at each occurrence are independently selected from hydrogen, $C_{1-4}$alkyl, $C_{2-4}$alkenyl, halogen, hydroxy, cyano, nitro, $CF_3$, $OC_{1-4}$alkyl, $OCF_3$, and $C(=O)C_{1-4}$alkyl (preferably Z is —$(CH_2)_{2-}$).

A preferred compound of formula VI is (1R,2S)-2-((S)-3-(benzyloxycarbonylamino)-2-oxopyrrolidin-1-yl)-5-oxocyclohexanecarboxylic acid or a salt thereof.

In a 30th embodiment, the disclosure provides a compound of formula VI that is (1R,2S)-2-((S)-3-(benzyloxycarbonylamino)-2-oxopyrrolidin-1-yl)-5-oxocyclohexanecarboxylic acid or a salt thereof.

In a 31st embodiment, the disclosure provide a novel compound of formula VII, or a salt thereof:

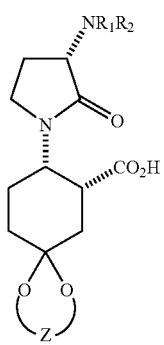

VII wherein:

$R_1$ and $R_2$ are independently selected from hydrogen and an amine-protecting group selected from BOC, Cbz, and benzyl (preferably $R_1$ is hydrogen and $R_2$ is Cbz);

Z is —$(CT_1T_2)_{2-}$, —$(CT_1T_2)_{3-}$, or

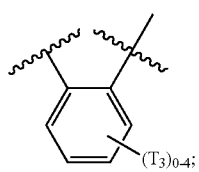

and $T_1$, $T_2$ and $T_3$ at each occurrence are independently selected from hydrogen, $C_{1-4}$alkyl, $C_{2-4}$alkenyl, halogen, hydroxy, cyano, nitro, $CF_3$, $OC_{1-4}$alkyl, $OCF_3$, and $C(=O)C_{1-4}$alkyl (preferably Z is —$(CH_2)_{2-}$).

A preferred compound of formula VII is (7R,8S)-8-((3S)-3-(((benzyloxy)carbonyl)amino)-2-oxo-1-pyrrolidinyl)-1,4-dioxaspiro[4.5]decane-7-carboxylic acid.

In a 32nd embodiment, the disclosure provides a compound of formula VII that is (7R,8S)-8-(3S)-3-(((benzyloxy)carbonyl)amino)-2-oxo-1-pyrrolidinyl)-1,4-dioxaspiro[4.5]decane-7-carboxylic acid, or a salt thereof.

In a 33rd embodiment, the disclosure provides novel compounds of formula VIIa, or a salt thereof:

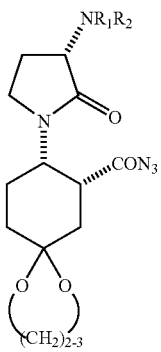

VIIa wherein:

$R_1$ and $R_2$ are independently selected from hydrogen and an amine-protecting group selected from BOC, Cbz, and benzyl (preferably $R_1$ is hydrogen and $R_2$ is Cbz);

Z is —$(CT_1T_2)_{2-}$, —$(CT_1T_2)_{3-}$, or

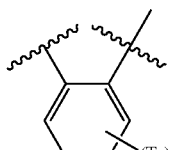

and $T_1$, $T_2$ and $T_3$ at each occurrence are independently selected from hydrogen, $C_{1-4}$alkyl, $C_{2-4}$alkenyl, halogen, hydroxy, cyano, nitro, $CF_3$, $OC_{1-4}$alkyl, $OCF_3$, and $C(=O)C_{1-4}$alkyl (preferably Z is —$(CH_2)_{2-}$).

A preferred compound of formula VIIa is benzyl ((3S)-1-(7R,8S)-7-(azidocarbonyl)-1,4-dioxaspiro[4.5]dec-8-yl)-2-oxo-3-pyrrolidinyl)carbamate.

In a 34th embodiment, the disclosure provides a compound of formula VIIa that is benzyl ((3S)-1-(7R,8S)-7-(azidocarbonyl)-1,4-dioxaspiro[4.5]dec-8-yl)-2-oxo-3-pyrrolidinyl) carbamate, or a salt thereof.

In a 35th embodiment, the disclosure provides a compound of formula VIII, or a salt thereof:

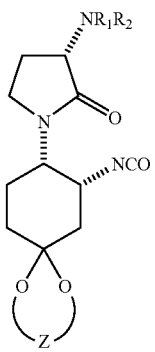

wherein:

$R_1$ and $R_2$ are independently selected from hydrogen and an amine-protecting group selected from BOC, Cbz, or benzyl (preferably $R_1$ is hydrogen and $R_2$ is Cbz);

Z is —(CT$_1$T$_2$)$_{2-}$, —(CT$_1$T$_2$)$_{3-}$, or

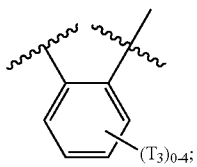

and

T$_1$, T$_2$ and T$_3$ at each occurrence are independently selected from hydrogen, C$_{1-4}$alkyl, C$_{2-4}$alkenyl, halogen, hydroxy, cyano, nitro, CF$_3$, OC$_{1-4}$alkyl, OCF$_3$, and C(=O)C$_{1-4}$alkyl (preferably Z is —(CH$_2$)$_2$—).

A preferred compound of formula VIII is benzyl ((3S)-1-(7R,8S)-7-isocyanato-1,4-dioxaspiro[4.5]dec-8-yl)-2-oxo-3-pyrollidinyl)carbamate.

In a 36$^{th}$ embodiment, the disclosure provides a compound of formula VIII that is benzyl ((3S)-1-(7R,8S)-7-isocyanato-1,4-dioxaspiro[4.5]dec-8-yl)-2-oxo-3-pyrrolidinyl)carbamate, or a salt thereof.

In a 37$^{th}$ embodiment, the disclosure provides a compound of formula IX, or a salt thereof

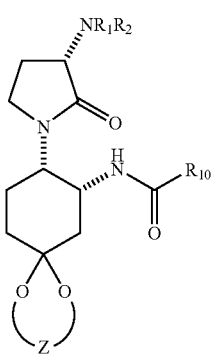

IX wherein:

R$_1$ and R$_2$ are independently selected from hydrogen and an amine-protecting group selected from BOC, Cbz, or benzyl (preferably R$_1$ is hydrogen and R$_2$ is Cbz);

Z is —(CT$_1$T$_2$)$_{2-}$, —(CT$_1$T$_2$)$_{3-}$, or

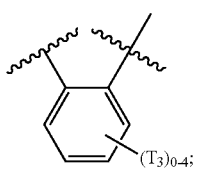

T$_1$, T$_2$ and T$_3$ at each occurrence are independently selected from hydrogen, C$_{1-4}$alkyl, C$_{2-4}$alkenyl, halogen, hydroxy, cyano, nitro, CF$_3$, OC$_{1-4}$alkyl, OCF$_3$, and C(=O)C$_{1-4}$alkyl (preferably Z is —(CH$_2$)$_2$—); and R$_{10}$ is C$_{1-6}$alkyl (preferably methyl).

A preferred compound of formula IX is benzyl ((3,5)-1-((7R,8S)-7-acetamido-1,4-dioxaspiro[4.5]dec-8-yl)-2-oxo-3-pyrrolidinyl)carbamate.

In a 38$^{th}$ embodiment, the disclosure provides a compound of formula IX that is benzyl ((3S)-1-((7R,8S)-7-acetamido-1,4-dioxaspiro[4.5]dec-8-yl)-2-oxo-3-pyrrolidinyl)carbamate, or a salt thereof.

In a 39$^{th}$ embodiment, the disclosure provides a compound of formula X, or a salt thereof:

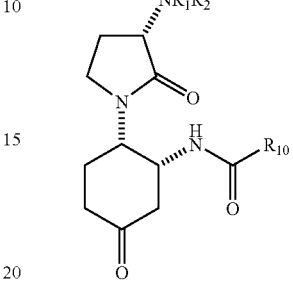

X wherein:

R$_1$ and R$_2$ are independently hydrogen or an amine-protecting group selected from BOC, Cbz, and benzyl; and R$_{10}$ is C$_{1-6}$alkyl.

Preferably R$_1$ is hydrogen, R$_2$ is Cbz and R$_{10}$ is methyl. A preferred compound of formula X is benzyl ((3S)-1-((1S,2R)-2-acetamido-4-oxocyclohexyl)-2-oxo-3-pyrrolidinyl) carbamate.

In a 40$^{th}$ embodiment, the disclosure provides a compound of formula X that is benzyl ((3S)-1-(1S,2R)-2-acetamido-4-oxocyclohexyl)-2-oxo-3-pyrrolidinyl)carbamate, or a salt thereof.

In a 40$^{th}$ embodiment, the disclosure provides a compound of formula XI, or a salt thereof:

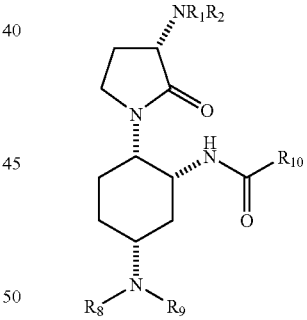

XI wherein:

R$_1$ and R$_2$ are independently hydrogen or an amine-protecting group selected from BOC, Cbz, and benzyl;

R$_8$ and R$_9$ are independently hydrogen or C$_{1-6}$alkyl; and

R$_{10}$ is C$_{1-6}$alkyl.

Preferably R$_1$ is hydrogen, R$_2$ is Cbz, R$_8$ is hydrogen, R$_9$ is tert-butyl, and R$_{10}$ is methyl. A preferred compound of formula XI is benzyl ((3S)-1-((1S,2R,4R)-2-acetamido-4-(tert-butylamino)cyclohexyl)-2-oxo-3-pyrrolidinyl)carbamate.

In a 41$^{st}$ embodiment, the disclosure provides a compound of formula XI that is benzyl ((3S)-1-((1S,2R,4R)-2-acetamido-4-(tert-butylamino)cyclohexyl)-2-oxo-3-pyrrolidinyl) carbamate, or a salt thereof.

In a 42$^{nd}$ embodiment, the disclosure provides a compound of formula XII, or a salt thereof:

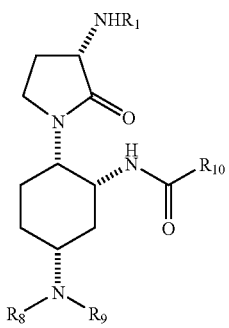

wherein:
R₁ is hydrogen or an amine-protecting group selected from BOC, Cbz, and benzyl;
$R_8$ and $R_9$ are independently hydrogen or $C_{1-6}$alkyl; and
$R_{10}$ is $C_{1-6}$alkyl.

Preferably $R_1$ is hydrogen, $R_8$ is hydrogen, $R_9$ is tert-butyl, and $R_{10}$ is methyl. A preferred compound of formula XII is N-((1R,2S,5R)-2-((3S)-3-amino-2-oxo-1-pyrrolidinyl)-5-(tert-butylamino)cyclohexyl)acetamide.

In a 43$^{rd}$ embodiment, the disclosure provides a compound of formula XII that is N-((1R,2S,5R)-2-((3S)-3-amino-2-oxo-1-pyrrolidinyl)-5-(tert-butylamino)cyclohexyl)acetamide, or a salt thereof.

In a 44$^{th}$ embodiment, the disclosure provides a compound selected from:
(7R,8S)-8-((3S)-3-(((benzyloxy)carbonyl)amino)-2-oxo-1-pyrrolidinyl)-1,4-dioxaspiro[4.5]decane-7-carboxylic acid, or a salt thereof;
benzyl ((3S)-1-((7R,8S)-7-(azidocarbonyl)-1,4-dioxaspiro[4.5]dec-8-yl)-2-oxo-3-pyrrolidinyl)carbamate, or a salt thereof;
benzyl ((3S)-1-((7R,8S)-7-isocyanato-1,4-dioxaspiro[4.5]dec-8-yl)-2-oxo-3-pyrrolidinyl)carbamate, or a salt thereof; benzyl ((3S)-1-((7R,8S)-7-acetamido-1,4-dioxaspiro[4.5]dec-8-yl)-2-oxo-3-pyrrolidinyl)carbamate, or a salt thereof;
benzyl ((3S)-1-((1S,2R)-2-acetamido-4-oxocyclohexyl)-2-oxo-3-pyrrolidinyl)carbamate, or a salt thereof; and
benzyl ((5S)-1-((1S,2R,4R)-2-acetamido-4-(tert-butylamino)cyclohexyl)-2-oxo-3-pyrrolidinyl)carbamate, or a salt thereof.

In a 45$^{th}$ embodiment, the disclosure provides a process wherein:
a compound of formula VII is (7R,8S)-8-(3S)-3-(((benzyloxy)carbonyl)amino)-2-oxo-1-pyrrolidinyl)-1,4-dioxaspiro[4.5]decane-7-carboxylic acid, or a salt thereof;
a compound of formula VIIa is benzyl ((3S)-1-((7R,8S)-7-(azidocarbonyl)-1,4-dioxaspiro[4.5]dec-8-yl)-2-oxo-3-pyrrolidinyl)carbamate, or a salt thereof;
a compound of formula VIII is benzyl ((3S)-1-((7R,8S)-7-isocyanato-1,4-dioxaspiro[4.5]dec-8-yl)-2-oxo-3-pyrrolidinyl)carbamate, or a salt thereof;
a compound of formula IX is benzyl ((3S)-1-((7R,8S)-7-acetamido-1,4-dioxaspiro[4.5]dec-8-yl)-2-oxo-3-pyrrolidinyl)carbamate, or a salt thereof;
the compound of formula X is benzyl ((3S)-1-((1S,2R)-2-acetamido-4-oxocyclohexyl)-2-oxo-3-pyrrolidinyl)carbamate, or a salt thereof; and
a compound of formula XI is benzyl ((3S)-1-((1S,2R,4R)-2-acetamido-4-(tert-butylamino)cyclohexyl)-2-oxo-3-pyrrolidinyl)carbamate, or a salt thereof.

In a 46$^{th}$ embodiment, the disclosure provides a process wherein a compound of formula I is N-((1R,2S,5R)-5-(tert-butylamino)-2-((S)-2-oxo-3-(6-(trifluoromethyl)quinazolin-4-ylamino)pyrrolidin-1-yl)cyclohexyl)acetamide or a salt thereof.

The present invention may be embodied in other specific forms without departing from the spirit or essential attributes thereof. Thus, the above embodiments should not be considered limiting. Any and all embodiments of the present invention may be taken in conjunction with any other embodiment or embodiments to describe additional embodiments. Each individual element (including preferred aspects) of the embodiments is its own independent embodiment. Furthermore, any element of an embodiment is meant to be combined with any and all other elements from any embodiment to describe an additional embodiment. In addition, the present invention encompasses combinations of different embodiment, parts of embodiments, definitions, descriptions, and examples of the invention noted herein.

Definitions

The following are definitions of terms used in this specification and appended claims. The initial definition provided for a group or term herein applies to that group or term throughout the specification and claims, individually or as part of another group, unless otherwise indicated.

The term "alkyl" refers to straight or branched chain hydrocarbon groups having 1 to 12 carbon atoms, preferably 1 to 6 carbon atoms. When numbers appear in a subscript after the symbol "C", the subscript defines with more specificity the number of carbon atoms that a particular group may contain. For example, "$C_{1-6}$alkyl" refers to straight and branched chain alkyl groups with one to six carbon atoms, such as methyl, ethyl, n-propyl, isopropyl, n-butyl, t-butyl, n-pentyl, and so forth. The subscript "0" refers to a bond. Thus, the term hydroxy($C_{0-2}$)alkyl or ($C_{0-2}$)hydroxyalkyl includes hydroxy, hydroxymethyl and hydroxyethyl. Alkyl groups may be substituted with one to three groups selected from ($C_{1-6}$)alkyl, ($C_{2-6}$)alkenyl, hydroxy, halogen, cyano, nitro, $CF_3$, $O(C_{1-6}alkyl)$, $OCF_3$, $C(=O)H$, $C(=O)(C_{1-6}alkyl)$, $CO_2H$, $CO_2(C_{1-6}alkyl)$, $NHCO_2(C_{1-6}alkyl)$, $-S(C_{1-6}alkyl)$, $NH_2$, $NH(C_{1-6}alkyl)$, $N(C_{1-6}alkyl)_2$, $N(CH_3)_3^+$, $SO_2(C_{1-6}alkyl)$, $C(=O)(C_{1-4}alkylene)NH_2$, $C(=O)(C_{1-4}alkylene)NH$ (alkyl), $C(=O)(C_{1-4}alkylene)N(C_{1-4}alkyl)_2$, $C_{3-7}$cycloalkyl, phenyl, benzyl, phenylethyl, phenyloxy, benzyloxy, napthyl, a four- to seven-membered heterocylo, and/ or a five- to six-membered heteroaryl. When a substituted alkyl is substituted with an aryl, heterocyclo, cycloalkyl, or heteroaryl group, said ringed systems are as defined below and thus may have zero, one, two, or three substituents, also as defined below.

When the term "alkyl" is used together with another group, such as in "arylalkyl", this conjunction defines with more specificity at least one of the substituents that the substituted alkyl will contain. For example, "arylalkyl" refers to a substituted alkyl group as defined above where at least one of the substituents is an aryl, such as benzyl. Thus, the term aryl($C_{0-4}$)alkyl includes a substituted lower alkyl having at least one aryl substituent and also includes an aryl directly bonded to another group, i.e., aryl($C_0$)alkyl.

The term "alkenyl" refers to straight or branched chain hydrocarbon groups having 2 to 12 carbon atoms and at least one double bond. Alkenyl groups of 2 to 6 carbon atoms and having one double bond are most preferred. Alkenyl groups may be substituted as described above for alkyl groups.

The team "alkynyl" refers to straight or branched chain hydrocarbon groups having 2 to 12 carbon atoms and at least one triple bond. Alkynyl groups of 2 to 6 carbon atoms and having one triple bond are most preferred. Alkynyl groups may be substituted as described above for alkyl groups.

The term "alkylene" refers to bivalent straight or branched chain hydrocarbon groups having 1 to 12 carbon atoms, preferably 1 to 8 carbon atoms, e.g., $\{'CH_2-\}_n$, wherein n is 1 to 12, preferably 1-8. Lower alkylene groups, that is, alkylene groups of 1 to 2 carbon atoms, are most preferred. The terms "alkenylene" and "alkynylene" refer to bivalent radicals of alkenyl and alkynyl groups, respectively, as defined above. Alkenylene groups may be substituted as described above for alkyl groups.

The term "alkoxy" refers to an oxygen atom substituted by alkyl, as defined herein. For example, the term "alkoxy" or includes the group —O—$C_{1-6}$alkyl.

When a subscript is used with reference to an alkoxy, thioalkyl or aminoalkyl, the subscript refers to the number of carbon atoms that the group may contain in addition to heteroatoms.

It should be understood that the selections for all groups, including for examples, alkoxy, thioalkyl, and aminoalkyl, will be made by one skilled in the field to provide stable compounds.

The term "carbonyl" refers to a bivalent carbonyl group —C(=O)—.

The term "acyl" refers to a carbonyl group linked to an organic radical, more particularly, the group C(=O)$R_e$, as well as the bivalent group —C(=O)$R_e$—, which are linked to organic radicals. The group $R_e$ can be selected from alkyl, alkenyl, alkynyl, cycloalkyl, heterocyclo, aryl, or heteroaryl as defined herein, or when appropriate, the corresponding bivalent group, e.g., alkylene.

The term "cycloalkyl" refers to fully saturated and partially unsaturated hydrocarbon rings (and therefore includes "cycloalkenyl rings") of 3 to 9, preferably 3 to 7 carbon atoms. The term "cycloalkyl" includes such rings having zero, one, two, or three substituents selected from ($C_{1-4}$)alkyl, ($C_{2-4}$)alkenyl, halogen, hydroxy, cyano, nitro, $CF_3$, O($C_{1-4}$alkyl), $OCF_3$, C(=O)H, C(=O)($C_{1-4}$alkyl), $CO_2$H, $CO_2$($C_{1-4}$alkyl), $NHCO_2$($C_{1-4}$alkyl), S($C_{1-4}$alkyl), $NH_2$, NH($C_{1-4}$alkyl), N($C_{1-4}$alkyl)$_2$, N($C_{1-4}$alkyl)$_3^+$, $SO_2$($C_{1-4}$alkyl), C(=O)($C_{1-4}$alkylene)$NH_2$, C(=O)($C_{1-4}$alkylene)NH(alkyl), and/or C(=O)($C_{1-4}$alkylene)N($C_{1-4}$alkyl)$_2$. The term "cycloalkyl" also includes such rings having a second ring fused thereto (e.g., including benzo, heterocyclo, or heteroaryl rings) or having a carbon-carbon bridge of 3 to 4 carbon atoms.

The term "halo" or "halogen" refers to chloro, bromo, fluoro and iodo.

The term "haloalkyl" means a substituted alkyl having one or more halo substituents. For example, "haloalkyl" includes mono, bi, and trifluoromethyl.

The teen "haloalkoxy" means an alkoxy group having one or more halo substituents. For example, "haloalkoxy" includes $OCF_3$.

The term "heteroatoms" shall include oxygen, sulfur and nitrogen.

The term "aryl" refers to phenyl, biphenyl, fluorenyl, 1-naphthyl and 2-naphthyl. The term "aryl" includes such rings having zero, one, two or three substituents selected from ($C_{1-4}$)alkyl, ($C_{2-4}$)alkenyl, halogen, hydroxy, cyano, nitro, $CF_3$, O($C_{1-4}$alkyl), $OCF_3$, C('O)H, C(=O)($C_{1-4}$alkyl), $CO_2$H, $CO_2$($C_{1-4}$alkyl), $NHCO_2$($C_{1-4}$alkyl), S($C_{1-4}$alkyl), $NH_2$, NH($C_{1-4}$alkyl), N($C_{1-4}$alkyl)$_3^+$, $SO_2$($C_{1-4}$alkyl), C(=O)($C_{1-4}$alkylene)$NH_2$, C(=O)($C_{1-4}$alkylene)NH(alkyl), and/or C(=O)($C_{1-4}$alkylene)N($C_{1-4}$alkyl)$_2$.

The terms "heterocyclo" or "heterocyclic" refers to substituted and unsubstituted non-aromatic (which may be partially or fully saturated) 3- to 15-membered rings having one to four heteroatoms. Such rings can be 3-to 7-membered monocyclic groups, 7-to 11-membered bicyclic groups, and 10-to 15-membered tricyclic groups. Each ring of the heterocyclo group containing a heteroatom can contain one or two oxygen or sulfur atoms and/or from one to four nitrogen atoms provided that the total number of heteroatoms in each ring is four or less, and further provided that the ring contains at least one carbon atom. The fused rings completing bicyclic and tricyclic groups may contain only carbon atoms and may be saturated, partially saturated, or unsaturated. The nitrogen and sulfur atoms may optionally be oxidized and the nitrogen atoms may optionally be quaternized. The heterocyclo group may be attached at any available nitrogen or carbon atom. The heterocyclo ring may contain zero, one, two or three substituents selected from ($C_{1-4}$)alkyl, ($C_{2-4}$)alkenyl, halogen, hydroxy, cyano, nitro, $CF_3$, O($C_{1-4}$alkyl), $OCF_3$, C(=O)H, C(=O)($C_{1-4}$alkyl), $CO_2$H, $CO_2$($C_{1-4}$alkyl), $NHCO_2$($C_{1-4}$alkyl), S($C_{1-4}$alkyl), $NH_2$, NH($C_{1-4}$alkyl), N($C_{1-4}$alkyl)$_2$, N($C_{1-4}$alkyl)$_3^+$, $SO_2$($C_{1-4}$alkyl), C(=O)($C_{1-4}$alkylene)$NH_2$, C(=O)($C_{1-4}$alkylene)NH(alkyl), and/or C(=O)($C_{1-4}$alkylene)N($C_{1-4}$alkyl)$_2$. Exemplary heterocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane, quinuclidinyl, and tetrahydro-1,1-dioxothienyl and the like.

The term "heteroaryl" refers to substituted and unsubstituted aromatic 3- to 14-membered rings having one to four heteroatoms selected from O, S, or N in at least one of the rings. Said rings can be 5- or 6-membered monocyclic groups, 9- or 10-membered bicyclic groups, and 11- to 14-membered tricyclic groups. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents selected from ($C_{1-4}$alkyl, ($C_{2-4}$)alkenyl, halogen, hydroxy, cyano, nitro, $CF_3$, O($C_{1-4}$alkyl), $OCF_3$, C(=O)H, C(=O)($C_{1-4}$alkyl), $CO_2$H, $CO_2$($C_{1-4}$alkyl), $NHCO_2$($C_{1-4}$alkyl), S($C_{1-4}$alkyl), $NH_2$, NH($C_{1-4}$alkyl), N($C_{1-4}$alkyl)$_2$, N($C_{1-4}$alkyl)$_3^+$, $SO_2$($C_{1-4}$alkyl), C(=O)($C_{1-4}$alkylene)$NH_2$, C(=O)($C_{1-4}$alkylene)NH(alkyl), and/or C(=O)($C_{1-4}$alkylene)N($C_{1-4}$alkyl)$_2$.

Exemplary heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl, indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl and the like. Particular heteroaryl groups include, for example, 6-substituted quinazolin-4-yl and 6-trifluoromethyl-quinazolin-4-yl.

Where a group is referred to as "optionally substituted", the term is defined herein to include both a substituted and unsubstituted group.

The compounds herein described may have asymmetric centers. Compounds of the present invention containing an asymmetrically substituted atom may be isolated in optically active or racemic forms. It is well known in the art how to prepare optically active fowls, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

One enantiomer of compounds disclosed herein may display superior activity compared with the other. Thus, all of the stereochemistries are considered to be a part of the present invention. When required, separation of the racemic material can be achieved by HPLC using a chiral column or by a resolution using a resolving agent such as camphonic chloride as in Steven D. Young, et al, *Antimicrobial Agents and Chemotherapy*, 1995, 2602-2605.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers which release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to inhibit MCP-1 or effective to treat or prevent disorders.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

The names used herein to characterize a specific form, e.g., "N-2", should not be considered limiting with respect to any other substance possessing similar or identical physical and chemical characteristics, but rather it should be understood that these designations are mere identifiers that should be interpreted according to the characterization information also presented herein.

The present invention provides, at least in part, crystalline forms of the free base of N-((1R,2S,5R)-5-(tert-butylamino)-2-((S)-2-oxo-3-(6-(trifluoromethyl)quinazolin-4-ylamino) pyrrolidin-1-yl)cyclohexyl)acetamide, as a novel material, in particular in a pharmaceutically acceptable form. In certain preferred embodiments, crystalline forms of the free base are in substantially pure form. Preferred embodiments of crystalline forms of the free base are disclosed in Example 2 as the E-1, HAC-1, JPA-1, N-2, RPG-3, H0.5-4, and H1.75-5 Forms.

As used herein "polymorph" refers to crystalline forms having the same chemical composition but different spatial arrangements of the molecules, atoms, and/or ions forming the crystal.

As used herein "solvate" refers to a crystalline form of a molecule, atom, and/or ions that further contains molecules of a solvent or solvents incorporated into the crystalline structure. The solvent molecules in the solvate may be present in a regular arrangement and/or a non-ordered arrangement. The solvate may comprise either a stoichiometric or nonstoichiometric amount of the solvent molecules. For example, a solvate with a nonstoichiometric amount of solvent molecules may result from partial loss of solvent from the solvate.

As used herein "amorphous" refers to a solid form of a molecule, atom, and/or ions that is not crystalline. An amorphous solid does not display a definitive X-ray diffraction pattern.

As used herein, "substantially pure," when used in reference to a crystalline form, means a compound having a purity greater than 90 weight %, including greater than 90, 91, 92, 93, 94, 95, 96, 97, 98 and 99 weight %, and also including equal to about 100 weight % of the compound, based on the weight of the compound. The remaining material comprises other form(s) of the compound, and/or reaction impurities and/or processing impurities arising from its preparation. For example, a crystalline form of N-((1R,2S,5R)-5-(tert-butylamino)-2-((S)-2-oxo-3-(6-(trifluoromethyl)quinazolin-4-ylamino)pyrrolidin-1-yl)cyclohexyl)acetamide may be deemed substantially pure in that it has a purity greater than 90 weight %, as measured by means that are at this time known and generally accepted in the art, where the remaining less than 10 weight % of material comprises other form(s) of N-((1R,2S,5R)-5-(tert-butylamino)-2-((S)-2-oxo-3-(6-(trifluoromethyl)quinazolin-4-ylamino)pyrrolidin-1-yl)cyclohexyl)acetamide and/or reaction impurities and/or processing impurities.

Samples of the crystalline forms may be provided with substantially pure phase homogeneity, indicating the presence of a dominant amount of a single crystalline form and optionally minor amounts of one or more other crystalline forms. The presence of more than one crystalline form in a sample may be determined by techniques such as powder X-ray diffraction (PXRD) or solid state nuclear magnetic resonance spectroscopy (SSNMR). For example, the presence of extra peaks in the comparison of an experimentally measured PXRD pattern with a simulated PXRD pattern may indicate more than one crystalline form in the sample. The simulated PXRD may be calculated from single crystal X-ray data. See Smith, D. K., "A FORTRAN Program for Calculating X-Ray Powder Diffraction Patterns," Lawrence Radiation Laboratory, Livermore, Calif., UCRL-7196 (April 1963).

Preferably, the crystalline form has substantially pure phase homogeneity as indicated by less than 10%, preferably less than 5%, and more preferably less than 2% of the total peak area in the experimentally measured PXRD pattern arising from the extra peaks that are absent from the simulated PXRD pattern. Most preferred is a crystalline form having substantially pure phase homogeneity with less than 1% of the total peak area in the experimentally measured PXRD pattern arising from the extra peaks that are absent from the simulated PXRD pattern.

Procedures for the preparation of crystalline forms are known in the art. The crystalline forms may be prepared by a variety of methods, including for example, crystallization or recrystallization from a suitable solvent, sublimation, growth from a melt, solid state transformation from another phase, crystallization from a supercritical fluid, and jet spraying. Techniques for crystallization or recrystallization of crystalline forms from a solvent mixture include, for example, evaporation of the solvent, decreasing the temperature of the solvent mixture, crystal seeding a supersaturated solvent mixture of the molecule and/or salt, freeze drying the solvent mixture, and addition of antisolvents (countersolvents) to the solvent mixture.

The forms may be characterized and distinguished using single crystal X-ray diffraction, which is based on unit cell and intensity measurements of a single crystal of a form at a fixed analytical temperature. A detailed description of unit cell and intensity analysis is provided in Stout & Jensen, X-Ray Structure Determination: A Practical Guide, Macmillan Co., New York (1968), Chapter 3, which is herein incorporated by reference. Alternatively, the unique arrangement of atoms in spatial relation within the crystalline lattice may be characterized according to the observed fractional atomic coordinates. See Stout & Jensen reference for experimental determination of fractional coordinates for structural analysis. Another means of characterizing the crystalline structure is by powder X-ray diffraction analysis in which the experimental or observed diffraction profile is compared to a simulated profile representing pure powder material, both at the same analytical temperature, and measurements for the subject form characterized as a series of $2\theta$ values and intensities.

The term "negligible weight loss," as employed herein, as characterized by TGA indicates the presence of a neat (non-solvated) crystal form.

The term "negligible % water uptake," as employed herein, as characterized by moisture-sorption isotherm indicates that the form tested is non-hygroscopic.

In one embodiment of the invention, a crystalline form of N-((1R,2S,5R)-5-(tert-butylamino)-2-((S)-2-oxo-3-(6-(trifluoromethyl)quinazolin-4-ylamino)pyrrolidin-1-yl)cyclohexyl)acetamide is provided in substantially pure form. This crystalline form may be employed in pharmaceutical compositions which may optionally include one or more other components selected, for example, from the group consisting of excipients, carriers, and one of other active pharmaceutical ingredients or active chemical entities of different molecular structures.

Preferably, the crystalline form has substantially pure phase homogeneity as indicated by less than 10%, preferably less than 5%, and more preferably less than 2% of the total peak area in the experimentally measured PXRD pattern arising from the extra peaks that are absent from the simulated PXRD pattern. Most preferred is a crystalline form having substantially pure phase homogeneity with less than 1% of the total peak area in the experimentally measured PXRD pattern arising from the extra peaks that are absent from the simulated PXRD pattern.

In another embodiment, a composition is provided consisting essentially of the crystalline forms of N-((1R,2S,5R)-5-(tert-butylamino)-2-((S)-2-oxo-3-(6-(trifluoromethyl)quinazolin-4-ylamino)pyrrolidin-1-yl)cyclohexyl) acetamide. The composition of this embodiment may comprise at least 90 weight % of the form, based on its weight in the composition.

The presence of reaction impurities and/or processing impurities may be determined by analytical techniques known in the art, such as, for example, chromatography, nuclear magnetic resonance spectroscopy, mass spectrometry or infrared spectroscopy.

Crystalline forms may be prepared by a variety of methods, including for example, crystallization or recrystallization from a suitable solvent, sublimation, growth from a melt, solid state transformation from another phase, crystallization from a supercritical fluid, and jet spraying. Techniques for crystallization or recrystallization of crystalline forms from a solvent mixture include, for example, evaporation of the solvent, decreasing the temperature of the solvent mixture, crystal seeding a supersaturated solvent mixture of the molecule and/or salt, freeze drying the solvent mixture, and addition of antisolvents (countersolvents) to the solvent mixture. High throughput crystallization techniques may be employed to prepare crystalline forms including polymorphs.

Crystals of drugs, including polymorphs, methods of preparation, and characterization of drug crystals are discussed in Solid-State Chemistry of Drugs, S. R. Byrn, R. R. Pfeiffer, and J. G. Stowell, 2nd Edition, SSCI, West Lafayette, Ind. (1999).

For crystallization techniques that employ solvent, the choice of solvent or solvents is typically dependent upon one or more factors, such as solubility of the compound, crystallization technique, and vapor pressure of the solvent. Combinations of solvents may be employed; for example, the compound may be solubilized into a first solvent to afford a solution, followed by the addition of an antisolvent to decrease the solubility of the compound in the solution and to afford the formation of crystals. An "antisolvent" is a solvent in which the compound has low solubility. Suitable solvents for preparing crystals include polar and nonpolar solvents.

In one method to prepare crystals, N-((1R,2S,5R)-5-(tert-butylamino)-2-((S)-2-oxo-3-(6-(trifluoromethyl)quinazolin-4-ylamino)pyrrolidin-1-yl)cyclohexyl)acetamide is suspended and/or stirred in a suitable solvent to afford a slurry, which may be heated to promote dissolution. The term "slurry," as used herein, means a saturated solution of the free base, which may also contain an additional amount of the compound to afford a heterogeneous mixture of the compound and a solvent at a given temperature. Suitable solvents in this regard include, for example, polar aprotic solvents and polar protic solvents, and mixtures of two or more of these, as disclosed herein.

Seed crystals may be added to any crystallization mixture to promote crystallization. As will be clear to the skilled artisan, seeding is used as a means of controlling growth of a particular crystalline form or as a means of controlling the particle size distribution of the crystalline product. Accordingly, calculation of the amount of seeds needed depends on the size of the seed available and the desired size of an average product particle as described, for example, in "Programmed cooling of batch crystallizers," J. W. Mullin and J. Nyvlt, *Chemical Engineering Science* 1971, 26, 369-377. In general, seeds of small size are needed to effectively control the growth of crystals in the batch. Seeds of small size may be generated by sieving, milling, or micronizing of larger crystals, or by micro-crystallization of solutions. Care should be taken that milling or micronizing of crystals does not result in any change in crystallinity from the desired crystal form (i.e., change to amorphous or to another polymorph).

A cooled mixture may be filtered under vacuum, and the isolated solids may be washed with a suitable solvent, such as cold recrystallization solvent, and dried under a nitrogen purge to afford the desired crystalline form. The isolated solids may be analyzed by a suitable spectroscopic or analytical technique, such as SSNMR, DSC, PXRD, or the like, to assure formation of the preferred crystalline form of the product. The resulting crystalline form is typically produced in an amount of greater than about 70 weight % isolated yield, but preferably greater than 90 weight % based on the weight of N-((1R,2S,5R)-5-(tert-butylamino)-2-((S)-2-oxo-3-(6-(trifluoromethyl)quinazolin-4-ylamino)pyrrolidin-1-yl)cyclohexyl)acetamide originally employed in the crystallization procedure. The product may be co-milled or passed through a mesh screen to de-lump the product, if necessary.

Crystalline forms may be prepared directly from the reaction medium of the final process step for preparing N-((1R,2S,5R)-5-(tert-butylamino)-2-((S)-2-oxo-3-(6-(trifluoromethyl)quinazolin-4-ylamino)pyrrolidin-1-yl)cyclohexyl) acetamide. This may be achieved, for example, by employing in the final process step a solvent or mixture of solvents from which the free base may be crystallized. Alternatively, crystalline forms may be obtained by distillation or solvent addition techniques. Suitable solvents for this purpose include any of those solvents described herein, including protic polar solvents, such as alcohols, and aprotic polar solvents, such as ketones.

By way of general guidance, the reaction mixture may be filtered to remove any undesired impurities, inorganic salts, and the like, followed by washing with reaction or crystallization solvent. The resulting solution may be concentrated to remove excess solvent or gaseous constituents. If distillation is employed, the ultimate amount of distillate collected may vary, depending on process factors including, for example, vessel size, stirring capability, and the like. By way of general guidance, the reaction solution may be distilled to about 1/10 the original volume before solvent replacement is carried out. The reaction may be sampled and assayed to determine the extent of the reaction and the wt % product in accordance with standard process techniques. If desired, additional reaction solvent may be added or removed to optimize reaction concentration. Preferably, the final concentration is adjusted to about 50 wt % at which point a slurry typically results.

It may be preferable to add solvents directly to the reaction vessel without distilling the reaction mixture. Preferred solvents for this purpose are those which may ultimately participate in the crystalline lattice, as discussed above in connection with solvent exchange. Although the final concentration may vary depending on desired purity, recovery and the like, the final concentration of the free base in solution is preferably about 4% to about 7%. The reaction mixture may be stirred following solvent addition and simultaneously warmed. By way of illustration, the reaction mixture may be stirred for about 1 hour while warming to about 70° C. The reaction is preferably filtered hot and washed with either the reaction solvent, the solvent added or a combination thereof. Seed crystals may be added to any crystallization solution to initiate crystallization.

The various fowls described herein may be distinguishable from one another through the use of various analytical techniques known to one of ordinary skill in the art. Such techniques include, but are not limited to, X-ray powder diffraction (PXRD) and/or thermogravimetric analysis (TGA). Specifically, the fowls may be characterized and distinguished using single crystal x-ray diffraction, which is based on unit cell measurements of a single crystal of a given form at a fixed analytical temperature. A detailed description of unit cells is provided in Stout & Jensen, X-Ray Structure Determination: A Practical Guide, Macmillan Co., New York (1968), Chapter 3, which is herein incorporated by reference. Alternatively, the unique arrangement of atoms in spatial relation within the crystalline lattice may be characterized according to the observed fractional atomic coordinates. Another means of characterizing the crystalline structure is by powder x-ray diffraction analysis in which the diffraction profile is compared to a simulated profile representing pure powder material, both run at the same analytical temperature, and measurements for the subject form characterized as a series of 2θ values (usually four or more).

Other means of characterizing the form may be used, such as solid state nuclear magnetic resonance (SSNMR) spectroscopy, differential scanning calorimetry (DSC), thermography and gross examination of the crystalline or amorphous morphology. These parameters may also be used in combination to characterize the subject form.

One of ordinary skill in the art will appreciate that an X-ray diffraction pattern may be obtained with a measurement error that is dependent upon the measurement conditions employed. In particular, it is generally known that intensities in a X-ray diffraction pattern may fluctuate depending upon measurement conditions employed and the shape or morphology of the crystal. It should be further understood that relative intensities may also vary depending upon experimental conditions and, accordingly, the exact order of intensity should not be taken into account. Additionally, a measurement error of diffraction angle for a conventional X-ray diffraction pattern is typically about 0.2° or less, preferably about 0.1° (as discussed hereinafter), and such degree of measurement error should be taken into account as pertaining to the aforementioned diffraction angles. Consequently, it is to be understood that the crystal forms of the instant invention are not limited to the crystal forms that provide X-ray diffraction patterns completely identical to the X-ray diffraction patterns depicted in the accompanying Figures disclosed herein. Any crystal forms that provide X-ray diffraction patterns substantially identical to those disclosed in the accompanying Figures fall within the scope of the present invention. The ability to ascertain substantial identities of X-ray diffraction patterns is within the purview of one of ordinary skill in the art.

Synthesis

Scheme 1
Hydrolysis of ketoester V to ketoacid VI

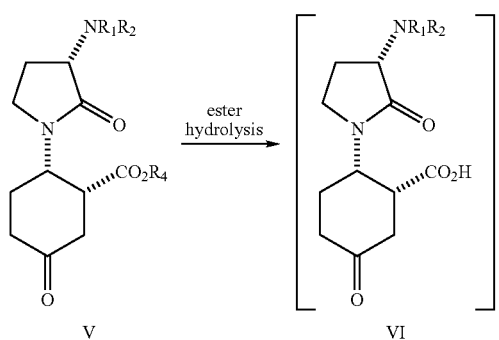

Ketoester V is hydrolyzed to its corresponding ketoacid VI by suspending V in an organic solvent partially miscible with water, such as acyclic or cyclic ethers including THF, 2-methyl THF, 1,2-dimethoxyethane, 1,4-dioxane, THF being preferred, and adding aqueous base such as aqueous solutions of alkali metal hydroxides MOH, where M is Li, Na or K, 1N NaOH being the preferred base, at −5° C. to +5° C. The biphasic mixture is then agitated at ≦5° C. for at least one hour. Low temperature for the base addition and reaction is important to minimize the epimerization at the carbon adjacent to the ester group. Water-nonmiscible solvent, preferably methyl tert-butyl ether is then added and the layers are separated. The product is then transferred from the aqueous back to the organic solvent, preferably dichloromethane, by adjusting the pH with acid, preferably 3N HCl, and VI is used in solution for the next step.

Scheme 2
Ketalization of ketoacid VI to ketal acid VII

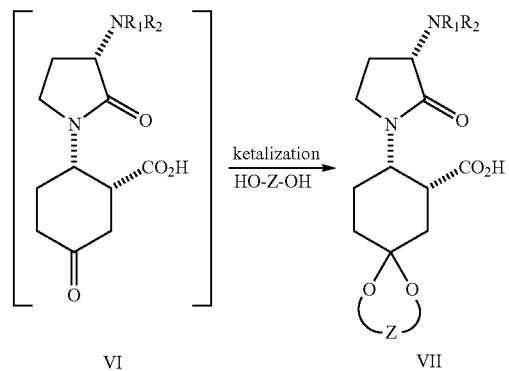

The solution of VI, preferably in dichloromethane, is exchanged via distillation into a non hygroscopic, higher boiling solvent, such as toluene, trifluorotoluene, xylenes, higher boiling esters such as n-butyl or isobutyl acetate, preferably toluene. A glycol of formula HO—Z—OH, (wherein Z is as defined supra) is then added, preferably ethylene glycol (1.2 eq), followed by a catalytic amount (0.5-2 M %) of an acid, preferably p-toulenesulfonic acid, and the mixture is distilled at atmospheric pressure until formation of compound VII is complete. The product VII crystallizes upon addition of ethyl acetate after cooling to approximately 70° C. After further cooling to room temperature, VII is isolated by filtration and subsequent drying in about 70% yield (for HO(CH$_2$)$_2$OH, R$_1$=H, R$_2$=CBz).

Scheme 3
Transformation of ketal acid VII to nonisolated ketal isocyanate VIII and then to ketal amide IX via acid activation/azidation, Curtius rearrangement and acylation

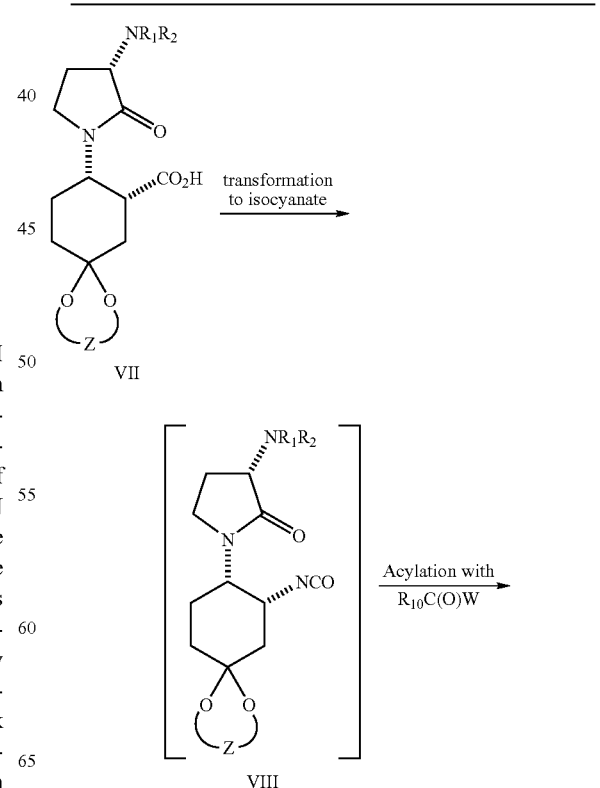

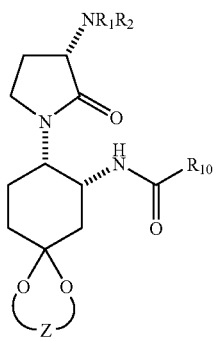

The ketoacid VII is first activated by transforming it to its mixed anhydride using tertiary amines, preferably triethylamine, and haloformates, preferably isobutyl chloroformate in dry solvents, such as toluene, trifluorotoluene, 1,2-dichloroethane, 1-chlorobutane, xylenes, preferably dry toluene, by addition of a haloformate to a precooled solution of VII and trialkylamine. The preferred temperature for mixed anhydride formation is −10° C. to 0° C. After approximately 30 min, an aqueous solution of alkali metal azide, preferably ~30 wt % sodium azide and a phase transfer catalyst, such as tetralkylammonium salts, preferably tetrabutylammonium bromide (5 mol %) is added and the biphasic mixture is vigorously agitated for about 1 h at −10° C. to 0° C. The organic phase is then separated and the resulting acyl azide solution is dried, 4 Å molecular sieves being preferred drying agent. The Curtius rearrangement and the concomitant trapping of the isocyanate VIII in situ with a carboxylic acid to form a ketal amide IX is accomplished by first adding a carboxylic acid, preferably acetic acid, and its corresponding anhydride, preferably acetic anhydride, to a dry solution of the acyl azide, and then heating the mixture 80-90° C. for 1-4 hours. The use of an anhydride in conjunction with carboxylic acid is critical to minimize impurity formation. After partial removal of the solvent and carboxylic acid by distillation, the product crystallizes upon cooling to room temperature. IX is isolated by filtration and drying in 65-78% yield (for Z=—(CH$_2$)$_2$—, R$_1$=H, R$_2$=CBz, R$_{10}$=Me).

Scheme 4
Hydrolysis of ketal amide IX to ketoamide X

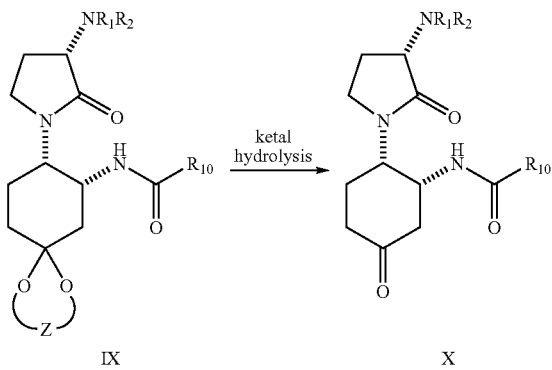

The ketal hydrolysis of compound IX to the ketoamide X is accomplished by heating a solution of IX in organic, water miscible solvent, preferably acetone and an aqueous solution of strong acid, preferably 1N HCl, for 2-4 hrs. The preferred temperature for hydrolysis is 45-55° C. After removal of acetone, the product is extracted to dichloromethane, which is exchanged to ethyl acetate by distillation. The product X crystallizes from ethyl acetate upon cooling to room temperature, and is isolated by filtration and drying in 85-90% yield (for HO(CH$_2$)$_2$OH, R$_1$=H, R$_2$=CBz, R$_{10}$=Me), Scheme 5
Reductive amination of ketoamide X to the aminoamide XI

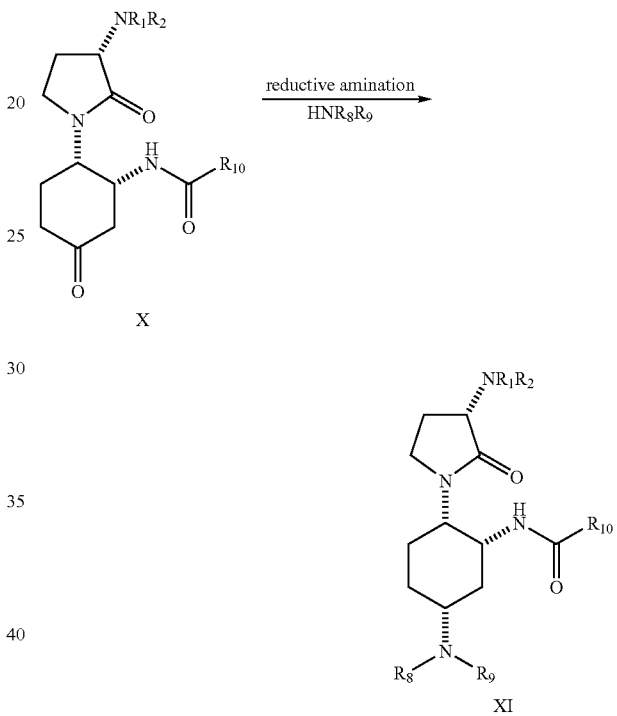

To a dry solution of X, preferably in dichloromethane, a primary or secondary amine is added, preferably tert-butylamine (5 eq), followed by a Lewis acid, preferably TiCl$_2$(OPr-i)$_2$ (1.2 eq), at −20° C. to 0° C. The resulting imine mixture is warmed to 10-20° C. and borane (1.1-1.2 eq) is added as a complex with dimethyl sulfide or THF, preferably dimethyl sulfide. The reaction mixture is agitated for 4-6 h and ethyl acetate saturated with water is then added. The titanium salts are removed by filtration and the product XI is extracted from the organic filtrate to water as its salt with an aqueous acid, preferably 1N HCl. Dichloromethane is then added and aqueous base, preferably concentrated ammonium hydroxide is added to the agitated biphasic mixture until pH is adjusted to 8.0-8.5. The product-rich dichloromethane phase is then separated and washed twice with aq ammonium chloride solution to remove the undesired trans isomer of XI, and finally with water. Dichloromethane is exchanged into ethyl acetate by distillation and XI crystallizes from ethyl acetate upon cooling and heptane addition. XI is isolated by filtration and drying in 65-70% yield (for R$_1$=H, R$_2$=CBz, R$_8$=H, R$_9$=tert-Bu, R$_{10}$=Me).

Scheme 6
Deprotection of pyrrolidonyl amine XI

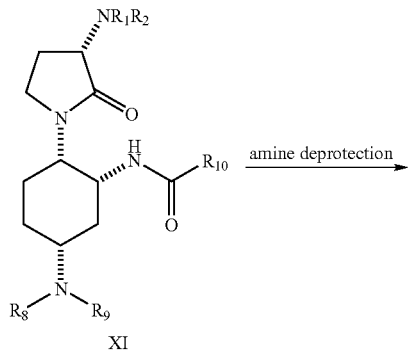

XI

Removal of the amine protecting group $R_2$, where $R_2$ is $CO_2CH_2Ph$ or $CH_2Ph$, is accomplished by hydrogenating a solution of XI in an alcohol, preferably methanol, in the presence of Pd catalyst, preferably 5 wt % Pd/C, for several hours. The catalyst is then removed by filtration, and methanol is exchanged into ethyl acetate by distillation. The product XII, which crystallizes from ethyl acetate upon cooling and heptane addition, is isolated by filtration and drying in 90-95% yield (for $R_1$=H, $R_2$=CBz, $R_8$=H, $R_9$=tert-Bu, $R_{10}$=Me).

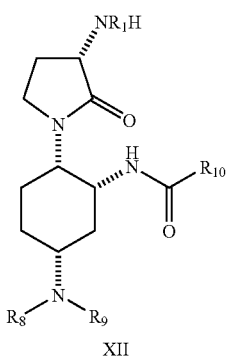

XII

Scheme 7
Coupling of amine XII with heterocycle bearing a leaving group HET-LG

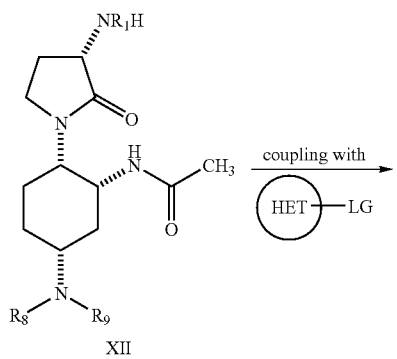

XII

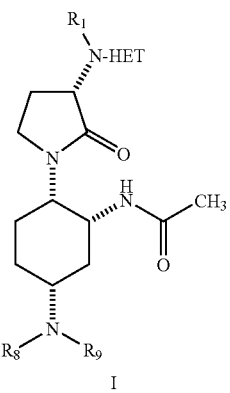

I

Synthesis of compound I is accomplished by coupling the pyrrolidonylamine XII and a heterocycle bearing a leaving group in the presence of a tertiary amine, preferably triethylamine, in a compatible solvent, such as dichloromethane, isopropanol or acetonitrile, dichloromethane being preferred. All components are therefore combined and the solution is reacted for 24-48 hrs at room temperature. A solution of previously prepared crude heterocyclic component may also be employed. After reaction completion, dichloromethane is washed with dilute acid, preferably aqueous 5 wt % acetic acid, the aqueous phase is separated and dichloromethane is then exchanged into ethyl acetate by distillation. The product I, which crystallizes from ethyl acetate upon cooling and heptane addition, is isolated by filtration and drying in 75-80% yield (for $R_1$=H, $R_8$=H, $R_9$=tert-Bu, HET=6-(trifluoromethyl)quinazolin-4-yl).

For the process of this invention, starting materials are commercially available or can be readily prepared by one or ordinary skill in the art. Solvents, temperatures, pressures, starting materials having the desired groups, and other reaction conditions, may be readily selected as appropriate by one of ordinary skill in the art. The process can be scaled up in order to prepare larger quantities of the compound of formula I, such as in a commercial production facility.

EXAMPLES

The following Examples illustrate embodiments of the inventive compounds and starting materials, and are not intended to limit the scope of the claims.

As appropriate, reactions were conducted under an atmosphere of dry nitrogen (or argon). For anhydrous reactions, Dri-Solv solvents from EM were employed. For other reactions, reagent grade or HPLC grade solvents were utilized. Unless otherwise stated, all commercially obtained reagents were used as received.

LC/MS measurements were obtained using a Shimadzu HPLC/Waters ZQ single quadropole mass spectrometer hybrid system. Data for the peak of interest are reported from positive-mode electrospray ionization. NMR (nuclear magnetic resonance) spectra were typically obtained on Bruker or JEOL 400 MHz and 500 MHz instruments in the indicated solvents. All chemical shifts are reported in ppm from tetramethylsilane with the solvent resonance as the internal standard. $^1$H-NMR spectral data are typically reported as follows: chemical shift, multiplicity (s=singlet, br s=broad singlet, d=doublet, dd=doublet of doublets, t=triplet, q=quartet, sep=septet, m=multiplet, app=apparent), coupling constants (Hz), and integration.

One of skill in the art will recognize the standard abbreviations utilized herein, throughout the specification. For ease of reference, the abbreviations include, but are not necessarily limited to: sat.=saturated, HPLC=high-performance liquid chromatography, AP=area percent, KF=Karl-Fischer, RT=room temperature, mmol=millimoles, HRMS=high-resolution mass spectroscopy, TBTU=O-benzotriazol-2-yl-N,N,N',N'-tetramethyluronium tetrafluoroborate, MTBE=TBME=tert-butyl methyl ether, EDAC=N-(3-dimethylaminopropyl)-N'-ethylcarbodiimide hydrochloride, EDC=N-(3-dimethylaminopropyl)-N'-ethylcarbodiimide, TEA=triethylamine, DPPA=diphenyl phosphoryl azide, IPA=isopropyl alcohol, TFA=trifluoroacetic acid, DCM=dichloromethane, THF=tetrahydrofuran, DMF=N,N-dimethylformamide, BOP=(benzotriazol-1-yloxy)tris(dimethylamino)phosphonium hexafluorophosphate, EtOAc=Ethyl acetate, DMSO=dimethylsulfoxide, ° C.=degrees Celsius, eq=equivalent or equivalents, g=grain or grams, mg=milligram or milligrams, mL (or ml)=milliliter or milliliters, h=hour or hours, M=molar, N=normal, min=minute or minutes, MHz=megahertz, tlc=thin layer chromatography, v/v=volume to volume ratio, and ca.=about.

"α", "β", "R" and "S" are stereochemical designations familiar to those skilled in the art.

Example 1

N-((1R,2S,5R)-5-(tert-butylamino)-2-((S)-2-oxo-3-(6-(trifluoromethyl)quinazolin-4-ylamino)pyrrolidin-1-yl)cyclohexyl)acetamide

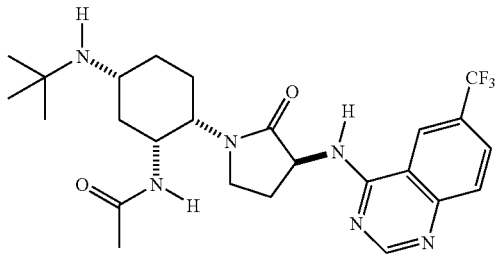

Example 1, Step 1

(1R,2S,5R)-tert-Butyl 2-benzyloxycarbonylamino-7-oxo-6-aza-bicyclo[3.2.1]octane-6-carboxylate (89.6 g, 0.24 mol, see: P. H. Carter, et al. PCT application WO 2005/021500) was dissolved in ethyl acetate (1.5 L) and the resulting solution was washed with sat. NaHCO$_3$ (2×0.45 L) and sat. NaCl (1×0.45 L). The solution was dried (Na$_2$SO$_4$) and then filtered directly into a 3-necked 3 L round-bottom flask. The solution was purged with direct nitrogen injection before being charged with 10% Pd/C (13.65 g) under nitrogen atmosphere. The flask was evacuated and back-filled with hydrogen; this was repeated twice more. Hydrogen was bubbled through the solution for 30 min and then the reaction was stirred under 1 atm H$_2$ for 18 h. The flask was evacuated, back-filled with nitrogen, and charged with fresh catalyst (6 g of 10% Pd/C). Hydrogen was bubbled through the solution for 30 min and then the reaction was stirred under 1 atm H$_2$ for 18 h. The flask was evacuated and back-filled with nitrogen. The mixture was filtered through Celite; the filter pad was then washed with ethyl acetate. The filtrate (~1.6 L EtOAc volume) was diluted with acetonitrile (0.3 L) and charged sequentially with L-N-Cbz-methionine (68 g, 0.24 mol), TBTU (77 g, 0.24 mol), and N,N-diisopropylethylamine (42 mL, 0.24 mol). The reaction was stirred at room temperature for 4 h, during which time it changed from a suspension to a clear solution. The reaction was quenched with the addition of sat. NH$_4$Cl (0.75 L) and water (0.15 L); the mixture was diluted further with EtOAc (0.75 L). The phases were mixed and separated and the organic phase was washed with sat. Na$_2$CO$_3$ (2×0.9 L) and sat. NaCl (1×0.75 L). The solution was dried (Na$_2$SO$_4$), filtered, and concentrated in vacuo to give (1R,2S,5R)-tert-butyl 2-(5)-2-(benzyloxycarbonylamino)-4-(methylthio)butanamido)-7-oxo-6-aza-bicyclo[3.2.1]octane-6-carboxylate as an oil, which was taken into the next step without further purification. LC/MS for primary peak: [M-Boca+H]$^+$=406.3; [M+Na]$^+$=528.3. $^1$H-NMR (400 MHz, d$_4$-MeOH): δ 7.36 (m, 5H), 5.11 (s, 2H), 4.32 (m, 1H), 4.2 (m, 1H), 4.0 (m, 1H), 2.5-2.7 (m, 3H), 2.25 (m, 1H), 2.11 (s, 3H), 2.05 (m, 4H), 1.9 (m, 1H), 1.7 (m, 2H), 1.54 (s, 9H). Also present are EtOAc [1.26 (t), 2.03 (s), 4.12 (q)] and N,N,N,N-tetramethylurea [2.83 (s)].

Example 1, Step 2

A sample of (1R,2S,5R)-tert-butyl 2-(S)-2-(benzyloxycarbonylamino)-4-(methylthio)butanamido)-7-oxo-6-aza-bicyclo[3.2.1]octane-6-carboxylate (0.24 mol assumed; see previous procedure) was dissolved in iodomethane (1,250 g) and stirred for 48 h at room temperature. The reaction was concentrated in vacuo. The residue was dissolved in dichloromethane and concentrated in vacuo. This was repeated twice more. The resultant sludge was dissolved in dichloromethane (0.4 L) and poured into a rapidly stirring solution of MTBE (4.0 L). The resultant yellow solids were collected via suction filtration and dried under high vacuum to afford the sulfonium salt (179 g). This material was taken into the next step without further purification. LC/MS for primary peak: [M-Me$_2$S+H]$^+$=458.4; [M]$^+$=520.4. $^1$H-NMR (400 MHz, d$_4$-MeOH): δ 7.35 (m, 5H), 5.09 (s, 2H), 4.33 (m, 1H), 4.28 (m, 1H), 3.98 (m, 1H), 3.3-3.45 (m, 2H), 2.97 (s, 3H), 2.94 (s, 3H), 2.78 (m, 1H), 2.0-2.3 (m, 4H), 1.7 (m, 2H), 1.52 (s, 9H). Also present are MTBE [1.18 (s), 3.2 (s)] and traces of N,N,N,N-tetramethylurea [2.81 (s)].

Example 1, Step 3

All of the sulfonium salt from the previous step (0.24 mol assumed) was dissolved in DMSO (2.0 L). The resultant solution was stirred under nitrogen at room temperature and charged with cesium carbonate (216 g) portionwise. The suspension was stirred at room temperature for 3 h and then filtered to remove the solids. The solution was divided into ~0.22 L portions and worked up as follows: the reaction mixture (~0.22 L) was diluted with ethyl acetate (1.5 L) and washed successively with water (3×0.5 L) and brine (1×0.3 L). The organic phase was dried (Na$_2$SO$_4$), filtered, and concentrated in vacuo. The desired (1R,2S,5R)-tert-butyl 2-((S)-3-(benzyloxycarbonylamino)-2-oxopyrrolidin-1-yl)-7-oxo-6-azabicyclo[3.2.1]octane-6-carboxylate (90.8 g, 83%) was obtained as a microcrystalline foam, free from tetramethyl urea impurity. LC/MS for primary peak: [M-Boc+H]$^+$=358.4; [M+Na]$^+$=480.4. $^1$H-NMR (400 MHz, d$_4$-MeOH): δ 7.35 (m, 5H), 5.12 (s, 2H), 4.35 (m, 2H), 4.2 (m, 1H), 3.6 (m, 1H), 3.3 (m, 1H), 2.64 (m, 1H), 2.28-2.42 (m, 2H), 2.15 (m, 1H), 1.7-2.0 (m, 5H), 1.55 (s, 9H). If desired, this material can be isolated as a solid by dissolving in MTBE (1 volume), adding to heptane (3.3 volumes), and collecting the resultant precipitate.

Example 1, Step 4

A stirring solution of (1R,2S,5R)-tert-butyl 2-((S)-3-(benzyloxycarbonylamino)-2-oxopyrrolidin-1-yl)-7-oxo-6-azabicyclo[3.2.1]octane-6-carboxylate (108 g, 0.236 mol) in THF (1 L) was charged with lithium hydroxide monohydrate (21.74 g, 0.519 mol). Water (0.3 L) was added slowly, such that the temperature did not exceed 20° C. The reaction was stirred at room temperature overnight and the volatiles were removed in vacuo. The pH was adjusted to ~4 through the addition of 1N HCl (450 mL) and $NaH_2PO_4$. The resultant white precipitates were collected by filtration and washed with water (2×1 L). The solid was dissolved in dichloromethane (1.5 L) and water (~1 L). The organic layer was dried ($Na_2SO_4$), filtered, and concentrated in vacuo. The residue was dissolved in EtOAc (0.7 L) and the resultant solution was heated at reflux for 1 h. Solids separated after cooling to RT, and were collected via filtration. These solids were purified by recrystallization in isopropanol to afford the desired (1R,2S,5R)-2-((S)-3-(benzyloxycarbonylamino)-2-oxopyrrolidin-1-yl)-5-(tert-butoxycarbonylamino)cyclohexanecarboxylic acid as a white solid (104.5 g, 93% yield). LC/MS for primary peak: $[M-tBu+H]^+=420.2$; $[M-Boc+H]^+=376.2$; $[M+H]^+=476.2$. $^1$H-NMR (400 MHz, $d_4$-MeOH): δ 7.35 (m, 5H), 5.11 (s, 2H), 4.35 (m, 2H), 3.71 (m, 1H), 3.45-3.6 (m, 2H), 2.99 (m, 1H), 2.41 (m, 1H), 2.15 (m, 1H), 2.0 (m, 2H), 1.6-1.9 (m, 4H), 1.46 (s, 9H).

Example 1, Step 5

A 3 L round bottom flask was charged with (1R,2S,5R)-2-((S)-3-(benzyloxycarbonylamino)-2-oxopyrrolidin-1-yl)-5-(tert-butoxycarbonylamino)cyclohexanecarboxylic acid (75.5 g, 0.158 mol), EDC*HCl (33.5 g, 0.175 mol), 1-hydroxybenzotriazole (23.6 g, 0.175 mol), and dichloromethane (1 L). The reaction was stirred at room temperature for 2 h, during which time it changed from a white suspension to a clear solution. Ammonia (gas) was bubbled into the solution until the pH was strongly basic (paper) and the reaction was stirred for 10 min; this ammonia addition was repeated and the reaction was stirred for an additional 10 min. Water was added. The organic phase was washed with sat. $NaHCO_3$, $NaH_2PO_4$, and brine before being concentrated in vacuo. The residue was slurried with acetonitrile (0.5 L) and then concentrated in to give (1R,2S,5R)-2-((S)-3-(benzyloxycarbonylamino)-2-oxopyrrolidin-1-yl)-5-(tert-butoxycarbonylamino)cyclohexanecarboxamide as a white solid (75.9 g, ~100%), which was used in the next step without further purification. LC/MS for primary peak: $[M-Boc+H]^+=375.3$; $[M±H]^+=475.4$; $[M-tBu+H]^+=419.3$. $^1$H-NMR (400 MHz, $d_4$-MeOH): δ 7.35 (m, 5H), 5.11 (s, 2H), 4.25 (m, 2H), 3.70 (m, 1H), 3.6 (m, 1H), 3.45 (m, 1H), 2.91 (m, 1H), 2.38 (m, 1H), 2.12 (m, 1H), 1.9-2.05 (m, 2H), 1.65-1.9 (m, 4H), 1.46 (s, 9H).

Example 1, Step 6

The reaction was run in three equal portions and combined for aqueous workup. A 5 L, 3-necked round bottom flask was charged with (1R,2S,5R)-2-((S)-3-(benzyloxycarbonylamino)-2-oxopyrrolidin-1-yl)-5-(tert-butoxycarbonylamino)cyclohexanecarboxamide (25.3 g, 53 mmol), acetonitrile (1.9 L), and 2.6 L of water/ice. The mixture was stirred and cooled to 0° C. Iodobenzene diacetate (25.77 g, 80 mmol) was added and the reaction was stirred for 2 h; another 0.5 eq of iodobenzene diacetate was added. The reaction was stirred for 9 h (reaction temp <10° C.). The mixture was charged with 8 eq N,N-diisopropylethylamine and 2 eq acetic anhydride. Over the next thirty minutes, 4 eq N,N-diisopropylethylamine and 2 eq acetic anhydride were added every ten minutes, until the reaction had proceeded to completion (HPLC). The acetonitrile was removed in vacuo; some solid separated from the residue, and this was collected by filtration. The remaining residue was extracted with dichloromethane (3 L, then 1 L). The organic phase was washed sequentially with water, sat. $NaHCO_3$, and brine. The collected solids were added to the organic phase, along with activated carbon (15 g). The mixture was stirred for 30 minutes at 40° C. before being filtered and concentrated in vacuo. The residue was dissolved in EtOAc (1 L), and the resultant solution was stirred at 75° C. for 1 h before being allowed to cool to room temperature. A solid separated and was collected by filtration. This solid was purified further by recrystallization: it was first dissolved in 0.5 L $CH_2Cl_2$, then concentrated in vacuo, then re-crystallized from 1 L EtOAc; this was repeated three times. The solids obtained from the mother liquors of the above were recrystallized three times using the same method. The combined solids were recrystallized twice more from acetonitrile (0.7 L) to provide 66 g (84%) of tert-butyl (1R,3R,4S)-3-acetamido-4-((S)-3-(benzyloxycarbonylamino)-2-oxopyrrolidin-1-yl)cyclohexylcarbamate (purity >99.5% by HPLC). LC/MS for primary peak: $[M+H]^+=489.4$; $[M-tBu+H]^+=433.3$. $^1$H-NMR (400 MHz, $d_4$-MeOH): δ 7.3-7.4 (m, 5H), 5.11 (s, 2H), 4.35 (m, 1H), 4.15 (m, 1H), 4.04 (m, 1H), 3.8 (m, 1H), 3.6 (m, 2H), 2.44 (m, 1H), 2.12 (m, 1H), 1.87-2.05 (m, 4H), 1.87 (s, 3H), 1.55-1.7 (m, 2H), 1.46 (s, 9H). The stereochemical fidelity of the Hofmann rearrangement was confirmed through X-ray crystal structure analysis of this compound, as shown in FIG. 1.

Example 1, Step 7

To a solution of tert-butyl (1R,3R,4S)-3-acetamido-4-((S)-3-(benzyloxycarbonylamino)-2-oxopyrrolidin-1-yl)cyclohexylcarbamate (100 g, 0.205 mol) in dichloromethane (400 ml) was added TFA (400 ml) at −20° C. The reaction solution was stirred at room temperature for 2 h. The solvent and most of TFA were removed under reduced pressure, and the residue was diluted with dichloromethane (2 L) and aqueous $K_2CO_3$ solution (2 L). The pH was adjusted to 10 with 1N HCl. The aqueous layer was extracted with dichloromethane (3×1 L). The combined organic layer was dried over $Na_2SO_4$, and concentrated to give benzyl (S)-1-((1S,2R,4R)-2-acetamido-4-aminocyclohexyl)-2-oxopyrrolidin-3-ylcarbamate as an oil (81 g, 100% yield). This amine was used directly in the next step without further purification.

Example 1, Step 8

A solution of benzyl (S)-1-((1S,2R,4R)-2-acetamido-4-aminocyclohexyl)-2-oxopyrrolidin-3-ylcarbamate (13.3 g, 34 mmol) and 3,5-di-tert-butylcyclohexa-3,5-diene-1,2-dione (7.54 g, 34 mmol) in methanol (160 ml) was stirred at room temperature for 2 h. The solution was concentrated and diluted with acetone (132 ml) and water (33 ml), followed by addition of Dowex-50WX8-200 (33 g). The reaction was stirred at room temperature for 2 h. Dowex-50WX8-200 was removed by filtration and washed with dichloromethane (300 ml). The filtrate was concentrated under vacuum to remove most of acetone. The residue was diluted with dichloromethane (200 ml) and washed with aqueous $NaHCO_3$ solution (200 ml) and brine (200 ml). The combined aqueous layers were extracted with dichloromethane (2×100 ml). The combined organic extracts were dried over $Na_2SO_4$ and concentrated. The product benzyl (S)-1-((1S,2R)-2-acetamido-4-oxocyclohexyl)-2-oxopyrrolidin-3-ylcarbamate was obtained as a solid (12 g, 90% yield) by crystallization in EtOAc (100 ml) and Hexane (200 ml). $^1$H-NMR (500 MHz, DMSO-$d_6$) δ ppm 7.99 (d, J=9.35 Hz, 1H), 7.44 (d, J=8.80 Hz, 1H), 7.28-7.39 (m, 5H), 5.03 (s, 2H), 4.50 (s, 1H), 4.31 (d, J=12.10 Hz, 1H), 4.18 (q, J=8.98 Hz, 1H), 3.27 (m, 2H), 2.82 (dd, J=15.12, 5.22 Hz, 1H), 2.52-2.65 (m, 1H), 2.40 (dd, J=12.92, 4.67 Hz, 1H), 2.15-2.31 (m, 2H), 2.09 (d, J=15.40 Hz, 1H), 1.90 (m, 1H), 1.81 (s, 3H), 1.68 (m, 1H). m/z: 388.46 [M+H].

Example 1, Step 9

To a solution of $TiCl_4$ (1M in dichloromethane, 36 ml, 36 mmol) in dichloromethane (30 ml) at 0° C. was added Ti(O-iPr)$_4$ (10.8 ml, 36 mmol). The mixture was then stirred at room temperature for 10 min. To a solution of benzyl (S)-1-((1S,2R)-2-acetamido-4-oxocyclohexyl)-2-oxopyrrolidin-3-ylcarbamate (23.25 g, 60 mmol) in dichloromethane (600 ml) was added tert-butylamine (30 ml, 300 mmol) at room temperature, followed by the addition of the TiCl$_4$/Ti(OiPr)$_4$ solution at −50° C. The reaction was allowed to warm slowly to room temperature. The reaction was finished after 2 h (The reaction was monitored on HPLC by quenching an HPLC sample with NaBH$_4$ in methanol). The solution was cooled to 10° C. and BH$_3$.SMe$_2$ (1M in dichloromethane, 66 ml, 66 mmol) was added. The mixture was stirred at room temperature for 5 h then quenched with Na$_2$CO$_3$ aqueous solution (300 ml). The precipitate was filtered off. The two layers were separated and the aqueous layer was extracted with dichloromethane (600 ml). The combined dichloromethane layers were extracted with 1N HCl twice (150 ml and 15 ml). (The product and the undesired trans isomer were both in the acidic aqueous phase.) The combined acidic aqueous layers were neutralized with 12 M aqueous solution of NH$_4$OH (12 ml) to pH~8 and extracted with dichloromethane twice (600 ml, 450 ml). (The product was in organic phase, while the trans isomer was still in aqueous layer.) The combined organic layers were washed with NH$_4$Cl aqueous solution 3 times (3×200 ml) until there was no trans isomer left in organic layer. The organic layer was dried over Na$_2$SO$_4$ and concentrated. The residue was purified by crystallization in EtOAc/Hexane(200 ml/800 ml) to give the desired benzyl (S)-1-((1S,2R,4R)-2-acetamido-4-(tert-butylamino)cyclohexyl)-2-oxopyrrolidin-3-ylcarbamate (20.80 g, 78% yield) as a white solid with 99.5% purity. $^1$H-NMR (500 MHz, DMSO-$d_6$) δ ppm 8.76 (s, 1H), 7.27-7.46 (m, 6H), 5.03 (m, 2H), 4.14 (m, 1 H), 4.07 (q, J=8.80 Hz, 1H), 3.83(m, 1H), 3.36 (m, 2H), 2.91 (s, 1H), 2.18 (m, 1H), 2.04 (m, 1H), 1.78 (s, 3H), 1.41-1.74 (m, 7H), 1.04 (s, 9H). m/z: 445.54 [M+H].

Example 1, Step 10

To a solution of benzyl (S)-1-((1S,2R,4R)-2-acetamido-4-(tert-butylamino)cyclohexyl)-2-oxopyrrolidin-3-ylcarbamate (43.3 g, 98 mmol) in methanol (400 ml), 10% wet Pd/C (4.34 g) was added. The mixture was evacuated and backfilled with hydrogen with a hydrogen balloon. The mixture was stirred at room temperature for 5 h. The mixture was filtered and washed with methanol (500 ml) and concentrated under vacuum to dryness. The crude product obtained was distilled with IPA (2×100 ml) under reduced pressure to give product N-((1R,2S,5R)-2-((S)-3-amino-2-oxopyrrolidin-1-yl)-5-(tert-butylamino)cyclohexyl)acetamide as an oil (30 g, 98% yield). This amine was used in the next step without further purification.

Example 1, Step 11

To a solution of N-((1R,2S,5R)-2-((S)-3-amino-2-oxopyrrolidin-1-yl)-5-(tert-butylamino)cyclohexyl)acetamide (30 g, 97 mmol) in IPA (400 ml) was added TEA (27 ml, 195 mmol) and 4-chloro-6-(trifluoromethyl)quinazoline (25 g, 107 mmol; see P. H. Carter, et al. PCT application WO 2005/021500). The mixture was stirred at room temperature overnight and then stirred at 70° C. for 1 h. The resulted solution was concentrated under reduced pressure to dryness. The residue was dissolved in dichloromethane (1 L) and extracted with acetic acid solution I (prepared by combining 700 mL of water and 22.6 mL of glacial acetic acid) twice (500 ml, 200 ml). The acidic aqueous layer (pH 4-5) was extracted with dichloromethane (2×300 ml). The dichloromethane layer was extracted with acetic acid solution II (300 ml; prepared by combining 300 mL water with 4 mL of glacial acetic acid). The combined acetic acid layers were basified with 1 M NaOH to pH>12 and extracted with dichloromethane (3×700 ml). The combined organic layers were dried and concentrated to give the crude product as a solid (45.6 g, 93% yield), The crude product was purified by recrystallization from EtOAc (400 ml)/Hexane (900 ml) to give 42.86 g (88%) N-((1R,2S,5R)-5-(tert-butylamino)-2-((S)-2-oxo-3-(6-(trifluoromethyl)quinazolin-4-ylamino)pyrrolidin-1-yl)cyclohexyl)acetamide with 99.7% purity. $^1$H-NMR (500 MHz, DMSO-$d_6$) δ ppm 9.71 (1H, br. s.), 9.02 (1H, s), 8.71 (1H, d, J=7.97 Hz), 8.59 (1H, s), 8.04 (1H, dd, J=8.66, 1.79 Hz), 7.88 (1H, d, J=8.52 Hz), 4.91-5.13 (1H, m), 4.30-4.57 (1H, m), 3.86(1H, dt, J=11.89, 3.71, 3.64 Hz), 3.43-3.57 (1H, m), 3.35-3.45 (1H, m), 3.04 (1H, t, J=3.85 Hz), 2.23-2.40 (1H, m), 2.05-2.22 (1H, m), 1.90-1.98 (1H, m), 1.86-1.93 (3H, m), 1.50-1.78 (5H, m), 0.98-1.15 (9H, m). $^{13}$C-NMR (126 MHz, DMSO-$d_6$) δ ppm 171.23, 169.35, 159.54, 156.87, 151.17, 128.97, 128.20, 125.76 (1C, q, J=30.52 Hz), 121.55 (1C, br. s.), 124.04 (1C, q, J=272.11 Hz), 114.31, 53.26, 52.39, 50.81, 47.56, 45.70, 42.77, 34.52, 32.17, 29.14 (3C, s), 26.49, 23.29, 20.30. $^{19}$F-NMR (471 MHz, DMSO-$d_6$) δ ppm −60.34 (s). m/z: 507.0 [M+H]. Anal. Calcd for $C_{25}H_{33}N_6O_2F_3$: C, 59.27; H, 6.56; N, 16.59; F, 11.25 Found: C, 59.44; H, 6.64; N, 16.74; F, 10.99.

ALTERNATIVE PREPARATION OF EXAMPLE 1

Example 1, Alternative Preparation, Step 1

An oven-dried 3-neck round-bottom flask was equipped with a dried stir bar, a dried reflux condenser, and two septa. After cooling under N$_2$, the flask was charged sequentially with (1R,2S,5R)-2-((S)-3-(benzyloxycarbonylamino)-2-oxopyrrolidin-1-yl)-5-(tert-butoxycarbonylamino)cyclohexanecarboxylic acid (60 g, 126 mmol; see Example 1, Step 4), acetonitrile (800 mL), N-methylmorpholine (273 mL, 252 mmol), and diphenylphosphoryl azide (29.9 mL, 139 mmol). The reaction was stirred at RT for 1 h 40 min, at which time 2-trimethylsilylethanol (90 mL, 631 mmol) was added. The reaction was set to heat, and reached reflux 30 min. later. It was allowed to reflux for 1 h, at which time it was allowed to cool to 50° C. gradually and then cooled to 15° C. with external cooling. The reaction was quenched with the addition of acetic acid (1.734 mL, 30.3 mmol). The reaction was concentrated in vacuo and then dissolved in EtOAc (1.2 L). It was washed sequentially with water (1×0.3 L), sat. NaHCO$_3$ (2×0.3 L), 1N HCl (1×0.3 L), and brine (2×0.3 L). The organic phase was dried (Na$_2$SO$_4$), filtered, and concentrated in vacuo. A solid appeared very early on in the concentration process. After the volatiles were removed, 800 mL 10%

EtOAc/Hexanes was added, and the mixture was stirred overnight. The solid was collected and dried to yield tent-butyl (1R,3R,4S)-4-((S)-3-benzyloxycarbonylamino-2-oxopyrrolidin-1-yl)-3-((2-trimethylsilyl)ethoxycarbonylamino)cyclohexylcarbamate (60.5 g, 102 mmol, 81% yield). HPLC showed that the material was 72% pure, with two 12% impurities. This material was taken into the next step without purification. The filtrate was later concentrated to yield another 4.38 g of product. Total yield=64.9 g (87%).

Example 1, Alternative Preparation, Step 2

A dry 500 mL round-bottom flask was equipped with a stir bar and charged sequentially with tert-butyl (1R,3R,4S)-4-((S)-3-benzyloxycarbonylamino-2-oxopyrrolidin-1-yl)-3-((2-trimethylsilyl)ethoxycarbonylamino)cyclohexylcarbamate (60.5 g), $CH_2Cl_2$ (180 mL), and a solution of para-toluenesulfonic acid monohydrate (19.48 g, 102 mmol) in $CH_2Cl_2$ (120 mL) and methanol (30 mL). The mixture was placed on a rotary evaporator and the bulk of the $CH_2Cl_2$ was removed (bath temp ca. 20° C.). When the mixture began to foam, the vacuum was released, and the bath temperature increased to 46° C. (the temperature varied between 44 and 51° C.; it was controlled with the addition of external ice). The mixture was rotated at this temperature for exactly one hour (gas evolution was visible throughout) and then diluted with EtOAc (1 L). The organic phase was washed with 0.5 N $NH_4OH$ (2×250 mL). The aqueous washes were combined and set aside. The organic phase was washed with sat. $NH_4Cl$ (1×250 mL) and sat. NaCl (1×250 mL); these aqueous washes were discarded. The initial combined $NH_4OH$ washes were back-extracted with EtOAc (1×250 mL), and that organic extract was washed with sat. $NH_4Cl$ (1×60 mL) and sat. NaCl (1×60 mL). All of the organic extracts were combined, dried ($Na_2SO_4$), filtered, and concentrated. The residue was purified by elution through a $SiO_2$ plug (13 cm wide×7.5 cm tall). The first eluant was pure EtOAc (ca. 4 L). The second eluant was 1:9 (10% $NH_4OH$ in MeOH)/$CH_2Cl_2$ (ca. 5 L). The fractions containing the desired product were pooled together and evaporated to afford the desired 2-(trimethylsilyl)ethyl (1R,2S,5R)-5-amino-2-((S)-3-benzyloxycarbonylamino-2-oxopyrrolidin-1-yl)cyclohexylcarbamate (31.6 g, 64.4 mmol, 63% yield).

Example 1, Alternative Preparation, Step 3

A stirring solution of 2-(trimethylsilyl)ethyl (1R,2S,5R)-5-amino-2-((S)-3-benzyloxycarbonylamino-2-oxopyrrolidin-1-yl)cyclohexylcarbamate (400 mg, 0.82 mmol) in acetonitrile (3 mL) was charged sequentially with diisopropylethylamine (315.8 mg, 3 eq) and bromoacetonitrile (109.5 mg, 1.1 eq). The mixture was stirred at 40° C. for 30 h. The solvent was removed under reduce pressure. The residue was purified by silica gel column chromatography, using 1.5% of methanol in dichloromethane as the eluant. The desired 2-(trimethylsilyl)ethyl(1R,2S,5R)-2-((S)-3-benzyloxycarbonylamino-2-oxopyrrolidin-1-yl)-5-(cyanomethylamino)cyclohexylcarbamate was obtained as a white solid (400 mg, 93%). LC/MS found $[M+H]^+$=530.

Example 1, Alternative Preparation, Step 4

A stirring solution of 2-(trimethylsilyl)ethyl(1R,2S,5R)-2-((S)-3-benzyloxycarbonylamino-2-oxopyrrolidin-1-yl)-5-(cyanomethylamino)cyclohexylcarbamate (400 mg, 0.76 mmol) in dichloromethane (5 mL), was cooled to 0° C. and charged with m-CPBA (372.6 mg, 2.2 eq) in portions. The mixture was stirred at room temperature for 1.5 h. Saturated $Na_2S_2O_3$ solution (3 mL) and saturated $NaHCO_3$ solution (3 mL) were added and the mixture was stirred at room temperature for 0.5 h. The mixture was diluted with dichloromethane (80 mL), washed with saturated $NaHCO_3$ (20 mL) and brine (20 mL). The solution was dried over anhydrous $Na_2SO_4$, filtered, and concentrated in vacuo. The residue obtained was dissolved in methanol (5 mL) and the solution was charged with $NH_2OH$—HCl (262.7 mg, 5 eq). The mixture was stirred at 60° C. for 2.5 h. After cooling to room temperature, the mixture was diluted with dichloromethane (80 mL) and filtered through a pad of celite. The filtrate was washed with saturated $NaHCO_3$ (2×20 mL). The aqueous washes were extracted with dichloromethane (30 mL). The dichloromethane layers were combined and washed with brine (30 mL). The solution was dried over anhydrous $Na_2SO_4$, filtered, and concentrated in vacuo to give 2-(trimethylsilyl)ethyl (1R,2S,5R)-2-((S)-3-benzyloxycarbonylamino-2-oxopyrrolidin-1-yl)-5-(hydroxyamino)cyclohexylcarbamate (350 mg, 91%). LC/MS found $[M+H]^+$=507.

Example 1, Alternative Preparation, Step 5

A solution of 2-(trimethylsilyl)ethyl (1R,2S,5R)-2-((S)-3-benzyloxycarbonylamino-2-oxopyrrolidin-1-yl)-5-(hydroxyamino)cyclohexylcarbamate (350 mg, 0.69 mmol) in acetone (5 mL) was stirred at room temperature for 16 h. The mixture was concentrated in vacuo. The residue was dissolved in anhydrous THF (7 mL) and cooled to 0° C. A solution of MeMgBr (1.1 mL, 3M in diethyl ether, 5 eq) was added dropwise. The mixture was stirred at room temperature for 1.5 h. The reaction was quenched with water (5 mL) at 0° C. The mixture was diluted with ethyl acetate (100 mL) and filtered through a pad of celite. The filtrate was washed with brine (30 mL). The solution was dried over anhydrous $MgSO_4$, filtered, and concentrated in vacuo. The residue was dissolved in 2 ml of acetonitrile and 1 ml of $CS_2$ was added. The mixture was stirred at room temperature for 1 hours. The solvent was removed and the crude product was purified by silica gel column chromatography, using 1.5% of methanol in dichloromethane as the eluant, to provide the desired 2-(trimethylsilyl)ethyl (1R,2S,5R)-2-((S)-3-benzyloxycarbonylamino-2-oxopyrrolidin-1-yl)-5-(tert-butylamino)cyclohexylcarbamate (160 mg, 42%). LC/MS found $[M+H]^+$=547.

Example 1, Alternative Preparation, Step 6

A stirring solution of 2-(trimethylsilyl)ethyl (1R,2S,5R)-2-((S)-3-benzyloxycarbonylamino-2-oxopyrrolidin-1-yl)-5-(tert-butylamino)cyclohexylcarbamate (100 mg, 0.183 mmol) in dichloromethane (3 mL) was charged with trifluoroacetic acid (2 mL). The reaction was stirred for 2 h at room temperature and concentrated in vacuo. The residue was dissolved in dichloromethane (50 mL) and washed with saturated $NaHCO_3$ (20 mL). The aqueous layer was extracted with dichloromethane (3×30 mL). The dichloromethane layers were combined and dried over anhydrous $Na_2SO_4$, filtered, and concentrated in vacuo to give benzyl (S)-1-((1S,2R,4R)-2-amino-4-(tert-butylamino)cyclohexyl)-2-oxopyrrolidin-3-ylcarbamate (66 mg, 90%). LC/MS found [M+H]=403.

Example 1, Alternative Preparation, Step 7

A solution of benzyl (S)-1-((1S,2R,4R)-2-amino-4-(tert-butylamino)cyclohexyl)-2-oxopyrrolidin-3-ylcarbamate (22 mg, 0.055 mmol) in dichloromethane (2 mL) was charged sequentially with triethylamine (11.1 mg, 2 eq) and acetic anhydride (6.1 mg, 1.1 eq). The reaction was stirred for 1.5 h at room temperature, diluted with dichloromethane (50 mL) and washed with saturated NaHCO$_3$ (20 mL). The organic phase was dried over anhydrous Na$_2$SO$_4$, filtered, and concentrated in vacuo to give benzyl (S)-1-((1S,2R,4R)-2-acetamido-4-(tert-butylamino)cyclohexyl)-2-oxopyrrolidin-3-yl-carbamate (22 mg, 90%). LC/MS found [M+H]=445.

Example 1, Alternative Preparation, Step 8

To a solution of benzyl (S)-1-((1S,2R,4R)-2-acetamido-4-(tert-butylamino)cyclohexyl)-2-oxopyrrolidin-3-ylcarbamate (22 mg, 0.05 mmol) in methanol (2 mL) was added Pd(OH)$_2$ (20 mg of 50% wet catalyst). The flask was evacuated and back-filled with hydrogen from a hydrogen balloon. The mixture was stirred at room temperature for 1 h and the catalyst was removed by filtration. The filtrate was concentrated in vacuo to provide N-((1R,2S,5R)-2-((S)-3-amino-2-oxopyrrolidin-1-yl)-5-(tert-butylamino)cyclohexyl)acetamide (13 mg, 85%). LC/MS found [M+H]$^+$=311.

Example 1, Alternative Preparation, Step 9

To a solution of N-((1R,2S,5R)-2-((S)-3-amino-2-oxopyrrolidin-1-yl)-5-(tert-butylamino)cyclohexyl)acetamide (70 mg, 0.225 mmol) in isopropanol (3 mL) was added 4-chloro-6-(trifluoromethyl)quinazoline (63 mg, 1.2 eq) and triethylamine (56.9 mg, 2.5 eq). The mixture was stirred at room temperature for 1.5 h. The solvent was removed under reduced pressure. The residue was purified with preparative HPLC to provide the title compound as its bis-TFA salt (110 mg, 67%). LC/MS found [M+H]$^+$=507.

2$^{ND}$ ALTERNATIVE PREPARATION OF EXAMPLE 1

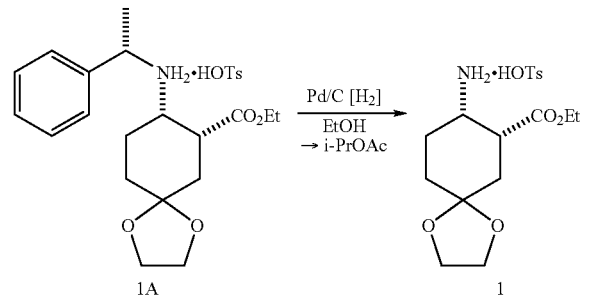

Example 1, 2$^{nd}$ Alternative Preparation, Step 1a

To a hydrogenator were charged ethyl (7R,8S)-8-((S)-1-phenyl-ethylamino)-1,4-dioxa-spiro[4.5]decane-7-carboxylate 4-toluenesulfonate salt 1A (1417 g, 2.8 moles, c.f: WO2004098516, prepared analogous to U.S. Pat. No. 6,835,841), ethanol (200 proof, 11.4 L), and 10% Pd/C catalyst (50% wet, 284 g). The mixture was inerted with nitrogen, then pressurized with hydrogen gas (45 psig) and agitated vigorously at approx. 40° C. until starting material was consumed (HPLC). The suspension was cooled, purged with nitrogen gas and the catalyst was removed by filtration while inerted. The spent catalyst was washed with ethanol (4.3 L). The filtrate and washings were combined and concentrated under vacuum to a volume of 2-3 L while maintaining the batch between 40°-60° C. Isopropyl acetate (5 L) was charged and the mixture was concentrated to a volume of ~2 L until most ethanol was removed (<0.5%) and residual moisture content was <1,000 ppm. Batch volume was adjusted to ~7.5 L by the addition of isopropyl acetate. The mixture was heated to 80° C. until clear, then cooled 65°-70° C. Seed crystals of 1 (5 g) were added and the batch was cooled to 50° C. over 2 hours, then further cooled to 20° C. over 4 hours and held for ~10 hours. The resulting slurry was filtered and the cake was washed with isopropyl acetate (2 L). The product was dried under vaccum at ~35° C. until volatiles were reduced below ~1% (LOD). Ethyl (7R,8S)-8-amino-1,4-dioxa-spiro[4.5]decane-7-carboxylate 4-toluenesulfonate salt 1 was obtained as a white, crystalline solid (936 g, 83% yield; HPLC purity: 99.8%). $^1$H-NMR: (300 MHz, CDCl$_3$) 8.14-7.89 (brs, 3H), 7.75 (d, J 9.0 Hz, 2H), 7.15 (d, J 8.0 Hz, 2H), 4.22-4.04 (m, 2H), 4.01-3.77 (m, 4H), 3.55-3.43 (m, 1H,), 3.20-3.13 (m, 1H), 2.40-2.27 (m, 4H), 2.21-1.94 (m, 2H), 1.81-1.51 (m, 3H), 1.23 (t, J 7.0 Hz, 3H); HPLC: Waters Xterra MS C18 4.6 mm×150 mm i.d., 3.5 μm particle size, 0.05% NH4OH (5% ACN, 95% H$_2$O, solvent A), to 0.05% NH$_4$OH (95% ACN, 5% H$_2$O, solvent B), 5% B to 20% B in 10 minutes, changed to 95% B in 25 minutes, and then changed to 5% B in 1 minute; 11.1 minutes (aminoester 1).

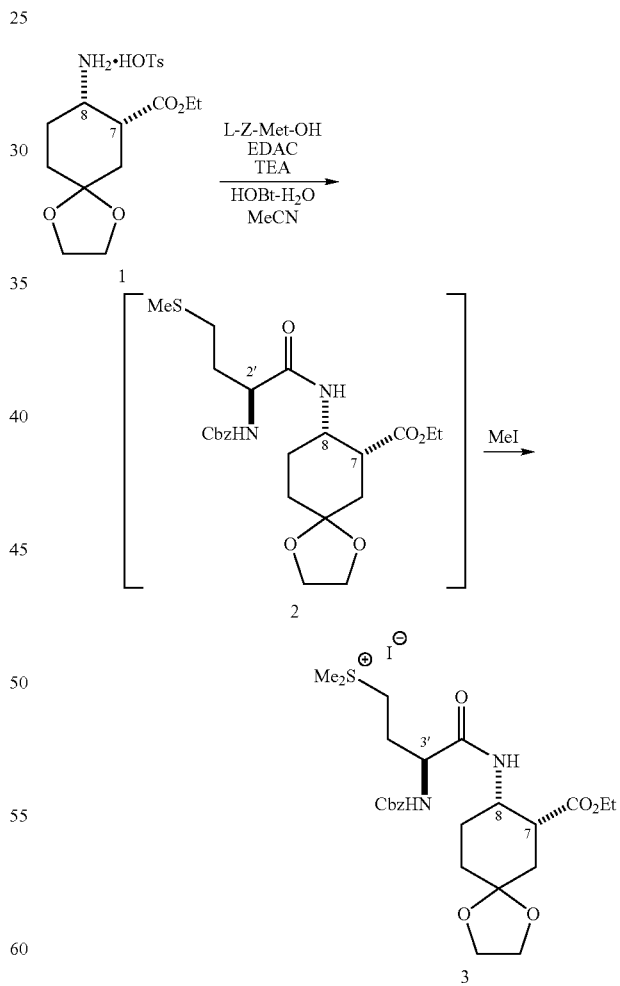

Example 1, 2$^{nd}$ Alternative Preparation, Step 1b

Ethyl (7R,8S)-8-amino-1,4-dioxa-spiro[4.5]decane-7-carboxylate 4-toluenesulfonate salt 1 (450.1 g; the product of reductive deprotection of a known compound—see R. J. Chemey, WO 2004/098516 and G. V. Delucca & S. S. Ko, WO 2004/110993), was combined with 1-ethyl-3-(3-dimethyl-amino-propyl)carbo-diimide hydrochloride (236.3 g), 1-hydroxy benzotriazole hydrate (171.9 g), N-carbobenzyloxy-L-methionine (333.4 g) and acetonitrile (3.1 L). To the stirred mixture was added triethylamine (249.5 g) below 30° C. Upon reaction completion (HPLC), the mixture was diluted with ethyl acetate (8.2 L) and washed with aqueous 25% potassium bicarbonate solution (2×4.5 L) followed by water (4.5 L). The organic phase was separated and concentrated under reduced pressure to obtain a solution of ethyl (7R,8S)-8-((S)-2-benzyloxycarbonylamino-4-methylsulfanyl-butyrylamino)-1,4-dioxa-spiro[4.5]decane-7-carboxylate 2 (1.4 L). Methyl iodide (2.39 kg) was added, the vessel was shielded from light and the mixture was held under slow agitation for approx. 24 h. To the thick yellow precipitate was added methyl tert-butyl ether (2.7 L) and the mixture was held for approx. 1 h. The product was isolated by filtration and the cake was washed with methyl tert-butyl ether (2×1.4 L), then dried under vacuum, yielding [(S)-3-benzyloxy-carbonylamino-3-(7R,8S)-7-ethoxycarbonyl-1,4-dioxa-spiro[4.5]dec-8-ylcarbamoyl)-propyl]-dimethylsulfonium iodide 3 (671.4 g, ~94% yield) as an off-white solid (HPLC purity 99.9%).

nylamino-2-oxo-pyrrolidin-1-yl)-1,4-dioxa-spiro[4.5]decane-7-carboxylate 4 in ethyl acetate (~0.8 L). Acetone (2.55 L) was added, followed by aqueous 0.5 M hydrochloric acid solution (2.3 L). With good mixing, the solution was heated to 50 to 60° C. until conversion of 4 to ethyl (1R,2S)-2-((S)-3-benzyloxycarbonylamino-2-oxo-pyrrolidin-1-yl)-5-oxo-cyclohexanecarboxylate 5 was complete (HPLC). The mixture was concentrated under reduced pressure while below 40° C., cooled to ~30° C., and water (4.1 L) was added. The resulting slurry was cooled to 5 to 10° C. and agitated for ~1 hour. The product was filtered and the cake was washed with water (2×2.5 L). Upon deliquoring, the cake was dried to a constant weight below 40° C. in a vacuum oven. Cyclohexanone 5 (272 g, 70% yield) was obtained (HPLC purity 98.7%).

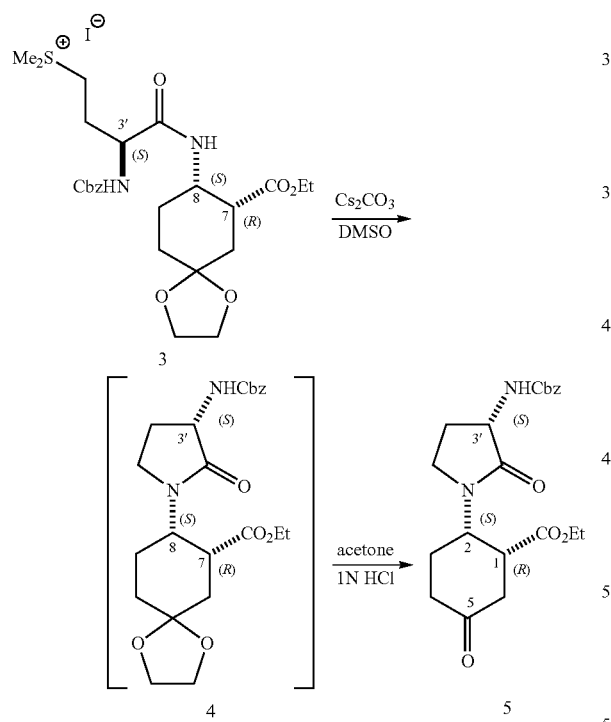

Example 1, 2$^{nd}$ Alternative Preparation, Step 2

Sulfonium salt 3 (619.4 g), and cesium carbonate (416.8 g) and anhydrous dimethyl sulfoxide (6.2 L) were combined in a reactor equipped with a scrubber to neutralize volatile sulfides. Vigorous agitation was maintained until complete conversion was obtained (HPLC). Ethyl acetate (12.4 L) was added, followed by 20% brine (3 L). The organic phase was separated, washed twice with brine (2×3 L) and evaporated to obtain a solution of ethyl (7R,8S)-8-((S)-3-benzyloxycarbo-

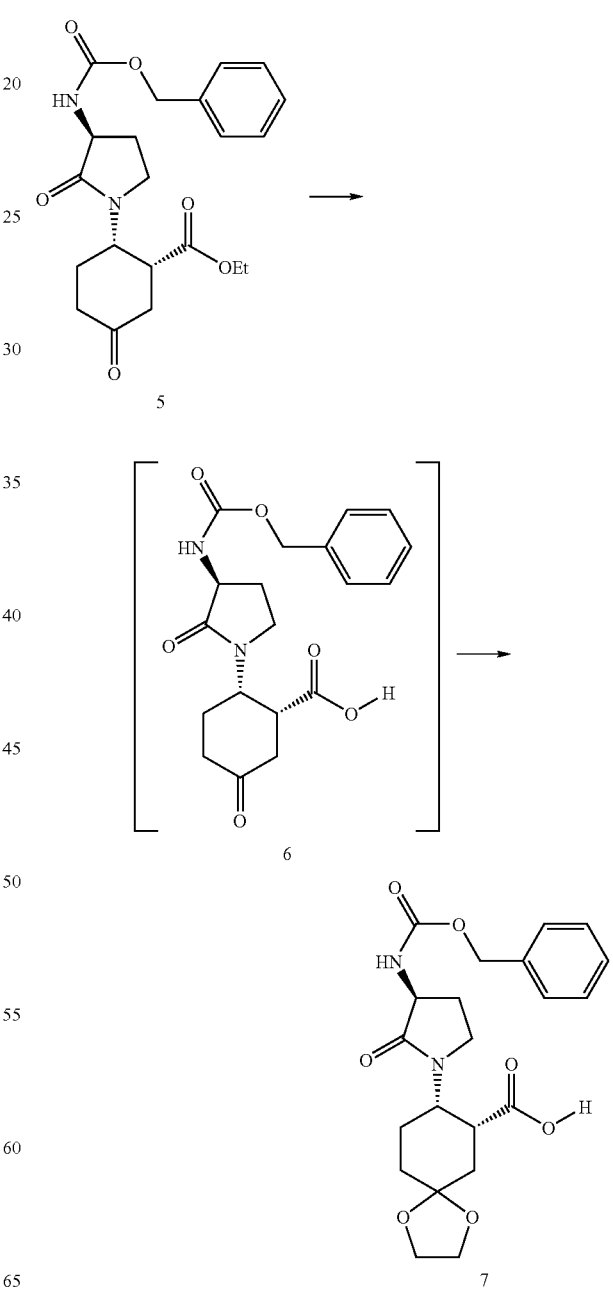

Example 1, 2nd Alternative Preparation, Step 3

Cyclohexanone 5 (100 g) was suspended in THF (500 mL) and cooled to 0° C. 1N NaOH (271 g) was added at 0-5° C. and the biphasic mixture was agitated at ≦5° C. for at least one hour. MTBE (500 mL) was added and the layers were separated. The bottom aqueous layer was washed again with MTBE (500 mL) and the layers were separated. Dichloromethane (500 mL) was charged to the product-rich aqueous layer, and the mixture was cooled to 0° C. 3N HCl (156 g) was charged maintaining ≦5° C. After stirring for at least 10 min, the mixture was warmed to 20-25° C., and the layers were separated. The aqueous layer was extracted with dichloromethane (100 mL). The organic layers were combined and solvent was exchanged into toluene via distillation. The toluene solution volume was adjusted to approximately 1L, and p-toluenesulfonic acid monohydrate (0.24 g) was added. Ethylene glycol (16.22 g) was added, and the mixture was distilled at atmospheric pressure until formation of compound 7 was complete and the pot volume was approximately 500-700 mL. The solution was cooled to approximately 70° C., and ethyl acetate (500 mL) was added maintaining approximately 70° C. The mixture was cooled and filtered to give 73 g (70% yield) of compound 7, (7R,8S)-8-((3S)-3-(((benzyloxy)carbonyl)amino)-2-oxo-1-pyrrolidinyl)-1,4-dioxaspiro[4.5]decane-7-carboxylic acid.

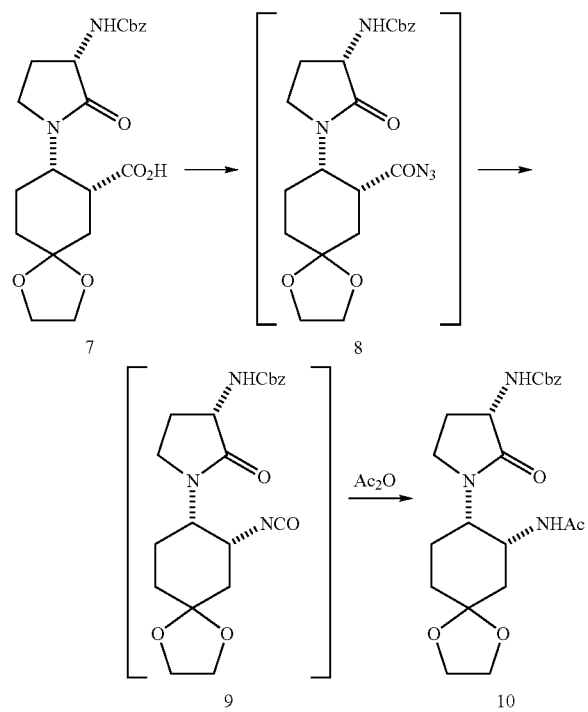

Example 1, 2nd Alternative Preparation, Step 4

To a slurry of compound 7 (147 g) in dry toluene (370 mL) was charged triethylamine (32.7 g) at 15-25° C. After the slurry became a solution after 10-15 min stirring at 25° C., the flask was cooled to −10° C. and isobutyl chloroformate (44.1 g) was charged at −10°-0° C. The mixture was agitated at −10°-0° C. for about 30 min. A solution of sodium azide (42 g) and tetrabutylammonium bromide (5.2 g) in water (130 mL) was added at −10°-0° C. The biphasic slurry was vigorously agitated for at least one hour and toluene (1750 mL) followed by water (300 mL) were added. The two phases were stirred for at least 10 min and the top organic layer was separated and dried with 4 Å molecular sieves. Acetic anhydride (76 mL) and acetic acid (28 mL) were added and the solution was heated to 80-90° C. for 1-4 hours, until <2 AP of intermediate 9 was detected by HPLC. The solvent was partially distilled off to approximately two thirds of the initial volume under atmospheric pressure, the solution was cooled to ambient temperature and the resultant slurry was stirred for 16 hours. Heptane (350 mL) was slowly added and the slurry was stirred for 1 h. The solids were filtered, washed with toluene/heptane 4:1 (300 mL), and dried to give 109 g (78% yield) of compound 10, benzyl ((3S)-1-((7R,8S)-7-acetamido-1,4-dioxaspiro[4.5]dec-8-yl)-2-oxo-3-pyrrolidinyl)carbamate.

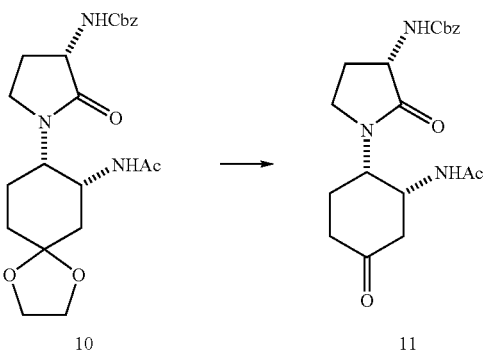

Example 1, 2nd Alternative Preparation, Step 5

To a solution of compound 10 (109 g) in acetone (760 mL) was charged 1N HCl (760 mL). The mixture was heated to 50° C. for 2.5 hours. The acetone was distilled off under reduced pressure and the product was extracted with dichloromethane twice 1×1 L and 1×0.5 L. Dichloromethane layers were combined and dichloromethane was exchanged into ethyl acetate by distillation until the b.p. on the kettle reached 78° C. and the final volume was approximately 10 mL/g compound 10 input. The ethyl acetate slurry was cooled to ambient temperature, agitated for 16 hrs and the solids were filtered and washed with ethyl acetate (400 mL). The solid was dried to give 84 g (87% yield) of compound 11, benzyl ((3S)-1-((1S,2R)-2-acetamido-4-oxocyclohexyl)-2-oxo-3-pyrrolidinyl)carbamate.

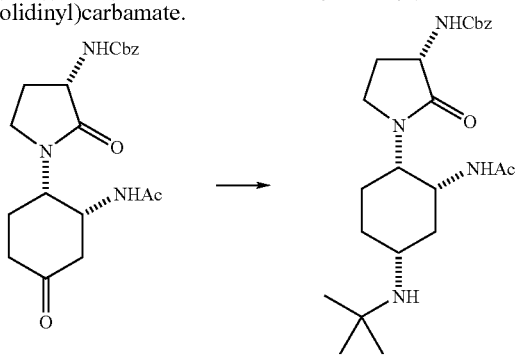

Example 1, 2nd Alternative Preparation, Step 6

The TiCl$_2$(OPr$^i$)$_2$ reagent was pre-formed by adding Ti(O$^i$Pr)$_4$ (11.5 mL) to a solution of 1M TiCl$_4$ in dichloromethane (39 mL) at 5-10° C. and subsequent stirring at ambient temperature for 15 min. Compound 11 (25 g) was dissolved in dichloromethane (500 mL) and t-butylamine (34 mL) was added at room temperature. After 10 min the solution was cooled to −25 to −20° C. and the preformed titanium reagent solution was added at a temperature below −20° C. The mixture was allowed to warm to ambient temperature and it was agitated for 1 h. A sample was taken to confirm the complete imine formation by miniquench with sodium borohydride in methanol (absence of alcohols indicated the complete consumption of the starting ketone 11). Borane dimethyl sulfide (7.0 mL) was then added at 0-5° C. and the reaction mixture was warmed to ambient temperature and stirred for at least 5 hours. Dichloromethane was partially (about half) evaporated under reduced pressure and wet ethyl acetate (300 mL, preformed by agitating ethyl acetate with water) was added within 30-60 min. The resulting slurry was agitated for at least 4 h, the solids were filtered and washed several times with dichloromethane until no more than 5 M % of the product was retained in the cake. The filtrate and washes were combined, 1 N HCl (200 mL) was added and the biphasic mixture was agitated for at least 30 min (gas evolution ceased after ~20 min). The product rich aqueous layer (upper phase) was separated and dichloromethane (500 mL) was added. Concentrated ammonium hydroxide was added to the agitated biphasic mixture until pH was adjusted to 8-8.5 (~15 mL). The organic phase was separated and washed 2×100 mL with 14 wt % ammonium chloride, to remove the undesired trans isomer of compound 12, and finally with water (25 mL). Dichloromethane was exchanged into ethyl acetate by distillation under normal pressure until the b.p. on the kettle reached 78° C. and the final volume was approximately 5 mL/g compound 11 input (~140 mL). The solution was cooled to ambient temperature. Heptane (250 mL) was added slowly at 40-50° C. and compound 12 started to crystallize. The slurry was agitated at room temperature for 3 hrs and the solids were filtered, washed with heptane (100 mL) and dried to give 20.1 g (70% yield) of compound 12, benzyl ((3S)-1-((1S,2R,4R)-2-acetamido-4-(tert-butylamino)cyclohexyl)-2-oxo-3-pyrrolidinyl)carbamate, as white, fluffy crystals.

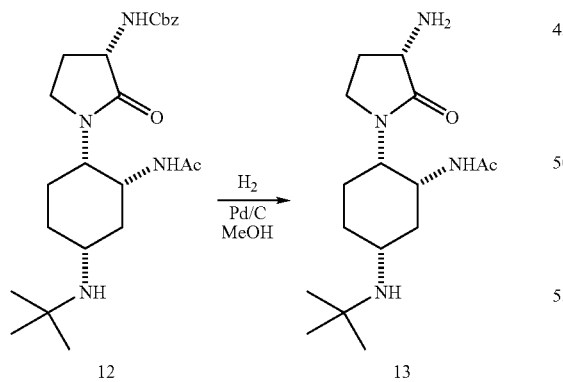

Example 1, 2$^{nd}$ Alternative Preparation, Step 7

Compound 12 (20 g) was dissolved in methanol (400 mL) and 5% Pd/C catalyst (1.8 g, 9 wt %) was added. The mixture was hydrogenated at 25° C. and 25 psig for 3 h. The catalyst was removed by filtration, and the methanol was exchanged into ethyl acetate by continuous distillation. The product crystallized from ethyl acetate (160 mL) upon cooling. Heptane (160 mL) was added at 25° C., the slurry was agitated for 1 h and the product was filtered, washed with heptane and dried to give 12.8 g (94% yield) of compound 13, N-((1R,2S,5R)-2-((3S)-3-amino-2-oxo-1-pyrrolidinyl)-5-(tert-butylamino)cyclohexyl)acetamide.

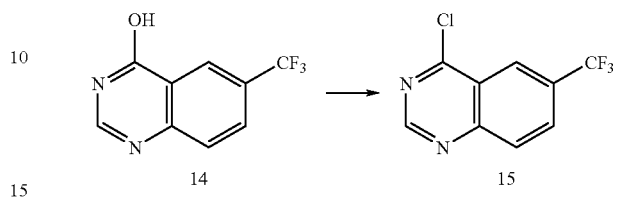

Example 1, 2$^{nd}$ Alternative Preparation, Step 8

6-(trifluoromethyl)-4-quinazolinol, 14 (5 g; see P. H. Carter, et al. PCT application WO 2005/021500) was suspended in dichloromethane (100 mL). N,N-diisopropylethylamine (4.2 mL, 1.05 eq) and DMF (0.4 mL, 0.2 eq) were added. Oxalyl chloride (3.0 mL, 1.5 eq) was then added to the agitated slurry at 20-25° C. under cooling (exothermic addition). The orange slurry was agitated at 30-35° C. for 2 h. Steady gas evolution was observed for ~1.5 hrs at which point the slurry became an orange solution. After cooling to 20° C., the reaction solution was added dropwise to 20 wt % aq K$_2$HPO$_4$ (50 mL) under vigorous agitation and gas evolution. The lower organic phase was separated and washed one more time with 20 wt % aq K$_2$HPO$_4$ (50 mL). The organic solution was used as is for the next step within 16 h.

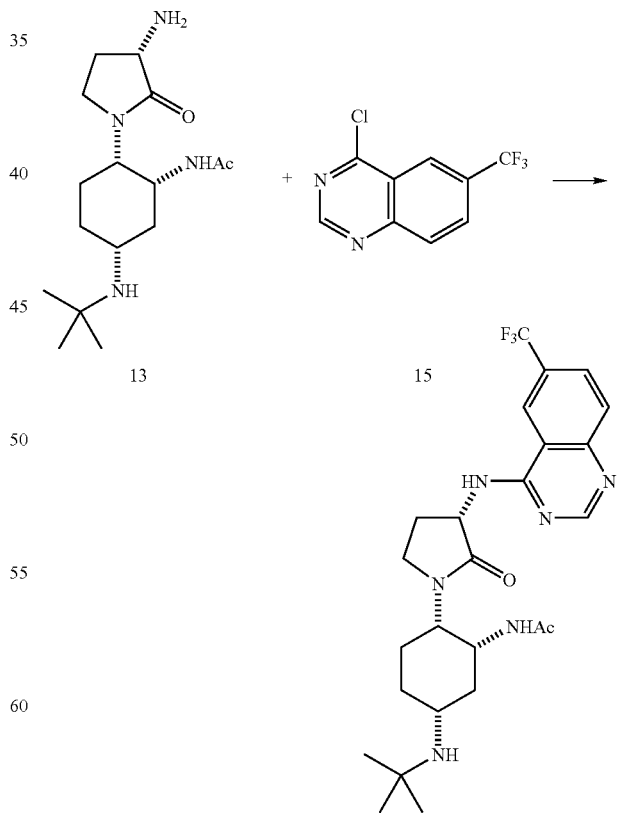

Example 1

Example 1, 2$^{nd}$ Alternative Preparation, Step 8

To a solution of 15 in dichloromethane (22 mL, 5.5 mmol), solid 13 (1.55 g, 5 mmol) was added and the mixture was agitated at room temperature until the solids dissolved. Triethylamine (1.4 mL, 11 mmol) was added and the mixture was agitated for 24 hrs at ambient temperature. Water (10 mL) was added, the two phases were agitated for 10 min and the organic phase was separated. Dichloromethane was exchanged into ethyl acetate by continuous distillation until the b.p. on the kettle reached 78° C. and the final volume was approximately 10 mL/g compound 13 input (~15 mL). The slurry was cooled to ambient temperature, heptane (15 mL) was slowly added and the slurry was agitated for 16 h. The solids were filtered, washed with heptane/ethyl acetate 1:1 (5 mL) and dried to give 1.83 g (72% yield) of beige crystals (form N-2 by XRD) of N-((1R,2S,5R)-5-(tert-butylamino)-2-((S)-2-oxo-3-(6-(trifluoromethyl)quinazolin-4-ylamino)pyrrolidin-1-yl)cyclohexyl)acetamide, Example 1.

Example 2

Crystal Forms of N-((1R,2S,5R)-5-(tert-butylamino)-2-((S)-2-oxo-3-(6-(trifluoromethyl)quinazolin-4-ylamino)pyrrolidin-1-yl)cyclohexyl)acetamide Various crystal forms of N-((1R,2S,5R)-5-(tert-butylamino)-2-((S)-2-oxo-3-(6-(trifluoromethyl)quinazolin-4-ylamino)pyrrolidin-1-yl)cyclohexyl)acetamide, free base were prepared and characterized as described below.

PROCEDURES FOR CHARACTERIZING THE FORMS

Single Crystal Data

Data were collected on a Bruker-Nonius (BRUKER AXS, Inc., 5465 East Cheryl Parkway Madison, Wis. 53711 USA) CAD4 serial diffractometer. Unit cell parameters were obtained through least-squares analysis of the experimental diffractometer settings of 25 high-angle reflections. Intensities were measured using Cu Kα radiation (λ=1.5418 Å) at a constant temperature with the θ-2θ variable scan technique and were corrected only for Lorentz-polarization factors. Background counts were collected at the extremes of the scan for half of the time of the scan. Alternately, single crystal data were collected on a Bruker-Nonius Kappa CCD 2000 system using Cu Kα radiation (λ=1.5418 Å). Indexing and processing of the measured intensity data were carried out with the HKL2000 software package (Otwinowski, Z. & Minor, W. (1997) in *Macromolecular Crystallography*, eds. Carter, W. C. Jr & Sweet, R. M. (Academic, NY), Vol. 276, pp. 307-326) in the Collect program suite. (Collect Data collection and processing user interface: Collect: Data collection software, R. Hooft, Nonius B. V., 1998.) Alternately, single crystal data were collected on a Bruker-AXS APEX2 CCD system using Cu Kα radiation (λ=1.5418 Å). Indexing and processing of the measured intensity data were carried out with the APEX2 software package/program suite (APEX2 Data collection and processing user interface: APEX2 User Manual, v1.27; BRUKER AXS, Inc., 5465 East Cheryl Parkway Madison, Wis. 53711 USA).

When indicated, crystals were cooled in the cold stream of an Oxford cryo system (Oxford Cryosystems Cryostream cooler: J. Cosier and A. M. Glazer, J. Appl. Cryst., 1986, 19, 105) during data collection.

The structures were solved by direct methods and refined on the basis of observed reflections using either the SDP (SDP, Structure Determination Package, Enraf-Nonius, Bohemia N.Y. 11716. Scattering factors, including f' and f", in the SDP software were taken from the "International Tables for Crystallography", Kynoch Press, Birmingham, England, 1974; Vol. IV, Tables 2.2A and 2.3.1) software package with minor local modifications or the crystallographic packages MAXUS (maXus solution and refinement software suite: S. Mackay, C. J. Gilmore, C. Edwards, M. Tremayne, N. Stewart, K. Shankland. maXus: a computer program for the solution and refinement of crystal structures from diffraction data or SHELXTL[4]. The derived atomic parameters (coordinates and temperature factors) were refined through full matrix least-squares. The function minimized in the refinements was $\Sigma_w(|F_O|-|F_C|)^2$. R is defined as $\Sigma||F_O|-|F_C||/\Sigma||F_O|$ while $R_w=[\Sigma_w(|F_O|-|F_C|)^2/\Sigma_w|F_O|^2]^{1/2}$ where w is an appropriate weighting function based on errors in the observed intensities. Difference maps were examined at all stages of refinement. Hydrogens were introduced in idealized positions with isotropic temperature factors, but no hydrogen parameters were varied.

X-Ray Powder Diffraction Data (PXRD)

PXRD data were obtained using a Bruker C2 GADDS. The radiation was Cu Kα (40 KV, 50 mA). The sample-detector distance was 15 cm. Powder samples were placed in sealed glass capillaries of 1 mm or less in diameter; the capillary was rotated during data collection. Data were collected for $3 \leq 2\theta \leq 35°$ with a sample exposure time of at least 2000 seconds. The resulting two-dimensional diffraction arcs were integrated to create a traditional 1-dimensional PXRD pattern with a step size of 0.02 degrees 2θ in the range of 3 to 35 degrees 2θ.

Differential Scanning Calorimetry (DSC)

DSC experiments were performed in a TA Instruments™ model Q1000 or 2920. The sample (about 2-6 mg) was weighed in an aluminum pan and recorded accurately recorded to a hundredth of a milligram, and transferred to the DSC. The instrument was purged with nitrogen gas at 50 mL/min. Data were collected between room temperature and 300° C. at 10° C./min heating rate. The plot was made with the endothermic peaks pointing down, Thermal Gravimetric Analysis (TGA)

TGA experiments were performed in a TA Instruments™ model Q500 or 2950. The sample (about 10-30 mg) was placed in a platinum pan previously tared. The weight of the sample was measured accurately and recorded to a thousandth of a milligram by the instrument. The furnace was purged with nitrogen gas at 100 mL/min. Data were collected between room temperature and 300° C. at 10° C./min heating rate.

PREPARATION AND ANALYSIS OF THE FORMS

The unit cell data and other properties for these examples are presented in Table 1. The unit cell parameters were obtained from single crystal X-ray crystallographic analysis. A detailed account of unit cells can be found in Chapter 3 of Stout & Jensen, *X-Ray Structure Determination: a Practical Guide*, (MacMillian, 1968).

Fractional atomic coordinates for Examples 2a, b, c, d, e, f, and g, and the conditions at which they were measured are presented in Tables 2-9.

Additionally, characteristic powder x-ray diffraction peak positions (degrees 2θ±0.1)@RT for Examples 2a, b, c, d, e, and f are presented in Table 9, all of which are based on high quality patterns collected with a diffractometer (CuKα) with a spinning capillary with 2θ calibrated with a NIST other suitable standard.

Figure 11:
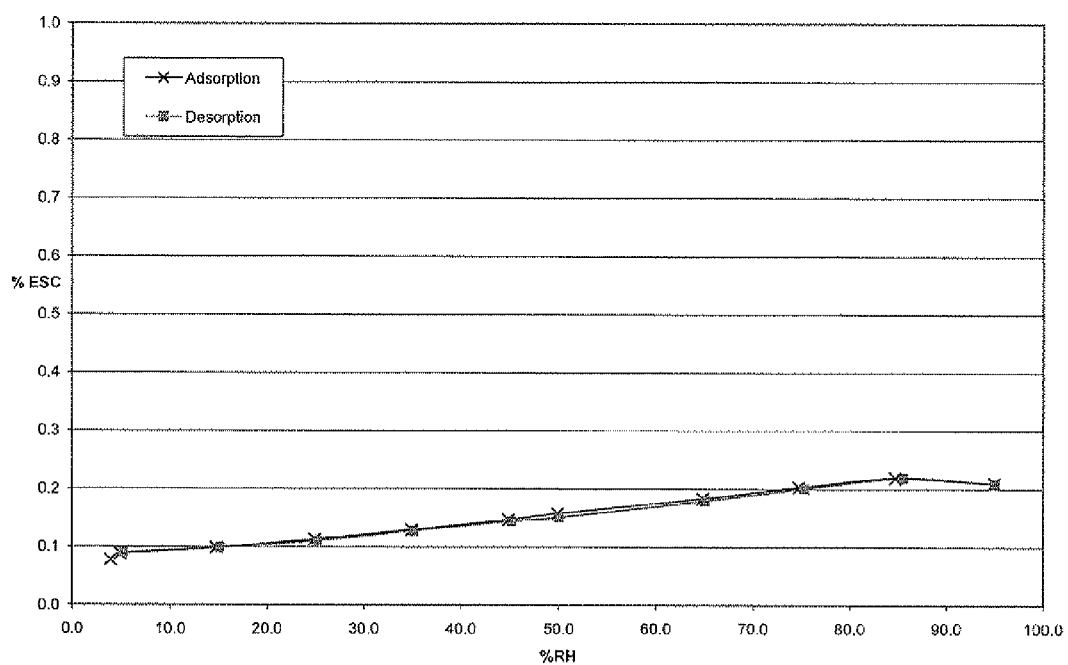
FIG. 11. Vapor Sorption Isotherm of N-((1R,2S,5R)-5-(tert-butylamino)-2-((S)-2-oxo-3-(6-(trifluoromethyl)quinazolin-4-ylamino)pyrrolidin-1-yl)cyclohexyl)acetamide, free base, Form N-2 at 25° C.
Figure 12:
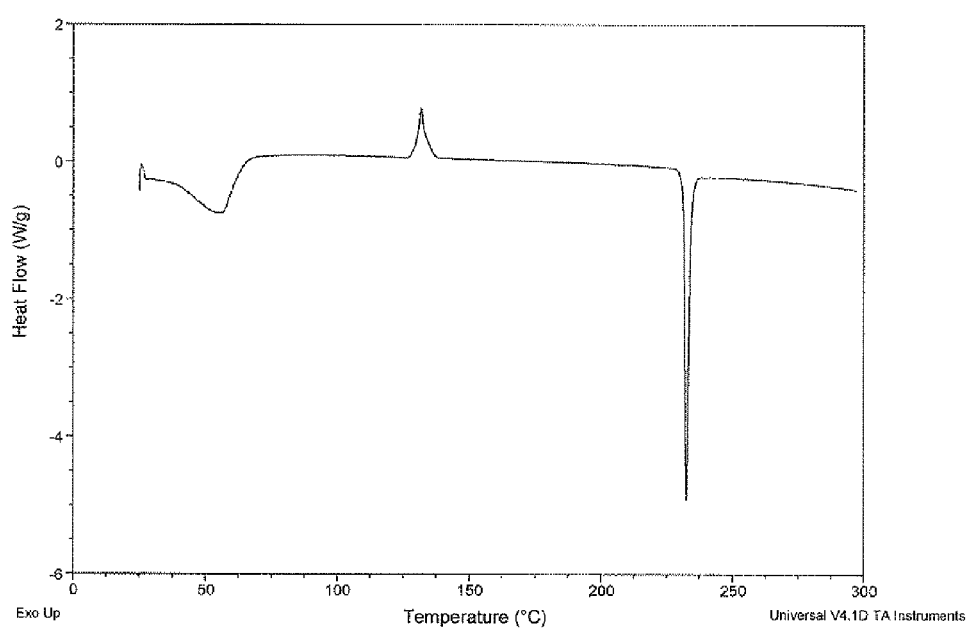
FIG. 12. DSC of N-((1R,2S,5R)-5-(tert-butylamino)-2-((S)-2-oxo-3-(6-(trifluoromethyl)quinazolin-4-ylamino)pyrrolidin-1-yl)cyclohexyl)acetamide, 1.75 moles $H_2O$, Form H1.75-5.
Figure 13:
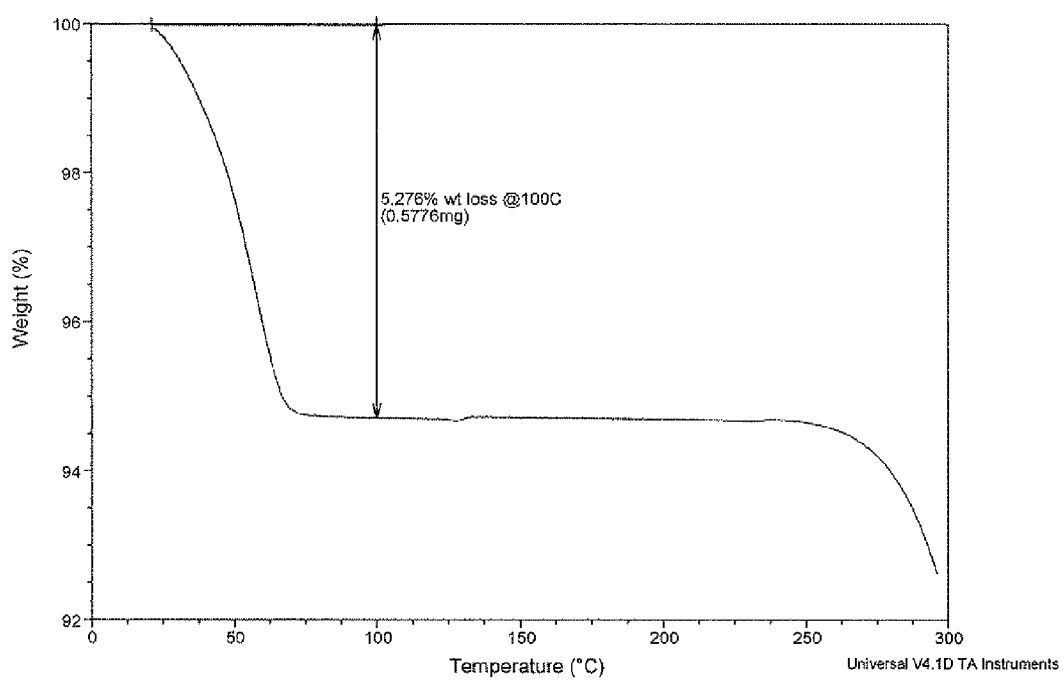
FIG. 13. TGA of N-((1R,2S,5R)-5-(tert-butylamino)-2-((S)-2-oxo-3-(6-(trifluoromethyl)quinazolin-4-ylamino)pyrrolidin-1-yl)cyclohexyl)acetamide, 1.75 moles $H_2O$, Form H1.75-5.
Figure 14:
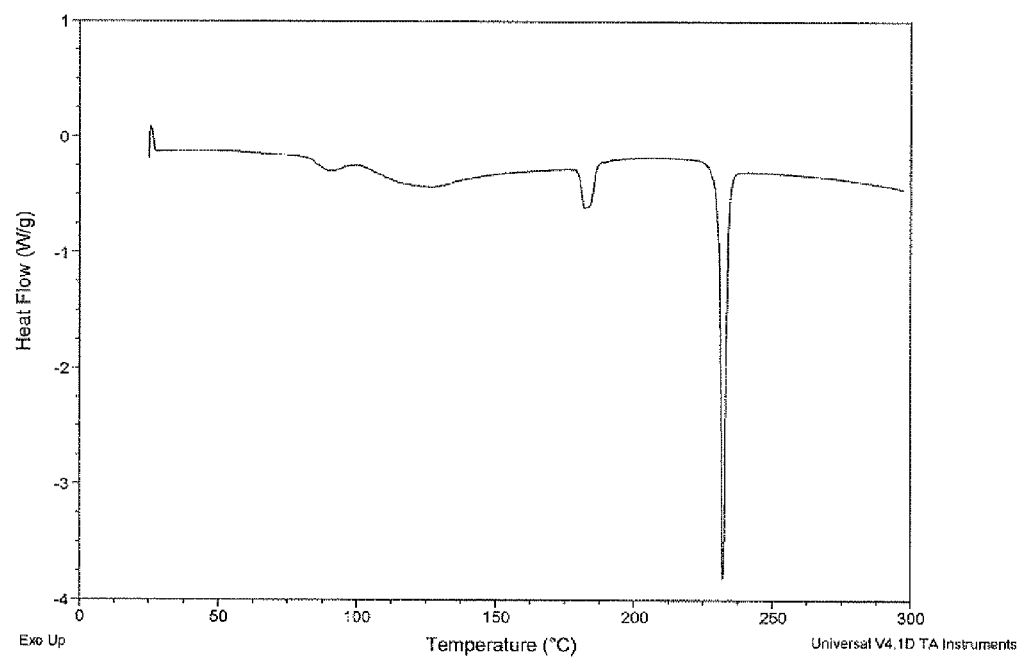
FIG. 14. DSC of N-((1R,2S,5R)-5-(tert-butylamino)-2-((S)-2-oxo-3-(6-(trifluoromethyl)quinazolin-4-ylamino)pyrrolidin-1-yl)cyclohexyl)acetamide, mono-acetic acid solvate, Form HAC-1.
Figure 15:
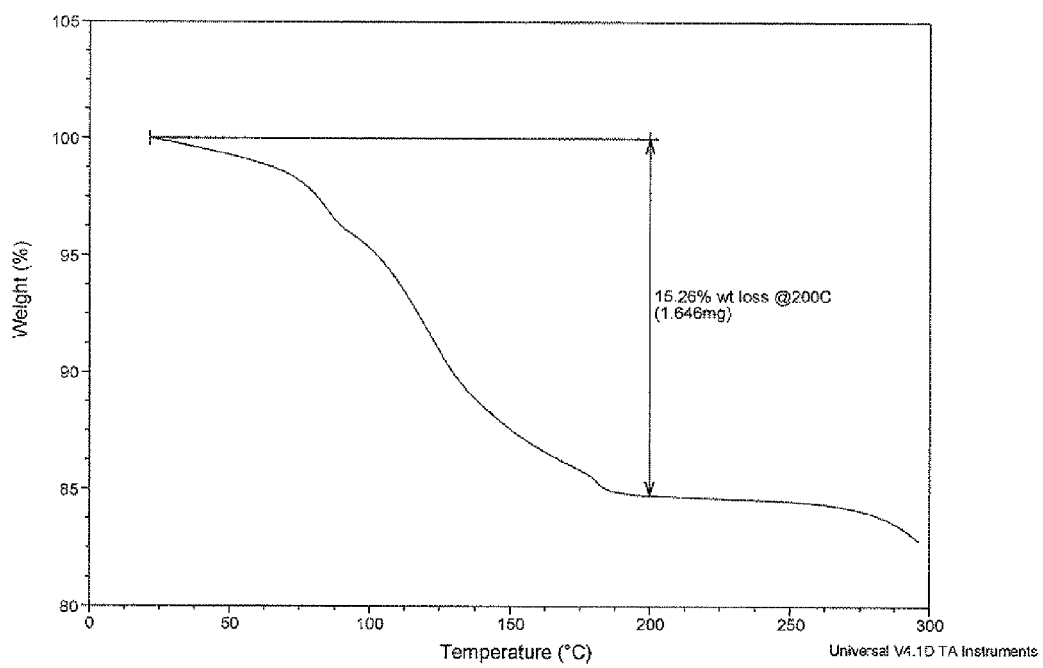
FIG. 15. TGA of N-((1R,2S,5R)-5-(tert-butylamino)-2-((S)-2-oxo-3-(6-(trifluoromethyl)quinazolin-4-ylamino)pyrrolidin-1-yl)cyclohexyl)acetamide, mono-acetic acid solvate, Form HAC-1.
Figure 16:
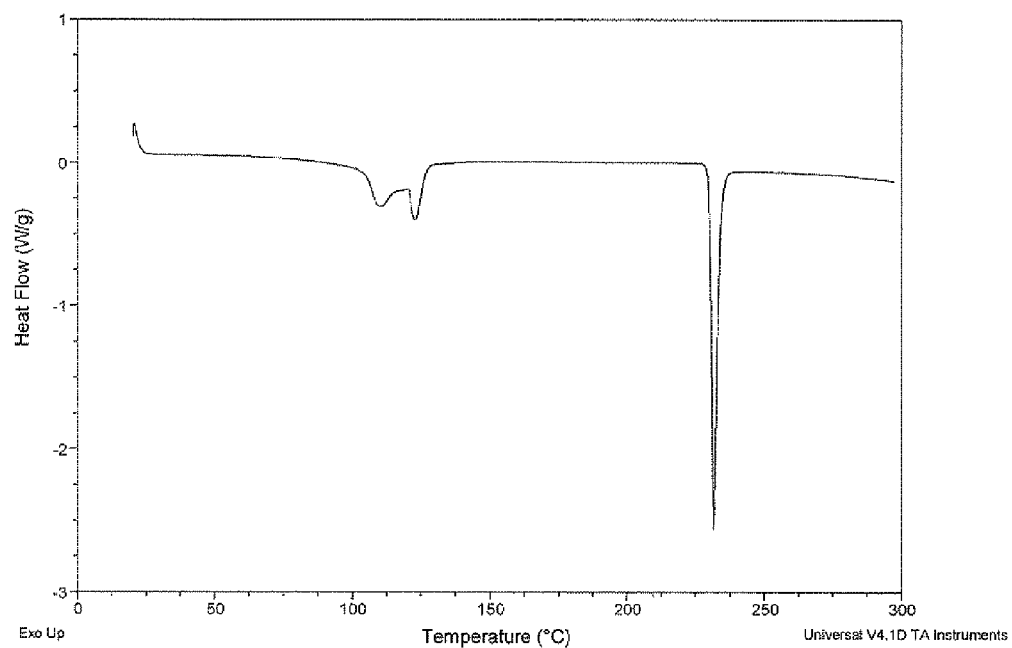
FIG. 16. DSC of N-((1R,2S,5R)-5-(tert-butylamino)-2-((S)-2-oxo-3-(6-(trifluoromethyl)quinazolin-4-ylamino)pyrrolidin-1-yl)cyclohexyl)acetamide, mono-ethanol solvate, Form E-1.
Figure 17:
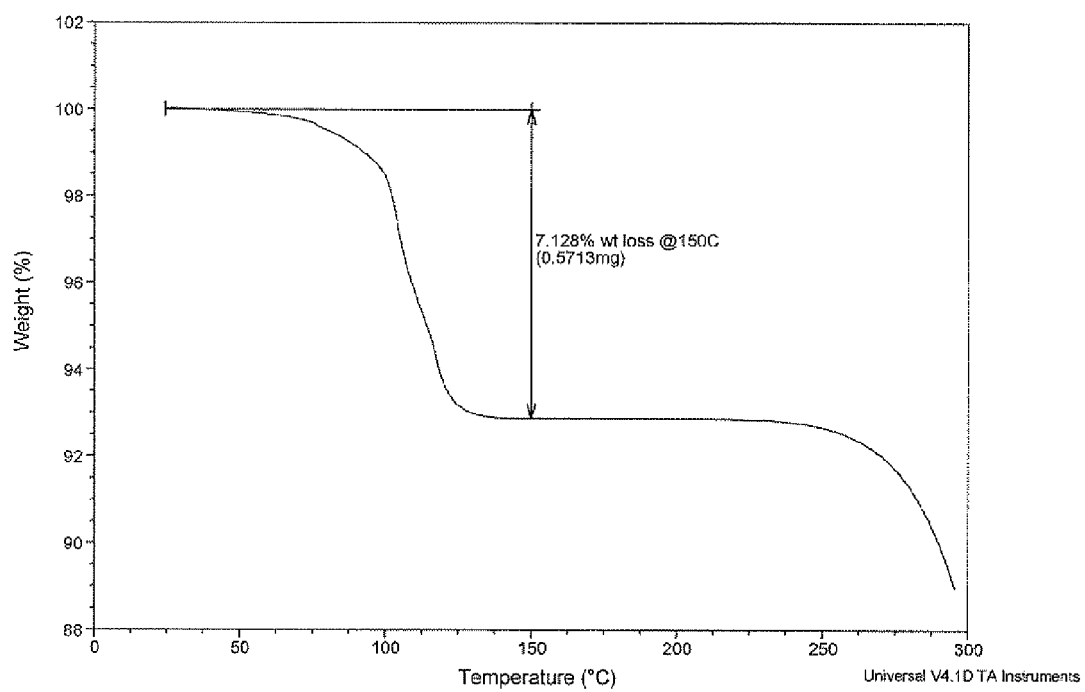
FIG. 17. TGA of N-((1R,2S,5R)-5-(tert-butylamino)-2-((S)-2-oxo-3-(6-(trifluoromethyl)quinazolin-4-ylamino)pyrrolidin-1-yl)cyclohexypacetamide, mono-ethanol solvate, Form E-1.
Figure 18:
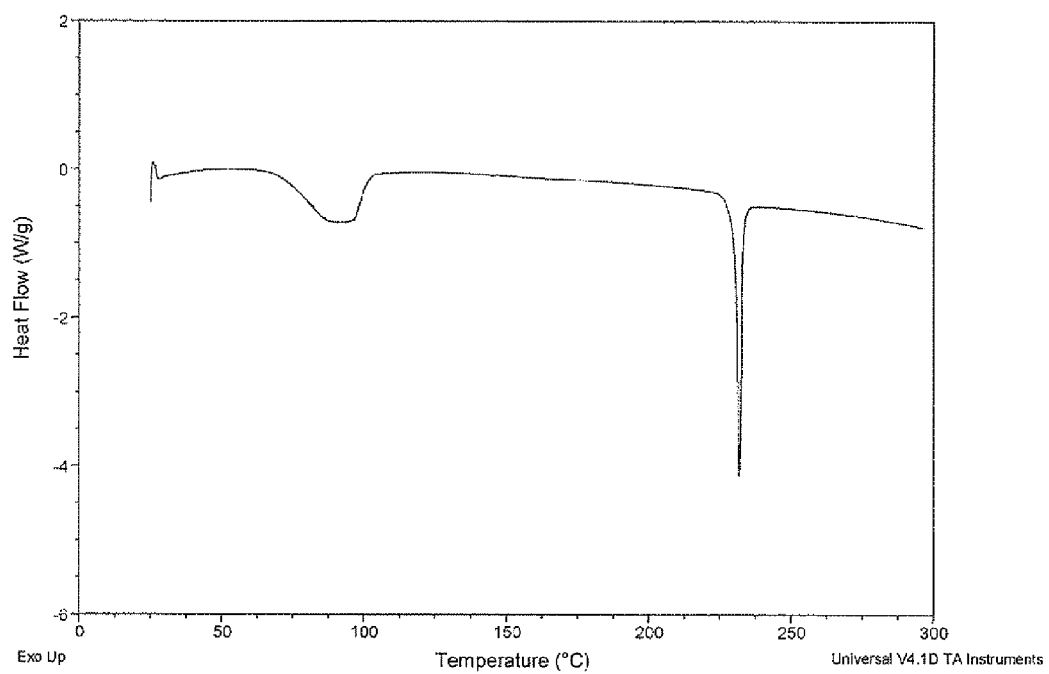
FIG. 18. DSC of N-((1R,2S,5R)-5-(tert-butylamino)-2-((S)-2-oxo-3-(6-(trifluoromethyl)quinazolin-4-ylamino)pyrrolidin-1-yl)cyclohexyl)acetamide, mono-R-propylene glycol solvate, Form RPG-3.
Figure 19:
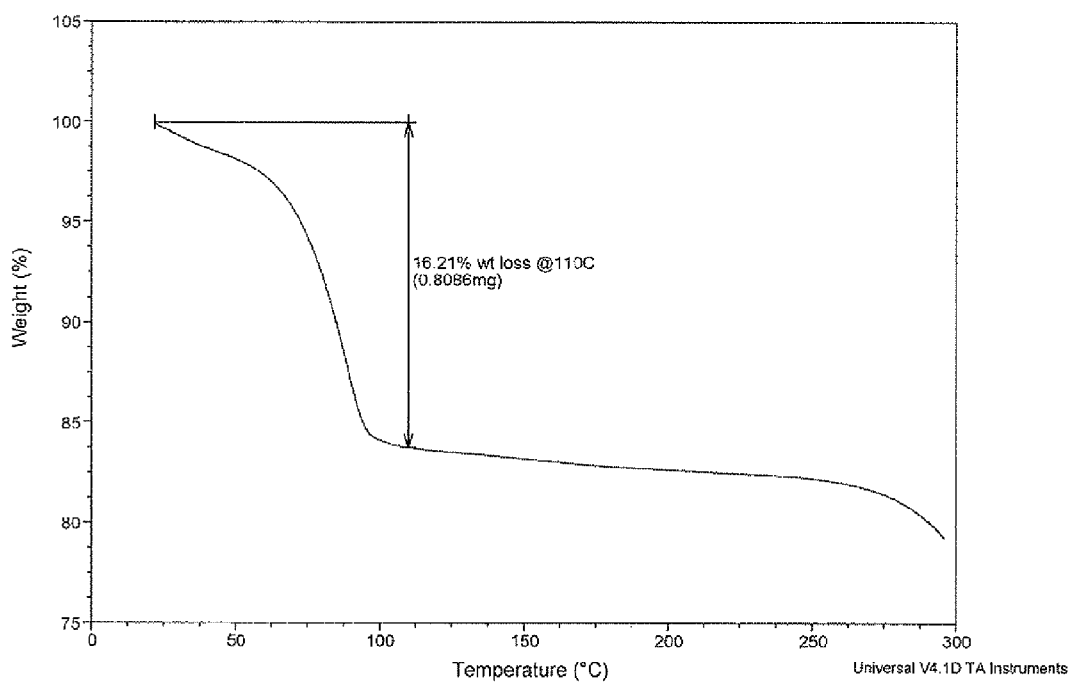
FIG. 19. TGA of N-((1R,2S,5R)-5-(tert-butylamino)-2-((S)-2-oxo-3-(6-(trifluoromethyl)quinazolin-4-ylamino)pyrrolidin-1-yl)cyclohexyl)acetamide, mono-R-propylene glycol solvate, Form RPG-3.

Finally, FIGS. 1, 2, 3, 4, 5, and 6 present XRPD patterns for Examples 2a, b, c, e, d and f, respectively. FIGS. 8, 10, 13, 15, 17 and 19 disclose the TGA of Examples 2a, b, c, d, e and f, respectively. FIGS. 7, 9, 12, 14, 16 and 18 disclose the DSC of Examples 2a, b, c, d, e and f, respectively. FIG. 11 discloses the Vapor Sorption Isotherm of Example 2b.

Form Preparation, DSC and TGA Characterization

Example 2a, Form H0.5-4

150 mg of N-((1R,2S,5R)-5-(tert-butylamino)-2-((S)-2-oxo-3-(6-(trifluoromethyl)quinazolin-4-ylamino)pyrrolidin-1-yl)cyclohexyl)acetamide, free base was dissolved in warm n-butyl acetate saturated with water. Heptane was added until a persistent cloud was observed. The slurry was allowed to cool to RT. Form H0.5-4 is characterized by 0.5 mole water per mole N-((1R,2S,5R)-5-(tert-butylamino)-2-((S)-2-oxo-3-(6-(trifluoromethyl)quinazolin-4-ylamino)pyrrolidin-1-yl)cyclohexyl)acetamide, free base. Form H0.5-4 was characterized by a DSC thermogram having a broad endotherm onset typically in the range between ca. RT and ca. 67° C. in agreement with the TGA curve; at higher temperatures other events may ensue. Form H0.5-4 was characterized by a TGA thermal curve having a weight loss typically from 0.6% to about 1.4% up to ca. 100° C. The theoretical weight loss for Form H0.5-4 is 1.7%, however, it is not unusual for unstable hydrates to become partially dehydrated upon drying.

Example 2b, Form N-2

1 g of N-((1R,2S,5R)-5-(tert-butylamino)-2-((S)-2-oxo-3-(6-(trifluoromethyl)quinazolin-4-ylamino)pyrrolidin-1-yl)cyclohexyl)acetamide, free base was dissolved in 10 mL of water-free EtOAc at 77° C. The solution was cooled to 70° C. 10 mg of seeds of N-2 were added. To the slurry, 18 mL of n-heptane was added over 1 hour with a syringe pump. The slurry was cooled from 70° C. to 20° C. over 1 hour, and agitated at 20° C. overnight. The solid was isolated by filtration, washed with 3 mL of n-heptane, dried at 50° C. in a vacuum oven overnight. Form N-2 is N-((1R,2S,5R)-5-(tert-butylamino)-2-((S)-2-oxo-3-(6-(trifluoromethyl)quinazolin-4-ylamino)pyrrolidin-1-yl)cyclohexyl)acetamide, free base, a neat fowl (without additional molecules of water or solvent). Form N-2 was characterized by a DSC thermogram having an endothermic onset typically between ca. 230° C. and ca. 232° C. as a single melt with no other transformations. Form N-2 was characterized by a TGA curve having negligible weight loss at up to ca. 200° C. and in agreement with the single-crystal structure.

Example 2c, Form H1.75-5

A slurry of 50 mg of N-((1R,2S,5R)-5-(tert-butylamino)-2-((S)-2-oxo-3-(6-(trifluoromethyl)quinazolin-4-ylamino)pyrrolidin-1-yl)cyclohexyl)acetamide, free base was vigorously agitated in 1 mL water for more than 16 hours. Form H1.75-5 is characterized by 1.75 moles of water per one mole of N-((1R,2S,5R)-5-(tert-butylamino)-2-((S)-2-oxo-3-(6-(trifluoromethyl)quinazolin-4-ylamino)pyrrolidin-1-yl)cyclohexyl)acetamide, free base. Form H1.75-5 was characterized by a DSC thermogram having an endotherm onset typically between ca. RT and ca. 70° C. in agreement with the TGA curve; at higher temperatures other events may ensue.

Form H1.75-5 was characterized by TGA curve having a weight loss of ca. 4.3% to ca. 5.3% at temperatures up to ca 100° C. Theoretical weight loss is ca. 5.9%, however, it is not unusual for unstable hydrates to become partially dehydrated upon drying.

Example 2d, HAC-1

100 mg of N-((1R,2S,5R)-5-(tert-butylamino)-2-((S)-2-oxo-3-(6-(trifluoromethyl)quinazolin-4-ylamino)pyrrolidin-1-yl)cyclohexyl)acetamide, free base was dissolved in 0.1 mL of HOAc at 80° C. To this, 0.2 mL of t-BuOAc was added and the solution was cooled to 20° C. The solution was evaporated to dryness. The resulting solid was agitated in heptane at 50° C. for 15 hours, followed by cooling to 20° C. HAC-1 was filtered and dried at 25° C. under vacuum overnight. Form HAC-1 is characterized by 1 mole of acetic acid per one mole of N-((1R,2S,5R)-5-(tert-butylamino)-2-((S)-2-oxo-3-(6-(trifluoromethyl)quinazolin-4-ylamino)pyrrolidin-1-yl)cyclohexyl)acetamide, free base. Form HAC-1 was characterized by a DSC thermogram having an endothermic onset typically at ea. 100° C. in agreement with the TGA curve; at higher temperatures other events may ensue. Form HAC-1 was also characterized by a TGA curve having ea, 15.3% weight loss up to ca. 200° C. Theoretical weight loss is ca. 10.5%, however it is not unusual for minor amount of high boiling point solvents to remain associated with the solid. In cases like this, PXRD is diagnostic of form but not sensitive to small amounts of adventitious solvent.

Example 2e, Form E-1

50 mg of N-((1R,2S,5R)-5-(tert-butylamino)-2-((S)-2-oxo-3-(6-(trifluoromethyl)quinazolin-4-ylamino)pyrrolidin-1-yl)cyclohexyl)acetamide, free base was dissolved in <1 mL of boiling ethanol. The solution was cooled to RT and allowed to slowly evaporate. Form E-1 is characterized by 1 mole of ethanol per one mole of N-((1R,2S,5R)-5-(tert-butylamino)-2-((S)-2-oxo-3-(6-(trifluoromethyl)quinazolin-4-ylamino)pyrrolidin-1-yl)cyclohexyl)acetamide, free base. Form E-1 was characterized by a DSC thermogram having an endothermic onset typically at ca. 100° C. in agreement with the TGA curves; at higher temperatures other events may ensue. Form E-1 was characterized by a TGA thermal curve having a weight loss of ca. 7.1% to ca. 7.6% up to ca. 150° C. Theoretical weight loss is ca. 8.3%, however, it is not unusual for unstable solvates to become partially desolvated upon drying.

Example 2f, RPG-3

30 to 40 mg of N-((1R,2S,5R)-5-(tert-butylamino)-2-((S)-2-oxo-3-(6-(trifluoromethyl)quinazolin-4-ylamino)pyrrolidin-1-yl)cyclohexyl)acetamide, free base was dissolved in 2 mL of racemic propylene glycol. Water was added until a cloud was observed. The solvent was allowed to slowly evaporate to dryness. Form RPG-3 is characterized by 1 molecule of R-propylene glycol per one molecule of N-((1R,2S,5R)-5-(tert-butylamino)-2-((S)-2-oxo-3-(6-(trifluoromethyl)quinazolin-4-ylamino)pyrrolidin-1-yl)cyclohexyl) acetamide, free base. Form RPG-3 was characterized by a DSC thermogram having an endothermic onset at ca. 70° C. in agreement with the TGA curve, at higher tempratures other events may ensue. Form RPG-3 was characterized by a TGA curve having a weight loss of ca.16.4% up to ca. 110° C. Theoretical weight loss is ca. 13.1%, however it is not unusual for minor amount of high boiling-point solvents to remain associated with the solid. In cases like this, PXRD is diagnostic of foam but not sensitive to small amounts of adventitious solvent.

Example 2g, Form IPA-1

40 mg of N-((1R,2S,5R)-5-(tert-butylamino)-2-((S)-2-oxo-3-(6-(trifluoromethyl)quinazolin-4-ylamino)pyrrolidin-1-yl)cyclohexyl)acetamide, free base was slurried in <1 mL of isopropyl alcohol. The slurry was gently heated to dissolve the remaining solid. The solution was cooled to RT and allowed to slowly evaporate until crystals were observed. Form IPA-1 is characterized by 1 mole of isopropyl alcohol per one mole of N-((1R,2S,5R)-5-(tert-butylamino)-2-((S)-2-oxo-3-(6-(trifluoromethyl)quinazolin-4-ylamino)pyrrolidin-1-yl)cyclohexyl)acetamide, free base.

TABLE 1

Unit Cell Parameters

| Compound | Form | T | a(Å) | b(Å) | c(Å) | α° | β° | γ° | V(Å$^3$) |
|---|---|---|---|---|---|---|---|---|---|
| Exp 2a | H0.5-4 | −50 | 17.7845(7) | 7.6215(3) | 20.9510(9) | 90 | 109.062(3) | 90 | 2684.1(2) |
| Exp 2b | N-2 | RT | 18.7240(4) | 8.0171(2) | 19.6568(5) | 90 | 114.935(2) | 90 | 2675.7(1) |
| Exp 2c | H1.75-5 | −70 | 12.7648(2) | 34.3194(7) | 12.9659(2) | 90 | 99.053(1) | 90 | 5609.4(2) |
| Exp 2d | HAC-1 | RT | 7.9766(7) | 11.058(2) | 33.348(4) | 90 | 90 | 90 | 2941.4(6) |
| Exp 2e | E-1 | −50 | 7.9866(3) | 11.2594(6) | 32.680(2) | 90 | 90 | 90 | 2938.7(2) |
| Exp 2f | RPG-3 | −50 | 10.3004(3) | 10.5475(4) | 15.4784(6) | 90.045(3) | 102.476(2) | 109.083(2) | 1547.0(1) |
| Exp 2g | IPA-1 | RT | 8.4487(2) | 11.6615(3) | 31.3800(9) | 90 | 90 | 90 | 3091.7(1) |

| Compound | Z' | Vm | sg | dcalc |
|---|---|---|---|---|
| Exp 2a | 2 | 671 | P2$_1$ | 1.235 |
| Exp 2b | 2 | 669 | P2$_1$ | 1.258 |
| Exp 2c | 4 | 701 | P2$_1$ | 1.274 |
| Exp 2d | 1 | 735 | P2$_1$2$_1$2$_1$ | 1.279 |
| Exp 2e | 1 | 735 | P2$_1$2$_1$2$_1$ | 1.249 |
| Exp 2f | 2 | 774 | P1 | 1.257 |
| Exp 2g | 1 | 773 | P2$_1$2$_1$2$_1$ | 1.217 |

The variables used in Table 1 are defined below:
T=temperature in Centigrade for the crystallographic data (RT is room temperature which is about +22° C.)
V=volume of unit cell
Z'=number of drug molecules per asymmetric unit
Vm=V(unit cell)/(Z drug molecules per cell)
sg=space group
dcalc=calculated crystal density

TABLE 2

Atomic Coordinates for Example 2a, Form H0.5-4

| Atom | X | Y | Z | Atom | X | Y | Z |
|---|---|---|---|---|---|---|---|
| F1 | 0.1718 | 0.5612 | 0.2388 | F138 | 0.9730 | 0.9700 | 0.6210 |
| F2 | 0.1576 | 0.4167 | 0.1518 | F139 | 1.0220 | 0.7300 | 0.6430 |
| F3 | 0.1277 | 0.6827 | 0.1463 | F140 | 0.9470 | 0.7710 | 0.5532 |
| N7 | 0.3729 | 0.0177 | −0.0187 | O137 | 0.5289 | 1.1320 | 0.2702 |
| N9 | 0.3967 | 0.3613 | 0.0716 | H10 | 0.3464 | 0.3422 | 0.0601 |
| N11 | 0.5034 | 0.5324 | 0.1275 | H16 | 0.1889 | −0.1347 | −0.0192 |
| N12 | 0.1513 | −0.3723 | −0.0803 | H85 | 0.2780 | 0.4332 | 0.1193 |
| N15 | 0.2070 | −0.0340 | −0.0258 | H88 | 0.4895 | 0.3182 | 0.0357 |
| N18 | 0.4944 | 0.7660 | 0.2016 | H90 | 0.2688 | −0.4938 | −0.1162 |
| O23 | 0.3677 | 0.2704 | −0.0786 | H91 | 0.2791 | −0.3427 | −0.1635 |
| O25 | 0.2371 | 0.2420 | 0.0154 | H93 | 0.2277 | 0.1128 | −0.0967 |
| C82 | 0.2630 | 0.6176 | 0.1822 | H95 | 0.3290 | −0.0521 | −0.1140 |
| C83 | 0.4281 | 0.4888 | 0.1165 | H99 | 0.3760 | −0.3135 | −0.0574 |
| C84 | 0.3027 | 0.5269 | 0.1466 | H100 | 0.3100 | −0.3067 | −0.0228 |
| C86 | 0.3810 | 0.5754 | 0.1513 | H102 | 0.5234 | 0.0450 | 0.0773 |
| C87 | 0.4447 | 0.2515 | 0.0409 | H103 | 0.4804 | 0.1033 | 0.1290 |
| C89 | 0.2647 | −0.3681 | −0.1237 | H105 | 0.1184 | −0.0766 | −0.1500 |
| C92 | 0.2304 | −0.0122 | −0.0852 | H106 | 0.1831 | −0.0821 | −0.1859 |

TABLE 2-continued

Atomic Coordinates for Example 2a, Form H0.5-4

| Atom | X | Y | Z | Atom | X | Y | Z |
|---|---|---|---|---|---|---|---|
| C94 | 0.3163 | −0.0776 | −0.0729 | H110 | 0.3980 | 0.9063 | 0.2542 |
| C96 | 0.4172 | 0.7161 | 0.1933 | H112 | 0.4292 | −0.1628 | 0.0516 |
| C97 | 0.1821 | 0.5681 | 0.1800 | H113 | 0.3692 | −0.0449 | 0.0742 |
| C98 | 0.3221 | −0.2755 | −0.0632 | H115 | 0.2715 | 0.8230 | 0.2452 |
| C101 | 0.4735 | 0.0847 | 0.0816 | H117 | 0.0540 | −0.3914 | −0.0071 |
| C104 | 0.1724 | −0.1130 | −0.1448 | H118 | 0.1047 | −0.5613 | −0.0042 |
| C107 | 0.3915 | 0.1858 | −0.0261 | H119 | 0.0122 | −0.5664 | −0.0392 |
| C108 | 0.2116 | 0.0919 | 0.0195 | H121 | 0.0157 | −0.2070 | −0.1065 |
| C109 | 0.3748 | 0.8103 | 0.2276 | H122 | −0.0438 | −0.3568 | −0.1418 |
| C111 | 0.4081 | −0.0451 | 0.0507 | H123 | 0.0156 | −0.2818 | −0.1762 |
| C114 | 0.2994 | 0.7605 | 0.2220 | H126 | 0.1446 | −0.3645 | −0.1779 |
| C116 | 0.0592 | −0.4960 | −0.0309 | H128 | 0.5835 | 0.7006 | 0.1755 |

TABLE 2-continued

Atomic Coordinates for Example 2a, Form H0.5-4

| Atom | X | Y | Z | Atom | X | Y | Z |
|---|---|---|---|---|---|---|---|
| C120 | 0.0087 | −0.3106 | −0.1338 | H130 | 0.2266 | 0.0448 | 0.1189 |
| C124 | 0.0696 | −0.4465 | −0.0977 | H131 | 0.1603 | −0.0732 | 0.0701 |
| C125 | 0.1783 | −0.3101 | −0.1359 | H132 | 0.1430 | 0.1249 | 0.0800 |
| C127 | 0.5309 | 0.6696 | 0.1690 | H134 | 0.0091 | −0.6633 | −0.1497 |
| C129 | 0.1827 | 0.0426 | 0.0774 | H135 | 0.1005 | −0.6984 | −0.1175 |
| C133 | 0.0611 | −0.6143 | −0.1412 | H136 | 0.0686 | −0.5851 | −0.1833 |
| F4 | 0.9541 | 0.9380 | 0.5714 | H141 | 0.1830 | −0.4440 | −0.0580 |
| F5 | 0.9826 | 0.6800 | 0.5759 | H14 | 0.6945 | 1.0312 | 0.5339 |
| F6 | 1.0259 | 0.8300 | 0.6655 | H21 | 0.7741 | 1.5073 | 0.4379 |
| N8 | 0.6040 | 1.3694 | 0.4758 | H28 | 0.7049 | 1.4602 | 0.3064 |
| N13 | 0.6631 | 1.0203 | 0.5573 | H29 | 0.6130 | 1.4814 | 0.2902 |
| N17 | 0.7581 | 1.7462 | 0.3780 | H32 | 0.5464 | 1.0615 | 0.5430 |
| N19 | 0.6266 | 0.8793 | 0.6383 | H34 | 0.6724 | 1.6789 | 0.4661 |
| N20 | 0.7501 | 1.4082 | 0.4350 | H35 | 0.5807 | 1.7062 | 0.4509 |
| N22 | 0.7080 | 0.6517 | 0.7080 | H38 | 0.8152 | 0.9372 | 0.5749 |
| O24 | 0.7581 | 1.1336 | 0.4774 | H41 | 0.5545 | 1.4575 | 0.3823 |
| O26 | 0.5442 | 1.1244 | 0.4164 | H44 | 0.5540 | 1.3350 | 0.5873 |
| C27 | 0.6643 | 1.5023 | 0.3242 | H45 | 0.6406 | 1.2709 | 0.6290 |
| C30 | 0.6817 | 0.9034 | 0.6081 | H48 | 0.6272 | 1.8887 | 0.3818 |
| C31 | 0.5921 | 1.1293 | 0.5402 | H49 | 0.5627 | 1.7587 | 0.3377 |
| C33 | 0.6205 | 1.6624 | 0.4324 | H52 | 0.6566 | 1.2721 | 0.3752 |
| C36 | 0.5758 | 1.2019 | 0.4701 | H55 | 0.6234 | 1.5433 | 0.5534 |
| C37 | 0.8201 | 0.8496 | 0.6069 | H56 | 0.6965 | 1.4170 | 0.5619 |
| C39 | 0.7568 | 0.8126 | 0.6288 | H58 | 0.8887 | 1.9136 | 0.4290 |
| C40 | 0.6067 | 1.4694 | 0.4172 | H59 | 0.9292 | 1.8759 | 0.3743 |
| C42 | 0.8902 | 0.7591 | 0.6317 | H60 | 0.9085 | 1.7203 | 0.4146 |
| C43 | 0.6042 | 1.2934 | 0.5840 | H62 | 0.6632 | 1.7578 | 0.2922 |
| C46 | 0.7651 | 0.6822 | 0.6794 | H64 | 0.8824 | 1.3038 | 0.5620 |
| C47 | 0.6162 | 1.7663 | 0.3697 | H65 | 0.8870 | 1.4370 | 0.5064 |

TABLE 2-continued

Atomic Coordinates for Example 2a, Form H0.5-4

| Atom | X | Y | Z | Atom | X | Y | Z |
|---|---|---|---|---|---|---|---|
| C50 | 0.8099 | 1.8166 | 0.3410 | H66 | 0.9097 | 1.2396 | 0.5019 |
| C51 | 0.6689 | 1.3952 | 0.3877 | H69 | 0.7263 | 1.9822 | 0.2803 |
| C53 | 0.7895 | 1.2775 | 0.4740 | H70 | 0.8132 | 2.0339 | 0.2846 |
| C54 | 0.6389 | 1.4243 | 0.5469 | H71 | 0.7823 | 2.0761 | 0.3450 |
| C57 | 0.8917 | 1.8331 | 0.3947 | H73 | 0.8374 | 1.5813 | 0.3078 |
| C61 | 0.6751 | 1.6998 | 0.3362 | H74 | 0.8486 | 1.7393 | 0.2638 |
| C63 | 0.8750 | 1.3182 | 0.5148 | H75 | 0.7629 | 1.6701 | 0.2558 |
| C67 | 0.9615 | 0.8066 | 0.6143 | H77 | 0.8443 | 0.5011 | 0.7349 |
| C68 | 0.7802 | 1.9934 | 0.3099 | H79 | 0.9456 | 0.5638 | 0.6960 |
| C72 | 0.8152 | 1.6904 | 0.2872 | H81 | 0.6060 | 0.7320 | 0.7067 |
| C76 | 0.8381 | 0.5893 | 0.7029 | H142 | 0.7500 | 1.8390 | 0.4090 |
| C78 | 0.8982 | 0.6264 | 0.6799 | H143 | 0.5333 | 1.1298 | 0.3123 |
| C80 | 0.6445 | 0.7516 | 0.6862 | H144 | 0.5194 | 1.0278 | 0.2538 |

TABLE 3

Atomic Coordinates for Example 2b, Base Form N-2

| Atom | X | Y | Z | Atom | X | Y | Z |
|---|---|---|---|---|---|---|---|
| N1 | 0.7824 | 1.3195 | 0.3238 | C71 | 0.9289 | 1.4591 | 0.5167 |
| N2 | 0.1685 | 0.3056 | −0.0178 | H72 | 0.9378 | 1.4237 | 0.5668 |
| H3 | 0.1633 | 0.1989 | −0.0196 | H73 | 0.9764 | 1.4359 | 0.5102 |
| N4 | 0.6223 | 0.8215 | 0.1887 | C74 | 0.8719 | 1.7574 | 0.6080 |
| N5 | 0.2627 | 0.4840 | −0.0849 | C75 | 0.6719 | 1.2862 | 0.4846 |
| N6 | 0.6868 | 0.9765 | 0.2943 | H76 | 0.6246 | 1.2933 | 0.4390 |
| H7 | 0.7030 | 0.9877 | 0.3420 | H77 | 0.6814 | 1.3914 | 0.5103 |
| N8 | 0.4185 | 0.9718 | 0.0742 | H78 | 0.6660 | 1.2009 | 0.5162 |
| N9 | 0.0989 | 0.0258 | −0.1003 | C79 | 0.9173 | 1.6199 | 0.6639 |
| N10 | 0.7913 | 1.3680 | 0.4754 | H80 | 0.8851 | 1.5217 | 0.6541 |
| H11 | 0.7826 | 1.4618 | 0.4918 | H81 | 0.9305 | 1.6578 | 0.6742 |
| N12 | 0.5331 | 0.6005 | 0.1813 | H82 | 0.9647 | 1.5943 | 0.6584 |
| N13 | 0.3353 | 0.7474 | 0.0475 | C83 | 0.9176 | 1.9198 | 0.6225 |
| H14 | 0.3028 | 0.6896 | 0.0583 | H84 | 0.9680 | 1.8999 | 0.6220 |
| N15 | 0.8501 | 1.6946 | 0.5311 | H85 | 0.9252 | 1.9631 | 0.6707 |
| N16 | 0.4567 | 1.1267 | 0.1887 | H86 | 0.8887 | 1.9992 | 0.5842 |
| O17 | 0.7470 | 1.1042 | 0.4435 | C87 | 0.7960 | 1.7901 | 0.6131 |
| O18 | 0.2114 | 0.7470 | −0.1165 | H88 | 0.7660 | 1.8705 | 0.5758 |
| O19 | 0.2229 | 0.5239 | 0.0583 | H89 | 0.8064 | 1.8325 | 0.6526 |
| O20 | 0.8588 | 1.0890 | 0.3360 | H90 | 0.7667 | 1.6881 | 0.6048 |
| F21 | 0.5881 | 0.9034 | 0.4961 | C91 | 0.2069 | 0.3753 | 0.0494 |
| F22 | 0.4828 | 0.7754 | 0.4659 | C92 | 0.1886 | 0.3981 | −0.1294 |
| F23 | 0.5874 | 0.6500 | 0.5199 | H93 | 0.1617 | 0.4641 | −0.1751 |
| C24 | 0.1049 | −0.1653 | −0.0049 | C94 | 0.1345 | 0.3960 | −0.0889 |
| H25 | 0.1473 | −0.2167 | −0.0125 | H95 | 0.1249 | 0.5115 | −0.0787 |
| H26 | 0.0773 | −0.2487 | 0.0097 | C96 | 0.3636 | 0.8982 | 0.1612 |
| H27 | 0.1257 | −0.0826 | 0.0338 | C97 | 0.0560 | 0.3169 | −0.1396 |
| C28 | 0.0052 | −0.2107 | −0.1371 | H98 | 0.0300 | 0.3865 | −0.1836 |
| H29 | −0.0334 | −0.1565 | −0.1806 | H99 | 0.0226 | 0.3123 | −0.1131 |
| H30 | −0.0204 | −0.2889 | −0.1178 | C100 | 0.0655 | 0.1409 | −0.1647 |
| H31 | 0.0423 | −0.2685 | −0.1506 | H101 | 0.0138 | 0.0994 | −0.1999 |
| C32 | −0.0102 | 0.0236 | −0.0618 | C102 | 0.2651 | 0.6526 | −0.0801 |
| H33 | 0.0176 | 0.1111 | −0.0276 | C103 | 0.3727 | 0.8727 | 0.0930 |
| H34 | −0.0371 | −0.0447 | −0.0399 | C104 | 0.3129 | 0.8065 | 0.1831 |
| H35 | −0.0478 | 0.0713 | −0.1077 | H105 | 0.2826 | 0.7213 | 0.1525 |
| C36 | 0.6347 | 0.8573 | 0.2590 | C106 | 0.4090 | 1.0275 | 0.2081 |
| C37 | 0.7956 | 1.1614 | 0.3094 | H107 | 0.1998 | 0.2249 | −0.1544 |
| C38 | 0.5429 | 0.6399 | 0.2526 | H108 | 0.2268 | 0.1548 | −0.1108 |
| C39 | 0.5969 | 0.8058 | 0.3661 | H109 | 0.2321 | 0.2314 | −0.1820 |
| C40 | 0.6303 | 0.8901 | 0.3943 | H110 | 0.0479 | −0.0823 | −0.0781 |
| C41 | 0.5928 | 0.7673 | 0.2949 | C111 | 0.3943 | 0.5437 | −0.0102 |
| C42 | 0.7174 | 1.0886 | 0.2543 | H112 | 0.4319 | 0.5306 | 0.0416 |
| H43 | 0.7243 | 1.0288 | 0.2140 | H113 | 0.4226 | 0.5469 | −0.0417 |
| C44 | 0.8437 | 1.4188 | 0.3806 | C114 | 0.1202 | 0.1477 | −0.2041 |
| H45 | 0.8919 | 1.4020 | 0.3733 | H115 | 0.0955 | 0.2128 | −0.2496 |
| C46 | 0.8266 | 1.6034 | 0.3730 | H116 | 0.1283 | 0.0355 | −0.2179 |
| H47 | 0.7791 | 1.6255 | 0.3797 | C117 | 0.3076 | 0.8411 | 0.2485 |
| H48 | 0.8177 | 1.6396 | 0.3230 | C118 | 0.2292 | 0.2619 | 0.1158 |
| C49 | 0.5524 | 0.7201 | 0.3942 | H119 | 0.2846 | 0.2720 | 0.1469 |
| C50 | 0.6668 | 1.2414 | 0.2237 | H120 | 0.2172 | 0.1487 | 0.0989 |
| H51 | 0.6690 | 1.2785 | 0.1776 | H121 | 0.2001 | 0.2924 | 0.1441 |
| H52 | 0.6125 | 1.2182 | 0.2137 | H122 | 0.3349 | 0.4024 | −0.0337 |
| C53 | 0.8609 | 1.3569 | 0.4595 | H123 | 0.3502 | 0.3144 | −0.0588 |

TABLE 3-continued

Atomic Coordinates for Example 2b, Base Form N-2

| Atom | X | Y | Z | Atom | X | Y | Z |
|---|---|---|---|---|---|---|---|
| H54 | 0.8773 | 1.2398 | 0.4636 | H124 | 0.3290 | 0.3556 | 0.0092 |
| H55 | 0.4991 | 0.5496 | 0.2836 | C125 | 0.3458 | 0.7009 | −0.0200 |
| H56 | 0.4668 | 0.4624 | 0.2569 | H126 | 0.3682 | 0.7937 | −0.0371 |
| C57 | 0.7010 | 1.3718 | 0.2841 | C127 | 0.4561 | 1.0941 | 0.1233 |
| H58 | 0.6975 | 1.4822 | 0.2628 | H128 | 0.4859 | 1.1659 | 0.1085 |
| H59 | 0.6744 | 1.3722 | 0.3171 | H129 | 0.4030 | 1.0567 | 0.2762 |
| C60 | 0.9137 | 1.6472 | 0.5099 | H130 | 0.4339 | 1.1390 | 0.3084 |
| H61 | 0.9621 | 1.7039 | 0.5438 | C131 | 0.2548 | 0.7395 | 0.2713 |
| C62 | 0.7404 | 1.2441 | 0.4666 | C132 | 0.3536 | 0.9679 | 0.2955 |
| C63 | 0.5039 | 0.5898 | 0.3526 | H133 | 0.3500 | 0.9907 | 0.3403 |
| H64 | 0.4747 | 0.5300 | 0.3726 | F134 | 0.1847 | 0.7359 | 0.2156 |
| C65 | 0.5722 | 0.6959 | 0.1556 | F135 | 0.2364 | 0.8060 | 0.3220 |
| H66 | 0.5642 | 0.6734 | 0.1065 | F136 | 0.2859 | 0.5920 | 0.2960 |
| C67 | 0.8949 | 1.7014 | 0.4308 | F137 | 0.1977 | 0.8329 | 0.2710 |
| H68 | 0.9412 | 1.6866 | 0.4211 | F138 | 0.2168 | 0.6170 | 0.2301 |
| H69 | 0.8818 | 1.8193 | 0.4256 | F139 | 0.2934 | 0.6790 | 0.3395 |
| C70 | 0.5532 | 0.7632 | 0.4678 | H140 | 0.8280 | 1.7679 | 0.5060 |
|  |  |  |  | H141 | 0.1330 | −0.0400 | −0.1062 |

TABLE 4

Atomic Coordinates for Example 2c, Base Form H1.75-5

| Atom | X | Y | Z | Atom | X | Y | Z |
|---|---|---|---|---|---|---|---|
| C1 | 0.3942 | 0.1176 | 0.2183 | C51 | 0.6094 | 0.0443 | −0.0547 |
| C2 | 0.2287 | 0.1174 | 0.0897 | C52 | 0.6750 | 0.0382 | 0.0420 |
| N3 | 0.1192 | 0.1293 | 0.0594 | C53 | 0.9963 | 0.1572 | 0.4974 |
| N4 | 0.1798 | 0.0501 | 0.1322 | C54 | 0.7176 | −0.0005 | 0.0684 |
| N5 | 0.3753 | 0.0509 | 0.2822 | C55 | 1.1985 | 0.0503 | 0.7049 |
| N6 | −0.0927 | 0.1070 | −0.1055 | C56 | 1.1539 | 0.1133 | 0.4965 |
| N7 | −0.3691 | 0.1154 | −0.3165 | C57 | 1.0229 | 0.1608 | 0.6162 |
| N8 | −0.2260 | 0.1440 | −0.1970 | C58 | 1.0367 | 0.1185 | 0.4572 |
| O9 | 0.1323 | 0.1298 | −0.1137 | C59 | 0.7341 | 0.1669 | 0.3280 |
| O10 | 0.0301 | 0.0456 | 0.0130 | C60 | 1.1829 | 0.1168 | 0.6162 |
| C11 | 0.0785 | 0.1332 | −0.0419 | C61 | 1.1435 | 0.1563 | 0.6496 |
| C12 | 0.2431 | 0.0735 | 0.0697 | C62 | 0.5636 | 0.1744 | 0.0306 |
| C13 | −0.2272 | 0.0747 | −0.2281 | C63 | 0.6973 | 0.1581 | 0.4320 |
| C14 | 0.0812 | 0.0382 | 0.0995 | C64 | 0.7972 | 0.1517 | 0.5115 |
| C15 | 0.4135 | 0.0738 | 0.2008 | C65 | 1.3015 | 0.0605 | 0.7775 |
| C16 | 0.2774 | 0.1283 | 0.2010 | C66 | 1.2257 | 0.0279 | 0.6122 |
| C17 | 0.3592 | 0.0623 | 0.0929 | C67 | 1.1287 | 0.0258 | 0.7652 |
| C18 | −0.3242 | 0.0799 | −0.2978 | C68 | 0.9017 | 0.0664 | 0.4282 |
| C19 | −0.1859 | −0.0329 | −0.2601 | C69 | 0.8592 | 0.0308 | 0.4749 |
| C20 | −0.3192 | 0.1441 | −0.2671 | F70 | 0.7706 | −0.0040 | 0.1659 |
| C21 | −0.1804 | 0.1091 | −0.1748 | F71 | 0.7890 | −0.0119 | 0.0101 |
| C22 | −0.1842 | 0.0372 | −0.2149 | F72 | 0.6477 | −0.0283 | 0.0583 |
| C23 | 0.0394 | 0.1336 | 0.1281 | N73 | 0.7366 | 0.2979 | 0.1640 |
| C24 | −0.3330 | 0.0112 | −0.3340 | N74 | 0.9286 | 0.2769 | 0.3415 |
| C25 | −0.2347 | 0.0067 | −0.2683 | N75 | 0.9490 | 0.3548 | 0.4399 |
| C26 | 0.0308 | 0.0146 | 0.1792 | N76 | 0.6679 | 0.2686 | 0.0076 |
| C27 | −0.3753 | 0.0465 | −0.3473 | N77 | 0.5468 | 0.3015 | −0.1239 |
| C28 | −0.0381 | 0.1410 | −0.0545 | N78 | 1.1302 | 0.3587 | 0.6021 |
| C29 | 0.4391 | 0.0161 | 0.3216 | O79 | 0.7689 | 0.2552 | 0.3756 |
| C30 | 0.4331 | −0.0152 | 0.2365 | O80 | 0.8000 | 0.3561 | 0.3182 |
| C31 | −0.0565 | 0.1490 | 0.0571 | C81 | 0.6779 | 0.3005 | 0.0685 |
| C32 | 0.5574 | 0.0267 | 0.3640 | C82 | 0.8021 | 0.2636 | 0.1953 |
| C33 | 0.3907 | 0.0006 | 0.4127 | C83 | 0.6253 | 0.3363 | 0.0330 |
| F34 | −0.1107 | −0.0374 | −0.1835 | C84 | 0.8293 | 0.2641 | 0.3145 |
| F35 | −0.1514 | −0.0419 | −0.3469 | C85 | 0.9704 | 0.2829 | 0.4523 |
| F36 | −0.2560 | −0.0605 | −0.2519 | C86 | 0.9612 | 0.3232 | 0.6101 |
| N37 | 0.9782 | 0.0854 | 0.4895 | C87 | 1.0815 | 0.3238 | 0.6395 |
| N38 | 0.8832 | 0.1624 | 0.4564 | C88 | 0.6395 | 0.3717 | 0.0871 |
| N39 | 0.6198 | 0.1729 | 0.1273 | C89 | 0.9221 | 0.3194 | 0.4932 |
| N40 | 0.7167 | 0.1350 | 0.2533 | C90 | 0.5107 | 0.3694 | −0.1081 |
| N41 | 0.5429 | 0.1472 | −0.0401 | C91 | 0.5605 | 0.3350 | −0.0649 |
| N42 | 1.1331 | 0.0855 | 0.6708 | C92 | 0.6021 | 0.2715 | −0.0843 |
| O43 | 0.9140 | 0.1821 | 0.2960 | C93 | 0.5266 | 0.4037 | −0.0538 |
| O44 | 0.8654 | 0.0771 | 0.3382 | C94 | 0.9119 | 0.2659 | 0.1620 |
| C45 | 0.8542 | 0.1720 | 0.3563 | C95 | 0.5911 | 0.4051 | 0.0443 |
| C46 | 0.5876 | 0.1117 | −0.0112 | C96 | 1.1535 | 0.3924 | 0.6738 |
| C47 | 0.6629 | 0.1387 | 0.1561 | C97 | 0.6068 | 0.4429 | 0.0984 |
| C48 | 0.6954 | 0.0688 | 0.1114 | C98 | 0.8832 | 0.3710 | 0.3595 |

TABLE 4-continued

Atomic Coordinates for Example 2c, Base Form H1.75-5

| Atom | X | Y | Z | Atom | X | Y | Z |
|---|---|---|---|---|---|---|---|
| C49 | 0.6512 | 0.1060 | 0.0865 | C99 | 1.0912 | 0.2839 | 0.4757 |
| C50 | 0.5679 | 0.0801 | −0.0813 | C100 | 1.1264 | 0.2872 | 0.5933 |
| C101 | 0.9810 | 0.2861 | 0.2520 | O151 | 0.4292 | 0.1756 | 0.7593 |
| C102 | 0.9190 | 0.4094 | 0.3235 | O152 | 0.3473 | 0.1636 | 0.8339 |
| C103 | 1.0516 | 0.4113 | 0.6921 | H153 | 0.4310 | 0.1254 | 0.2979 |
| C104 | 1.2130 | 0.3807 | 0.7821 | H154 | 0.4349 | 0.1341 | 0.1645 |
| C105 | 1.2167 | 0.4208 | 0.6206 | H155 | 0.2779 | 0.1337 | 0.0447 |
| F106 | 0.6836 | 0.4427 | 0.1806 | H156 | 0.2164 | 0.0417 | 0.2100 |
| F107 | 0.5186 | 0.4543 | 0.1375 | H157 | 0.3714 | 0.0703 | 0.3474 |
| F108 | 0.6281 | 0.4715 | 0.0364 | H158 | −0.0576 | 0.0785 | −0.0868 |
| N109 | 0.3031 | 0.2523 | 0.0895 | H159 | 0.2173 | 0.0675 | −0.0123 |
| N110 | 0.3202 | 0.3294 | 0.1970 | H160 | 0.4992 | 0.0681 | 0.2061 |
| N111 | 0.5022 | 0.3356 | 0.3522 | H161 | 0.2372 | 0.1127 | 0.2569 |
| N112 | 0.0946 | 0.2741 | −0.0674 | H162 | 0.2676 | 0.1594 | 0.2134 |
| N113 | −0.0336 | 0.2377 | −0.1697 | H163 | 0.3639 | 0.0302 | 0.0854 |
| N114 | −0.2016 | 0.2650 | −0.2433 | H164 | 0.4006 | 0.0751 | 0.0350 |
| O115 | 0.1682 | 0.3314 | 0.0829 | H165 | −0.3534 | 0.1727 | −0.2828 |
| O116 | 0.1499 | 0.2237 | 0.1243 | H166 | −0.1099 | 0.0321 | −0.1626 |
| C117 | 0.2052 | 0.2373 | 0.0644 | H167 | 0.0215 | 0.1059 | 0.1611 |
| C118 | 0.2992 | 0.2930 | 0.2475 | H168 | 0.0659 | 0.1539 | 0.1907 |
| C119 | −0.0515 | 0.3401 | −0.0764 | H169 | −0.3750 | −0.0142 | −0.3730 |
| C120 | 0.3416 | 0.2960 | 0.3644 | H170 | −0.0484 | 0.0061 | 0.1467 |
| C121 | −0.1222 | 0.3701 | −0.0923 | H171 | 0.0783 | −0.0115 | 0.2000 |
| C122 | 0.4698 | 0.2615 | 0.2174 | H172 | 0.0297 | 0.0317 | 0.2489 |
| C123 | −0.1737 | 0.2997 | −0.1931 | H173 | −0.4526 | 0.0496 | −0.3983 |
| C124 | −0.0044 | 0.2713 | −0.1206 | H174 | −0.0573 | 0.1673 | −0.1021 |
| C125 | −0.2438 | 0.3311 | −0.2090 | H175 | 0.4770 | −0.0409 | 0.2650 |
| C126 | −0.0754 | 0.3040 | −0.1278 | H176 | 0.3484 | −0.0242 | 0.2146 |
| C127 | 0.1701 | 0.2420 | −0.0535 | H177 | 0.4596 | −0.0045 | 0.1679 |
| C128 | 0.3488 | 0.2578 | 0.2007 | H178 | −0.1282 | 0.1348 | 0.0707 |
| C129 | 0.5097 | 0.2640 | 0.3350 | H179 | −0.0650 | 0.1804 | 0.0686 |
| C130 | 0.4624 | 0.2986 | 0.3883 | H180 | 0.5963 | −0.0009 | 0.3924 |
| C131 | −0.0968 | 0.4077 | −0.0362 | H181 | 0.5930 | 0.0381 | 0.3032 |
| C132 | 0.3460 | 0.2683 | 0.0015 | H182 | 0.5596 | 0.0461 | 0.4284 |
| C133 | −0.1317 | 0.2372 | −0.2271 | H183 | 0.4332 | −0.0251 | 0.4433 |
| C134 | 0.5253 | 0.3677 | 0.4289 | H184 | 0.3902 | 0.0220 | 0.4712 |
| C135 | −0.2190 | 0.3662 | −0.1602 | H185 | 0.3084 | −0.0081 | 0.3820 |
| C136 | 0.2745 | 0.2511 | −0.0941 | H186 | 0.9987 | 0.0754 | 0.5691 |
| C137 | 0.5618 | 0.4023 | 0.3689 | H187 | 0.7487 | 0.1066 | 0.2786 |
| C138 | 0.6152 | 0.3567 | 0.5186 | H188 | 1.1096 | 0.0983 | 0.7400 |
| C139 | 0.4264 | 0.3788 | 0.4754 | H189 | 0.7448 | 0.0641 | 0.1858 |
| C140 | 0.2540 | 0.3461 | 0.1186 | H190 | 0.5192 | 0.0845 | −0.1565 |
| C141 | 0.2900 | 0.3831 | 0.0758 | H191 | 0.5930 | 0.0200 | −0.1086 |
| F142 | 0.0020 | 0.4176 | −0.0257 | H192 | 1.0402 | 0.1792 | 0.4633 |
| F143 | −0.1497 | 0.4372 | −0.0806 | H193 | 1.1791 | 0.0849 | 0.4744 |
| F144 | −0.1239 | 0.4079 | 0.0550 | H194 | 1.1975 | 0.1355 | 0.4619 |
| O145 | 0.4346 | 0.1106 | 0.5123 | H195 | 0.9975 | 0.1890 | 0.6409 |
| O146 | 0.1371 | 0.2037 | 0.3256 | H196 | 0.9825 | 0.1382 | 0.6530 |
| O147 | 0.6629 | 0.2454 | 0.5702 | H197 | 1.0259 | 0.1190 | 0.3726 |
| O148 | 0.4523 | 0.2291 | 0.5970 | H198 | 0.6972 | 0.1932 | 0.2915 |
| O149 | 0.3986 | 0.3042 | 0.6776 | H199 | 1.2687 | 0.1146 | 0.6366 |
| O150 | 0.3459 | 0.1840 | 0.4326 | H200 | 1.1831 | 0.1795 | 0.6123 |
| H201 | 1.1631 | 0.1593 | 0.7328 | H251 | 1.1684 | 0.4299 | 0.5453 |
| H202 | 0.5306 | 0.2029 | 0.0082 | H252 | 0.3950 | 0.3437 | 0.2241 |
| H203 | 0.6519 | 0.1824 | 0.4545 | H253 | 0.5749 | 0.3293 | 0.3230 |
| H204 | 0.6483 | 0.1323 | 0.4245 | H254 | 0.1193 | 0.3022 | −0.0335 |
| H205 | 0.8029 | 0.1216 | 0.5375 | H255 | 0.2147 | 0.2880 | 0.2355 |
| H206 | 0.7957 | 0.1702 | 0.5801 | H256 | 0.0233 | 0.3437 | −0.0249 |
| H207 | 1.3466 | 0.0340 | 0.8006 | H257 | 0.3083 | 0.3215 | 0.3958 |
| H208 | 1.3500 | 0.0795 | 0.7383 | H258 | 0.3160 | 0.2703 | 0.4028 |
| H209 | 1.2843 | 0.0747 | 0.8476 | H259 | 0.5050 | 0.2366 | 0.1841 |
| H210 | 1.2710 | 0.0024 | 0.6388 | H260 | 0.4927 | 0.2878 | 0.1790 |
| H211 | 1.1517 | 0.0185 | 0.5635 | H261 | −0.3192 | 0.3277 | −0.2606 |
| H212 | 1.2687 | 0.0462 | 0.5671 | H262 | 0.1323 | 0.2153 | −0.0854 |
| H213 | 1.1703 | −0.0007 | 0.7926 | H263 | 0.3327 | 0.2320 | 0.2439 |
| H214 | 1.1105 | 0.0421 | 0.8313 | H264 | 0.4885 | 0.2372 | 0.3700 |
| H215 | 1.0556 | 0.0182 | 0.7149 | H265 | 0.5951 | 0.2670 | 0.3470 |
| H216 | 0.7976 | 0.0176 | 0.4203 | H266 | 0.4874 | 0.2957 | 0.4712 |
| H217 | 0.9226 | 0.0100 | 0.4973 | H267 | 0.3419 | 0.2998 | 0.0019 |
| H218 | 0.8269 | 0.0390 | 0.5453 | H268 | 0.4278 | 0.2594 | 0.0040 |
| H219 | 0.7349 | 0.3217 | 0.2190 | H269 | −0.1537 | 0.2100 | −0.2663 |
| H220 | 1.0259 | 0.3684 | 0.4660 | H270 | −0.2738 | 0.3905 | −0.1734 |
| H221 | 1.2052 | 0.3497 | 0.5802 | H271 | 0.3087 | 0.2249 | −0.1215 |
| H222 | 0.7595 | 0.2370 | 0.1705 | H272 | 0.2609 | 0.2719 | −0.1576 |
| H223 | 0.9510 | 0.2576 | 0.4964 | H273 | 0.5805 | 0.4266 | 0.4203 |
| H224 | 0.9305 | 0.2994 | 0.6498 | H274 | 0.6328 | 0.3938 | 0.3368 |
| H225 | 0.9306 | 0.3505 | 0.6365 | H275 | 0.5006 | 0.4101 | 0.3051 |
| H226 | 1.1023 | 0.3226 | 0.7234 | H276 | 0.6311 | 0.3804 | 0.5741 |
| H227 | 0.6892 | 0.3732 | 0.1634 | H277 | 0.5931 | 0.3310 | 0.5600 |
| H228 | 0.8361 | 0.3164 | 0.4802 | H278 | 0.6878 | 0.3500 | 0.4880 |
| H229 | 0.4622 | 0.3687 | −0.1842 | H279 | 0.4455 | 0.4020 | 0.5307 |
| H230 | 0.5955 | 0.2449 | −0.1310 | H280 | 0.3644 | 0.3877 | 0.4139 |
| H231 | 0.4887 | 0.4301 | −0.0865 | H281 | 0.4001 | 0.3535 | 0.5147 |
| H232 | 0.9411 | 0.2373 | 0.1483 | H282 | 0.2315 | 0.3935 | 0.0139 |
| H233 | 0.9065 | 0.2830 | 0.0906 | H283 | 0.3050 | 0.4046 | 0.1373 |
| H234 | 1.1232 | 0.2576 | 0.4474 | H284 | 0.3642 | 0.3778 | 0.0457 |
| H235 | 1.1194 | 0.3088 | 0.4371 | H297 | 0.5031 | 0.1166 | 0.5720 |
| H236 | 1.2129 | 0.2887 | 0.6081 | H298 | 0.4013 | 0.1383 | 0.4827 |
| H237 | 1.1010 | 0.2618 | 0.6307 | H291 | 0.1415 | 0.2116 | 0.2456 |
| H238 | 0.9841 | 0.3173 | 0.2399 | H292 | 0.0561 | 0.1944 | 0.3301 |
| H239 | 1.0614 | 0.2747 | 0.2630 | H285 | 0.7189 | 0.2533 | 0.6386 |
| H240 | 0.8608 | 0.4208 | 0.2603 | H286 | 0.7007 | 0.2488 | 0.5014 |
| H241 | 0.9250 | 0.4304 | 0.3884 | H287 | 0.4531 | 0.2087 | 0.6605 |
| H242 | 0.9943 | 0.4069 | 0.2987 | H288 | 0.5334 | 0.2354 | 0.5869 |
| H243 | 1.0681 | 0.4363 | 0.7411 | H289 | 0.4187 | 0.2763 | 0.6478 |
| H244 | 1.0091 | 0.4217 | 0.6147 | H290 | 0.4459 | 0.3091 | 0.7532 |
| H245 | 1.0017 | 0.3911 | 0.7227 | H293 | 0.3695 | 0.2054 | 0.4921 |
| H246 | 1.2276 | 0.4062 | 0.8315 | H294 | 0.2663 | 0.1913 | 0.3921 |
| H247 | 1.1658 | 0.3601 | 0.8194 | H295 | 0.4701 | 0.1653 | 0.8329 |
| H248 | 1.2882 | 0.3671 | 0.7752 | H296 | 0.4645 | 0.1639 | 0.6962 |
| H249 | 1.2341 | 0.4465 | 0.6673 | H299 | 0.2731 | 0.1523 | 0.8513 |
| H250 | 1.2881 | 0.4078 | 0.6030 | H300 | 0.4117 | 0.1542 | 0.8909 |

TABLE 5

Atomic Coordinates for Example 2e, Base Form E-1

| Atom | X | Y | Z | Atom | X | Y | Z |
|---|---|---|---|---|---|---|---|
| F18 | 0.2662 | 0.4002 | 0.0274 | F23 | 0.0301 | 0.3722 | 0.0039 |
| F19 | 0.0473 | 0.4191 | 0.0033 | C18 | 0.1648 | 0.3165 | 0.0297 |
| F20 | 0.1401 | 0.2386 | 0.0059 | H31 | 0.2375 | 0.5477 | 0.2387 |
| O2 | 0.3035 | 0.7582 | 0.1985 | H41 | 0.5018 | 0.4801 | 0.2585 |
| O28 | 0.4277 | 0.5819 | 0.1087 | H42 | 0.4761 | 0.3850 | 0.2161 |
| N1 | 0.5559 | 0.6627 | 0.1978 | H51 | 0.6480 | 0.5043 | 0.1733 |
| N6 | 0.2412 | 0.4989 | 0.1766 | H52 | 0.7376 | 0.5463 | 0.2204 |
| N8 | 0.0422 | 0.3993 | 0.2139 | H61 | 0.2881 | 0.5282 | 0.1472 |
| N10 | −0.1606 | 0.2714 | 0.1828 | H91 | −0.1519 | 0.3157 | 0.2435 |
| N27 | 0.6744 | 0.6813 | 0.1115 | H111 | −0.2586 | 0.1707 | 0.1140 |
| N29 | 0.9824 | 0.8036 | 0.1064 | H121 | −0.1207 | 0.1964 | 0.0469 |
| C2 | 0.3877 | 0.6687 | 0.2028 | H141 | 0.2343 | 0.4431 | 0.0976 |
| C3 | 0.3235 | 0.5438 | 0.2136 | H211 | 0.5921 | 0.8399 | 0.1984 |
| C4 | 0.4827 | 0.4775 | 0.2252 | H221 | 0.4827 | 0.7942 | 0.1303 |
| C5 | 0.6231 | 0.5426 | 0.2028 | H231 | 0.6846 | 0.8993 | 0.0877 |
| C7 | 0.1130 | 0.4242 | 0.1780 | H232 | 0.6444 | 0.9699 | 0.1348 |
| C9 | −0.0900 | 0.3261 | 0.2139 | H241 | 0.9421 | 0.9813 | 0.1221 |
| C11 | −0.1488 | 0.2295 | 0.1107 | H251 | 1.0517 | 0.8711 | 0.1826 |
| C12 | −0.0761 | 0.2450 | 0.0735 | H252 | 0.8644 | 0.9484 | 0.1930 |
| C13 | 0.0600 | 0.3235 | 0.0687 | H261 | 0.8551 | 0.7433 | 0.2231 |
| C14 | 0.1243 | 0.3844 | 0.1017 | H262 | 0.8872 | 0.6821 | 0.1741 |
| C15 | −0.0857 | 0.2914 | 0.1453 | H271 | 0.8051 | 0.6804 | 0.1028 |
| C16 | 0.0498 | 0.3680 | 0.1409 | H291 | 1.0794 | 0.7695 | 0.1261 |
| C17 | 0.1207 | 0.3503 | 0.0270 | H294 | 0.7893 | 0.5312 | 0.0656 |
| C21 | 0.6470 | 0.7650 | 0.1817 | H292 | 0.6583 | 0.4189 | 0.0854 |
| C22 | 0.6168 | 0.7817 | 0.1361 | H293 | 0.5951 | 0.5011 | 0.0421 |
| C23 | 0.7030 | 0.8953 | 0.1212 | H311 | 0.9885 | 0.9169 | 0.0098 |
| C24 | 0.8922 | 0.8952 | 0.1304 | H312 | 0.8322 | 0.8277 | 0.0324 |
| C25 | 0.9185 | 0.8727 | 0.1765 | H313 | 0.8750 | 0.9701 | 0.0523 |
| C26 | 0.8353 | 0.7590 | 0.1910 | H321 | 1.2632 | 0.9515 | 0.0466 |
| C28 | 0.5782 | 0.5936 | 0.0987 | H322 | 1.1556 | 1.0063 | 0.0897 |
| C29 | 0.6596 | 0.5024 | 0.0711 | H323 | 1.2983 | 0.8878 | 0.0951 |
| C30 | 1.0633 | 0.8393 | 0.0676 | H331 | 1.1943 | 0.7459 | 0.0197 |
| C31 | 0.9326 | 0.8931 | 0.0389 | H332 | 1.2251 | 0.6857 | 0.0690 |
| C32 | 1.2044 | 0.9276 | 0.0745 | H333 | 1.0345 | 0.6616 | 0.0430 |
| C33 | 1.1314 | 0.7245 | 0.0492 | H971 | −0.8355 | 0.1305 | 0.1615 |
| O99 | −0.4402 | 0.1232 | 0.1894 | H972 | −0.7164 | 0.0043 | 0.1747 |
| C97 | −0.7313 | 0.0985 | 0.1797 | H973 | −0.7551 | 0.1157 | 0.2115 |
| C98 | −0.5812 | 0.1608 | 0.1676 | H981 | −0.5951 | 0.2544 | 0.1716 |

TABLE 5-continued

Atomic Coordinates for Example 2e, Base Form E-1

| Atom | X | Y | Z | Atom | X | Y | Z |
|---|---|---|---|---|---|---|---|
| F21 | 0.3052 | 0.3620 | 0.0283 | H982 | −0.5565 | 0.1430 | 0.1349 |
| F22 | 0.1907 | 0.2403 | 0.0143 | H991 | −0.3383 | 0.1855 | 0.1847 |

TABLE 6

Atomic Coordinates for Example 2d, Base Form HAC-1

| Atom | X | Y | Z | Atom | X | Y | Z |
|---|---|---|---|---|---|---|---|
| C1 | 0.0418 | 0.3612 | 0.1413 | H32 | −0.1504 | 0.2133 | 0.0512 |
| N2 | −0.1614 | 0.2566 | 0.1827 | H21 | 0.2024 | 0.4361 | 0.1001 |
| N3 | 0.5574 | 0.6476 | 0.1969 | H19 | −0.2633 | 0.1786 | 0.1141 |
| O4 | 0.4002 | 0.5938 | 0.1104 | H15 | −0.1260 | 0.2877 | 0.2400 |
| N5 | 0.0480 | 0.3793 | 0.2136 | H6 | 0.2703 | 0.5248 | 0.1514 |
| N6 | 0.2349 | 0.4911 | 0.1766 | H14 | 0.2507 | 0.5355 | 0.2354 |
| N7 | 0.6581 | 0.6819 | 0.1120 | H25A | 0.5017 | 0.4595 | 0.2502 |
| O9 | 0.3141 | 0.7518 | 0.2032 | H25B | 0.4643 | 0.3765 | 0.2131 |
| C10 | 0.6548 | 0.7519 | 0.1823 | H22A | 0.6302 | 0.4915 | 0.1724 |
| C11 | 0.1091 | 0.4116 | 0.1779 | H22B | 0.7255 | 0.5203 | 0.2124 |
| C12 | 0.6143 | 0.7805 | 0.1389 | H10 | 0.6208 | 0.8184 | 0.1990 |
| C13 | −0.0977 | 0.2822 | 0.1453 | H12 | 0.4961 | 0.7944 | 0.1361 |
| C14 | 0.3251 | 0.5321 | 0.2128 | H31A | 0.7369 | 0.5221 | 0.0663 |
| C15 | −0.0849 | 0.3037 | 0.2135 | H31B | 0.5607 | 0.5108 | 0.0459 |
| C16 | 0.5496 | 0.5972 | 0.0993 | H31C | 0.6086 | 0.4250 | 0.0815 |
| C17 | 0.8422 | 0.7397 | 0.1888 | H17A | 0.8651 | 0.7215 | 0.2164 |
| N18 | 0.9734 | 0.7976 | 0.1050 | H17B | 0.8826 | 0.6751 | 0.1722 |
| C19 | −0.1674 | 0.2302 | 0.1113 | H23A | 0.6885 | 0.9061 | 0.0978 |
| C20 | 0.0380 | 0.3268 | 0.0698 | H23B | 0.6640 | 0.9626 | 0.1405 |
| C21 | 0.1085 | 0.3827 | 0.1029 | H28A | 0.8869 | 0.9177 | 0.1920 |
| C22 | 0.6188 | 0.5229 | 0.1991 | H28B | 1.0495 | 0.8473 | 0.1796 |
| C23 | 0.7063 | 0.8942 | 0.1260 | H27 | 0.9448 | 0.9635 | 0.1263 |
| C24 | 0.3943 | 0.6572 | 0.2042 | H18 | 1.0626 | 0.7570 | 0.1189 |
| C25 | 0.4808 | 0.4583 | 0.2218 | H39A | 1.2479 | 0.9507 | 0.0498 |
| C27 | 0.8951 | 0.8864 | 0.1321 | H39B | 1.2853 | 0.8792 | 0.0894 |
| C28 | 0.9305 | 0.8535 | 0.1757 | H39C | 1.1647 | 0.9911 | 0.0903 |
| F29 | 0.2449 | 0.4047 | 0.0277 | H38A | 0.9706 | 0.9352 | 0.0175 |
| C30 | 1.0501 | 0.8412 | 0.0669 | H38B | 0.8802 | 0.9740 | 0.0573 |
| C31 | 0.6205 | 0.5052 | 0.0708 | H38C | 0.8310 | 0.8527 | 0.0360 |
| C32 | −0.1018 | 0.2511 | 0.0743 | H40A | 1.1575 | 0.7492 | 0.0195 |
| C33 | 0.1058 | 0.3467 | 0.0300 | H40B | 1.0092 | 0.6805 | 0.0403 |
| F36 | 0.1168 | 0.2494 | 0.0085 | H40C | 1.1861 | 0.6845 | 0.0608 |
| F37 | 0.0041 | 0.4132 | 0.0068 | H7 | 0.7708 | 0.6743 | 0.1022 |
| C38 | 0.9217 | 0.9066 | 0.0421 | H35A | −0.8134 | 0.1022 | 0.1656 |
| C39 | 1.2014 | 0.9229 | 0.0747 | H35B | −0.7586 | 0.1045 | 0.2107 |
| C40 | 1.1073 | 0.7290 | 0.0448 | H35C | −0.7035 | −0.0029 | 0.1830 |
| O8 | −0.4446 | 0.1296 | 0.1963 | H8 | −0.3548 | 0.1817 | 0.1876 |
| C26 | −0.5724 | 0.1491 | 0.1735 | | | | |
| O34 | −0.5673 | 0.2213 | 0.1458 | | | | |
| C35 | −0.7251 | 0.0824 | 0.1840 | | | | |

TABLE 7

Atomic Coordinates for Example 2g, Base Form IPA-1

| Atom | X | Y | Z | Atom | X | Y | Z |
|---|---|---|---|---|---|---|---|
| F1 | 0.1519 | 0.3786 | 0.0243 | H4B | 0.8724 | 0.7912 | 0.1232 |
| F3 | −0.0140 | 0.2540 | −0.0043 | H3 | 0.6171 | 0.6809 | 0.1026 |
| F2 | 0.0260 | 0.4241 | 0.0085 | H1 | 0.1162 | 0.5505 | 0.1460 |
| N4 | 0.8062 | 0.8075 | 0.1016 | H10 | 0.3362 | 0.7935 | 0.1099 |
| N3 | 0.5159 | 0.6834 | 0.1054 | H9 | 0.3991 | 0.8799 | 0.1736 |
| N2 | 0.3481 | 0.7197 | 0.1890 | H6A | 0.4782 | 0.9618 | 0.1051 |
| N1 | 0.0675 | 0.5440 | 0.1700 | H6B | 0.5369 | 0.8805 | 0.0686 |
| N5 | −0.1311 | 0.4643 | 0.2095 | H22 | 0.0665 | 0.4473 | 0.0929 |
| N6 | −0.2941 | 0.3121 | 0.1828 | H5 | 0.7491 | 0.9735 | 0.1042 |
| O1 | 0.1140 | 0.8031 | 0.1697 | H21 | −0.3360 | 0.1865 | 0.1167 |
| O2 | 0.2925 | 0.5779 | 0.1031 | H12A | 0.5507 | 0.4357 | 0.0989 |
| C10 | 0.4463 | 0.7911 | 0.1197 | H12B | 0.6252 | 0.5211 | 0.0660 |
| C9 | 0.4471 | 0.8051 | 0.1677 | H12C | 0.4678 | 0.4565 | 0.0549 |
| C4 | 0.9030 | 0.8194 | 0.0629 | H8A | 0.6698 | 0.7392 | 0.1786 |
| C24 | −0.0632 | 0.3232 | 0.0669 | H8B | 0.6137 | 0.8216 | 0.2153 |
| C19 | −0.0909 | 0.3946 | 0.1378 | H16 | 0.0302 | 0.6334 | 0.2243 |
| C6 | 0.5348 | 0.8912 | 0.0992 | H13A | 0.4882 | 0.6277 | 0.2283 |
| C20 | −0.2139 | 0.3158 | 0.1454 | H13B | 0.4421 | 0.5607 | 0.1863 |
| C11 | 0.4342 | 0.5879 | 0.0964 | H3B | 0.9771 | 0.9859 | 0.0712 |
| C22 | −0.0159 | 0.3962 | 0.0980 | H3C | 1.0944 | 0.9144 | 0.0431 |
| C5 | 0.7048 | 0.9021 | 0.1156 | H3D | 1.0915 | 0.8973 | 0.0926 |
| C17 | −0.0508 | 0.4684 | 0.1726 | H23 | −0.2112 | 0.1922 | 0.0537 |
| C21 | −0.2559 | 0.2399 | 0.1123 | H18 | −0.3052 | 0.3848 | 0.2368 |
| C14 | 0.1869 | 0.7250 | 0.1863 | H2A | 0.7158 | 0.7853 | 0.0234 |
| C12 | 0.5279 | 0.4917 | 0.0774 | H2B | 0.8604 | 0.8380 | −0.0010 |
| C8 | 0.6155 | 0.8107 | 0.1847 | H2C | 0.7518 | 0.9169 | 0.0270 |
| C16 | 0.1187 | 0.6161 | 0.2052 | H7A | 0.6551 | 0.9825 | 0.1718 |
| C13 | 0.4041 | 0.6134 | 0.2080 | H7B | 0.8129 | 0.9118 | 0.1736 |
| C3 | 1.0281 | 0.9129 | 0.0679 | H1A | 1.0319 | 0.6803 | 0.0846 |
| C23 | −0.1824 | 0.2437 | 0.0749 | H1B | 1.0662 | 0.7077 | 0.0366 |
| C18 | −0.2485 | 0.3861 | 0.2114 | H1C | 0.9087 | 0.6458 | 0.0495 |
| C2 | 0.7981 | 0.8420 | 0.0246 | H15A | 0.2542 | 0.5916 | 0.2593 |
| C7 | 0.7045 | 0.9108 | 0.1635 | H15B | 0.2564 | 0.4841 | 0.2288 |
| C1 | 0.9852 | 0.7023 | 0.0579 | H3A | −0.4990 | 0.1985 | 0.1863 |
| C15 | 0.2577 | 0.5672 | 0.2298 | H27 | −0.6926 | 0.2734 | 0.1759 |
| C25 | 0.0153 | 0.3263 | 0.0246 | H26A | −0.7745 | 0.0861 | 0.1320 |
| F4 | 0.1640 | 0.2980 | 0.0315 | H26B | −0.6492 | 0.1771 | 0.1173 |
| F5 | −0.0739 | 0.3770 | −0.0036 | H26C | −0.8259 | 0.2136 | 0.1243 |
| F6 | 0.0440 | 0.2214 | 0.0112 | H28A | −0.8028 | 0.1216 | 0.2237 |
| O3 | −0.5666 | 0.1486 | 0.1890 | H28B | −0.9203 | 0.1527 | 0.1868 |
| C27 | −0.7093 | 0.1903 | 0.1763 | H28C | −0.8515 | 0.2497 | 0.2160 |
| C26 | −0.7420 | 0.1648 | 0.1343 | | | | |
| C28 | −0.8290 | 0.1780 | 0.2024 | | | | |
| C29 | −0.8460 | 0.1070 | 0.1744 | | | | |
| C30 | −0.6990 | 0.2550 | 0.1410 | | | | |

TABLE 8

Atomic Coordinates for Example 2f, Base Form RPG-3

| Atom | X | Y | Z | Atom | X | Y | Z |
|---|---|---|---|---|---|---|---|
| F1 | 1.4700 | 0.5720 | 0.6614 | N2 | 0.6350 | 0.3813 | 0.3765 |
| F7 | 1.4119 | 0.5575 | 0.7000 | N6 | 0.2687 | 0.8628 | 0.3992 |
| F2 | 1.4315 | 0.5398 | 0.7741 | N4 | 0.3398 | 0.7349 | 0.3149 |
| F8 | 1.5600 | 0.5336 | 0.8131 | N1 | 0.8898 | 0.3354 | 0.4598 |
| F3 | 1.6320 | 0.5630 | 0.7860 | N5 | 0.0527 | 0.9107 | 0.3489 |
| F9 | 1.6111 | 0.5864 | 0.6960 | C12 | 0.4202 | 0.2078 | 0.3911 |
| N9 | 0.7997 | −0.0295 | 0.8348 | O1 | 0.6129 | 0.7507 | 0.2839 |
| N8 | 0.7989 | 0.1232 | 0.9974 | C10 | 0.7273 | 0.4981 | 0.3447 |
| N11 | 1.1628 | −0.0946 | 0.6829 | C6 | 0.8597 | 0.4735 | 0.3332 |
| N10 | 1.0937 | 0.0679 | 0.7424 | C9 | 0.7661 | 0.6239 | 0.4071 |
| N7 | 0.5331 | 0.0253 | 1.0441 | C20 | 0.1173 | 0.7695 | 0.2548 |
| N12 | 1.3802 | −0.0414 | 0.6342 | C19 | 0.0264 | 0.8385 | 0.2716 |
| O3 | 0.8190 | 0.0931 | 0.7142 | C5 | 0.9561 | 0.4627 | 0.4193 |
| O4 | 1.0177 | 0.2159 | 0.9737 | C17 | 0.2435 | 0.7914 | 0.3234 |
| C34 | 0.7187 | 0.1296 | 0.9094 | C8 | 0.8573 | 0.6109 | 0.4957 |

TABLE 8-continued

Atomic Coordinates for Example 2f, Base Form RPG-3

| Atom | X | Y | Z | Atom | X | Y | Z |
|---|---|---|---|---|---|---|---|
| C45 | 1.3119 | 0.1383 | 0.6926 | O2 | 0.4273 | 0.3887 | 0.2980 |
| C37 | 0.6769 | 0.0002 | 0.8509 | C24 | −0.0460 | 0.6680 | 0.1174 |
| C30 | 0.4799 | 0.0412 | 0.9508 | C16 | 0.4606 | 0.7449 | 0.3864 |
| C42 | 1.1869 | 0.0349 | 0.7058 | C22 | 0.0802 | 0.6875 | 0.1776 |
| C31 | 0.5850 | 0.1596 | 0.9161 | C14 | 0.5786 | 0.7190 | 0.3544 |
| C49 | 1.4737 | 0.3643 | 0.7029 | C7 | 0.9892 | 0.5850 | 0.4828 |
| C33 | 0.5750 | −0.1179 | 0.8869 | C23 | −0.1359 | 0.7367 | 0.1342 |
| C47 | 1.3487 | 0.2751 | 0.7153 | C18 | 0.1707 | 0.9200 | 0.4061 |
| C40 | 0.8584 | 0.0198 | 0.7679 | C25 | −0.0848 | 0.5788 | 0.0372 |
| C32 | 0.4447 | −0.0846 | 0.8933 | C13 | 0.5736 | 0.6259 | 0.4906 |
| C41 | 0.9773 | −0.0327 | 0.7663 | C21 | −0.1010 | 0.8179 | 0.2096 |
| C39 | 1.0115 | −0.0750 | 0.8618 | C4 | 0.9438 | 0.1985 | 0.3554 |
| C35 | 0.9405 | 0.1730 | 1.0250 | C3 | 0.9469 | 0.2256 | 0.4509 |
| C38 | 0.8681 | −0.1166 | 0.8863 | C15 | 0.4317 | 0.6466 | 0.4565 |
| C28 | 0.4760 | 0.0765 | 1.1130 | C2 | 1.0956 | 0.2572 | 0.5066 |
| C43 | 1.2625 | −0.1234 | 0.6483 | C11 | 0.4953 | 0.3347 | 0.3508 |
| C44 | 1.4064 | 0.0935 | 0.6556 | C1 | 0.8466 | 0.1026 | 0.4843 |
| C46 | 1.5338 | 0.1870 | 0.6430 | F4 | −0.1040 | 0.4554 | 0.0598 |
| C48 | 1.5649 | 0.3202 | 0.6666 | F5 | 0.0211 | 0.6100 | −0.0030 |
| C36 | 1.0000 | 0.1703 | 1.1211 | F6 | −0.1869 | 0.5900 | −0.0238 |
| C29 | 0.5552 | 0.0482 | 1.2020 | F10 | −0.2221 | 0.5070 | 0.0190 |
| C27 | 0.3192 | 0.0052 | 1.1006 | F11 | −0.0370 | 0.4791 | 0.0400 |
| C26 | 0.5156 | 0.2276 | 1.1108 | F12 | −0.0360 | 0.6334 | −0.0302 |
| C50 | 1.5103 | 0.5068 | 0.7292 | O7 | 0.3015 | 0.5242 | 0.1820 |
| N3 | 0.6420 | 0.6560 | 0.4169 | O8 | 0.5067 | 0.7155 | 0.1016 |
| C55 | 0.4573 | 0.5719 | 0.0792 | H12C | 0.3410 | 0.1518 | 0.3473 |
| C56 | 0.3131 | 0.5089 | 0.0936 | H10A | 0.6770 | 0.5138 | 0.2867 |
| C54 | 0.4592 | 0.5517 | −0.0152 | H6A | 0.8326 | 0.3912 | 0.2958 |
| O5 | 1.1135 | 0.3136 | 0.8309 | H6B | 0.9113 | 0.5467 | 0.3027 |
| O6 | 0.9224 | 0.3638 | 0.6775 | H9 | 0.8236 | 0.6994 | 0.3801 |
| C52 | 0.9658 | 0.4383 | 0.7607 | H95 | 1.0446 | 0.4603 | 0.4067 |
| C53 | 1.0998 | 0.4403 | 0.8150 | H8B | 0.8035 | 0.5371 | 0.5249 |
| C51 | 0.9706 | 0.5801 | 0.7445 | H8C | 0.8845 | 0.6928 | 0.5336 |
| H8 | 0.7521 | 0.0843 | 1.0354 | H16 | 0.4967 | 0.8363 | 0.4153 |
| H10 | 1.1043 | 0.1515 | 0.7516 | H22 | 0.1413 | 0.6448 | 0.1660 |
| H34 | 0.7767 | 0.2034 | 0.8813 | H7A | 1.0479 | 0.6636 | 0.4601 |
| H37 | 0.6246 | 0.0147 | 0.7931 | H77B | 1.0425 | 0.5720 | 0.5399 |
| H30 | 0.3926 | 0.0620 | 0.9462 | H23 | −0.2199 | 0.7261 | 0.0931 |
| H31A | 0.5395 | 0.1776 | 0.8580 | H18 | 0.1897 | 0.9731 | 0.4584 |
| H31B | 0.6110 | 0.2396 | 0.9557 | H13A | 0.6288 | 0.6865 | 0.5425 |
| H33A | 0.5480 | −0.1985 | 0.8476 | H13B | 0.5604 | 0.5340 | 0.5057 |
| H33B | 0.6213 | −0.1349 | 0.9450 | H21 | −0.1626 | 0.8605 | 0.2204 |
| H47 | 1.2884 | 0.3066 | 0.7391 | H4A | 0.8479 | 0.1679 | 0.3217 |
| H32A | 0.3953 | −0.0742 | 0.8343 | H4B | 0.9856 | 0.1305 | 0.3502 |
| H32B | 0.3818 | −0.1587 | 0.9172 | H4C | 0.9960 | 0.2797 | 0.3330 |
| H41 | 0.9434 | −0.1120 | 0.7240 | H15A | 0.3587 | 0.5626 | 0.4312 |
| H39A | 1.0471 | −0.1496 | 0.8633 | H15B | 0.4034 | 0.6838 | 0.5038 |
| H39B | 1.0801 | −0.0006 | 0.9013 | H2A | 1.1552 | 0.3410 | 0.4913 |
| H38A | 0.8152 | −0.2110 | 0.8689 | H2B | 1.1310 | 0.1867 | 0.4955 |
| H38B | 0.8786 | −0.0998 | 0.9495 | H2C | 1.0948 | 0.2640 | 0.5683 |
| H43 | 1.2434 | −0.2140 | 0.6327 | H1A | 0.8496 | 0.1213 | 0.5456 |
| H46 | 1.5955 | 0.1582 | 0.6190 | H1B | 0.8758 | 0.0261 | 0.4785 |
| H48 | 1.6483 | 0.3822 | 0.6582 | H1C | 0.7522 | 0.0839 | 0.4497 |
| H36A | 1.0650 | 0.1213 | 1.1285 | H99 | 0.9009 | 0.3500 | 0.5070 |
| H36B | 0.9249 | 0.1270 | 1.1498 | H7 | 0.3628 | 0.5029 | 0.2157 |
| H36C | 1.0484 | 0.2607 | 1.1471 | H8A | 0.5335 | 0.7307 | 0.1555 |
| H29A | 0.5101 | −0.0427 | 1.2144 | H55 | 0.5214 | 0.5322 | 0.1164 |
| H29B | 0.5546 | 0.1090 | 1.2479 | H56A | 0.2502 | 0.5475 | 0.0555 |
| H29C | 0.6509 | 0.0606 | 1.1995 | H56B | 0.2814 | 0.4136 | 0.0755 |
| H27A | 0.2727 | 0.0063 | 1.0399 | H54A | 0.4034 | 0.5980 | −0.0510 |
| H27B | 0.2829 | 0.0501 | 1.1386 | H54B | 0.4208 | 0.4574 | −0.0335 |
| H27C | 0.3022 | −0.0863 | 1.1155 | H54C | 0.5546 | 0.5867 | −0.0221 |
| H26A | 0.6150 | 0.2666 | 1.1142 | H5 | 1.0835 | 0.2863 | 0.8748 |
| H26B | 0.4925 | 0.2636 | 1.1602 | H6 | 0.9213 | 0.2865 | 0.6847 |
| H26C | 0.4641 | 0.2486 | 1.0564 | H52 | 0.8933 | 0.3997 | 0.7941 |
| H100 | 0.5160 | −0.0550 | 1.0510 | H53A | 1.1740 | 0.4907 | 0.7866 |
| H2 | 0.6741 | 0.3386 | 0.4153 | H53B | 1.1148 | 0.4884 | 0.8717 |
| H4 | 0.3295 | 0.6914 | 0.2656 | H51A | 1.0458 | 0.6226 | 0.7158 |
| H12A | 0.3879 | 0.2319 | 0.4404 | H51B | 0.9866 | 0.6294 | 0.8002 |
| H12B | 0.4843 | 0.1597 | 0.4113 | H51C | 0.8826 | 0.5788 | 0.7073 |

TABLE 9

Characteristic powder x-ray diffraction peak positions
(degrees 2θ ± 0.1) @ RT for Examples 2a, b, d,
c, d, e, f, and g based on a high quality pattern collected
with a diffractometer (CuKα) with a spinning capillary
with 2θ calibrated with a NIST other suitable standard

| Exp 2a | Exp 2b | Exp 2c | Exp 2d | Exp 2e | Exp 2f | Exp 2g |
|---|---|---|---|---|---|---|
| 5.2 | 5.5 | 5.1 | 5.3 | 5.4 | 6.3 | 6.9 |
| 7.9 | 9.1 | 6.9 | 9.6 | 9.4 | 9.0 | 8.7 |
| 17.1 | 12.1 | 7.4 | 13.7 | 11.2 | 11.7 | 9.8 |
| 17.6 | 14.0 | 10.2 | 14.7 | 13.7 | 15.0 | 10.3 |
| 19.6 | 19.2 | 18.0 | 19.5 | 19.1 | 17.6 | 11.8 |

Comparative Pharmacological Characteristics

Assays and data comparing the pharmacological characteristics of Example 1 and compounds found in WO2005021500 (corresponding to U.S. Pat. No. 7,163,937, assigned to present Applicant) are presented below.

Human Peripheral Blood Mononuclear Cell Binding ("CCR2 Binding")

See e.g. Yoshimura et al., *J. Immunol.* 1990, 145, 292. The human CCR2 binding assay was established with human peripheral blood mononuclear cells (hPBMCs) using $^{125}$I-human MCP-1 as the tracer ligand. hPBMCs were isolated from human leukopak (Biological Specialty Inc.) using a standard protocol with Ficoll-Hypaque (Mediatech Cellgro). Isolated hPBMCs were washed and diluted to $1\times10^7$/ml in binding buffer (RPMI-1640, 0.1% BSA, 20 mM Hepes, pH 7.4). $^{125}$I-MCP-1 (NEN/Perk Elmer) was diluted to 0.45 nM in binding buffer. The compound was diluted in binding buffer at 3-fold the final concentrations used in the binding assay. The binding assay was performed using a 96-well filter plate (Millipore). Total $^{125}$I-MCP-1 binding was assessed as follows: to each reaction of a total volume of 150 µl were added $5\times10^5$ cells, 0.15 nM $^{125}$I-MCP-1, and compound such that the final concentration ranged from 0 to 100 nM. The plate was incubated at room temperature for 30 minutes followed by three washes with RPMI-1640, 0.1% BSA, 0.4 M NaCl, 20 mM Hepes, pH 7.4 using a vacuum manifold filtration (Millipore). After washing, the plate was air-dried for 60 minutes at room temperature. This was followed by adding 25 µl of Microscint 20 into each well. The plate was sealed and counted on the Trilux for 1 minute. Non-specific binding was determined in the presence of 300 nM cold MCP-1 (Pepro-Tech Inc.). Specific $^{125}$I-MCP-1 was calculated as the difference between total and non-specific binding. All conditions were tested in duplicate. The IC50 is defined as the concentration of competing compound required to reduce specific binding by 50%.

hERG Flux

HEK293 cells stably-expressing hERG channels were grown (37° C., 5% $CO_2$) in Dulbecco's Modified Eagle's Media supplemented with 10% Sigma fetal bovine serum, non-essential amino acids, 2 mM L-glutamine and 500 µg/ml G418, at incubator. Cell dissociation buffer was used to extract the cells from flasks, which were then plated into 384-well Corning poly-D-lysine coated black/clear plates at a density of $2\times10^4$ cells per well (20 µl) in 10% serum media, and incubated for 15-24 hours at 37° C. in a 5% $CO_2$ incubator until a confluent monolayer of cells was obtained.

A 2 mM stock of BTC-AM dye (Molecular Probes, Eugene, Oreg.) was prepared in 100% DMSO and then added 1:1 to 10% (w/v) pluronic acid in DMSO on the day of assay. The dye was then diluted in hERG external EP buffer (140 mM NaCl, 4.0 mM KCl, 1.8 mM $CaCl_2$, 1.0 mM $MgCl_2$, 10 mM HEPES, pH 7.3 and 10 mM glucose; all buffer components obtained from Sigma Chemical). This BTC dye mixture (30 µl) was added to the cells and produced a final loading concentration of 2.5 µM. Cells are incubated at 21° C. for 45 minutes.

Test compounds were diluted to 10 mM DMSO in 60 µl. These compounds were then serially-diluted at a 1:2 ratio in DMSO in columns 1-10 and 11-20 of a 384-well plate. Assay-ready plates were generated by stamping 2.5 µl from the DMSO serially diluted plate, which was prepared on the Velocity 11 BioCel. Aqueous plates were created by adding 48 µl of EP buffer and then were diluted 30-45 minutes before the assay was read on the FLIPR. After dye loading, aqueous-diluted compounds were added to the cells of the three replicate plates (10 µl) yielding a ten point concentration range of 80 µM to 0.156 nM. Final DMSO concentration in the assay is 1%. Assay-ready aqueous plates were prepared and diluted on a Cybio liquid handler.

Cells loaded with dye were read on the FLIPR384 (Molecular Devices, Sunnyvale, Calif.), which excites the dye using the 488 nm line of an argon laser. Emission was filtered using a 540±30 nm bandpass filter. hERG channels are stimulated to open by the addition of 20 µl/well EP buffer containing 66 mM $K_2SO_4$ and 1.3 mM $Tl_2SO_4$ (Sigma/Aldrich). For each plate, data were collected every second for a period of 12 seconds, at which time the $Tl^+$-containing stimulus buffer was added. Data collection proceeded every second for 48 seconds, and then continued every three seconds for an additional 2 minutes.

The dynamic range of the assay was determined from blanks and totals wells. The totals wells (columns 21 and 22) define maximal hERG activation for the plate (no test compound present), and the blanks wells (columns 23 and 24) define 100% hERG inhibition. The blanks wells contain 400 nM of either of the standard hERG inhibitors dofetilide (Ficker et al., 1998) or E-4031. Raw data points in each sample well were first corrected for cell/signal variation, negative control (blanks) background, and normalized to the positive controls (totals) using the online FLIPR software. Test compound concentration response curves for the hERG $Tl^+$ flux data were then fit using Excel Fit (ID Business Solutions Limited, Surrey, UK) with a single-site logistic equation, $Y=A+((B-A)/1+((C/X)^\wedge D)))$ where A=maximal inhibition. Data were analyzed by fitting maximum amplitudes of change in fluorescence for $Tl^+$ flux for a given condition of test compound. Potencies ($IC_{50}$ values) of compounds were calculated from the average of triplicate wells.

Sodium Channel, Site 2 Binding Assay

See also: W. A. Catterall, et al. *J. Biol. Chem.* 1981, 256, 8922. The standard binding buffer contained 50 mM HEPES, 50 mM Tris-HCl, pH 7.4, 130 mM Choline Chloride, 5.4 mM KCl, 0.8 mM $MgCl_2$, 5.5 mM glucose, 40 µg/mL LqT. Binding reactions were initiated by adding synaptosomes (prepared from Wistar rat brain) to the reaction mixture containing 5 nM [$^3$H]-Batrachotoxin in a standard binding buffer and the compound to be tested at the desirable concentration. Samples were then mixed and incubated at 37° C. for 60 minutes. The reactions were stopped by adding ice-cold washing buffer containing 50 mM HEPES, 50 mM Tris-HCl, pH 7.4, 1.8 mM $CaCl_2$, 0.8 mM $MgCl_2$ and 1 mg/mL bovine serum albumin. The synaptosomes were immediately collected onto glass fiber filters and washed 3 times with washing buffers. The radioactivity of [$^3$H]-Batrachotoxin remaining on the filters was counted using liquid scintillation spectrometers.

Parallel Artificial Membrane Permeability Assay (PAMPA)

The Parallel Artificial Membrane Permeability Assay (PAMPA) consists of a specially formulated lecithin-based lipid combination referred to as the gastrointestinal tract (GIT) lipid. The GU lipid is used to form a membrane in a sandwich plate assembly similar to that used in the Caco-2 assays. The GIT lipid closely resembles in vivo membrane composition and performance as measured by standard compounds that are known to be passively absorbed in humans. PAMPA is widely used as an in vitro model for permeability screening of discovery compounds. The rate of passage of compounds through the PAMPA membrane is used to determine a permeability coefficient (Pc), which can be related to the in vivo passive permeability of the compound.

The permeability coefficient (Pc) of a particular compound is examined in a pH-dependent setting with apical and basolateral pH of 7.4. All experiments are conducted in triplicate determinations.

Compounds (10 mM stocks in 100% DMSO) were diluted 1:100 in pH 7.4 donor well buffer (pION CAT #110151), providing a 100 µM assay solution in 1% DMSO. Compound diluted in donor well buffer was transferred to a Whatman Unifilter plate and filtered prior to dispensing 200 µl into the donor well of the assay plate (pION CAT #110163). The PAMPA membrane was formed by pipetting 4 µl of the lipid solution (pION CAT #110169) onto the filter plate (VWR CAT #13503). The membrane was then covered with 200 µl of acceptor well buffer at pH 7.4 (pION CAT #110139). The PAMPA assay plate (donor side and acceptor side) was combined and allowed to incubate at room temperature for 4 hours. The plate was then disassembled and spectrophotometer plates (VWR CAT #655801) were filled (150 µl/well). The donor, acceptor, reference, and blank plates were read in the SpectraMax UV plate reader. Data was captured by the pION software, which analyzes the spectra and generates Pc values.

CCR2 Chemotaxis

The human CCR2 chemotaxis assay was conducted with the human monocytic cell line, THP-1. THP-1 cells were first labeled with the fluorescent dye Calcein-AM in phenol red-free, BSA-free RPMI-1640 (pH 7.4) at 37° C. for 30 minutes with gentle mixing every 15 minutes. The labeled cells were then washed and re-suspended at $1\times10^5$/ml in chemotaxis buffer (phenol red-free RPMI-1640, 0.1% BSA, pH 7.4). The test compound was diluted in chemotaxis buffer such that the final assay concentration ranged from 0.01 nM to 1 µM. The ligand MCP-1 (PeproTech Inc.) was diluted to 20 nM in chemotaxis buffer. To perform the assay, an equal volume of test compound dilutions was mixed with an equal volume of labeled THP-1 cells (Mixture 1), and an equal volume of test compound dilutions was mixed with an equal volume of diluted MCP-1 ligand (Mixture 2). Both mixtures were incubated independently at 37° C. for 10 minutes followed by gentle mixing. MCP-1-induced chemotaxis was then measured in a chemotaxis plate (Becton Dickinson) by placing 50 µl of Mixture 1 in the top chamber and 225 µl of Mixture 2 in the bottom chamber. The plate was covered with a lid and incubated at 37° C. for 30 minutes. 30 minutes later, the plate was read on a Cytofluor. All conditions were tested in duplicate. For signal to noise determination, 50 µl of labeled THP-1 cells alone ($5\times10^4$/well) were placed into the top chamber and 225 µl of ligand MCP-1 alone was placed in the bottom chamber (final concentration of 10 nM). The inhibition achieved by graded concentrations of test compound was calculated as a percentage of the compound-free MCP-1 control. The IC50 is defined as the concentration of test compound required to reach 50% inhibition of cellular chemotaxis.

hERG Patch Clamp

Whole-cell patch-clamp was used to directly measure hERG currents in HER-293 cells stably expressing the cloned hERG potassium channel α subunit. The compound was tested in an aqueous buffer with pH 7.4 at room temperature. Repetitive test pulses (0.05 Hz) were applied from a holding potential of −80 mV to +20 mV for 2 seconds and tail currents were elicited following the test pulses by stepping the voltage to −65 mV. The effects from the compound were calculated by measuring inhibition of peak tail current Sodium Channel Patch Clamp Whole-cell patch-clamp was used to directly measure inward sodium currents in HEK-293 cells expressing the human cardiac sodium channel, SCN5A. The compound was tested at a protein-free aqueous buffer. For determining steady state inhibition, sodium currents were elicited every 5 seconds using the following voltage protocol: cells were held at a potential of −90 mV and stepped to −20 mV for 60 ms. Effects were calculated by measuring inhibition of peak current during the test pulse to −20 mV. Rate-dependence of inhibition was assessed by stimulation at frequencies of 1 Hz and 4 Hz.

Single-Dose Pharmacokinetics in Rats

Male Sprague-Dawley rats (250-300 g) were used for the pharmacokinetic studies. Rats were fasted overnight prior to PO dosing and fed 4 h post dose. Blood samples (~0.3 mL) were collected from the jugular vein into $K_2$EDTA-containing tubes and then centrifuged at 4° C. (1500-2000×g) to obtain plasma. In an oral bioavailability study, 2 groups of animals (N=2-3 per group) received the test compound either as an intravenous (IV) infusion (over 10 min) via the jugular vein or by oral gavage. Serial blood samples were obtained at 0.17 (for IV only), 0.25, 0.5, 0.75, 1, 2, 4, 6, 8, and 24 h post dose. Plasma samples, obtained by centrifugation at 4° C. (1500-2000×g), were stored at −20° C. until analysis by LC/MS/MS.

Single-Dose Pharmacokinetics in Monkeys

The pharmacokinetics of various test compounds were evaluated in male Cynomolgus monkeys in a crossover-design. Monkeys were fasted overnight prior to PO dosing and fed 4 h post dose. A group of 1-3 animals (3 to 5 kg) received the compound by IV infusion (over 10 min) via a femoral vein and by oral gavage, with a 1-week washout between treatments. Serial blood samples (~0.3 mL) were collected from a femoral artery at 0.17 (IV only), 0.25, 0.5, 0.75, 1, 2, 4, 6, 8, and 24 h post dose, and centrifuged at 4° C. (1500-2000×g) to obtain plasma. Samples were stored at −20° C. until analysis by LC/MS/MS.

Data Analysis for Pharmacokinetic Assays

The pharmacokinetic parameters were obtained by non-compartmental analysis of plasma concentration vs. time data (KINETICA™ software, Version 4.2, InnaPhase Corporation, Philadelphia, Pa.). The peak concentration (Cmax) and time for Cmax were recorded directly from experimental observations. The area under the curve from time zero to the last sampling time (AUC(0-T)) was calculated using a combination of linear and log trapezoidal summations. The total plasma clearance (CLTp), steady-state volume of distribution (Vss), apparent elimination half-life (T1/2) and mean residence time (MRT) were estimated after IV administration. Estimations of T1/2 was made using a minimum of 3 time points with quantifiable concentrations. The absolute oral bioavailability (F) was estimated as the ratio of dose-normalized AUC values following oral and IV doses.

Find below data for each compound as measured in the assays described above.

TABLE 10

Comparative In Vitro Data

| Compound | CCR2 Binding $IC_{50}$ (nM) | hERG FLUX $IC_{50}$ (nM) | $Na^+$ channel binding (% inhibition) | PAMPA permeability (nm/sec) |
|---|---|---|---|---|
| Example 12as, WO2005021500 | 0.27 (1) | 2,800 | Not available | Not available |
| Example 12aj WO2005021500 | 0.43 ± 0.06 (2) | 770 | Not available | Not available |
| Example 2k WO2005021500 | 0.88 ± 0.60 (23) | 51,000 | 97%, 10,000 nM | 529 ± 157 (9) |
| Example 12bd WO2005021500 | 1.15 ± 0.07 (2) | >80,000 | 54%, 10,000 nM | 392 |
| Example 8a WO2005021500 | 1.83 ± 0.80 (12) | >80,000 | 3%, 10,000 nM<br>33%, 30,000 nM | 94 ± 58 (10) |
| Example 8e, WO2005021500 | 2.20 ± 0.03 (2) | >80,000 | 6%, 10,000 nM | 2 ± 2 (2) |
| Example 9c, WO2005021500 | 0.96 ± 0.26 (19) | >80,000 | 48%, 10,000 nM<br>75%, 30,000 nM | 145 ± 71 (8) |
| Example 1 Present Invention | 2.74 ± 1.34 (15) | >80,000 | 13%, 10,000 nM<br>32%, 30,000 nM | 560 ± 86 (5) |

TABLE 11a

Additional Comparative In Vitro Data

| Compound | CCR2 Chemotaxis $IC_{50}$ (nM) | hERG patch clamp (% Inhib.) | $Na^+$ channel patch clamp (% Inhib.) |
|---|---|---|---|
| Example 2k WO2005021500 | 0.24 ± 0.16 (12) | 83%, 10,000 nM | 52%, 10,000 nM<br>90%, 30,000 nM |
| Example 8a WO2005021500 | 2.63 ± 1.24 (4) | 4%, 10,000 nM | 22%, 10,000 nM<br>49%, 30,000 nM |
| Example 9c, WO2005021500 | 0.21 | 4%, 10,000 nM | 19%, 10,000 nM<br>39%, 30,000 nM |
| Example 1, Present Invention | 0.75 ± 0.42 (16) | 12%, 10,000 nM<br>19%, 30,000 nM | 29%, 30,000 nM |

TABLE 11b

Comparative In Vivo Pharmacokinetic Data in the Rat

| Compound | Dose IV/PO (mg/kg) | Cl (mL/min/kg) | F % | Oral AUC (nM*h) |
|---|---|---|---|---|
| Example 2k WO2005021500 | 2.5/25 | 40 | 68 | 9294 |
| Example 8a WO2005021500 | 6/72 | 42 | 1.4 | 690 |
| Example 9c, WO2005021500 | 4/43 | 54 | 14 | 1855 |
| Example 1, Present Invention | 2/10 | 25 | 79 | 10169 |

TABLE 11c

Comparative In Vivo Pharmacokinetic Data in the Monkey

| Compound | Dose IV/PO (mg/kg) | Cl (mL/min/kg) | F % | Oral AUC (nM*h) |
|---|---|---|---|---|
| Example 2k WO2005021500 | 1/1.4 | 25 | 46 | 862 |
| Example 8a WO2005021500 | 1/11 | 14 | 9.4 | 1896 |

TABLE 11c-continued

Comparative In Vivo Pharmacokinetic Data in the Monkey

| Compound | Dose IV/PO (mg/kg) | Cl (mL/min/kg) | F % | Oral AUC (nM*h) |
|---|---|---|---|---|
| Example 9c, WO2005021500 | 1/10 | 12 | 26 | 6763 |
| Example 1, Present Invention | 1/1 | 12 | 95 | 2352 |

Utility

Representative compounds of the examples are shown to be modulators of chemokine receptor activity using assays know by those skilled in the art. In this section, we describe such assays and give their literature reference. More assays are described herein in the section titled "Comparative Pharmacological Characteristics", supra. By displaying activity in these assays of MCP-1 antagonism, compounds of the examples are expected to be useful in the treatment of human diseases associated with chemokines and their cognate receptors. The definition of activity in these assays is a compound demonstrating an $IC_{50}$ of 30 µM or lower in concentration when measured in a particular assay.

Antagonism of MCP-1 Binding to Human PBMC
(Yoshimura et al., *J. Immunol.* 1990, 145, 292)

At least one compounds described in the examples have activity in the antagonism of MCP-1 binding to human PBMC (human peripheral blood mononuclear cells) described here.

Millipore filter plates (#MABVN1250) are treated with 100 µl of binding buffer (0.5% bovine serum albumin, 20 mM HEPES buffer and 5 mM magnesium chloride in RPMI 1640 media) for thirty minutes at room temperature. To measure binding, 50 µl of binding buffer, with or without a known concentration compound, is combined with 50 µl of $^{125}I$ labeled human MCP-1 (to give a final concentration of 150 pM radioligand) and 50 µl of binding buffer containing $5\times10^5$ cells. Cells used for such binding assays can include human peripheral blood mononuclear cells isolated by Ficoll-Hypaque gradient centrifugation, human monocytes (Weiner et al., *J. Immunol. Methods.* 1980, 36, 89), or the THP-1 cell line which expresses the endogenous receptor. The mixture of compound, cells and radioligand are incubated at room temperature for thirty minutes. Plates are placed onto a vacuum manifold, vacuum applied, and the plates washed three times with binding buffer containing 0.5M NaCl. The plastic skirt is removed from the plate, the plate allowed to air dry, the wells punched out and counted. The percent inhibition of binding is calculated using the total counts obtained in the absence of any competing compound and the background binding determined by addition of 100 nM MCP-1 in place of the test compound.

Antagonism of MCP-1-Induced Calcium Influx
(Sullivan, et al. *Methods Mol. Biol.*, 114, 125-133 (1999))

At least one compounds described in the examples have activity in the antagonism of MCP-1-induced calcium influx assay described here.

Calcium mobilization is measured using the fluorescent $Ca^{2+}$ indicator dye, Fluo-3. Cells are incubated at $8\times10^5$ cells/ml in phosphate-buffered saline containing 0.1% bovine serum albumin, 20 mM HEPES buffer, 5 mM glucose, 1% fetal bovine serum, 4 µM Fluo-3 AM and 2.5 mM probenecid for 60 minutes at 37° C. Cells used for such calcium assays can include human monocytes isolated as described by Weiner et al., *J. Immunol. Methods*, 36, 89-97 (1980) or cell lines which expresses the endogenous CCR2 receptor such as THP-1 and MonoMac-6. The cells are then washed three times in phosphate-buffered saline containing 0.1% bovine serum albumin, 20 mM HEPES, 5 mM glucose and 2.5 mM probenecid. The cells are resuspended in phosphate-buffered saline containing 0.5% bovine serum albumin, 20 mM HEPES and 2.5 mM probenecid at a final concentration of $2\text{-}4\times10^6$ cells/ml. Cells are plated into 96-well, black-wall microplates (100 µl/well) and the plates centrifuged at 200×g for 5 minutes. Various concentrations of compound are added to the wells (50 µl/well) and after 5 minutes, 50 µl/well of MCP-1 is added to give a final concentration of 10 nM. Calcium mobilization is detected by using a fluorescent-imaging plate reader. The cell monolayer is excited with an argon laser (488 nM) and cell-associated fluorescence measured for 3 minutes, (every second for the first 90 seconds and every 10 seconds for the next 90 seconds). Data are generated as arbitrary fluorescence units and the change in fluorescence for each well determined as the maximum-minimum differential. Compound-dependent inhibition is calculated relative to the response of MCP-1 alone.

Antagonism of MCP-1-Induced Human PBMC Chemotaxis
(Bacon et al., *Brit. J. Pharmacol.* 1988, 95, 966)

At least one compounds described in the examples have activity in the antagonism of MCP-1-induced human PBMC chemotaxis assay described here.

Neuroprobe MBA96-96-well chemotaxis chamber, Polyfiltronics MPC 96 well plate, and Neuroprobe polyvinylpyrrolidone-free polycarbonate PFDS 8-micron filters are warmed in a 37° C. incubator. Human Peripheral Blood Mononuclear Cells (PBMCs) (Boyum et al., *Scand. J. Clin. Lab Invest. Suppl.* 1968, 97, 31), freshly isolated via the standard ficoll density separation method, are suspended in DMEM at $1\times10^7$ c/ml and warmed at 37° C. A 60 nM solution of human MCP-1 is also warmed at 37° C. Dilutions of test compounds are made up at 2× the concentration needed in DMEM. The PBMC suspension and the 60 nm MCP-1 solution are mixed 1:1 in polypropylene tubes with prewarmed DMEM with or without a dilution of the test compounds. These mixtures are warmed in a 37° C. tube warmer. To start the assay, add the MCP-1/compound mixture into the wells of the Polyfiltronics MPC 96 well plate that has been placed into the bottom part of the Neuroprobe chemotaxis chamber. The approximate volume is 400 µl to each well and there should be a positive meniscus after dispensing. The 8 micron filter is placed gently on top of the 96 well plate, a rubber gasket is attached to the bottom of the upper chamber, and the chamber is assembled. A 200 µl volume of the cell suspension/compound mixture is added to the appropriate wells of the upper chamber. The upper chamber is covered with a plate sealer, and the assembled unit is placed in a 37° C. incubator for 45 minutes. After incubation, the plate sealer is removed and all the remaining cell suspension is aspirated off. The chamber is disassembled and the filter gently removed. While holding the filter at a 90 degree angle, unmigrated cells are washed away using a gentle stream of phosphate buffered saline and the top of the filter wiped with the tip of a rubber squeegee. Repeat this wash twice more. The filter is air dried and then immersed completely in Wright Geimsa stain for 45 seconds. The filter is then washed by soaking in distilled water for 7 minutes, and then a 15 second additional wash in fresh distilled water. The filter is again air dried. Migrated cells on the filter are quantified by visual microscopy.

Mammalian chemokine receptors provide a target for interfering with or promoting immune cell function in a mammal, such as a human. Compounds that inhibit or promote chemokine receptor function are particularly useful for modulating immune cell function for therapeutic purposes. Accordingly, the present invention is directed to compounds which are useful in the prevention and/or treatment of a wide variety of inflammatory, infectious, and immunoregulatory disorders and diseases, including asthma and allergic diseases, infection by pathogenic microbes (which, by definition, includes viruses), as well as autoimmune pathologies such as the rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation or infectious disease. As a result, one or more inflammatory process, such as leukocyte emigration, adhesion, chemotaxis, exocytosis (e.g., of enzymes, histamine) or inflammatory mediator release, is inhibited.

Similarly, an instant compound which promotes one or more functions of the mammalian chemokine receptor (e.g., a human chemokine) as administered to stimulate (induce or enhance) an immune or inflammatory response, such as leukocyte emigration, adhesion, chemotaxis, exocytosis (e.g., of enzymes, histamine) or inflammatory mediator release, resulting in the beneficial stimulation of inflammatory processes. For example, eosinophils can be recruited to combat parasitic infections. In addition, treatment of the aforementioned inflammatory, allergic and autoimmune diseases can also be contemplated for an instant compound which promotes one or more functions of the mammalian chemokine receptor if one contemplates the delivery of sufficient compound to cause the loss of receptor expression on cells through the induction of chemokine receptor internalization or the delivery of compound in a manner that results in the misdirection of the migration of cells.

In addition to primates, such as humans, a variety of other mammals can be treated according to the method of the present invention. For instance, mammals, including but not limited to, cows, sheep, goats, horses, dogs, cats, guinea pigs, rats or other bovine, ovine, equine, canine, feline, rodent or murine species can be treated. However, the method can also be practiced in other species, such as avian species. The subject treated in the methods above is a mammal, male or female, in whom modulation of chemokine receptor activity is desired. "Modulation" as used herein is intended to encompass antagonism, agonism, partial antagonism and/or partial agonism.

CCR5 Binding and Functional Assays

Cell derivation and cell culture: A pool of HT1080 cells stably expressing endogenous CC chemokine receptor 5 (CCR5) were developed using the methods outlined by Harrington, Sherf, and Rundlett (see U.S. Pat. No. 6,361,972 and U.S. Pat. No. 6,410,266). The highest-expressing clones were isolated using repetitive flow cytometry, followed by subcloning. These cells were then cultured in 6-well dishes at $3 \times 10^5$ cells/well and transfected with a DNA vector containing the chimeric HA-tagged G protein Gqi5 (Molecular Devices; 5 micrograms of linearized vector DNA in 15 microL of Ex-Gen from Permeates was used for the transfection). Two days after transfection, the wells were combined and plated into P100 plates. Seven days after plating, colonies were picked, expanded, and analyzed for Gqi5 content by Western blot. A clone (designated as 3559.1.6) having high expression of Gqi5 (from transfection) and of CCR5 (endogenous) was selected and used for the experiments described below. The HT1080 cells (clone 3559.1.6) were cultured with alpha-MEM supplemented with 10% dialyzed fetal bovine serum, 2% penicillin/streptomycin/glutamine, and 500 microgram/mL hygromycin B (final concentration) at 37° C. with 5% $CO_2$ in a humidified atmosphere.

Membrane Preparation: A cell pellet containing $1 \times 10^8$ HT1080 cells (clone 3559.1.6) was resuspended in 5 mL of ice-cold Membrane Prep Buffer (50 mM HEPES, 5 mM $MgCl_2$, 1 mM $CaCl_2$) and homogenized at high-speed on a Polytron homogenizer for 20 sec on ice. The homogenate was diluted with another 25 mL of Membrane Prep Buffer and centrifuged for 12 min (48,000×g at 4° C.). The cell pellet was resuspended in 5 mL of Membrane Prep Buffer before being rehomogenized as described previously. The homogenate was diluted with 5 mL of Membrane Prep Buffer and assayed for CCR5 protein concentration.

Binding assay: The freshly-prepared homogenate from the Membrane Preparation described above was diluted in Binding buffer (50 mM HEPES, 5 mM $MgCl_2$, 1 mM $CaCl_2$, 0.1% BSA; one complete protease inhibitor tablet was added before assay) to achieve a final protein concentration of 10 micrograms/well (solid white 96-well plates from Corning, Inc.). This membrane preparation was mixed with WGA-SPA beads (Amerhsam; pre-soaked in Binding buffer) to give a concentration of 200 micrograms/well. The membrane/SPA bead mix (100 microliters/well) was then added to a plate that had been pre-dotted with 2 microliters DMSO containing various concentrations of test articles (pure DMSO for negative control; various concentrations of examples of this invention for test articles; 500 nM MIP-1 beta as a positive control). The binding assay was initiated through the addition of 50 microliters of [$^{125}$I]-MIP-1 beta (Perkin Elmer; material was diluted in Binding buffer such that the addition of 50 microliters/well gives a final concentration of 0.1 nM [$^{125}$I]-MIP-1 beta). The plate was sealed and allowed to stand at room temperature for 4-6 h before being counted on a Packard TopCount. The percentage bound for the test article was calculated, using negative and positive controls to define the window for each experiment.

Fluorometric Imaging Plate Reader (FLIPR)-Based Functional assay: HT1080 cells (clone 3559.1.6) were plated at 10,000 cells/well (30 microliters) in 384-well plates (black/clear bottom Biocoat PDL, Beckton Dickinson) and charged with 30 microliters/well of Fluro-4 AM fluorescent dye (prepared by dissolving 1 mg Fluro-4 AM in 440 microliters DMSO and diluting with 100 microliters of pluronic solution before diluting further with 10 mL of Hanks buffer). The cells were incubated at 37° C. with 5% $CO_2$ for 30 min before being washed three times and suspended in Assay Buffer (20 mM HEPES, 1.2 mM $CaCl_2$, 5 mM $MgCl_2$, 2.5 mM Probenecid, 0.5% BSA, 1× Hanks). The test article was serially diluted in DMSO and then diluted 1:10 with Assay Buffer before being added to the cells (10 microliters/well). Using FLIPR, the plates were read (10-70 sec) for induction of flux (i.e. agonist activity). The cells were then further charged with Agonist Solution (30 microliters/well; prepared by diluting 30 microliters of 100 microMolar MIP-1 beta in 100 mL of Assay Buffer; this protocol delivers a final concentration of 5 nM MIP-1 beta in the assay) and the plates were read using FLIPR for one minute. Antagonist activity of the test article was determined relative to 0.4% DMSO/Buffer negative control.

At least one compound of the disclosure is an inhibitor of both CCR2 and CCR5 and may be used to treat diseases associated with either chemokine. The compounds of the present invention are considered dual antagonists.

Diseases or conditions of human or other species which can be treated with inhibitors of chemokine receptor function, include, but are not limited to: inflammatory or allergic diseases and conditions, including respiratory allergic diseases such as asthma, allergic rhinitis, hypersensitivity lung diseases, hypersensitivity pneumonitis, eosinophilic cellulitis (e.g., Well's syndrome), eosinophilic pneumonias (e.g., Loeffler's syndrome, chronic eosinophilic pneumonia), eosinophilic fasciitis (e.g., Shulman's syndrome), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymositis or dermatomyositis); systemic anaphylaxis or hypersensitivity responses, drug allergies (e.g., to penicillin, cephalosporins), eosinophilia-myalgia syndrome due to the ingestion of contaminated tryptophan, insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as an dermatitis, eczema, atopic dermatitis, allergic contact dermatitis, urticaria; vasculitis (e.g., necrotizing, cutaneous, and hypersensitivity vasculitis); eosinophilic myositis, eosinophilic fasciitis; cancers with leukocyte infiltration of the skin or organs. Other diseases or conditions in which undesirable inflammatory responses are to be inhibited can be treated, including, but not limited to, vasculitis, vulnerable plaques, venous neointimal hyperplasia reperfusion injury, dialysis-graft neointimal hyperplasia, artio-venous shunt intimal hyperplasia, atherosclerosis, certain hematologic malignancies, cytokine-induced toxicity (e.g., septic shock, endotoxic shock), polymyositis, dermatomyositis. Infectious diseases or conditions of human or other species which can be treated with inhibitors of chemokine receptor function, include, but are not limited to, HIV.

Diseases or conditions of humans or other species which can be treated with promoters of chemokine receptor function, include, but are not limited to: immunosuppression, such as that in individuals with immunodeficiency syndromes such as AIDS or other viral infections, individuals undergoing radiation therapy, chemotherapy, therapy for autoimmune disease or drug therapy (e.g., corticosteroid therapy), which causes immunosuppression; immunosuppression due to congenital deficiency in receptor function or other causes; and infections diseases, such as parasitic diseases, including, but not limited to helminth infections, such as nematodes (round worms); (Trichuriasis, Enterobiasis, Ascariasis, Hookworm, Strongyloidiasis, Trichinosis, filariasis); trematodes (flukes) (Schistosomiasis, Clonorchiasis), cestodes (tape worms) (Echinococcosis, Taeniasis saginata, Cysticercosis); visceral worms, visceral larva migraines (e.g., Toxocara), eosinophilic gastroenteritis (e.g., *Anisaki* sp., *Phocanema* sp.), cutaneous larva migraines (*Ancylostona braziliense, Ancylostoma caninum*). The compounds of the present invention are accordingly useful in the prevention and treatment of a wide variety of inflammatory, infectious and immunoregulatory disorders and diseases.

In addition, treatment of the aforementioned inflammatory, allergic and autoimmune diseases can also be contemplated for promoters of chemokine receptor function if one contemplates the delivery of sufficient compound to cause the loss of receptor expression on cells through the induction of chemokine receptor internalization or delivery of compound in a manner that results in the misdirection of the migration of cells.

In another aspect, the instant invention may be used to evaluate the putative specific agonists or antagonists of a G protein coupled receptor. The present invention is directed to the use of these compounds in the preparation and execution of screening assays for compounds that modulate the activity of chemokine receptors. Furthermore, the compounds of this invention are useful in establishing or determining the binding site of other compounds to chemokine receptors, e.g., by competitive inhibition or as a reference in an assay to compare its known activity to a compound with an unknown activity. When developing new assays or protocols, compounds according to the present invention could be used to test their effectiveness. Specifically, such compounds may be provided in a commercial kit, for example, for use in pharmaceutical research involving the aforementioned diseases. The compounds of the instant invention are also useful for the evaluation of putative specific modulators of the chemokine receptors, In addition, one could utilize compounds of this invention to examine the specificity of G protein coupled receptors that are not thought to be chemokine receptors, either by serving as examples of compounds which do not bind or as structural variants of compounds active on these receptors which may help define specific sites of interaction.

Compounds disclosed herein are useful to treat or prevent disorders selected from rheumatoid arthritis, osteoarthritis, septic shock, atherosclerosis, aneurism, fever, cardiovascular effects, haemodynamic shock, sepsis syndrome, post ischemic reperfusion injury, malaria, Crohn's disease, inflammatory bowel diseases, mycobacterial infection, meningitis, psoriasis, congestive heart failure, fibrotic diseases, cachexia, graft rejection, autoimmune diseases, skin inflammatory diseases, multiple sclerosis, radiation damage, hyperoxic alveolar injury, HIV, HIV dementia, non-insulin dependent diabetes mellitus, asthma, allergic rhinitis, atopic dermatitis, idiopathic pulmonary fibrosis, bullous pemphigoid, helminthic parasitic infections, allergic colitis, eczema, conjunctivitis, transplantation, familial eosinophilia, eosinophilic cellulitis, eosinophilic pneumonias, eosinophilic fasciitis, eosinophilic gastroenteritis, drug induced eosinophilia, cystic fibrosis, Churg-Strauss syndrome, lymphoma, Hodgkin's disease, colonic carcinoma, Felty's syndrome, sarcoidosis, uveitis, Alzheimer, Glomerulonephritis, and systemic lupus erythematosus, esophageal squamous cell carcinoma, neuropathic pain, and obesity.

In another aspect, the compounds are useful to treat or prevent inflammatory disorders selected from rheumatoid arthritis, osteoarthritis, atherosclerosis, aneurism, fever, cardiovascular effects, Crohn's disease, inflammatory bowel diseases, psoriasis, congestive heart failure, multiple sclerosis, autoimmune diseases, skin inflammatory diseases.

In another aspect, the compounds are used to treat or prevent inflammatory disorders selected from rheumatoid arthritis, osteoarthritis, atherosclerosis, Crohn's disease, inflammatory bowel diseases, and multiple sclerosis.

In another aspect, examples disclosed herein may be useful in for the treatment of a variety of cancers, including, but not limited to, the following:

carcinoma including that of the bladder (including accelerated and metastatic bladder cancer), breast, colon (including colorectal cancer), kidney, liver, lung (including small and non-small cell lung cancer and lung adenocarcinoma), ovary, prostate, testes, genitourinary tract, lymphatic system, rectum, larynx, pancreas (including exocrine pancreatic carcinoma), esophagus, stomach, gall bladder, cervix, thyroid, and skin (including squamous cell carcinoma);

hematopoietic tumors of lymphoid lineage including leukemia, acute lymphocytic leukemia, acute lymphoblastic leukemia, B-cell lymphoma, T-cell lymphoma, Hodgkin's lymphoma, non-Hodgkin's lymphoma, hairy cell lymphoma, histiocytic lymphoma, and Burketts lymphoma;

hematopoietic tumors of myeloid lineage including acute and chronic myelogenous leukemias, myelodysplastic syndrome, myeloid leukemia, and promyelocytic leukemia;

tumors of the central and peripheral nervous system including astrocytoma, neuroblastoma, glioma, and schwannomas;

tumors of mesenchymal origin including fibrosarcoma, rhabdomyoscarcoma, and osteosarcoma; and other tumors including melanoma, xenoderma pigmentosum, keratoactanthoma, seminoma, thyroid follicular cancer, and teratocarcinoma.

In another embodiment, disclosed herein are methods of treating cancer, wherein the cancer is selected from breast cancer, liver cancer, prostate cancer, and melanoma. Additionally, compounds disclosed herein may be useful in the treatment of ovarian cancer, and multiple myeloma.

The present invention provides methods for the treatment of a variety of non-cancerous proliferative diseases.

Combined therapy to prevent and treat inflammatory, infectious and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities. For example, in the treatment or prevention of inflammation, the present compounds may be used in conjunction with an anti-inflammatory or analgesic agent such as an opiate agonist, a lipoxygenase inhibitor, a cyclooxygenase-2 inhibitor, an interleukin inhibitor, such as an interleukin-1 inhibitor, a tumor necrosis factor inhibitor, an NMDA antagonist, an inhibitor or nitric oxide or an inhibitor of the synthesis of nitric oxide, a non-steroidal anti-inflammatory agent, a phosphodiesterase inhibitor, or a cytokine-suppressing anti-inflammatory agent, for example with a compound such as acetaminophen, aspirin, codeine, fentaynl, ibuprofen, indomethacin, ketorolac, morphine, naproxen, phenacetin, piroxicam, a steroidal analgesic, sufentanyl, sunlindac, interferon alpha and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levodesoxy-ephedrine; and antitussive such as codeine, hydrocodone, caramiphen, carbetapentane, or dextramethorphan; a diuretic; and a sedating or non-sedating antihistamine. Likewise, compounds disclosed herein may be used in combination with other drugs that are used in the treatment/prevention/suppression or amelioration of the diseases or conditions for which compound of the present invention are useful. Such other drugs may be administered, by a route and in an amount commonly used therefore, contemporaneously or sequentially with a compound of the present invention. When a compound is used contemporaneously with one or more other drugs, a pharmaceutical composition containing such other drugs in addition to the compound of the present invention may be used. Accordingly, the pharmaceutical compositions include those that also contain one or more other active ingredients, in addition to a compound of the present disclosure.

Examples of other active ingredients that may be combined with a compound of the present invention, either administered separately or in the same pharmaceutical compositions, include, but are not limited to: (a) integrin antagonists such as those for selectins, ICAMs and VLA-4; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as b2-agonists (terbutaline, metaproterenol, fenoterol, isoetharine, albuteral, bitolterol, and pirbuterol), theophylline, cromolyn sodium, atropine, ipratropium bromide, leukotriene antagonists (zafirlukast, montelukast, pranlukast, iralukast, pobilukast, SKB-102, 203), leukotriene biosynthesis inhibitors (zileuton, BAY-1005); (f) non-steroidal antiinflammatory agents (NSAIDs) such as propionic acid derivatives (alminoprofen, benxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (i) other antagonists of the chemokine receptors; (j) cholesterol lowering agents such as HMG-COA reductase inhibitors (lovastatin, simvastatin and pravastatin, fluvastatin, atorvsatatin, and other statins), sequestrants (cholestyramine and colestipol), nicotonic acid, fenofibric acid derivatives (gemfibrozil, clofibrat, fenofibrate and benzafibrate), and probucol; (k) anti-diabetic agents such as insulin, sulfonylureas, biguanides (metformin), a-glucosidase inhibitors (acarbose) and glitazones (troglitazone and pioglitazone); (l) preparations of interferons (interferon alpha-2a, interferon-2B, interferon alpha-N3, interferon beta-1a, interferon beta-1b, interferon gamma-1b); (m) antiviral compounds such as efavirenz, nevirapine, indinavir, ganciclovir, lamivudine, famciclovir, and zalcitabine; (o) other compound such as 5-aminosalicylic acid and prodrugs thereof, antimetabolites such as azathioprine and 6-mereaptopurine, and cytotoxic cancer chemotherapeutic agents. The weight ratio of the compound of the present invention to the second active ingredient may be varied and will depend upon the effective doses of each ingredient.

Generally, an effective dose of each will be used. Thus, for example, when a compound is combined with an NSAID the weight ratio of the compound of the present invention to the NSAID will generally range from about 1000:1 to about 1:1000, or alternatively from about 200:1 to about 1:200. Combinations of a compound of the present invention and other active ingredients will generally also be within the aforementioned range, but in each case, an effective dose of each active ingredient should be used.

In treating cancer, a combination of chemotherapeutic agents and/or other treatments (e.g., radiation therapy) is often advantageous. The second (or third) agent may have the same or different mechanism of action than the primary therapeutic agent. It may be especially useful to employ cytotoxic drug combinations wherein the two or more drugs being administered act in different manners or in different phased of the cell cycle, and/or where the two or more drugs have overlapping toxicities or side effects, and/or where the drugs being combined each has a demonstrated efficacy in treating the particular disease state manifested by the patient.

Accordingly, compounds disclosed herein (or other formulae disclosed herein) may be administered in combination with other anti-cancer and cytotoxic agents and treatments useful in the treatment of cancer or other proliferative diseases. The invention herein further comprises use of the compounds herein (or other formulae disclosed herein), in preparing medicaments for the treatment of cancer, and/or it comprises the packaging of the compounds of herein together with instructions that the compounds be used in combination with other anti-cancer or cytotoxic agents and treatments for the treatment of cancer. The present invention further comprises combinations of the compounds of and one or more additional agents in kit form, e.g., where they are packaged together or placed in separate packages to be sold together as a kit, or where they are packaged to be formulated together.

The second (or more) anti-cancer agents may be selected from any one or more of the following:

alkylating agents (including nitrogen mustards, alkyl sulfonates, nitrosoureas, ethylenimine derivatives, and triazenes); anti-angiogenics (including matrix metalloproteinase inhibitors); antimetabolites (including adenosine deaminase inhibitors, folic acid antagonists, purine analogues, and pyrimidine analogues); antibiotics or antibodies (including monoclonal antibodies, CTLA-4 antibodies, anthracyclines); aromatase inhibitors;

cell-cycle response modifiers; enzymes; farnesyl-protein transferase inhibitors;

hormonal and antihormonal agents and steroids (including synthetic analogs, glucocorticoids, estrogens/anti-estrogens [e.g., SERMs], androgens/anti-androgens, progestins, progesterone receptor agonists, and luteinizing hormone-releasing [LHRH] agonists and antagonists); insulin-like growth factor (IGF)/insulin-like growth factor receptor (IGFR) system modulators (including IGFR1 inhibitors); integrin-signaling inhibitors; kinase inhibitors (including multi-kinase inhibitors and/or inhibitors of Src kinase or Src/abl, cyclin dependent kinase [CDK] inhibitors, panther, Her-1 and Her-2 antibodies, VEGF inhibitors, including anti-VEGF antibodies, EGFR inhibitors, mitogen-activated protein [MAP] inhibitors, MEK inhibitors, Aurora kinase inhibitors, PDGF inhibitors, and other tyrosine kinase inhibitors or serine/threonine kinase inhibitors;

microtubule-disruptor agents, such as ecteinascidins or their analogs and derivatives; microtubule-stabilizing agents such as taxanes, and the naturally-occurring epothilones and their synthetic and semi-synthetic analogs;

microtubule-binding, destabilizing agents (including vinca alkaloids); and topoisomerase inhibitors; prenyl-protein transferase inhibitors; platinum coordination complexes; signal transduction inhibitors; and other agents used as anti-cancer and cytotoxic agents such as biological response modifiers, growth factors, and immune modulators.

Additionally, the compounds of the present invention can be formulated or co-administered with other therapeutic agents that are selected for their particular usefulness in addressing side effects associated with the aforementioned conditions. For example, compounds of the invention may be formulated with agents to prevent nausea, hypersensitivity and gastric irritation, such as antiemetics, and $H_1$ and $H_2$ antihistaminics.

The above other therapeutic agents, when employed in combination with the compounds of the present invention, can be used, for example, in those amounts indicated in the Physicians' Desk Reference (PDR) or as otherwise determined by one of ordinary skill in the art.

The compounds are administered to a mammal in a therapeutically effective amount. By "therapeutically effective amount" it is meant an amount of a compound of the present disclosure that, when administered alone or in combination with an additional therapeutic agent to a mammal, is effective to prevent or ameliorate the disease condition or the progression of the disease.

Dosage and Formulation

The compounds of this disclosure can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the disorder.

By way of general guidance, the daily oral dosage of each active ingredient, when used for the indicated effects, will range between about 0.001 to 1000 mg/kg of body weight, or between about 0.01 to 100 mg/kg of body weight per day, or alternatively, between about 1.0 to 20 mg/kg/day. Intravenously, the doses will range from about 1 to about 10 mg/kg/minute during a constant rate infusion. Compounds of this invention may be administered in a single daily dose, or the total daily dosage may be administered in divided doses of two, three, or four times daily. In one embodiment, the daily oral dosage of the active ingredient is between 3 and 600 mg either administered once daily or in divided doses administered twice daily. Alternatively, the active ingredient may be administered in doses of 10-20 mg administered twice daily or 40 to 100 mg administered once daily. Alternatively, the active ingredient may be administered a dose of 12.5 mg twice a day or 75 mg once a day. Alternatively, the active ingredient may be administered in doses of 3, 10, 30, 100, 300, and 600 mg administered either once or twice a day.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration may contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil may be prepared and injected by means of a positive displacement pump into gelatin to fowl soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where the compounds of this invention are combined with other anticoagulant agents, for example, a daily dosage may be about 0.1 to 100 milligrams of the compound of Formula I and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where two or more of the foregoing second therapeutic agents are administered with the compound of the examples, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of the examples and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional bather to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

Additionally, certain compounds disclosed herein may be useful as metabolites of other compounds. Therefore, in one embodiment, compounds may be useful either as a substantially pure compound, which may also then be incorporated into a pharmaceutical composition, or may be useful as metabolite which is generated after administration of the prodrug of that compound. In one embodiment, a compound may be useful as a metabolite by being useful for treating disorders as described herein.

"Substantially pure" as used herein is intended to include a compound having a purity greater than about 90 weight percent, including about 90, 91, 92, 93, 94, 95, 96, 97, 98, 99, and 100 percent.

As one example, a compound disclosed herein may be substantially pure in having a purity greater than about 90 percent (by weight), where the remaining less than about 10 percent of material comprises other metabolite of the compound, a prodrug of the compound, and/or reaction and/or processing impurities arising from its preparation.

Obviously, numerous modifications and variations of the present invention are possible in light of the above teachings. It is therefore to be understood that within the scope of the appended claims, the invention may be practiced otherwise that as specifically described herein.

IN VIVO ASSAYS AND EFFICACY

N-((1R,2S,5R)-5-(tert-butylamino)-2-((S)-2-oxo-3-(6-(trifluorornethyl)quinazolin-4-ylamino)pyrrolidin-1-yl)cyclohexyl)acetamide (also referred to as "Example 1") was evaluated in the following in vivo assays as described below.
Section 1. Example 1 Blocked Mononuclear Cell Recruitment to the Skin Following Intradermal (ID) MCP-1 Challenge in Cynomolgus Monkey.

Intradermal injection of MCP-1 results in the infiltration of mononuclear cells to the injection site. This model was initially developed to assess the inhibitory effect of CCR2 antagonists on the infiltration of mononuclear cells to the skin tissue injected with human MCP-1. The cellular infiltrate can be measured semi-quantitatively by histological scoring.
Methods Each monkey was dosed with Example 1 or its vehicle control (0.05 N HCl) once daily for three days. Example 1 was orally administered at doses of 0, 5, 10, or 20 mg/kg to groups of 4 cynomolgus monkeys (2 per sex per group). Immediately after dosing on Day 3, all animals received 2 intradermal injections of 10 μg (50 μL/injection) of human MCP-1 (R & D Systems) and 2 intradermal injections of its DPBS control (50 μl/injection) at separate sites on the dorsal thorax. Dermal biopsies of all sites were obtained at approximately 18 hours following MCP-1 (or DPBS) challenge. Biopsies were processed for semi-quantitative histological evaluation. Representative sections of skin samples were examined by light microscopy; microscopic lesions and cellular infiltration were noted and their incidences were tabulated.

Figure 20:
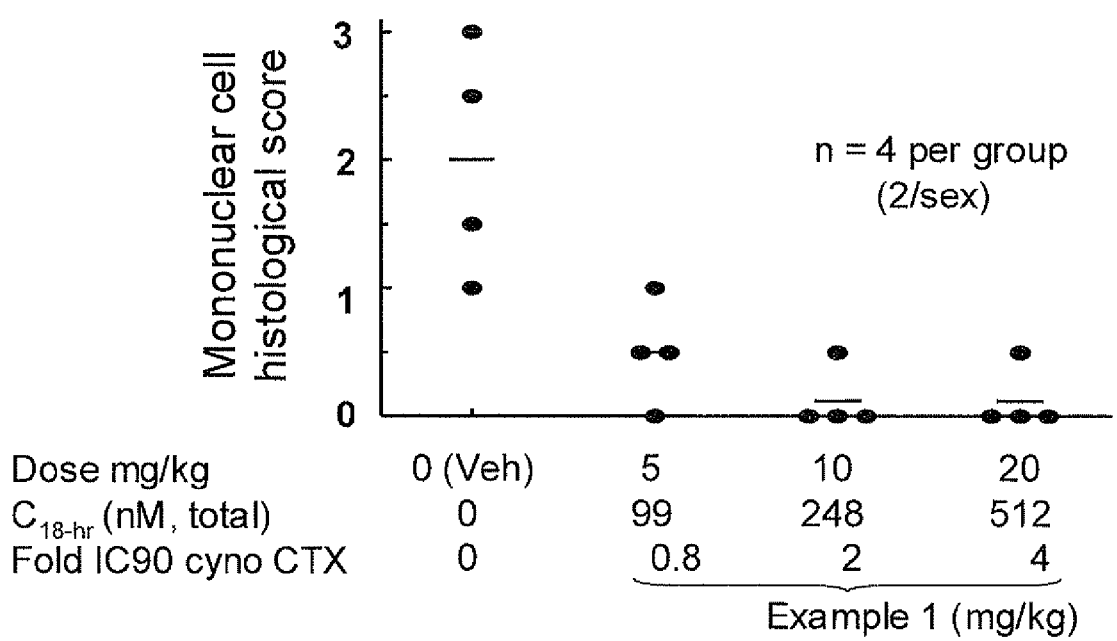
FIG. 20. Intradermal challenge model in cynomolgus monkey: Example 1 inhibited mononuclear cell recruitment to skin.

In addition to biopsy analysis, blood was collected and evaluated for complete blood counts and cell differentials. Also evaluated were plasma samples for compound (and metabolite) concentrations, and serum samples for systemic MCP-1 levels.
Results The recruitment of mononuclear cells to the skin of vehicle-treated control animals in response to MCP-1 challenge was significant (mean histologic score of 2.0 with a range of 1-3, Table 10). Example 1 at 5, 10, and 20 mg/kg inhibited this dermal mononuclear cell infiltration by 75%, 95% and 95%, respectively (Table 10 and FIG. 20). The compound also blocked the infiltration of other cell types such as eosinophils and neutrophils (Table 12). The plasma concentrations of Example 1 at 18 hours and their relationship to levels of inhibition and Cyno chemotaxis IC90 values are summarized in Table 12. Based on the IC50 value of 7.1±2.7 nM for Example 1 in cyno chemotaxis assay, the 5, 10 and 20 mg/kg doses resulted in free plasma concentrations of 0.8-, 2.1-, and 4.3-fold the chemotaxis IC90 at 18 hours post dosing (Table 12).

TABLE 12

Summary of effects of Example 1 on infiltration of mononuclear cells and other cell types in response to MCP-1 challenge in cynomolgus monkeys[a,b]

| Doses mg/kg | Free plasma concentration (nM) | Fold Chemotaxis IC90 | Mononuclear cell score (range) (inhibition %) | PMN[c] score (range) | Eos[d] score (range) | Total cell score (range) |
|---|---|---|---|---|---|---|
| 0 | 0 | 0 | 2.0 (1-3) (0%) | 0.3 (0-1) | 1.5 (0.5-3) | 4.0 (2-6[e]) |

TABLE 12-continued

Summary of effects of Example 1 on infiltration of mononuclear cells and other cell types in response to MCP-1 challenge in cynomolgus monkeys[a,b]

| Doses mg/kg | Free plasma concentration (nM) | Fold Chemotaxis IC90 | Mononuclear cell score (range) (inhibition %) | PMN[c] score (range) | Eos[d] score (range) | Total cell score (range) |
|---|---|---|---|---|---|---|
| 5 | 99 | 0.8 | 0.5 (0-1) (75%) | 0.1 (0-0.5) | 1.4 (1-2) | 2.0 (1-3) |
| 10 | 248 | 2.1 | 0.1 (0-0.5) (95%) | 0.1 (0-0.5) | 0.8 (0.5-1) | 1.0 (0.5-2) |
| 20 | 512 | 4.3 | 0.1 (0-0.5) (95%) | 0 (0-0) | 0.8 (0.5-1) | 0.9 (0.5-1) |

[a]An arbitrary scaling system from 0 to 4 was utilized with each number representing a particular designation of inflammatory infiltrate as follows: 0, unremarkable number of inflammatory cells; 0.5, trace; 1, minimal; 2, mild; 3, moderate; 4, marked infiltration.
[b]Mean values are an average of 8 MCP-1 site biopsies, representing 2 separate biopsies from 4 monkeys per group. Ranges represent the spread of average histological scores for 2 biopsies per animal.
[c]PMN stands for polymorphonuclear cell (neutrophil).
[d]Eos is an abbreviation for eosinophils.
[e]Total score is a mathematical sum of mean values for each cell type to demonstrate the dose response.

Evaluation of changes in serum inflammatory mediators showed an increase (approximately 3-4 fold) in MCP-1 level in Example 1-treated groups relative to vehicle control. In addition, complete blood count (CBC) analysis showed an increase (~2-fold) in neutrophils in Example 1-treated groups, relative to vehicle control, at 18 hours on Day 4 following three days of dosing.

To refine the dose (concentration) response of Example 1 in a more readily quantifiable system, we used hCCR2 KI mice to evaluate the effect of Example 1 monocyte/macrophage infiltration in thioglycollate (TG)-induced peritonitis model with flow cytometry-based methodology.

Section 2. Example 1 Inhibited Monocyte/Macrophage Infiltration in 48-Hour TG Peritonitis Model in hCCR2 KI Mouse TG-induced peritonitis model has been used as a model of recruitment of monocytes/macrophages to inflammation site. Both in-house and published studies have demonstrated that monocyte/macrophage recruitment in this model is CCR2-dependent. See Boring L. et al., *Impaired monocyte migration and reduced type 1 (Th1) cytokine responses in C—C chemokine receptor 2 knockout mice*. J Clin Invest., 100(10): 2552-61. (1997); and Kuziel, W. A. et al., *Severe reduction in leukocyte adhesion and monocyte extravasation in mice deficient in CC chemokine receptor 2*. Proc Natl Acad Sci U S A. 94(22):12053-8 (1997).

Methods

For the 48-hour TG peritonitis study, Example 1 was dosed twice a day with the first dose given one hour prior to TG injection. Total peritoneal cell counts were obtained on isolated cells by a cell counter. Blood was also collected in heparin from the retro-orbital sinus at the end of each study for flow cytometry and in EDTA for determination of drug concentration.

For flow cytometric analysis, peritoneal exudate cells ($1\times10^6$) were washed once with FACS buffer (PBS/0.5% BSA) and resuspended in FACS buffer. Cells were incubated with an Fe-blocking antibody (BD Pharmingen) on ice for 15 min followed by addition of the following antibodies (BD Phainiingen): PE conjugated anti-F4/80, FITC conjugated anti-Ly6C, and Alexa 647 conjugated anti-hCCR2. After 45 min on ice, cells were fixed by BD Cytofix for 15 min on ice, washed twice with FACS buffer, and resuspended in 200 µl FACS buffer. Cellular events (40,000) were acquired for each sample and data were analyzed using FloJo software (TreeStar). A FSC/SSC gate was set to include all monocytes (low SSC, higher FSC) while excluding granulocytes from the analysis. This gated population was then analyzed for Ly6C (FITC), F4/80 (PE) expression. Peritoneal monocytes/macrophage numbers were determined by multiplying total peritoneal cell counts obtained by the cell counter and the percentage of monocytes/macrophages identified by F4/80+ cells from flow cytometry. Statistical significance of differences between means was analyzed using the paired two-tailed t test with significance set at p values below 0.05.

Results

Example 1 was evaluated in the hCCR2 KI mouse TG peritonitis model to determine its EC50 in inhibiting monocyte/macrophage infiltration. Mice were administered thioglycollate, and dosed orally with Example 1 at 1, 25, or 100 mg/kg BID. Forty eight hours post TG treatment, peritoneal lavage was obtained for cellular infiltrate analysis by flow cytometry.

Figure 21:
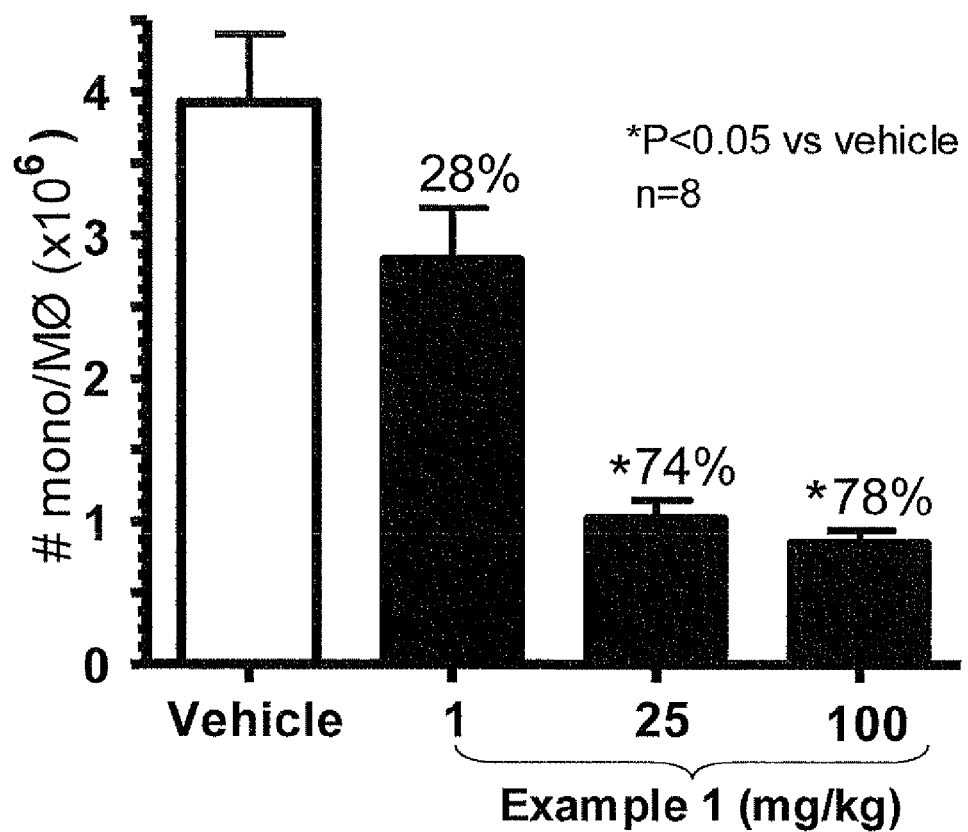
FIG. 21. 48-hour TG peritonitis in hCCR2 KI mouse: Example 1 inhibition of monocyte/macrophage infiltration into peritoneal cavity.

To distinguish between the recruited monocyte/macrophages versus resident macrophages and granulocytes, staining of both F4/80 and Ly6C monocyte/macrophage surface markers was used to define the recruited monocyte/macrophages. A dose-dependent inhibition in monocyte/macrophage infiltration was observed (FIG. 21). Doses of 1, 25, and 100 mg/kg gave an inhibition of 24%, 74% and 78%, respectively. In three separate studies with multiple doses, the average EC50 for inhibition of monocyte/macrophage infiltration by this analysis was estimated to be 3.9 nM.

To assess the in vivo level of receptor occupancy by Example 1 in the 48-hour thioglycolate peritonitis model in the hCCR2 KI mouse, plasma levels of both Example 1 and mouse MCP-1 were measured. The caveat for this estimation is that only CCR2 and its major ligand MCP-1, were taken into consideration. The receptor occupancy of a ligand in the presence of a competitive inhibitor is defined by the Gaddum equation:

$$\frac{[RL]}{[R]} = \frac{1}{1+(K_d/[L])(1+[I]/K_i)}$$

Since Example 1 is a competitive inhibitor of MCP-1 binding to CCR2, the amounts of both mouse MCP-1/CCR2 receptor complex and Example 1/CCR2 receptor complex can be determined using the serum levels of both mouse MCP-1 and protein-unbound Example 1 in plasma. The $K_d$ for mouse MCP-1 binding to hCCR2 is 0.91±0.08 nM (n=8) which was determined in cold competition ligand binding experiments using $^{125}$I-human MCP-1. The average $K_i$ for Example 1 binding to hCCR2 is 1.3 nM. The fraction of mouse MCP-1/CCR2 receptor complexes is determined using the form of the equation described above. To determine the fraction of Example 1/CCR2 complexes the equation is re-defined as:

$$\frac{[RI]}{[R]} = \frac{1}{1+(K_i/[I])(1+[L]/K_d)}$$

Finally, the amount of CCR2 free is determined from:

$[CCR2]_{total} = [CCR2]_{free} + [\text{mouse } MCP-1/CCR2] + [\text{Example } 1/CCR2]$ As shown in Table 13, the percent inhibition of monocyte/macrophage infiltration into the peritoneum at 48 hour reflects the percentage of Example 1/CCR2 receptor complex.

TABLE 13

Determination of in vivo receptor occupancy of Example 1 in blood of hCCR2 KI mice in the 48-hour TG peritonitis model

| Dose (mg/kg) | Concentration of Mouse MCP-1 in plasma (nM) | Concentration of free Example 1 in plasma (nM) (fold IC90 CCR2 binding) | % mouse MCP-1 bound CCR2 | % of Example 1-bound CCR2 | % free CCR2 | % inhibition of monocyte/ macrophage infiltration[a] |
|---|---|---|---|---|---|---|
| 100 | 0.015 | 53 (1.8) | 0.04 | 97.6 | 2.4 | 78 |
| 25 | 0.017 | 14 (0.5) | 0.16 | 91.2 | 8.6 | 74 |
| 1 | 0.005 | 1.4 (0.05) | 0.26 | 51.4 | 48.3 | 24 |
| 0 (vehicle) | 0 | 0 | 0 | 0 | 100 | 0 |

Section 3. Chronic Efficacy Studies
Experimental Autoimmune Encephalomyelitis (EAE) Methods To assess the effect of Example 1 on chronic models of disease, we used the EAE model of multiple sclerosis in hCCR2 KI mice. To study the effect of Example 1 on EAE model, 10 mice per group were used. On day 0, hCCR2 KI mice were immunized subcutaneously with a total of 200 μl of 300 μg myelin oligodendrocyte glycoprotein (MOG) 35-55 (Genemed Synthesis) mixed 1:1 with 300 μg Mycobacterium tuberculosis (H37Ra) (Becton-Dickinson) in incomplete Freund's adjuvant (IFA) (Sigma-Aldrich). On day 0 (two hours post-immunization) and day 2, mice were injected intraperitoneally with 100 μl of 400 ng pertussis toxin. Clinical scoring began on day 10, continued three times per week throughout the study, and was based on a scale of 0-5: 0, no signs of disease; 0.5, partial tail weakness; 1, limp tail or waddling gait with tail tonicity; 1.5, waddling gait with partial tail weakness; 2, wadding gait with limp tail (ataxia); 2.5 (ataxia with partial limb paralysis; 3, full paralysis of one limb; 3.5, full paralysis of one limb with partial paralysis of a second limb; 4, full paralysis of two limbs; 4.5, moribund; 5, death. Oral dosing of Example 1 at 25 mg/kg and 55 mg/kg (BID) was initiated on day 1.

Results

Figure 22:
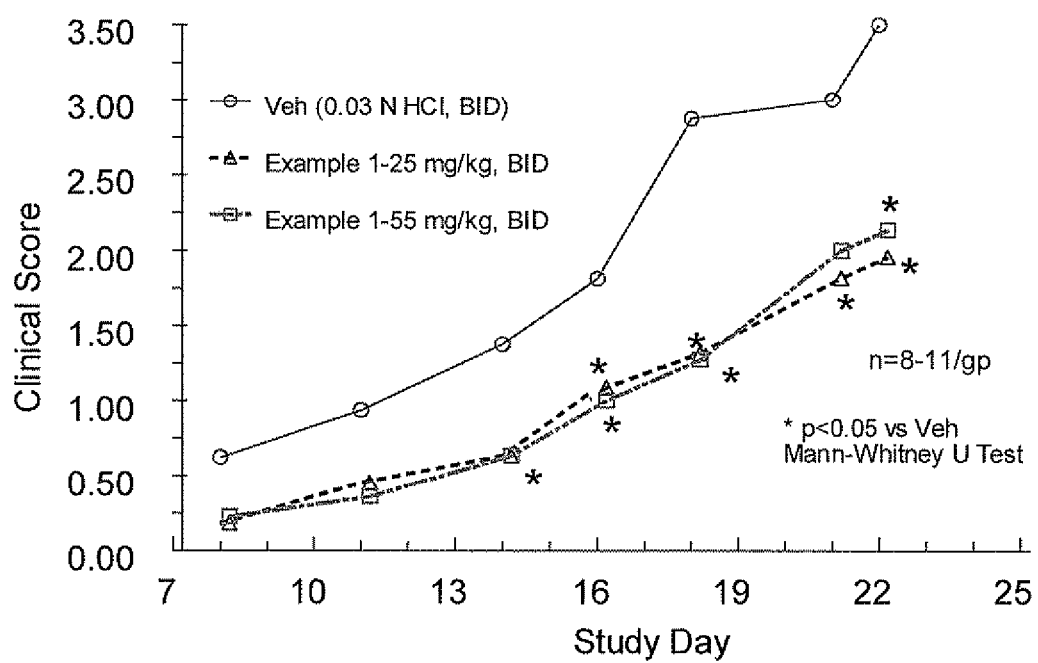
FIG. 22. hCCR2 KI mouse EAE (experimental autoimmune encephalomyelositis): Example 1 treatment reduced clinical score.

Example 1 at both doses reduced the area under curve (AUC) of the clinical score by 49% (p<0.05) (FIG. 22). The IC50 is 3.7 nM for Example 1 in $^{125}$I-mouse MCP-1 binding to hCCR2-expressing cells, hPBMCs (mimicking hCCR2 KI setting). Based on this IC50 value, the 25 and 55 mg/kg doses resulted in a free plasma trough concentration of 1- and 3-fold the binding IC90. Histological evaluation of the spinal cord on Day 22 did not demonstrate a significant difference in total inflammatory cellular infiltrate between mice treated with Example 1 versus vehicle. A marked neutrophil infiltrate was observed in mice treated with compound.

What is claimed is:

1. A compound selected from:

(7R,8S)-8-((3S)-3-(((benzyloxy)carbonyl)amino)-2-oxo-1-pyrrolidinyl)-1,4-dioxaspiro[4.5]decane-7-carboxylic acid, or a salt thereof;

benzyl ((3S)-1-(7R,8S)-7-(azidocarbonyl)-1,4-dioxaspiro[4.5]dec-8-yl)-2-oxo-3-pyrrolidinyl)carbamate, or a salt thereof;

benzyl ((3S)-1-(7R,8S)-7-isocyanato-1,4-dioxaspiro[4.5]dec-8-yl)-2-oxo-3-pyrrolidinyl)carbamate, or a salt thereof;

benzyl ((3S)-1-((7R,8S)-7-acetamido-1,4-dioxaspiro[4.5]dec-8-yl)-2-oxo-3-pyrrolidinyl)carbamate, or a salt thereof;

benzyl ((3S)-1-((1S,2R)-2-acetamido-4-oxocyclohexyl)-2-oxo-3-pyrrolidinyl)carbamate, or a salt thereof; and benzyl ((3S)-1-((1S,2R,4R)-2-acetamido-4-(tert-butylamino)cyclohexyl)-2-oxo-3-pyrrolidinyl)carbamate, or a salt thereof.

* * * * *

UNITED STATES PATENT AND TRADEMARK OFFICE
CERTIFICATE OF CORRECTION

PATENT NO. : 8,049,019 B2  
APPLICATION NO. : 12/606255  
DATED : November 1, 2011  
INVENTOR(S) : Boguslaw M. Mudryk, Michael E. Randazzo and Rulin Zhao Page 1 of 1

It is certified that error appears in the above-identified patent and that said Letters Patent is hereby corrected as shown below:

Column 104

Line 31, "(7R,8S)" should read -- ((7R,8S) --; and  
Line 54, "(7R,8S)" should read -- ((7R,8S) --.

Signed and Sealed this  
Twenty-ninth Day of May, 2012

David J. Kappos  
*Director of the United States Patent and Trademark Office*